US012540343B2

(12) United States Patent
Okita et al.

(10) Patent No.: US 12,540,343 B2
(45) **Date of Patent: *Feb. 3, 2026**

(54) METHOD FOR PRODUCING MICROBIAL OIL FROM LABYRINTHULID MICROORGANISM CAPABLE OF PRODUCING SAID MICROBIAL OIL

(71) Applicants: KYUSHU UNIVERSITY, NATIONAL UNIVERSITY CORPORATION, Fukuoka (JP); KONAN GAKUEN, Kobe (JP); NIPPON SUISAN KAISHA, LTD., Tokyo (JP)

(72) Inventors: Yuji Okita, Tokyo (JP); Makoto Ito, Fukuoka (JP); Rie Hamaguchi, Fukuoka (JP); Hatsumi Goda, Fukuoka (JP); Seiya Mochinaga, Fukuoka (JP); Daisuke Honda, Kobe (JP)

(73) Assignees: KYUSHU UNIVERSITY, NATIONAL UNIVERSITY CORPORATION, Fukuoka (JP); KONAN GAKUEN, Kobe (JP); NIPPON SUISAN KAISHA, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/411,156

(22) Filed: Jan. 12, 2024

(65) Prior Publication Data

US 2024/0294952 A1 Sep. 5, 2024

Related U.S. Application Data

(60) Division of application No. 17/401,894, filed on Aug. 13, 2021, now Pat. No. 11,898,190, which is a continuation of application No. 15/740,969, filed as application No. PCT/JP2016/069825 on Jul. 4, 2016, now abandoned.

(30) Foreign Application Priority Data

Jul. 3, 2015 (JP) ................................ 2015-134715

(51) Int. Cl.

| | |
|---|---|
| ***C12P 7/6432*** | (2022.01) |
| ***C10G 3/00*** | (2006.01) |
| ***C12N 1/00*** | (2006.01) |
| ***C12N 1/12*** | (2006.01) |
| ***C12N 15/09*** | (2006.01) |
| ***C12N 15/52*** | (2006.01) |
| ***C12N 15/79*** | (2006.01) |
| ***C12P 1/00*** | (2006.01) |
| ***C12P 7/64*** | (2022.01) |
| ***C12P 7/6427*** | (2022.01) |
| ***C12P 7/6472*** | (2022.01) |
| ***C12P 19/34*** | (2006.01) |
| ***C12R 1/00*** | (2006.01) |
| ***C12R 1/89*** | (2006.01) |

(52) U.S. Cl.

CPC ............ *C12P 7/6432* (2022.01); *C12N 15/09* (2013.01); *C12N 15/79* (2013.01); *C12P 1/00* (2013.01); *C12P 7/64* (2013.01); *C12P 7/6427* (2013.01); *C12P 7/6472* (2013.01); *C12P 19/34* (2013.01); *C10G 3/00* (2013.01); *C12N 1/00* (2013.01); *C12N 1/125* (2021.05); *C12N 15/52* (2013.01); *C12R 2001/00* (2021.05); *C12R 2001/89* (2021.05)

(58) Field of Classification Search

None

See application file for complete search history.

(56) References Cited

U.S. PATENT DOCUMENTS

| | | | |
|---|---|---|---|
| 5,130,242 | A | 7/1992 | Barclay |
| 5,340,594 | A | 8/1994 | Barclay |
| 5,340,742 | A | 8/1994 | Barclay |
| 5,518,918 | A | 5/1996 | Barclay |
| 5,656,319 | A | 8/1997 | Barclay |
| 5,688,500 | A | 11/1997 | Barclay |

(Continued)

FOREIGN PATENT DOCUMENTS

| | | |
|---|---|---|
| JP | 3127161 B2 | 1/2001 |
| JP | 3669372 B2 | 7/2005 |

(Continued)

OTHER PUBLICATIONS

Cohen, Z. et al. editors, "Single Cell OIls Microbial and Algal Oils", AOCS Press, 2010, 2nd Edition, p. 88; cited in the Specification.

Metz, J. G. et. al., "Production of Polyunsaturated Fatty Acids by Polyketide Synthases in Both Prokaryotes and Eukaryotes", Science, 13, Jul. 2001, vol. 293, pp. 290-293; cited in the Specification.

Ratlegde, C., "Omega-3 biotechnology: Erros and omissions", Biotechnology Advances 30, 2012, pp. 1746-1747; cited in the Specification.

Lippmeier, J.C. et al., "Characterization of Both Polyunsaturated Fatty Acid Biosynthetic Pathways in *Schizochytrium* sp.", Lipids, 2009, pp. 621-630; cited in the Specification and ISR.

(Continued)

*Primary Examiner* — Christian L Fronda

(74) *Attorney, Agent, or Firm* — WHDA, LLP

(57) ABSTRACT

A method for producing a microbial oil includes genetically modifying a labyrinthulid which belongs to the genus *Parietichytrium* or the genus *Schizochytrium* by disrupting and/or silencing a Δ4 desaturase gene, a C20 elongase gene, and/or a C18 elongase gene, or by being transformed with an ω3 desaturase gene; culturing the labyrinthulid; and collecting the microbial oil from the labyrinthulid. The labyrinthulid has an activity of synthesizing DHA via a PUFA-PKS pathway in an amount of not more than 1/100 of a total amount of DHA synthesized in the labyrinthulid or no activity of producing PUFAs via the PUFA-PKS pathway, and the labyrinthulid has an activity of producing PUFAs via an endogenous elongase-desaturase pathway.

10 Claims, 48 Drawing Sheets

Specification includes a Sequence Listing.

(56) References Cited

U.S. PATENT DOCUMENTS

| | | | | |
|---|---|---|---|---|
| 5,698,244 | A | 12/1997 | Barclay | |
| 9,062,315 | B2 * | 6/2015 | Sakaguchi | C12P 7/6434 |
| 9,150,891 | B2 * | 10/2015 | Sakaguchi | C12P 7/6409 |
| 10,815,505 | B2 * | 10/2020 | Sakaguchi | C12N 9/0083 |
| 11,203,763 | B2 * | 12/2021 | Sakaguchi | C12P 7/6409 |
| 11,898,190 | B2 * | 2/2024 | Okita | C12N 9/1029 |
| 2005/0014231 | A1 | 1/2005 | Mukerji et al. | |
| 2011/0177031 | A1 * | 7/2011 | Apt | C12N 1/125 435/243 |
| 2012/0322116 | A1 * | 12/2012 | Sakaguchi | C12N 9/0083 435/471 |
| 2013/0309772 | A1 * | 11/2013 | Sakaguchi | C12P 7/6434 554/1 |

FOREIGN PATENT DOCUMENTS

| | | | |
|---|---|---|---|
| WO | 2011037207 | A1 | 3/2011 |
| WO | 2012/043826 | A1 | 4/2012 |
| WO | 2013013211 | A1 | 1/2013 |

OTHER PUBLICATIONS

Matsuda, T. et. al., "Analysis of D12-fatty acid desaturase function revealed that two distinct pathways are active for the synthesis of PUFAs in T. aureum TCC 34304", Journal of Lipid Research, 2012, vol. 53, pp. 1210-1222; cited in the Specification and ISR.

Chang, M. L. "Marine microorganisms an unexpected source for anti-inflammatory fatty acids used to treat lipid disorders?", ASBMB Today, Jun. 2012, p. 30; cited in the Specification and ISR.

Sakaguchi, K. et. al., "Versatile Transformation System That Is Applicable to both Multiple Transgene Expression and Gene Targeting for Thraustochytrids", Applied and Environmental Microbiology, 2012, pp. 3193-3202; cited in the Specification and ISR.

Yazawa, K. "Production of Eicosapentaenoic Acid from Marine Bacteria", Supplement, 1996, vol. 31, pp. 297-300; cited in the Specification.

"Gene Knockout Construct Producation Method by PCR", Journal of the Japan Society for Bioscience, Biotechnology and Agrochem, 2003, pp. 150-153; with English Abstract; cited in the Specification.

"Illustrated Bio Experiments vol. 2 Fundamentals of Gene Analysis", 1995, pp. 63-68; with English Abstract; cited in the Specification.

Sanger, F. et. al., "DNA sequencing with chain-terminating inhibitors", Proc. Natl. Acad. Sci., Dec. 1997, vol. 74, No. 12, pp. 5463-5467; cited in the Specification.

Cigan, A. M. et. al., "Sequence and structural features associated with translational initiator regions in yeast—a review", Elsevier, 1987, pp. 1-18; cited in the Specification.

Qiu, X. et. al., "Identification of a D4 Fatty Acid Desaturase from *Thraustochytrium* sp. Involved in the Biosynthesis of Docosahezanoic Acid by Heterologous Expression in *Saccharomyces cerevisiae* and *Brassica juncea*", The Journal of Biological Chemistry, 2001, vol. 276, No. 34, pp. 31561-31566; cited in the Specification.

Abe, E. et. al., "A Novel Phosphatidylcholine Which Contains Pentadecanoic Acid at sn-1 and Docosahexaenoic Acid at sn-2 in *Schizochytrium* sp. F26-b", J. Blochem., 2006, pp. 247-253; cited in the Specification.

Bio-Experiments Illustrated, vol. 2, Illustrated Bio-Expericents vol. 2 Fundamentals of Gene Analysis, 1995, pp. o??•õ 17-128; with English Abstract; cited in the Specification.

"PCR DIG Probe Synthesis Kit", DIG Manual (Japanese Edition) 8th, Roche Applied Science; cited in the Specification.

Ohara, J. et. al., "Two Fatty Acid Elongases Processing C18-Delta 6/C18-Delta 9/C20-Delta 5 or C16-Delta 9 Elongase Activity in Thraustochytrium sp_ ATCC 26185", Mar. Biotechnol., 2013, vol. 15, pp. 476-486; cited in ISR.

Kobayashi, T. et. al., "Increase of Eicosapentaenoic Acid in Thraustochytrids through Thraustochytrid Ubiquitin Promoter-Driven Expression of a Fatty Acid D5 Desaturase Gene", Applied and Environmental Microbiology, Jun. 2011, vol. 77, No. 11, pp. 3870-3876; cited in ISR.

Matsuda, T. et. al., "Molecular cloning of a Pinguiochrysis pyriformis oleate-specific microsomal D12-fatty acid desaturase and functional analysis in yeasts and thraustochytrids", J. Biochem., 2011, vol. 150, No. 4, pp. 375-383; cited in ISR.

Matsuda, T. et. al., "Species-dependent pathway for production of PUFA in thraustochytrids revealed by analysis of D12 fatty acid desaturase", Chemistry and Physics of Lipids, 2011, vol. 164, p. S24; cited in ISR.

Martinez, M. et. al., "The D4-desaturation pathway for DHA biosynthesis is operative in the human species: Differences between normal controls and children with the Zellweger syndrome", Lipids in Health and Disease, 2010, pp. 1-10; cited in ISR.

Martins et al. Mar. Drugs 2013, 11, 2259-2281. (Year: 2013).

Chica et al. Curr Opin Biotechnol. Aug. 2005; 16(4):378-84. (Year: 2005).

Singh et al. Curr Protein Pept Sci. 2017, 18, 1-11 (Year: 2017.

Kizer et al. Appl Environ Microbial. May 2008;74(10):3229-41. (Year: 2008).

Prather et al. Curr Opin Biotechnol. Oct. 2008; 19(5):468-7 4. (Year: 2008).

Romanos, M. A. et. al., "Foreign Gene Expression in Yeast: a Review", Yeast, 1992, vol. 8, pp. 423-488; cited in the Specification.

Lindblad, V. et. al., "Yeast, Chapter 13", Current Protocols in Molecular Biology , 2003. (138 pages).

* cited by examiner

| COMPARISON WITH WILD-TYPE STRAIN | C20 −/− | SEK364 | FA |
|---|---|---|---|
| 54.4% | 1.16 | 2.13 | C14:0 |
| 6.5% | 0.02 | 0.38 | C15:0 |
| 65.4% | 17.55 | 26.83 | C16:0 |
| 31.6% | 0.24 | 0.76 | C17:0 |
| 12.0% | 0.05 | 0.42 | C17:1 |
| 29.4% | 4.66 | 15.84 | C18:0 |
| 49.5% | 12.91 | 26.08 | C18:1n−9 |
| − | 0.00 | 0.00 | C18:1n−7 |
| 289.4% | 7.38 | 2.55 | C18:2n−6(LA) |
| 36.3% | 0.02 | 0.06 | C19:0 |
| 368.7% | 1.91 | 0.52 | C18:3n−6(GLA) |
| 99.5% | 0.31 | 0.31 | C19:2 |
| 1673.7% | 8.62 | 0.51 | C20:3n−6(DGLA) |
| 1079.4% | 25.22 | 2.34 | C20:4n−6(ARA) |
| 722.8% | 0.56 | 0.08 | C20:4n−3(ETA) |
| 105.7% | 0.18 | 0.17 | C22:0 |
| 851.2% | 11.58 | 1.36 | C20:5n3(EPA) |
| 42.2% | 0.67 | 1.59 | C22:4n−6(DTA) |
| 23.1% | 1.64 | 7.07 | C22:5n−6(DPA) |
| 45.4% | 0.26 | 0.56 | C22:5n−3(DPA) |
| 20.0% | 1.28 | 6.38 | C22:6n−3(DHA) |

FIG. 13

| Fatty acid(%) | SEK364 | Δ4 desaturase KO | KO/SKE358 |
|---|---|---|---|
| C14:0 | 2.24 | 2.65 | 118% |
| C16:0 | 20.28 | 29.67 | 146% |
| C18:0 | 16.69 | 15.80 | 95% |
| C18:1n-9 | 33.63 | 27.71 | 82% |
| C18:2n-6(LA) | 2.71 | 4.05 | 150% |
| C18:3n-6(GLA) | 0.19 | 0.38 | 198% |
| C20:3n-6(DGLA) | 0.78 | 0.98 | 125% |
| C20:4n-6(ARA) | 1.30 | 1.59 | 122% |
| C20:4n-3(ETA) | 0.30 | 0.05 | 16% |
| C20:5n-3(EPA) | 1.44 | 0.79 | 55% |
| C22:4n-6(DTA) | 1.17 | 5.91 | 505% |
| C22:5n-6(n-6 DPA) | 4.29 | <0.005 | <0.12% |
| C22:5n-3(n-3 DPA) | 0.85 | 4.02 | 475% |
| C22:6n-3(DHA) | 4.94 | <0.005 | <0.11% |

FIG. 22

| C20 elongase KO | | SEK358 | FA |
|---|---|---|---|
| 101.0% | 1.41 | 1.40 | C14:0 |
| 32.0% | 2.44 | 7.63 | C15:0 |
| 62.1% | 13.49 | 21.73 | C16:0 |
| 26.6% | 1.96 | 7.34 | C17:0 |
| 39.6% | 2.95 | 7.46 | C18:0 |
| 22.0% | 3.19 | 14.47 | C18:1n-9 |
| 84.5% | 0.19 | 0.23 | C18:1n-7 |
| 269.4% | 4.28 | 1.59 | C18:2n-6(LA) |
| 247.0% | 2.61 | 1.06 | C18:3n-6(GLA) |
| 201.5% | 0.34 | 0.17 | C19:2 |
| 499.9% | 8.64 | 1.73 | C20:3n-6(DGLA) |
| 654.8% | 21.35 | 3.26 | C20:4n-6(ARA) |
| | 2.14 | 0.00 | C20:4n-3(ETA) |
| | 0.30 | 0.00 | C22:0 |
| 1068.6% | 23.83 | 2.23 | C20:5n3(EPA) |
| 8.0% | 0.26 | 3.28 | C22:4n-6(DTA) |
| 6.4% | 0.46 | 7.10 | C22:5n-6(DPA) |
| 21.6% | 0.23 | 1.06 | C22:5n-3(DPA) |
| 12.3% | 0.94 | 7.61 | C22:6n-3(DHA) |

| Fatty acid(%) | SKE 358 | Δ4 desaturase KO | KO/SKE358 |
|---|---|---|---|
| C14:0 | 2.37 | 2.94 | 124% |
| C16:0 | 26.42 | 23.57 | 89% |
| C18:0 | 13.58 | 6.70 | 49% |
| C18:1n-9 | 17.26 | 34.57 | 200% |
| C18:2n-6(LA) | 1.66 | 4.60 | 276% |
| C18:3n-6(GLA) | 0.51 | 0.78 | 152% |
| C20:3n-6(DGLA) | 2.21 | 1.35 | 61% |
| C20:4n-6(ARA) | 4.59 | 3.03 | 66% |
| C20:4n-3(ETA) | 0.16 | 0.03 | 20% |
| C20:5n-3(EPA) | 2.40 | 1.10 | 46% |
| C22:4n-6(DTA) | 3.72 | 7.88 | 212% |
| C22:5n-6(n-6 DPA) | 7.32 | <0.005 | <0.07% |
| C22:5n-3(n-3 DPA) | 1.67 | 5.10 | 305% |
| C22:6n-3(DHA) | 7.13 | <0.005 | <0.07% |

| C20 elongase KO | | SEK571 | FA |
|---|---|---|---|
| 43.8% | 0.98 | 2.23 | C14:0 |
| 197.0% | 4.86 | 2.47 | C15:0 |
| 40.6% | 14.13 | 34.78 | C16:0 |
| 152.7% | 4.80 | 3.14 | C17:0 |
| 43.4% | 4.71 | 10.86 | C18:0 |
| 85.5% | 3.66 | 4.28 | C18:1n-9 |
| 234.8% | 0.37 | 0.16 | C18:1n-7 |
| 251.6% | 1.70 | 0.67 | C18:2n-6(LA) |
| 228.8% | 1.07 | 0.47 | C18:3n-6(GLA) |
| 156.9% | 0.24 | 0.16 | C19:2 |
| 450.2% | 1.93 | 0.43 | C20:3n-6(DGLA) |
| 388.5% | 13.24 | 3.41 | C20:4n-6(ARA) |
| 1048.9% | 1.14 | 0.11 | C20:4n-3(ETA) |
| 182.8% | 0.43 | 0.24 | C22:0 |
| 796.8% | 29.58 | 3.71 | C20:5n3(EPA) |
| 9.0% | 0.15 | 1.61 | C22:4n-6(DTA) |
| 8.2% | 0.96 | 11.69 | C22:5n-6(DPA) |
| 34.0% | 0.25 | 0.75 | C22:5n-3(DPA) |
| 8.6% | 1.17 | 13.62 | C22:6n-3(DHA) |

FIG. 34

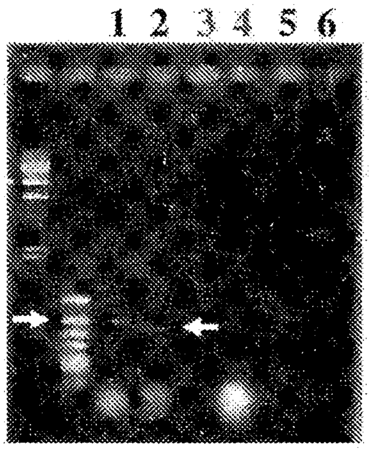
FIG. 35
FIG. 36A
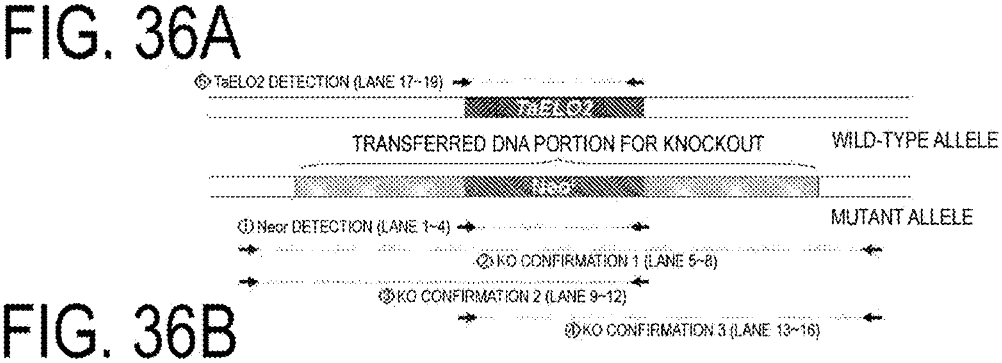
FIG. 36B
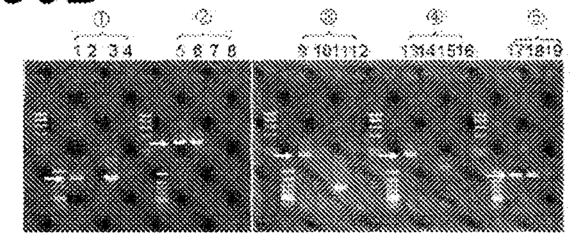
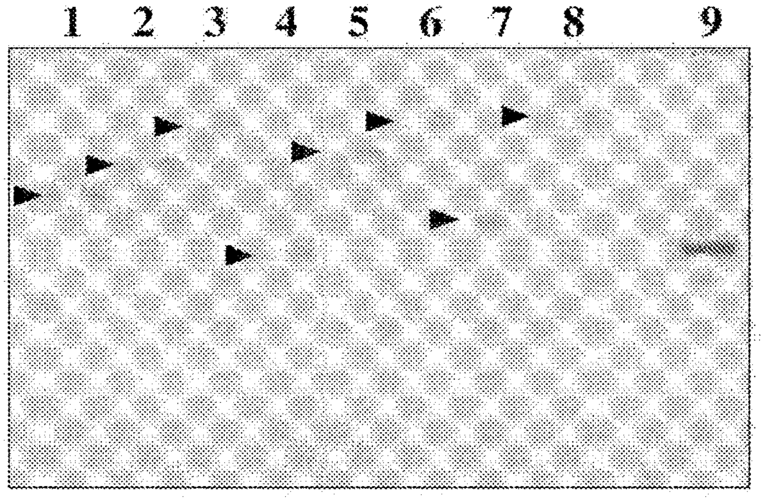
FIG. 37

14 CLONES THAT WERE POSITIVE IN (B)

FIG. 40A
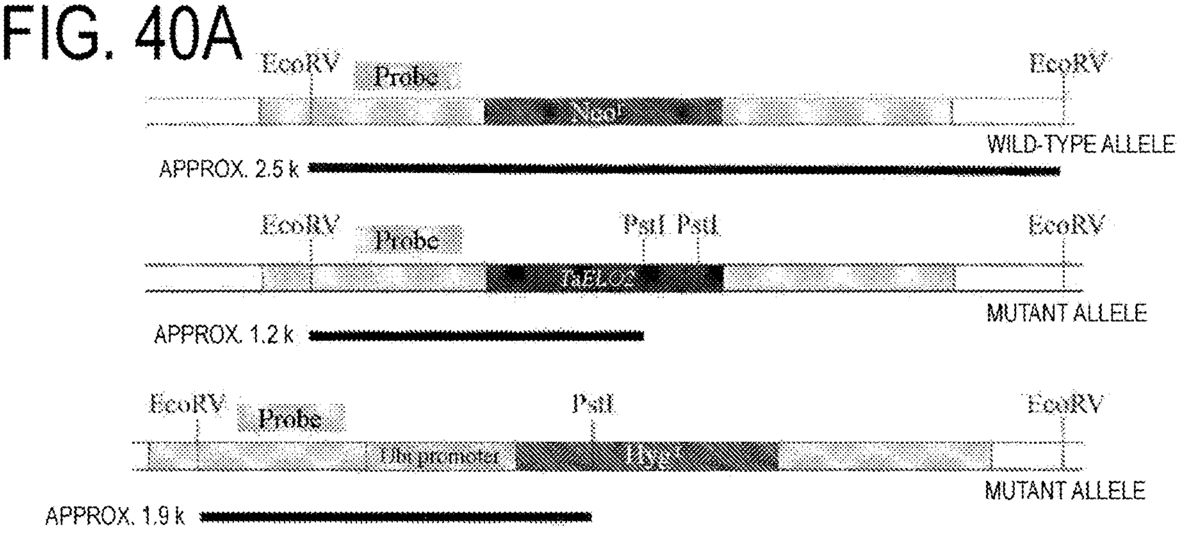
FIG. 40B
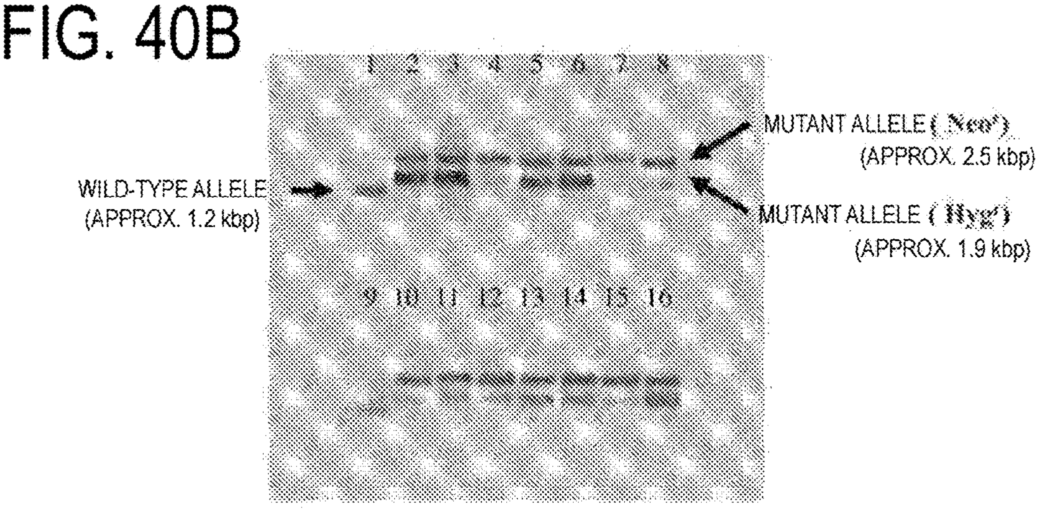
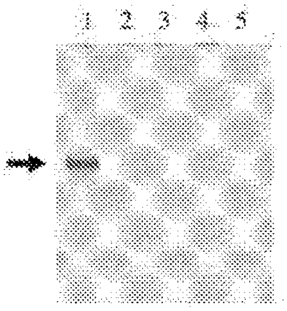
FIG. 41

| | Wild type | *TaELO2* KO |
|---|---|---|
| C14:0 | 0.30 ± 0.0 | 0.22 ± 0.0 |
| C15:0 | 5.11 ± 0.7 | 7.47 ± 1.4 |
| C16:0 | 11.83 ± 1.1 | 4.57 ± 0.9 |
| C17:0 | 3.94 ± 0.6 | 5.89 ± 0.3 |
| C17:1 | 0.33 ± 0.1 | 1.06 ± 0.2 |
| C18:0 | 1.14 ± 0.4 | 0.84 ± 0.0 |
| C18:1n9 | 0.30 ± 0.1 | 0.23 ± 0.1 |
| C181n7 | 0.32 ± 0.1 | 0.20 ± 0.0 |
| LA | 0.42 ± 0.1 | 0.75 ± 0.1 |
| GLA | 0.16 ± 0.1 | 0.35 ± 0.1 |
| C19:2 | 0.45 ± 0.0 | 0.46 ± 0/1 |
| DGLA | 0.14 ± 0.0 | 0.31 ± 0.1 |
| ARA | 2.82 ± 0.2 | 3.49 ± 0.5 |
| EPA | 8.31 ± 0.5 | 16.95 ± 0.7 |
| ω6 DPA | 9.48 ± 0.3 | 7.41 ± 0.4 |
| ω3 DPA | 0.55 ± 0.0 | 0.76 ± 0.1 |
| DHA | 54.38 ± 2.3 | 48.77 ± 1.3 |

| PKS(OrfA)KO | | T.aureum | FA |
|---|---|---|---|
| 121.2% | 0.33 | 0.27 | C14:0 |
| 60.9% | 7.07 | 11.61 | C15:0 |
| 151.2% | 13.21 | 8.74 | C16:0 |
| 82.8% | 11.97 | 14.46 | C17:0 |
| 83.4% | 2.30 | 2.76 | C17:1 |
| 153.7% | 2.77 | 1.80 | C18:0 |
| 172.6% | 1.21 | 0.70 | C18:1n-9 |
| 339.0% | 3.03 | 0.89 | C18:1n-7 |
| 130.6% | 1.07 | 0.82 | C18:2n-6(LA) |
| 101.5% | 1.02 | 1.01 | C19:0 |
| 105.2% | 0.77 | 0.73 | C18:3n-6(GLA) |
| 131.6% | 0.65 | 0.49 | C19:2 |
| 125.9% | 0.23 | 0.18 | C20:3n-6(DGLA) |
| 141.2% | 3.10 | 2.19 | C20:4n-6(ARA) |
| 164.6% | 0.04 | 0.02 | C20:4n-3(ETA) |
| 126.9% | 6.82 | 5.38 | C20:5n3(EPA) |
| 169.6% | 2.00 | 1.18 | C22:4n-6(DTA) |
| 196.3% | 10.66 | 5.43 | C22:5n-6(DPA) |
| 93.6% | 1.13 | 1.20 | C22:5n-3(DPA) |
| 66.5% | 22.58 | 33.97 | C22:6n-3(DHA) |

FIG. 52

| PKS AND C20 KO | | T.aureum | FA |
|---|---|---|---|
| 113.0% | 0.31 | 0.27 | C14:0 |
| 23.3% | 2.71 | 11.61 | C15:0 |
| 176.4% | 15.41 | 8.74 | C16:0 |
| 23.8% | 3.44 | 14.46 | C17:0 |
| 37.0% | 1.02 | 2.76 | C17:1 |
| 125.2% | 2.26 | 1.80 | C18:0 |
| 279.4% | 1.96 | 0.70 | C18:1n-9 |
| 443.0% | 3.96 | 0.89 | C18:1n-7 |
| 208.2% | 1.71 | 0.82 | C18:2n-6(LA) |
| 26.0% | 0.26 | 1.01 | C19:0 |
| 60.9% | 0.45 | 0.73 | C18:3n-6(GLA) |
| 163.7% | 0.81 | 0.49 | C19:2 |
| 996.6% | 1.81 | 0.18 | C20:3n-6(DGLA) |
| 889.0% | 19.50 | 2.19 | C20:4n-6(ARA) |
| 1550.6% | 0.31 | 0.02 | C20:4n-3(ETA) |
| 463.3% | 24.02 | 5.38 | C20:5n3(EPA) |
| 40.3% | 0.47 | 1.18 | C22:4n-6(DTA) |
| 108.6% | 5.90 | 5.43 | C22:5n-6(DPA) |
| 47.9% | 0.58 | 1.20 | C22:5n-3(DPA) |
| 20.0% | 6.78 | 33.97 | C22:6n-3(DHA) |

FIG. 64

| PKS and Δ4des KO | | T aureum | FA |
|---|---|---|---|
| 92.6% | 0.58 | 0.62 | C14:0 |
| 101.0% | 4.48 | 4.43 | C15:0 |
| 53.7% | 7.28 | 13.56 | C16:0 |
| 176.1% | 5.84 | 3.32 | C17:0 |
| 128.4% | 2.05 | 1.60 | C18:0 |
| 304.9% | 4.83 | 1.58 | C18:1 n-9 |
| 250.1% | 4.49 | 1.80 | C18:1 n-7 |
| 450.5% | 4.47 | 0.99 | C18:2n-6(LA) |
| 310.7% | 0.81 | 0.26 | C19:0 |
| 784.5% | 2.67 | 0.34 | C18:3n-6(GLA) |
| 229.0% | 0.59 | 0.26 | C19:2 |
| 353.7% | 0.90 | 0.25 | C20:3n-6(DGLA) |
| 164.2% | 6.35 | 3.87 | C20:4n-6(ARA) |
| 182.8% | 0.28 | 0.15 | C20:4n-3(ETA) |
| 78.1% | 6.22 | 7.96 | C20:5n3(EPA) |
| 2008.9% | 11.01 | 0.55 | C22:4n-6(DTA) |
| 2.4% | 0.21 | 8.79 | C22:5n-6(DPA) |
| 2695.8% | 15.78 | 0.59 | C22:5n-3(DPA) |
| 1.2% | 0.51 | 41.71 | C22:6n-3(DHA) |

FIG. 71

SEQUENCE LISTING

```
Sequence total quantity: 192
SEQ ID NO: 1            moltype = DNA  length = 34
FEATURE                 Location/Qualifiers
misc_feature            1..34
                        note = primer
source                  1..34
                        mol_type = other DNA
                        organism = synthetic construct
SEQUENCE: 1
cagatctgga tccgcgaaat gaccgaccaa gcga                        34

SEQ ID NO: 2            moltype = DNA  length = 24
FEATURE                 Location/Qualifiers
misc_feature            1..24
                        note = primer
source                  1..24
                        mol_type = other DNA
                        organism = synthetic construct
```

```
SEQUENCE: 2
acgcaattaa tgtgagatct agct                                          24

SEQ ID NO: 3            moltype = DNA  length = 342
FEATURE                 Location/Qualifiers
misc_feature            1..342
                        note = SV40 terminator
source                  1..342
                        mol_type = other DNA
                        organism = synthetic construct
SEQUENCE: 3
cagatctgga tccgcgaaat gaccgaccaa gcgacgccca acctgccatc acgagatttc  60
gattccaccg ccgccttcta tgaaaggttg ggcttcggaa tcgttttccg ggacgccggc  120
tggatgatcc tccagcgcgg ggatctcatg ctggagttct tcgcccaccc caacttgttt  180
attgcagctt ataatggtta caaataaagc aatagcatca caaatttcac aaataaagca  240
tttttttcac tgcattctag ttgtggtttg tccaaactca tcaatgtatc ttatcatgtc  300
tgtataccgt cgacctctag ctagatctca cattaattgc gt                      342

SEQ ID NO: 4            moltype = DNA  length = 619
FEATURE                 Location/Qualifiers
misc_feature            1..619
                        note = ubiquitin promoter
source                  1..619
                        mol_type = other DNA
                        organism = synthetic construct
SEQUENCE: 4
cccagatctg ccgcagcgcc tggtgcaccc gccgggcgtt gttggtgtgc tcttcttgcc  60
tccgagagag agagcggagc ggatgcatag gaaatcgggc cacgcgggag ggccatgcgt  120
tcgcccccaca cgccactttc cacgcccgct ctctctccgg ccggcaggca gcgcataact  180
ctccgacgct ggcaggctgg tagcaactgg cagggacaac tcgcgcgcgg gtcccggtcg  240
ttcgatgtgc caacccgaga gaatccagcc agcagggcgg ttggcctcat cgcccacctg  300
ctatggtgca gcgaaccaac tcccgaagcg gccggttctg cgattccctc ttctgaattc  360
tgaattctga actgattccg gaggagaacc ctctggaagc gcgggttgcc tctccagttc  420
tgccgaacta gacaggggag tgagcagaga gtgaccctga cgcgggagcg agctggttgc  480
tggaaaagtc gcgaacgctg ggctgtgtca cgcgtccact tcgggcagac cccaaacgac  540
aagcagaaca agcaacacca gcagcagcaa gcgacctaag caacactagc caacatgatt  600
gaacaggacg gccttcacg                                                619

SEQ ID NO: 5            moltype = DNA  length = 36
FEATURE                 Location/Qualifiers
misc_feature            1..36
                        note = primer
source                  1..36
                        mol_type = other DNA
                        organism = synthetic construct
SEQUENCE: 5
cccagatctg ccgcagcgcc tggtgcaccc gccggg                             36

SEQ ID NO: 6            moltype = DNA  length = 58
FEATURE                 Location/Qualifiers
misc_feature            1..58
                        note = primer
source                  1..58
                        mol_type = other DNA
                        organism = synthetic construct
SEQUENCE: 6
cgtgaaggcc gtcctgttca atcatgttgg ctagtgttgc ttaggtcgct tgctgctg    58

SEQ ID NO: 7            moltype = DNA  length = 826
FEATURE                 Location/Qualifiers
misc_feature            1..826
                        note = Neomycin resistance gene (Neor)
source                  1..826
                        mol_type = other DNA
                        organism = synthetic construct
SEQUENCE: 7
agcgacctaa gcaacactag ccaacatgat tgaacaggac ggccttcacg ctggctcgcc  60
cgctgcttgg gtggaacggc tgttcggcta cgactgggct cagcagacga tcggctgctc  120
ggacgcggcc gtgttccgcc ttagcgcgca gggccggccg gtcctgtttg tcaagaccga  180
ccttagcggc gccctcaacg agctccagga cgaagctgcc cgcctcagct ggcttgccac  240
gacgggggtt ccgtgcgccg ctgtgctcga cgtcgtcacc gaagccggcc gcgactggct  300
gctcctcggg gaagtgcccg gccaggacct cctcagcagc cacctcgcgc ccgctgagaa  360
ggtgtccatc atggccgacg ccatgcgccg cctgcacacc ctcgaccccg ccacctgccc  420
cttcgaccac caggcgaagc acaggatcga acgcgcccgc acgcggatgg aggctggcct  480
cgtcgaccaa gacgacctcg acgaggagca ccagggcctc gcgccggcgg aactgttcgc  540
caggcttaag gctaggatgc cggacggcga ggacctcgtg gtcacgcacg gcgacgcctg  600
cctccccaac atcatggtcg agaacggccg cttctcgggc tttatcgact gcgggcgcct  660
gggcgtggcg gaccgctacc aagacatcgc gctcgccacg cgggacatcg ccgaggagct  720
tggcggcgag tgggccgacc gctttctcgt gctctacggc atcgccgccc cggacagcca  780
```

```
gaggattgcg ttctaccgcc tcctggacga gttcttttga gatctg                826

SEQ ID NO: 8            moltype = DNA  length = 54
FEATURE                 Location/Qualifiers
misc_feature            1..54
                        note = primer
source                  1..54
                        mol_type = other DNA
                        organism = synthetic construct
SEQUENCE: 8
agcgacctaa gcaacactag ccaacatgat tgaacaggac ggccttcacg ctgg       54

SEQ ID NO: 9            moltype = DNA  length = 26
FEATURE                 Location/Qualifiers
misc_feature            1..26
                        note = primer
source                  1..26
                        mol_type = other DNA
                        organism = synthetic construct
SEQUENCE: 9
cagatctcaa aagaactcgt ccagga                                      26

SEQ ID NO: 10           moltype = DNA  length = 1395
FEATURE                 Location/Qualifiers
misc_feature            1..1395
                        note = fusion DNA (T. aureum ATCC 34304 ubiquitin
                         promoter/Neor)
source                  1..1395
                        mol_type = other DNA
                        organism = synthetic construct
SEQUENCE: 10
cccagatctg ccgcagcgcc tggtgcaccc gccgggcgtt gttggtgtgc tcttcttgcc  60
tccgagagag agagcggagc ggatgcatag gaaatcgggc cacgcgggag ggccatgcgt  120
tcgccccaca cgccactttc cacgcccgct ctctctccgg ccggcaggca gcgcataact  180
ctccgacgct ggcaggctgg tagcaactgg cagggacaac tcgcgcgcgg gtcccggtcg  240
ttcgatgtgc caacccgaga gaatccagcc agcagggcgg ttggcctcat cgcccacctg  300
ctatggtgca gcgaaccaac tcccgaagcg gccggttctg cgattccctc ttctgaattc  360
tgaattctga actgattccg gaggagaacc ctctggaagc gcgggttgcc tctccagttc  420
tgccgaacta gacaggggag tgagcagaga gtgaccctga cgcgggagcg agctggttgc  480
tggaaaagtc gcgaacgctg ggctgtgtca cgcgtccact tcgggcagac cccaaacgac  540
aagcagaaca agcaacacca gcagcagcaa gcgacctaag caacactagc caacatgatt  600
gaacaggacg gccttcacgc tggctcgccc gctgcttggg tggaacggct gttcggctac  660
gactgggctc agcagacgat cggctgctcg gacgcggccg tgttccgcct tagcgcgcag  720
ggccggccgg tcctgtttgt caagaccgac cttagcggcg ccctcaacga gctccaggac  780
gaagctgccc gcctcagctg gcttgccacg acgggggttc cgtgcgccgc tgtgctcgac  840
gtcgtcaccg aagccggccg cgactggctg ctcctcgggg aagtgcccgg ccaggacctc  900
ctcagcagcc acctcgcgcc cgctgagaag gtgtccatca tggccgacgc catgcgccgc  960
ctgcacaccc tcgaccccgc cacctgcccc ttcgaccacc aggcgaagca caggatcgaa  1020
cgcgcccgca cgcggatgga ggctggcctc gtcgaccaag acgacctcga cgaggagcac  1080
cagggcctcg cgccggcgga actgttcgcc aggcttaagg ctaggatgcc ggacggcgag  1140
gacctcgtgg tcacgcacgg cgacgcctgc ctccccaaca tcatggtcga gaacggccgc  1200
ttctcgggct ttatcgactg cgggcgcctg ggcgtggcgg accgctacca agacatcgcg  1260
ctcgccacgc gggacatcgc cgaggagctt ggcggcgagt gggccgaccg ctttctcgtg  1320
ctctacggca tcgccgcccc ggacagccag aggattgcgt tctaccgcct cctggacgag  1380
ttcttttgag atctg                                                  1395

SEQ ID NO: 11           moltype = DNA  length = 617
FEATURE                 Location/Qualifiers
misc_feature            1..617
                        note = ubiquitin promoter
source                  1..617
                        mol_type = other DNA
                        organism = synthetic construct
SEQUENCE: 11
cccagatctg ccgcagcgcc tggtgcaccc gccgggcgtt gttgtgtgct cttcttgcct  60
ccgagagaga gagcggagcg gatgcatagg aaatcgggcc acgcgggagg gccatgcgtt  120
cgccccacac gccactttcc acgcccgctc tctctccggc cggcaggcag cgcataactc  180
tccgacgctg gcaggctggt agcaactggc agggacaact cgcgcgcggg tcccggtcgt  240
tcgatgtgcc aacccgagag aatccagcca gcagggcggt tggcctcatc gcccacctgc  300
tatggtgcag cgaaccaact cccgaagcgg ccggttctgc gattccctct tctgaattct  360
gaattctgaa ctgattccgg aggagaaccc tctggaagcg cgggttgcct ctccagttct  420
gccgaactag acaggggagt gagcagagag tgaccctgac gcggagcgag ctggttgctg  480
gaaaagtcgc gaacgctggg ctgtgtcacg cgtccacttc gggcagaccc caaacgacaa  540
gcagaacaag caacaccagc agcagcaagc gacctaagca acactagcca acatgaaaaa  600
gcctgaactc accgcga                                                617

SEQ ID NO: 12           moltype = DNA  length = 58
FEATURE                 Location/Qualifiers
misc_feature            1..58
```

```
                        note = primer
source                  1..58
                        mol_type = other DNA
                        organism = synthetic construct
SEQUENCE: 12
tcgcggtgag ttcaggcttt ttcatgttgg ctagtgttgc ttaggtcgct tgctgctg    58

SEQ ID NO: 13           moltype = DNA  length = 1058
FEATURE                 Location/Qualifiers
misc_feature            1..1058
                        note = Hygromycin resistance gene (Hygr)
source                  1..1058
                        mol_type = other DNA
                        organism = synthetic construct
SEQUENCE: 13
agcgacctaa gcaacactag ccaacatgaa aaagcctgaa ctcaccgcga cgtctgtcga  60
gaagtttctg atcgaaaagt tcgacagcgt ctccgacctg atgcagctct cggagggcga  120
agaatctcgt gctttcagct tcgatgtagg agggcgtgga tatgtcctgc gggtaaatag  180
ctgcgccgat ggtttctaca aagatcgtta tgtttatcgg cactttgcat cggccgcgct  240
cccgattccg gaagtgcttg acattgggga attcagcgag agcctgacct attgcatctc  300
ccgccgtgca cagggtgtca cgttgcaaga cctgcctgaa accgaactgc ccgctgttct  360
gcagccggtc gcggaggcca tggatgcgat cgctgcggcc gatcttagcc agacgagcgg  420
gttcggccca ttcggaccgc aaggaatcgg tcaatacact acatggcgtg atttcatatg  480
cgcgattgct gatccccatg tgtatcactg gcaaactgtg atggacgaca ccgtcagtgc  540
gtccgtcgcg caggctctcg atgagctgat gctttgggcc gaggactgcc ccgaagtccg  600
gcacctcgtg cacgcggatt tcggctccaa caatgtcctg acggacaatg gccgcataac  660
agcggtcatt gactggagcg aggcgatgtt cggggattcc caatacgagg tcgccaacat  720
cttcttctgg aggccgtggt tggcttgtat ggagcagcag acgcgctact tcgagcggag  780
gcatccggag cttgcaggat cgccgcggct ccgggcgtat atgctccgca ttggtcttga  840
ccaactctat cagagcttgg ttgacggcaa tttcgatgat gcagcttggg cgcagggtcg  900
atgcgacgca atcgtccgat ccggagccgg gactgtcggg cgtacacaaa tcgcccgcag  960
aagcgcggcc gtctggaccg atggctgtgt agaagtactc gccgatagtg gaaaccgacg  1020
ccccagcact cgtccgaggg caaaggaata gagatctg                          1058

SEQ ID NO: 14           moltype = DNA  length = 56
FEATURE                 Location/Qualifiers
misc_feature            1..56
                        note = primer
source                  1..56
                        mol_type = other DNA
                        organism = synthetic construct
SEQUENCE: 14
agcgacctaa gcaacactag ccaacatgaa aaagcctgaa ctcaccgcga cgtctg      56

SEQ ID NO: 15           moltype = DNA  length = 36
FEATURE                 Location/Qualifiers
misc_feature            1..36
                        note = primer
source                  1..36
                        mol_type = other DNA
                        organism = synthetic construct
SEQUENCE: 15
cagatctcta ttcctttgcc ctcggacgag tgctgg                            36

SEQ ID NO: 16           moltype = DNA  length = 1625
FEATURE                 Location/Qualifiers
misc_feature            1..1625
                        note = fusion DNA (Thraustochytrium aureum ATCC 34304
                         ubiquitin promoter[pc]DNA 3.1/ Hygr)
source                  1..1625
                        mol_type = other DNA
                        organism = synthetic construct
SEQUENCE: 16
cccagatctg ccgcagcgcc tggtgcaccc gccgggcgtt gttgtgtgct cttcttgcct  60
ccgagagaga gagcggagcg gatgcatagg aaatcgggcc acgcgggagg gccatgcgtt  120
cgccccacac gccactttcc acgcccgctc tctctccggc cggcaggcag cgcataactc  180
tccgacgctg gcaggctggt agcaactggc agggacaact cgcgcgcggg tcccggtcgt  240
tcgatgtgcc aacccgagag aatccagcca gcagggcggt tggcctcatc gcccacctgc  300
tatggtgcag cgaaccaact cccgaagcgg ccggttctgc gattccctct tctgaattct  360
gaattctgaa ctgattccgg aggagaaccc tctggaagcg cgggttgcct ctccagttct  420
gccgaactag acaggggagt gagcagagag tgaccctgac gcggagcgag ctggttgctg  480
gaaaagtcgc gaacgctggg ctgtgtcacg cgtccacttc gggcagaccc caaacgacaa  540
gcagaacaag caacaccagc agcagcaagc gacctaagca acactagcca acatgaaaaa  600
gcctgaactc accgcgacgt ctgtcgagaa gtttctgatc gaaaagttcg acagcgtctc  660
cgacctgatg cagctctcgg agggcgaaga atctcgtgct ttcagcttcg atgtaggagg  720
gcgtggatat gtcctgcggg taaatagctg cgccgatggt ttctacaaag atcgttatgt  780
ttatcggcac tttgcatcgg ccgcgctccc gattccggaa gtgcttgaca ttggggaatt  840
cagcgagagc ctgacctatt gcatctcccg ccgtgcacag ggtgtcacgt tgcaagacct  900
gcctgaaacc gaactgcccg ctgttctgca gccggtcgcg gaggccatgg atgcgatcgc  960
```

```
tgcggccgat cttagccaga cgagcgggtt cggcccattc ggaccgcaag gaatcggtca  1020
atacactaca tggcgtgatt tcatatgcgc gattgctgat ccccatgtgt atcactggca  1080
aactgtgatg gacgacaccg tcagtgcgtc cgtcgcgcag gctctcgatg agctgatgct  1140
ttgggccgag gactgccccg aagtccggca cctcgtgcac gcggatttcg gctccaacaa  1200
tgtcctgacg gacaatggcc gcataacagc ggtcattgac tggagcgagg cgatgttcgg  1260
ggattcccaa tacgaggtcg ccaacatctt cttctggagg ccgtggttgg cttgtatgga  1320
gcagcagacg cgctacttcg agcggaggca tccggagctt gcaggatcgc cgcggctccg  1380
ggcgtatatg ctccgcattg gtcttgacca actctatcag agcttggttg acggcaattt  1440
cgatgatgca gcttgggcgc agggtcgatg cgacgcaatc gtccgatccg gagccgggac  1500
tgtcgggcgt acacaaatcg cccgcagaag cgcggccgtc tggaccgatg gctgtgtaga  1560
agtactcgcc gatagtggaa accgacgccc cagcactcgt ccgagggcaa aggaatagag  1620
atctg                                                              1625

SEQ ID NO: 17          moltype = DNA  length = 25
FEATURE                Location/Qualifiers
misc_feature           1..25
                       note = primer
source                 1..25
                       mol_type = other DNA
                       organism = synthetic construct
SEQUENCE: 17
ccttcggcgc tcctcttatg tatgt                                        25

SEQ ID NO: 18          moltype = DNA  length = 25
FEATURE                Location/Qualifiers
misc_feature           1..25
                       note = primer
source                 1..25
                       mol_type = other DNA
                       organism = synthetic construct
SEQUENCE: 18
caatgcaaga ggcgaactgg gagag                                        25

SEQ ID NO: 19          moltype = DNA  length = 25
FEATURE                Location/Qualifiers
misc_feature           1..25
                       note = primer
source                 1..25
                       mol_type = other DNA
                       organism = synthetic construct
SEQUENCE: 19
tggggctctg gaaccgctgc ttacg                                        25

SEQ ID NO: 20          moltype = DNA  length = 25
FEATURE                Location/Qualifiers
misc_feature           1..25
                       note = primer
source                 1..25
                       mol_type = other DNA
                       organism = synthetic construct
SEQUENCE: 20
cttccagctc tcccagttcg cctct                                        25

SEQ ID NO: 21          moltype = DNA  length = 25
FEATURE                Location/Qualifiers
misc_feature           1..25
                       note = primer
source                 1..25
                       mol_type = other DNA
                       organism = synthetic construct
SEQUENCE: 21
cgggttgttg atgttgagcg aggtg                                        25

SEQ ID NO: 22          moltype = DNA  length = 25
FEATURE                Location/Qualifiers
misc_feature           1..25
                       note = primer
source                 1..25
                       mol_type = other DNA
                       organism = synthetic construct
SEQUENCE: 22
cccacgccat ccacgagcac accac                                        25

SEQ ID NO: 23          moltype = DNA  length = 957
FEATURE                Location/Qualifiers
misc_feature           1..957
                       note = cDNA (Parietichytrium genomic DNA contains C20
                        elongase coding region)
source                 1..957
```

```
                          mol_type = other DNA
                          organism = synthetic construct
SEQUENCE: 23
cccggatcca tggcagctcg cgtggagaaa cagcaggcac ctgcgaaggc cgccaagaag  60
gtggggtcgc gtgtggaccg cagtgatggg ttctttcgca ctttcaacct ctgtgcgctg  120
tacggaagcg cgttcgcgta cgcttacaac aatgggccag tggacaacga cggcaagggc  180
ttgtactttt caaagtctcc attctacgca ttcctcgtct cggacgccat gaccttcggc  240
gctcctctta tgtatgtaat tgctgtcatg gcactcagcc gatacatggc agacaagcag  300
cccctcactg gcttcattaa aagctacatt cagccagttt acaacattgt gcaaatcgtg  360
gtgtgctcgt ggatggcgtg gggccttttg ccacaggtgg acatcttcaa cctcaaccca  420
ttcggtctca acaagcagcg tgatgccaac atcgagttct ttgtcatggt ccacctcctg  480
acaaagttcc tcgactggac cgacaccttc atcatgattt tcaagaagaa ctatgcacag  540
gtctcttttc tccaggtgtt ccaccatgcc accatcggaa tggtgtggtc cttcctcctc  600
cagcgcggct ggggctctgg aaccgctgct tacggagcgt tcatcaactc ggtcacccat  660
gtcatcatgt acactcatta ctttgtcacc tcgctcaaca tcaacaaccc gttcaagagg  720
tacatcaccg gcttccagct ctcccagttc gcctcttgca ttgtacatgc tctcctcgtc  780
cttgccttcg aggaggtgta ccccctcgag tacgcttacc ttcagatcag ctaccacatc  840
atcatgctct acctcttcgg caggagaatg aactggagcc ctctctggtg cactggcgag  900
gtcgacgggc ttgacgtcaa cgtcgagacc tccaagaagg ctcagtaagg atccggg     957

SEQ ID NO: 24             moltype = DNA  length = 32
FEATURE                   Location/Qualifiers
misc_feature              1..32
                          note = primer
source                    1..32
                          mol_type = other DNA
                          organism = synthetic construct
SEQUENCE: 24
cccggatcca tggcagctcg cgtggagaaa ca                                32

SEQ ID NO: 25             moltype = DNA  length = 33
FEATURE                   Location/Qualifiers
misc_feature              1..33
                          note = primer
source                    1..33
                          mol_type = other DNA
                          organism = synthetic construct
SEQUENCE: 25
cccggatcct tactgagcct tcttggaggt ctc                               33

SEQ ID NO: 26             moltype = DNA  length = 936
FEATURE                   Location/Qualifiers
misc_feature              1..936
                          note = genomic DNA (Parietichytrium C20 elongase gene)
source                    1..936
                          mol_type = other DNA
                          organism = synthetic construct
SEQUENCE: 26
atggcagctc gcgtggagaa acagcaggca cctgcgaagg ccgccaagaa ggtggggtcg  60
cgtgtggacc gcagtgatgg gttctttcgc actttcaacc tctgtgcgct gtacggaagc  120
gcgttcgcgt acgcttacaa caatgggcca gtggacaacg acggcaaggg cttgtacttt  180
tcaaagtctc cattctacgc attcctcgtc tcggacgcca tgaccttcgg cgctcctctt  240
atgtatgtaa ttgctgtcat ggcactcagc cgatacatgg cagacaagca gcccctcact  300
ggcttcatta aaagctacat tcagccagtt tacaacattg tgcaaatcgt ggtgtgctcg  360
tggatggcgt ggggcctttt gccacaggtg gacatcttca acctcaaccc attcggtctc  420
aacaagcagc gtgatgccaa catcgagttc tttgtcatgg tccacctcct gacaaagttc  480
ctcgactgga ccgacacctt catcatgatt ttcaagaaga actatgcaca ggtctctttt  540
ctccaggtgt tccaccatgc caccatcgga atggtgtggt ccttcctcct ccagcgcggc  600
tggggctctg gaaccgctgc ttacggagcg ttcatcaact cggtcaccca tgtcatcatg  660
tacactcatt actttgtcac ctcgctcaac atcaacaacc cgttcaagag gtacatcacc  720
ggcttccagc tctcccagtt cgcctcttgc attgtacatg ctctcctcgt ccttgccttc  780
gaggaggtgt acccccctcga gtacgcttac cttcagatca gctaccacat catcatgctc  840
tacctcttcg gcaggagaat gaactggagc cctctctggt gcactggcga ggtcgacggg  900
cttgacgtca acgtcgagac ctccaagaag gctcag                            936

SEQ ID NO: 27             moltype = AA  length = 312
FEATURE                   Location/Qualifiers
source                    1..312
                          mol_type = protein
                          organism = synthetic construct
SEQUENCE: 27
MAARVEKQQA PAKAAKKVGS RVDRSDGFFR TFNLCALYGS AFAYAYNNGP VDNDGKGLYF  60
SKSPFYAFLV SDAMTFGAPL MYVIAVMALS RYMADKQPLT GFIKSYIQPV YNIVQIVVCS  120
WMAWGLLPQV DIFNLNPFGL NKQRDANIEF FVMVHLLTKF LDWTDTFIMI FKKNYAQVSF  180
LQVFHHATIG MVWSFLLQRG WGSGTAAYGA FINSVTHVIM YTHYFVTSLN INNPFKRYIT  240
GFQLSQFASC IVHALLVLAF EEVYPLEYAY LQISYHIIML YLFGRRMNWS PLWCTGEVDG  300
LDVNVETSKK AQ                                                      312

SEQ ID NO: 28             moltype = DNA  length = 26
```

```
FEATURE                 Location/Qualifiers
misc_feature            1..26
                        note = primer
source                  1..26
                        mol_type = other DNA
                        organism = synthetic construct
SEQUENCE: 28
acaaagatct cgactggacc gacacc                                            26

SEQ ID NO: 29           moltype = DNA  length = 27
FEATURE                 Location/Qualifiers
misc_feature            1..27
                        note = primer
source                  1..27
                        mol_type = other DNA
                        organism = synthetic construct
SEQUENCE: 29
agtcgagatc tttgtcagga ggtggac                                           27

SEQ ID NO: 30           moltype = DNA  length = 935
FEATURE                 Location/Qualifiers
misc_feature            1..935
                        note = BglIIinserted C20 elongase
source                  1..935
                        mol_type = other DNA
                        organism = synthetic construct
SEQUENCE: 30
atggcagctc gcgtggagaa acagcaggca cctgcgaagg ccgccaagaa ggtggggtcg  60
cgtgtggacc gcagtgatgg gttctttcgc actttcaacc tctgtgcgct gtacggaagc  120
gcgttcgcgt acgcttacaa caatgggcca gtggacaacg acggcaaggg cttgtacttt  180
tcaaagtctc cattctacgc attcctcgtc tcggacgcca tgaccttcgg cgctcctctt  240
atgtatgtaa ttgctgtcat ggcactcagc cgatacatgg cagacaagca gcccctcact  300
ggcttcatta aaagctacat tcagccagtt tacaacattg tgcaaatcgt ggtgtgctcg  360
tggatggcgt ggggcctttt gccacaggtg gacatcttca acctcaaccc attcggtctc  420
aacaagcagc gtgatgccaa catcgagttc tttgtcatgg tccacctcct gacaaagatc  480
tcgactggac cgacaccttc atcatgattt tcaagaagaa ctatgcacag gtctcttttc  540
tccaggtgtt ccaccatgcc accatcggaa tggtgtggtc cttcctcctc cagcgcggct  600
ggggctctgg aaccgctgct tacggagcgt tcatcaactc ggtcacccat gtcatcatgt  660
acactcatta ctttgtcacc tcgctcaaca tcaacaaccc gttcaagagg tacatcaccg  720
gcttccagct ctcccagttc gcctcttgca ttgtacatgc tctcctcgtc cttgccttcg  780
aggaggtgta ccccctcgag tacgcttacc ttcagatcag ctaccacatc atcatgctct  840
acctcttcgg caggagaatg aactggagcc ctctctggtg cactggcgag gtcgacgggc  900
ttgacgtcaa cgtcgagacc tccaagaagg ctcag                                935

SEQ ID NO: 31           moltype = DNA  length = 2661
FEATURE                 Location/Qualifiers
misc_feature            1..2661
                        note = fusion DNA (Parietichytrium C20 elongase 5'
                         region/SV40 terminator/Neor/ubiquitin
                         promoter/Parietichytrium C20 elongase 3' region)
source                  1..2661
                        mol_type = other DNA
                        organism = synthetic construct
SEQUENCE: 31
cccggatcca tggcagctcg cgtggagaaa cagcaggcac ctgcgaaggc cgccaagaag  60
gtggggtcgc gtgtggaccg cagtgatggg ttctttcgca ctttcaacct ctgtgcgctg  120
tacggaagcg cgttcgcgta cgcttacaac aatgggccag tggacaacga cggcaagggc  180
ttgtactttt caaagtctcc attctacgca ttcctcgtct cggacgccat gaccttcggc  240
gctcctctta tgtatgtaat tgctgtcatg gcactcagcc gatacatggc agacaagcag  300
cccctcactg gcttcattaa aagctacatt cagccagttt acaacattgt gcaaatcgtg  360
gtgtgctcgt ggatggcgtg gggccttttg ccacaggtgg acatcttcaa cctcaaccca  420
ttcggtctca acaagcagcg tgatgccaac atcgagttct ttgtcatggt ccacctcctg  480
acaaagatct agctagaggt cgacggtata cagacatgat aagatacatt gatgagtttg  540
gacaaaccac aactagaatg cagtgaaaaa aatgctttat ttgtgaaatt tgtgatgcta  600
ttgctttatt tgtaaccatt ataagctgca ataaacaagt tggggtgggc gaagaactcc  660
agcatgagat ccccgcgctg gaggatcatc cagccggcgt cccggaaaac gattccgaag  720
cccaaccttt catagaaggc ggcggtggaa tcgaaatctc gtgatggcag gttgggcgtc  780
gcttggtcgg tcatttcgcg gatctcaaaa gaactcgtcc aggaggcggt agaacgcaat  840
cctctggctg tccggggcgg cgatgccgta gagcacgaga aagcggtcgg cccactcgcc  900
gccaagctcc tcggcgatgt cccgcgtggc gagcgcgatg tcttggtagc ggtccgccac  960
gcccaggcgc ccgcagtcga taaagcccga gaagcggccg ttctcgacca tgatgttggg  1020
gaggcaggcg tcgccgtgcg tgaccacgag gtcctcgccg tccggcatcc tagccttaag  1080
cctggcgaac agttccgccg gcgcgaggcc ctggtgctcc tcgtcgaggt cgtcttggtc  1140
gacgaggcca gcctccatcc gcgtgcgggc gcgttcgatc ctgtgcttcg cctggtggtc  1200
gaaggggcag gtggcggggt cgagggtgtg caggcggcgc atggcgtcgg ccatgatgga  1260
caccttctca gcgggcgcga ggtggctgct gaggaggtcc tggccgggca cttccccgag  1320
gagcagccag tcgcggccgg cttcggtgac gacgtcgagc acagcggcgc acggaacccc  1380
cgtcgtggca agccagctga ggcgggcagc ttcgtcctgg agctcgttga gggcgccgct  1440
aaggtcggtc ttgacaaaca ggaccggccg gccctgcgcg ctaaggcgga acacggccgc  1500
```

```
gtccgagcag ccgatcgtct gctgagccca gtcgtagccg aacagccgtt ccacccaagc  1560
agcgggcgag ccagcgtgaa ggccgtcctg ttcaatcatg ttggctagtg ttgcttaggt  1620
cgcttgctgc tgctggtgtt gcttgttctg cttgtcgttt ggggtctgcc cgaagtggac  1680
gcgtgacaca gcccagcgtt cgcgactttt ccagcaacca gctcgctccg cgtcagggtc  1740
actctctgct cactcccctg tctagttcgg cagaactgga gaggcaaccc gcgcttccag  1800
agggttctcc tccggaatca gttcagaatt cagaattcag aagagggaat cgcagaaccg  1860
gccgcttcgg gagttggttc gctgcaccat agcaggtggg cgatgaggcc aaccgccctg  1920
ctggctggat tctctcgggt tggcacatcg aacgaccggg acccgcgcgc gagttgtccc  1980
tgccagttgc taccagcctg ccagcgtcgg agagttatgc gctgcctgcc ggccggagag  2040
agagcgggcg tggaaagtgg cgtgtggggc gaacgcatgg ccctcccgcg tggcccgatt  2100
tcctatgcat ccgctccgct ctctctctcg gaggcaagaa gagcacacca acaacgcccg  2160
gcgggtgcac caggcgctgc ggcagatcca gatctcgact ggaccgacac cttcatcatg  2220
attttcaaga agaactatgc acaggtctct tttctccagg tgttccacca tgccaccatc  2280
ggaatggtgt ggtccttcct cctccagcgc ggctggggct ctggaaccgc tgcttacgga  2340
gcgttcatca actcggtcac ccatgtcatc atgtacactc attactttgt cacctcgctc  2400
aacatcaaca acccgttcaa gaggtacatc accggcttcc agctctccca gttcgcctct  2460
tgcattgtac atgctctcct cgtccttgcc ttcgaggagg tgtacccccct cgagtacgct  2520
taccttcaga tcagctacca catcatcatg ctctacctct tcggcaggag aatgaactgg  2580
agccctctct ggtgcactgg cgaggtcgac gggcttgacg tcaacgtcga gacctccaag  2640
aaggctcagt aaggatccgg g                                            2661
```

```
SEQ ID NO: 32           moltype = DNA  length = 2892
FEATURE                 Location/Qualifiers
misc_feature            1..2892
                        note = fusion DNA (Parietichytrium C20 elongase 5'
                         region/SV40 terminator/Hygr/ubiquitin
                         promoter/Parietichytrium C20 elongase 3' region)
source                  1..2892
                        mol_type = other DNA
                        organism = synthetic construct
SEQUENCE: 32
cccggatcca tggcagctcg cgtggagaaa cagcaggcac ctgcgaaggc cgccaagaag  60
gtggggtcgc gtgtggaccg cagtgatggg ttctttcgca ctttcaacct ctgtgcgctg  120
tacggaagcg cgttcgcgta cgcttacaac aatgggccag tggacaacga cggcaagggc  180
ttgtactttt caaagtctcc attctacgca ttcctcgtct cggacgccat gaccttcggc  240
gctcctctta tgtatgtaat tgctgtcatg gcactcagcc gatacatggc agacaagcag  300
cccctcactg gcttcattaa aagctacatt cagccagttt acaacattgt gcaaatcgtg  360
gtgtgctcgt ggatggcgtg gggccttttg ccacaggtgg acatcttcaa cctcaaccca  420
ttcggtctca acaagcagcg tgatgccaac atcgagttct ttgtcatggt ccacctcctg  480
acaaagatct agctagaggt cgacggtata cagacatgat aagatacatt gatgagtttg  540
gacaaaccac aactagaatg cagtgaaaaa aatgctttat ttgtgaaatt tgtgatgcta  600
ttgctttatt tgtaaccatt ataagctgca ataaacaagt tggggtgggc gaagaactcc  660
agcatgagat ccccgcgctg gaggatcatc cagccggcgt cccggaaaac gattccgaag  720
cccaaccttt catagaaggc ggcggtggaa tcgaaatctc gtgatggcag gttgggcgtc  780
gcttggtcgg tcatttcgcg gatctctatt cctttgccct cggacgagtg ctggggcgtc  840
ggtttccact atcggcgagt acttctacac agccatcggt ccagacggcc gcgcttctgc  900
gggcgatttg tgtacgcccg acagtcccgg ctccggatcg gacgattgcg tcgcatcgac  960
cctgcgccca agctgcatca tcgaaattgc cgtcaaccaa gctctgatag agttggtcaa  1020
gaccaatgcg gagcatatac gcccggagcc gcggcgatcc tgcaagctcc ggatgcctcc  1080
gctcgaagta gcgcgtctgc tgctccatac aagccaacca cggcctccag aagaagatgt  1140
tggcgacctc gtattgggaa tccccgaaca tcgcctcgct ccagtcaatg accgctgtta  1200
tgcggccatt gtccgtcagg acattgttgg agccgaaatc cgcgtgcacg aggtgccgga  1260
cttcggggca gtcctcggcc caaagcatca gctcatcgag agcctgcgcg acggacgcac  1320
tgacggtgtc gtccatcaca gtttgccagt gatacacatg gggatcagca atcgcgcata  1380
tgaaatcacg ccatgtagtg tattgaccga ttccttgcgg tccgaatggg ccgaacccgc  1440
tcgtctggct aagatcggcc gcagcgatcg catccatggc ctccgcgacc ggctgcagaa  1500
cagcgggcag ttcggtttca ggcaggtctt gcaacgtgac accctgtgca cggcgggaga  1560
tgcaataggt caggctctcg ctgaattccc caatgtcaag cacttccgga atcgggagcg  1620
cggccgatgc aaagtgccga taaacataac gatctttgta gaaaccatcg gcgcagctat  1680
ttacccgcag gacatatcca cgccctccta catcgaagct gaaagcacga gattcttcgc  1740
cctccgagag ctgcatcagg tcggagacgc tgtcgaactt ttcgatcaga aacttctcga  1800
cagacgtcgc ggtgagttca ggctttttca tgttggctag tgttgcttag gtcgcttgct  1860
gctgctggtg ttgcttgttc tgcttgtcgt ttggggtctg cccgaagtgg acgcgtgaca  1920
cagcccagcg ttcgcgactt ttccagcaac cagctcgctc cgcgtcaggg tcactctctg  1980
ctcactcccc tgtctagttc ggcagaactg gagaggcaac ccgcgcttcc agagggttct  2040
cctccggaat cagttcagaa ttcagaattc agaagaggga atcgcagaac cggccgcttc  2100
gggagttggt tcgctgcacc atagcaggtg ggcgatgagg ccaaccgccc tgctggctgg  2160
attctctcgg gttggcacat cgaacgaccg ggacccgcgc gcgagttgtc cctgccagtt  2220
gctaccagcc tgccagcgtc ggagagttat gcgctgcctg ccggccggag agagagcggg  2280
cgtggaaagt ggcgtgtggg gcgaacgcat ggccctcccg cgtggcccga tttcctatgc  2340
atccgctccg ctctctctct cggaggcaag aagagcacac aacaacgccc ggcgggtgca  2400
ccaggcgctg cggcagatcc agatctcgac tggaccgaca ccttcatcat gattttcaag  2460
aagaactatg cacaggtctc ttttctccag gtgttccacc atgccaccat cggaatggtg  2520
tggtccttcc tcctccagcg cggctggggc tctggaaccg ctgcttacgg agcgttcatc  2580
aactcggtca cccatgtcat catgtacact cattactttg tcacctcgct caacatcaac  2640
aacccgttca agaggtacat caccggcttc cagctctccc agttcgcctc ttgcattgta  2700
catgctctcc tcgtccttgc cttcgaggag gtgtaccccc tcgagtacgc ttaccttcag  2760
atcagctacc acatcatcat gctctacctc ttcggcagga gaatgaactg gagccctctc  2820
tggtgcactg gcgaggtcga cgggcttgac gtcaacgtcg agacctccaa gaaggctcag  2880
```

```
taaggatccg gg                                                          2892

SEQ ID NO: 33          moltype = DNA  length = 20
FEATURE                Location/Qualifiers
misc_feature           1..20
                       note = primer
source                 1..20
                       mol_type = other DNA
                       organism = synthetic construct
SEQUENCE: 33
ggttgacggc aatttcgatg                                                  20

SEQ ID NO: 34          moltype = DNA  length = 22
FEATURE                Location/Qualifiers
misc_feature           1..22
                       note = primer
source                 1..22
                       mol_type = other DNA
                       organism = synthetic construct
SEQUENCE: 34
cctcctacat cgaagctgaa ag                                               22

SEQ ID NO: 35          moltype = DNA  length = 21
FEATURE                Location/Qualifiers
misc_feature           1..21
                       note = primer
source                 1..21
                       mol_type = other DNA
                       organism = synthetic construct
SEQUENCE: 35
cttctcgggc tttatcgact g                                                21

SEQ ID NO: 36          moltype = DNA  length = 22
FEATURE                Location/Qualifiers
misc_feature           1..22
                       note = primer
source                 1..22
                       mol_type = other DNA
                       organism = synthetic construct
SEQUENCE: 36
taaggtcggt cttgacaaac ag                                               22

SEQ ID NO: 37          moltype = DNA  length = 24
FEATURE                Location/Qualifiers
misc_feature           1..24
                       note = primer
source                 1..24
                       mol_type = other DNA
                       organism = synthetic construct
SEQUENCE: 37
agtagtcccc gatttggtag ttga                                             24

SEQ ID NO: 38          moltype = DNA  length = 22
FEATURE                Location/Qualifiers
misc_feature           1..22
                       note = primer
source                 1..22
                       mol_type = other DNA
                       organism = synthetic construct
SEQUENCE: 38
ggcagagagc aaaaacacga gc                                               22

SEQ ID NO: 39          moltype = DNA  length = 5003
FEATURE                Location/Qualifiers
misc_feature           1..5003
                       note = cDNA contains delta4-desaturase
source                 1..5003
                       mol_type = other DNA
                       organism = synthetic construct
SEQUENCE: 39
gtttgaggag cgaggcattt cttcatttct tcgtggagaa gaaagggcac acctgcagac  60
taaacagcca agtaagaaaa gttatttatc atcatcacaa tatcctttct ggcctgtctc  120
caagagaaag aaactttttaa actttttaaa ttttaacttt tgcttgtgct cgtatgctta  180
caaaagcttg caacgaaaca cagcggaagc aagttcagaa cacgccaatg acatctttgc  240
tctccaaaat tgaaaattgt tttgtcaaat tttaaaaact gattctgtaa gaaaccttaa  300
tttttgcaaa caatcaaaaa atcgccgttg actgagtgtg attgaactca ctccaacgaa  360
agcgttagtc cctcttccta tactttacca taataatatc cctcttagat tccatcccga  420
cctgttccta ctacgagctt ataaacccct acgccccaag ccaggtaaga gagactagta  480
aattcttgac aatctgactg actatcctaa accttctcga ctactatgca aaggactagt  540
```

-continued

```
cgctgtagtc ccagttgtgt gtactatagc agtaaagcgt tggtgtactt aacagtaaaa  600
cagtaaaacc aaagcccccc taaattcccc aaacagaatg agttgtctca gtccgaaact  660
ttctttgcaa tgaaatacga ttggtttgga aagttgacag tgagtgaaaa gcctttcgat  720
tgattgattt gcttcggtca ttcattcact cattcattca ctcattcaaa ttgaaatgag  780
catgaaagtg gtcgaagtgg agtatctagg cgatctacat gaacgacttc aaggagcaag  840
agtgcgagag gtaaaaagta tgttaaagcg ttaaaagctg caaaagctgt aaaagtgaaa  900
gcccatctgg aaaccataga aacgttctca attcctcgat tcctcgattc ctcgtgcaga  960
ctgcagaaga agactgacaa agcatcggca ctggcactga catgcgggta cgagtaggta  1020
cggacagcga gtgcccacac agccccaagc ccacacattc attacattca ttcattgaac  1080
acattgaacg cattgaacaa tcaatcactc cacattgtca ctgtcaactg atgtcaactg  1140
gtaaacttgt aacttgtatt gtattgacct cgcttggtgc atagagtgcg tagagtgcgt  1200
agagtgcgta gccgtcgccc cggagagacg ctgttgactg acaactgtgt taaggtgtcg  1260
attacaacaa acaaacaaat aaacaaacaa ccaaacaaac acctcccaac acacgagctt  1320
tgacgtcctc accacccggt ttgccctcgc agtcgcggtc agttcagtgc cacgagtgcc  1380
acggggcgta aggaagttta ggaaggcgtg tttcgaatcc ctttacagcg cggcgctcgc  1440
gaactgaaga cgcggagata cgcagtagtg agtgggtgga gcaagaaaag tagagggccc  1500
ccgtacgtcc cggaggagag accgattgtg gattggactg ctggatcgtg gaataggcaa  1560
gatgacggcc ggatttgaag aagtgatcac catgaagcag gtgaaggacc ggaatacgcc  1620
ggacgatgcg tggtgcgtgg tgcatggcaa ggtgtacgac atcaccaagt tcaagaacgc  1680
tcaccccggt ggagatataa tcatgttggc ggctggcaag gacgccacca tcctgttcga  1740
gacttaccac atccgcggtg tgcccgatgc cgtgttgcgc aagtatcaga tcggcaaact  1800
tccggacgga aagaacaaag agggcggcaa cggcctcgac agcgcctcgt actactcctg  1860
ggacagcgag ttttaccgcg tccttcgcga gcgcgtcttg aagcgcctga acgagctcaa  1920
gctgtccaga cgcggaggct tcgagatttg ggccaaggct atctttctct tgaccggctt  1980
ctggtcttgc ctctacctca tgtgcacact caacccaaat gggcttgcga ttcctgccgc  2040
catgatgttg ggaatctttg ctgccttcgt aggaacctgc attcagcacg acgggaatca  2100
cggtgcgttc gcccaatctt cgtggcttaa caaggccgct ggttggactt tggacatgat  2160
tggttccagc gccatgacct gggagatgca gcacgtgctt ggacatcatc cgtacaccaa  2220
cttgattgaa atggagaatg gcaatcaaaa ggtctccggc aagcctgttg acaccaagac  2280
tgtcgaccag gagagcgacc ctgatgtctt tagcacctac cctatgcttc gccttcaccc  2340
ttggcacagc aaaaagtggt accacaaata ccagcacatc tatgcaccat tcatctttgg  2400
gttcatgacc atcaacaagg tcattgcaca ggacgtcggc gttatcacac gcaagcgtct  2460
cttccagatt gacgccaact gccgctacgc ttctccgact tacgtcgctc gcttctggat  2520
catgaaggtt cttaccgttc tctacatggt tggcctgcca atgtacatgc aaggtccatg  2580
ggagggtctc aagttgttct ttattgcgca ctttacttgc ggcgagctgc tggccacaat  2640
gttcatcgta aaccacatca tcgagggtgt cagctacgca agcaaagatg ccatcaaggg  2700
cgagatggct ccaccgaaaa cggtccgcgg tgtcaccccc atgcacgaga cgcaaaaggt  2760
tctcgaccag cgcgagaaag acatggacga aacttctaag aagagccgca tccctctcaa  2820
cgactgggcc gctgtacagt gccagacctc cgtgaactgg gctatcggtt cttggttctg  2880
gaaccacttt tccgggggcc tcaatcatca gattgagcat catctgttcc ccggcttgac  2940
tcacaccacc tatgttcact ttcacgatgt ggtcaaagat acttgcgctg agtacggggt  3000
tccataccag cacgaggaga gtctatacac tgcctacttt aagatgttga atcatctcaa  3060
gaccctaggc aacgagccaa tgcctgcctg ggacaagaac taacagtaaa caaacatcac  3120
gcgtcctcaa agcctgacta tcgcgggctg cgctttcact ttgcctgccg ttttggagga  3180
tatctgcttt tgcgatcaaa actaggaatg gagtgtacag ccagccactc gttcttcagt  3240
acgaatcaac gaagactttg tctcctttcc taaaaaagag gatgtttttc ttacctagct  3300
aacaaggcgg tgtctggcca ttgtaccttt ggattcgcta catacacaca tacatacacg  3360
cctttcgttg cgctgctcga aatttgtagt gacgtgagat gaaagataaa aaaaatagaa  3420
ttcaggtctc gttcaaaagt tcgtaattct cttctccaat tccattcgtc tccggagaaa  3480
gtctaggtcg gcattctgta ttgaagcaat gtgcagcagc gaaacagaaa aaacgagcag  3540
tcaaaagact agctactagt cttcgagtgg atcgcccccca gccaatctca aatacatctt  3600
tgcgaaaaca gacacttttg tttcctgaga gcttttgatg aaggtttccg tcaaagtatc  3660
tgacgaggcg ttgcacgggt tctcgaaacc cggcaaagca ggtagatcta actttctgag  3720
gctctccata aaaccctgca cacgatcttt ggcttttggc tcattcgtca aacgaaacaa  3780
aatgccaggc ttgtcgttgg ttccaactac ggttgtaaag ttgtatggcg agtgcactcg  3840
tttttcgtcg aaccagtctg gatgcttctg catcatggct ttcttgaagg caacagtttc  3900
cgtgaaagta gactccaggg ctgtataaga acctggagca agggtggtct tcatgccttg  3960
ctccatcatg tggatgacac tgtgactcac aaaattgcat ccaatctcag acatgtacat  4020
attgaggttg tagttttccg ggtccgtcac gttggagatg gagattccgc tcgccgaagc  4080
atcgcagcag taccaatgac ttgagcgatc cgccacccag tgtaggtata gtccaaatcg  4140
tacaatctct tcggggacag gatccccgtt gataagtgaa taaggtgcgc tcgagttgag  4200
atattcccca agctggcttg ccagtactac atccgtcatc ttgtagtttt cgttatggtc  4260
tgggtcctcg caggtcccgt tgcaagcgca agccggatca cagttgtagt taacgtattg  4320
ctcacctaac atcatatcgc ctccggcgag agggattgga ccgctcacca atttggagat  4380
gtgtttagaa gtgacggttc cgcttttagg gcaggtctcg ccagtgaatg gagatccatc  4440
agggccaatg ctagtatagc ctccaacaca aagcagatcc gtctctccaa aagcccatcg  4500
tcgagcagaa gcgagcgcac cctcgtaaaa gttgtcgtcc atatttgggg ccaggcccgg  4560
gcaatgcgca cggtaaaact catacgactt tttgaagcga tacctctgac agtcaccctc  4620
cttgccaccc gtgtgctcct tggcgctctc ggttaaaatg gagccattga agtgtccgat  4680
gtacgggatt cctaagtgcc gctgtgttcc tcccagcttg gtgtttgtac ggagaaaacc  4740
tctcataggt ggagtccacc actccaatcc catgtccgcg ccacagctgt caattgcgcg  4800
gtactgtacg aaatcaatcg cctgagaata cgcggccatg aagtaagcgt actctgcttt  4860
gaggccctgt gccacagcaa tataatagat cgcgtaaaag tgaatgaagc ctctgcaggc  4920
ggaggtatcg ttgaacccgg ttgtcatctg tgggagcaga cttgccagga tgcactttgg  4980
acgccagtca ttgtacgagc act                                          5003
```

```
SEQ ID NO: 40          moltype = DNA  length = 23
FEATURE                Location/Qualifiers
misc_feature           1..23
```

```
                        note = primer
source                  1..23
                        mol_type = other DNA
                        organism = synthetic construct
SEQUENCE: 40
gtttgaggag cgaggcattt ctt                                          23

SEQ ID NO: 41           moltype = DNA  length = 23
FEATURE                 Location/Qualifiers
misc_feature            1..23
                        note = primer
source                  1..23
                        mol_type = other DNA
                        organism = synthetic construct
SEQUENCE: 41
agtgctcgta caatgactgg cgt                                          23

SEQ ID NO: 42           moltype = DNA  length = 8020
FEATURE                 Location/Qualifiers
misc_feature            1..8020
                        note = plasmid
source                  1..8020
                        mol_type = other DNA
                        organism = synthetic construct
SEQUENCE: 42
tatagtgagt cgtattacaa ttcactggcc gtcgttttac aacgtcgtga ctgggaaaac  60
cctggcgtta cccaacttaa tcgccttgca gcacatcccc ctttcgccag ctggcgtaat  120
agcgaagagg cccgcaccga tcgcccttcc caacagttgc gcagcctgaa tggcgaatgg  180
acgcgccctg tagcggcgca ttaagcgcgg cgggtgtggt ggttacgcgc agcgtgaccg  240
ctacacttgc cagcgcccta gcgcccgctc ctttcgcttt cttcccttcc tttctcgcca  300
cgttcgccgg ctttccccgt caagctctaa atcgggggct ccctttaggg ttccgattta  360
gtgctttacg gcacctcgac cccaaaaaac ttgattaggg tgatggttca cgtagtgggc  420
catcgccctg atagacggtt tttcgccctt tgacgttgga gtccacgttc tttaatagtg  480
gactcttgtt ccaaactgga acaacactca accctatctc ggtctattct tttgatttat  540
aagggatttt gccgatttcg gcctattggt taaaaaatga gctgatttaa caaaaattta  600
acgcgaattt taacaaaata ttaacgctta caatttcctg atgcggtatt ttctccttac  660
gcatctgtgc ggtatttcac accgcatcag gtggcacttt tcggggaaat gtgcgcggaa  720
cccctatttg tttatttttc taaatacatt caaatatgta tccgctcatg agacaataac  780
cctgataaat gcttcaataa tattgaaaaa ggaagagtat gagtattcaa catttccgtg  840
tcgcccttat tccctttttt gcggcatttt gccttcctgt ttttgctcac ccagaaacgc  900
tggtgaaagt aaaagatgct gaagatcagt tgggtgcacg agtgggttac atcgaactgg  960
atctcaacag cggtaagatc cttgagagtt ttcgccccga agaacgtttt ccaatgatga  1020
gcacttttaa agttctgcta tgtggcgcgg tattatcccg tattgacgcc gggcaagagc  1080
aactcggtcg ccgcatacac tattctcaga atgacttggt tgagtactca ccagtcacag  1140
aaaagcatct tacggatggc atgacagtaa gagaattatg cagtgctgcc ataaccatga  1200
gtgataacac tgcggccaac ttacttctga caacgatcgg aggaccgaag gagctaaccg  1260
cttttttgca caacatgggg gatcatgtaa ctcgccttga tcgttgggaa ccggagctga  1320
atgaagccat accaaacgac gagcgtgaca ccacgatgcc tgtagcaatg gcaacaacgt  1380
tgcgcaaact attaactggc gaactactta ctctagcttc ccggcaacaa ttaatagact  1440
ggatggaggc ggataaagtt gcaggaccac ttctgcgctc ggcccttccg gctggctggt  1500
ttattgctga taaatctgga gccggtgagc gtgggtctcg cggtatcatt gcagcactgg  1560
ggccagatgg taagccctcc cgtatcgtag ttatctacac gacggggagt caggcaacta  1620
tggatgaacg aaatagacag atcgctgaga taggtgcctc actgattaag cattggtaac  1680
tgtcagacca agtttactca tatatacttt agattgattt aaaacttcat ttttaattta  1740
aaaggatcta ggtgaagatc ctttttgata atctcatgac caaaatccct taacgtgagt  1800
tttcgttcca ctgagcgtca gaccccgtag aaaagatcaa aggatcttct tgagatcctt  1860
tttttctgcg cgtaatctgc tgcttgcaaa caaaaaaacc accgctacca gcggtggttt  1920
gtttgccgga tcaagagcta ccaactcttt ttccgaaggt aactggcttc agcagagcgc  1980
agataccaaa tactgttctt ctagtgtagc cgtagttagg ccaccacttc aagaactctg  2040
tagcaccgcc tacatacctc gctctgctaa tcctgttacc agtggctgct gccagtggcg  2100
ataagtcgtg tcttaccggg ttggactcaa gacgatagtt accggataag gcgcagcggt  2160
cgggctgaac ggggggttcg tgcacacagc ccagcttgga gcgaacgacc tacaccgaac  2220
tgagatacct acagcgtgag ctatgagaaa gcgccacgct tcccgaaggg agaaaggcgg  2280
acaggtatcc ggtaagcggc agggtcggaa caggagagcg cacgagggag cttccagggg  2340
gaaacgcctg gtatctttat agtcctgtcg ggtttcgcca cctctgactt gagcgtcgat  2400
ttttgtgatg ctcgtcaggg gggcggagcc tatggaaaaa cgccagcaac gcggcctttt  2460
tacggttcct ggccttttgc tggccttttg ctcacatgtt ctttcctgcg ttatcccctg  2520
attctgtgga taaccgtatt accgcctttg agtgagctga taccgctcgc cgcagccgaa  2580
cgaccgagcg cagcgagtca gtgagcgagg aagcggaaga gcgcccaata cgcaaaccgc  2640
ctctccccgc gcgttggccg attcattaat gcagctggca cgacaggttt cccgactgga  2700
aagcgggcag tgagcgcaac gcaattaatg tgagttagct cactcattag gcaccccagg  2760
ctttacactt tatgcttccg gctcgtatgt tgtgtggaat tgtgagcgga taacaatttc  2820
acacaggaaa cagctatgac catgattacg ccaagctatt taggtgacac tatagaatac  2880
tcaagctatg catccaacgc gttgggagct ctcccatatg gtcgacctgc aggcggccgc  2940
gaattcacta gtgattgttt gaggagcgag gcatttcttc atttcttcgt ggagaagaaa  3000
gggcacacct gcagactaaa cagccaagta agaaaagtta tttatcatca tcacaatatc  3060
ctttctggcc tgtctccaag agaaagaaac ttttaaactt tttaaatttt aacttttgct  3120
tgtgctcgta tgcttacaaa agcttgcaac gaaacacagc ggaagcaagt tcagaacacg  3180
ccaatgacat ctttgctctc caaaattgaa aattgttttg tcaaatttta aaaactgatt  3240
```

-continued ctgtaagaaa ccttaatttt tgcaaacaat caaaaaatcg ccgttgactg agtgtgattg 3300
aactcactcc aacgaaagcg ttagtccctc ttcctatact ttaccataat aatatccctc 3360
ttagattcca tcccgacctg ttcctactac gagcttataa acccctacgc cccaagccag 3420
gtaagagaga ctagtaaatt cttgacaatc tgactgacta tcctaaacct tctcgactac 3480
tatgcaaagg actagtcgct gtagtcccag ttgtgtgtac tatagcagta aagcgttggt 3540
gtacttaaca gtaaaacagt aaaaccaaag ccccccctaaa ttccccaaac agaatgagtt 3600
gtctcagtcc gaaactttct ttgcaatgaa atacgattgg tttggaaagt tgacagtgag 3660
tgaaaagcct ttcgattgat tgatttgctt cggtcattca ttcactcatt cattcactca 3720
ttcaaattga aatgagcatg aaagtggtcg aagtggagta tctaggcgat ctacatgaac 3780
gacttcaagg agcaagagtg cgagaggtaa aaagtatgtt aaagcgttaa aagctgcaaa 3840
agctgtaaaa gtgaaagccc atctggaaac catagaaacg ttctcaattc ctcgattcct 3900
cgattcctcg tgcagactgc agaagaagac tgacaaagca tcggcactgg cactgacatg 3960
cgggtacgag taggtacgga cagcgagtgc ccacacagcc ccaagcccac acattcatta 4020
cattcattca ttgaacacat tgaacgcatt gaacaatcaa tcactccaca ttgtcactgt 4080
caactgatgt caactggtaa acttgtaact tgtattgtat tgacctcgct tggtgcatag 4140
agtgcgtaga gtgcgtagag tgcgtagccg tcgccccgga gagacgctgt tgactgacaa 4200
ctgtgttaag gtgtcgatta caacaaacaa acaaataaac aaacaaccaa acaaacacct 4260
cccaacacac gagctttgac gtcctcacca cccggtttgc cctcgcagtc gcggtcagtt 4320
cagtgccacg agtgccacgg ggcgtaagga agtttaggaa ggcgtgtttc gaatcccttt 4380
acagcgcggc gctcgcgaac tgaagacgcg gagatacgca gtagtgagtg ggtggagcaa 4440
gaaaagtaga gggcccccgt acgtcccgga ggagagaccg attgtggatt ggactgctgg 4500
atcgtggaat aggcaagatg acggccggat ttgaagaagt gatcaccatg aagcaggtga 4560
aggaccggaa tacgccggac gatgcgtggt gcgtggtgca tggcaaggtg tacgacatca 4620
ccaagttcaa gaacgctcac cccggtggag atataatcat gttggcggct ggcaaggacg 4680
ccaccatcct gttcgagact taccacatcc gcggtgtgcc cgatgccgtg ttgcgcaagt 4740
atcagatcgg caaacttccg gacggaaaga acaaagaggg cggcaacggc ctcgacagcg 4800
cctcgtacta ctcctgggac agcgagtttt accgcgtcct tcgcgagcgc gtcttgaagc 4860
gcctgaacga gctcaagctg tccagacgcg gaggcttcga gatttgggcc aaggctatct 4920
ttctcttgac cggcttctgg tcttgcctct acctcatgtg cacactcaac ccaaatgggc 4980
ttgcgattcc tgccgccatg atgttgggaa tctttgctgc cttcgtagga acctgcattc 5040
agcacgacgg gaatcacggt gcgttcgccc aatcttcgtg gcttaacaag gccgctggtt 5100
ggactttgga catgattggt tccagcgcca tgacctggga gatgcagcac gtgcttggac 5160
atcatccgta caccaacttg attgaaatgg agaatggcaa tcaaaaggtc tccggcaagc 5220
ctgttgacac caagactgtc gaccaggaga gcgaccctga tgtctttagc acctacccta 5280
tgcttcgcct tcacccttgg cacagcaaaa agtggtacca caaataccag cacatctatg 5340
caccattcat ctttgggttc atgaccatca acaaggtcat tgcacaggac gtcggcgtta 5400
tcacacgcaa gcgtctcttc cagattgacg ccaactgccg ctacgcttct ccgacttacg 5460
tcgctcgctt ctggatcatg aaggttctta ccgttctcta catggttggc ctgccaatgt 5520
acatgcaagg tccatgggag ggtctcaagt tgttctttat tgcgcacttt acttgcggcg 5580
agctgctggc cacaatgttc atcgtaaacc acatcatcga gggtgtcagc tacgcaagca 5640
aagatgccat caagggcgag atggctccac cgaaaacggt ccgcggtgtc accccaatgc 5700
acgagacgca aaaggttctc gaccagcgcg agaaagacat ggacgaaact tctaagaaga 5760
gccgcatccc tctcaacgac tggccgctg tacagtgcca gacctccgtg aactgggcta 5820
tcggttcttg gttctggaac cacttttccg ggggcctcaa tcatcagatt gagcatcatc 5880
tgttccccgg cttgactcac accacctatg ttcactttca cgatgtggtc aaagatactt 5940
gcgctgagta cggggttcca taccagcacg aggagagtct atacactgcc tactttaaga 6000
tgttgaatca tctcaagacc ctaggcaacg agccaatgcc tgcctgggac aagaactaac 6060
agtaaacaaa catcacgcgt cctcaaagcc tgactatcgc gggctgcgct ttcactttgc 6120
ctgccgtttt ggaggatatc tgcttttgcg atcaaaacta ggaatggagt gtacagccag 6180
ccactcgttc ttcagtacga atcaacgaag actttgtctc ctttcctaaa aaagaggatg 6240
tttttcttac ctagctaaca aggcggtgtc tggccattgt acctttggat tcgctacata 6300
cacacataca tacacgcctt tcgttgcgct gctcgaaatt tgtagtgacg tgagatgaaa 6360
gataaaaaaa atagaattca ggtctcgttc aaaagttcgt aattctcttc tccaattcca 6420
ttcgtctccg gagaaagtct aggtcggcat tctgtattga agcaatgtgc agcagcgaaa 6480
cagaaaaaac gagcagtcaa aagactagct actagtcttc gagtggatcg cccccagcca 6540
atctcaaata catctttgcg aaaacagaca cttttgtttc ctgagagctt ttgatgaagg 6600
tttccgtcaa agtatctgac gaggcgttgc acgggttctc gaaacccggc aaagcaggta 6660
gatctaactt tctgaggctc tccataaaac cctgcacacg atctttggct tttggctcat 6720
tcgtcaaacg aaacaaaatg ccaggcttgt cgttggttcc aactacggtt gtaaagttgt 6780
atggcgagtg cactcgtttt tcgtcgaacc agtctggatg cttctgcatc atggctttct 6840
tgaaggcaac agtttccgtg aaagtagact ccagggctgt ataagaacct ggagcaaggg 6900
tggtcttcat gccttgctcc atcatgtgga tgacactgtg actcacaaaa ttgcatccaa 6960
tctcagacat gtacatattg aggttgtagt tttccgggtc cgtcacgttg gagatggaga 7020
ttccgctcgc cgaagcatcg cagcagtacc aatgacttga gcgatccgcc acccagtgta 7080
ggtatagtcc aaatcgtaca atctcttcgg ggacaggatc cccgttgata agtgaataag 7140
gtgcgctcga gttgagatat tccccaagct ggcttgccag tactacatcc gtcatcttgt 7200
agttttcgtt atggtctggg tcctcgcagg tcccgttgca agcgcaagcc ggatcacagt 7260
tgtagttaac gtattgctca cctaacatca tatcgcctcc ggcgagaggg attggaccgc 7320
tcaccaattt ggagatgtgt ttagaagtga cggttccgct tttagggcag gtctcgccag 7380
tgaatggaga tccatcaggg ccaatgctag tatagcctcc aacacaaagc agatccgtct 7440
ctccaaaagc ccatcgtcga gcagaagcga gcgcaccctc gtaaaagttg tcgtccatat 7500
ttggggccag gcccgggcaa tgcgcacggt aaaactcata cgactttttg aagcgatacc 7560
tctgacagtc accctccttg ccacccgtgt gctccttggc gctctcggtt aaaatggagc 7620
cattgaagtg tccgatgtac gggattccta agtgccgctg tgttcctccc agcttggtgt 7680
ttgtacggag aaaacctctc ataggtggag tccaccactc caatcccatg tccgcgccac 7740
agctgtcaat tgcgcggtac tgtacgaaat caatcgcctg agaatacgcg gccatgaagt 7800
aagcgtactc tgctttgagg ccctgtgcca cagcaatata atagatcgcg taaaagtgaa 7860
tgaagcctct gcaggcggag gtatcgttga acccggttgt catctgtggg agcagacttg 7920
ccaggatgca ctttggacgc cagtcattgt acgagcacta atcgaattcc cgcggccgcc 7980

```
atggcggccg ggagcatgcg acgtcgggcc caattcgccc                       8020

SEQ ID NO: 43          moltype = DNA  length = 1542
FEATURE                Location/Qualifiers
source                 1..1542
                       mol_type = other DNA
                       organism = synthetic construct
SEQUENCE: 43
atgacggccg gatttgaaga agtgatcacc atgaagcagg tgaaggaccg gaatacgccg  60
gacgatgcgt ggtgcgtggt gcatggcaag gtgtacgaca tcaccaagtt caagaacgct  120
caccccggtg gagatataat catgttggcg gctggcaagg acgccaccat cctgttcgag  180
acttaccaca tccgcggtgt gcccgatgcc gtgttgcgca agtatcagat cggcaaactt  240
ccggacggaa agaacaaaga gggcggcaac ggcctcgaca gcgcctcgta ctactcctgg  300
gacagcgagt tttaccgcgt ccttcgcgag cgcgtcttga agcgcctgaa cgagctcaag  360
ctgtccagac gcggaggctt cgagatttgg gccaaggcta tctttctctt gaccggcttc  420
tggtcttgcc tctacctcat gtgcacactc aacccaaatg ggcttgcgat tcctgccgcc  480
atgatgttgg gaatctttgc tgccttcgta ggaacctgca ttcagcacga cgggaatcac  540
ggtgcgttcg cccaatcttc gtggcttaac aaggccgctg gttggacttt ggacatgatt  600
ggttccagcg ccatgacctg ggagatgcag cacgtgcttg gacatcatcc gtacaccaac  660
ttgattgaaa tggagaatgg caatcaaaag gtctccggca agcctgttga caccaagact  720
gtcgaccagg agagcgaccc tgatgtcttt agcacctacc ctatgcttcg ccttcaccct  780
tggcacagca aaaagtggta ccacaaatac cagcacatct atgcaccatt catctttggg  840
ttcatgacca tcaacaaggt cattgcacag gacgtcggcg ttatcacacg caagcgtctc  900
ttccagattg acgccaactg ccgctacgct tctccgactt acgtcgctcg cttctggatc  960
atgaaggttc ttaccgttct ctacatggtt ggcctgccaa tgtacatgca aggtccatgg  1020
gagggtctca agttgttctt tattgcgcac tttacttgcg gcgagctgct ggccacaatg  1080
ttcatcgtaa accacatcat cgagggtgtc agctacgcaa gcaaagatgc catcaagggc  1140
gagatggctc caccgaaaac ggtccgcggt gtcaccccaa tgcacgagac gcaaaaggtt  1200
ctcgaccagc gcgagaaaga catggacgaa acttctaaga agagccgcat ccctctcaac  1260
gactgggccg ctgtacagtg ccagacctcc gtgaactggg ctatcggttc ttggttctgg  1320
aaccactttt ccgggggcct caatcatcag attgagcatc atctgttccc cggcttgact  1380
cacaccacct atgttcactt tcacgatgtg gtcaaagata cttgcgctga gtacggggtt  1440
ccataccagc acgaggagag tctatacact gcctacttta agatgttgaa tcatctcaag  1500
accctaggca acgagccaat gcctgcctgg gacaagaact aa                    1542

SEQ ID NO: 44          moltype = DNA  length = 26
FEATURE                Location/Qualifiers
misc_feature           1..26
                       note = primer
source                 1..26
                       mol_type = other DNA
                       organism = synthetic construct
SEQUENCE: 44
ggcaagatct aactttctga ggctct                                      26

SEQ ID NO: 45          moltype = DNA  length = 26
FEATURE                Location/Qualifiers
misc_feature           1..26
                       note = primer
source                 1..26
                       mol_type = other DNA
                       organism = synthetic construct
SEQUENCE: 45
aagttagatc ttgcctattc cacgat                                      26

SEQ ID NO: 46          moltype = DNA  length = 26
FEATURE                Location/Qualifiers
misc_feature           1..26
                       note = primer
source                 1..26
                       mol_type = other DNA
                       organism = synthetic construct
SEQUENCE: 46
gtgcagacgc agaagaagac tgacaa                                      26

SEQ ID NO: 47          moltype = DNA  length = 25
FEATURE                Location/Qualifiers
misc_feature           1..25
                       note = primer
source                 1..25
                       mol_type = other DNA
                       organism = synthetic construct
SEQUENCE: 47
cttctgcgtc tgcacgagga atcga                                       25

SEQ ID NO: 48          moltype = DNA  length = 7579
FEATURE                Location/Qualifiers
misc_feature           1..7579
                       note = plasmid
```

-continued

```
source                 1..7579
                       mol_type = other DNA
                       organism = synthetic construct
SEQUENCE: 48
tatagtgagt cgtattacaa ttcactggcc gtcgttttac aacgtcgtga ctgggaaaac  60
cctggcgtta cccaacttaa tcgccttgca gcacatcccc ctttcgccag ctggcgtaat  120
agcgaagagg cccgcaccga tcgcccttcc caacagttgc gcagcctgaa tggcgaatgg  180
acgcgccctg tagcggcgca ttaagcgcgg cgggtgtggt ggttacgcgc agcgtgaccg  240
ctacacttgc cagcgcccta gcgcccgctc ctttcgcttt cttcccttcc tttctcgcca  300
cgttcgccgg ctttccccgt caagctctaa atcgggggct ccctttaggg ttccgattta  360
gtgctttacg gcacctcgac cccaaaaaac ttgattaggg tgatggttca cgtagtgggc  420
catcgccctg atagacggtt tttcgccctt tgacgttgga gtccacgttc tttaatagtg  480
gactcttgtt ccaaactgga acaacactca accctatctc ggtctattct tttgatttat  540
aagggatttt gccgatttcg gcctattggt taaaaaatga gctgatttaa caaaaattta  600
acgcgaattt taacaaaata ttaacgctta caatttcctg atgcggtatt ttctccttac  660
gcatctgtgc ggtatttcac accgcatcag gtggcacttt tcggggaaat gtgcgcggaa  720
cccctatttg tttatttttc taaatacatt caaatatgta tccgctcatg agacaataac  780
cctgataaat gcttcaataa tattgaaaaa ggaagagtat gagtattcaa catttccgtg  840
tcgcccttat tccctttttt gcggcatttt gccttcctgt ttttgctcac ccagaaacgc  900
tggtgaaagt aaaagatgct gaagatcagt tgggtgcacg agtgggttac atcgaactgg  960
atctcaacag cggtaagatc cttgagagtt ttcgccccga agaacgtttt ccaatgatga  1020
gcacttttaa agttctgcta tgtggcgcgg tattatcccg tattgacgcc gggcaagagc  1080
aactcggtcg ccgcatacac tattctcaga atgacttggt tgagtactca ccagtcacag  1140
aaaagcatct tacggatggc atgacagtaa gagaattatg cagtgctgcc ataaccatga  1200
gtgataacac tgcggccaac ttacttctga caacgatcgg aggaccgaag gagctaaccg  1260
cttttttgca caacatgggg gatcatgtaa ctcgccttga tcgttgggaa ccggagctga  1320
atgaagccat accaaacgac gagcgtgaca ccacgatgcc tgtagcaatg gcaacaacgt  1380
tgcgcaaact attaactggc gaactactta ctctagcttc ccggcaacaa ttaatagact  1440
ggatggaggc ggataaagtt gcaggaccac ttctgcgctc ggcccttccg gctggctggt  1500
ttattgctga taaatctgga gccggtgagc gtgggtctcg cggtatcatt gcagcactgg  1560
ggccagatgg taagccctcc cgtatcgtag ttatctacac gacggggagt caggcaacta  1620
tggatgaacg aaatagacag atcgctgaga taggtgcctc actgattaag cattggtaac  1680
tgtcagacca agtttactca tatatacttt agattgattt aaaacttcat ttttaattta  1740
aaaggatcta ggtgaagatc ctttttgata atctcatgac caaaatccct taacgtgagt  1800
tttcgttcca ctgagcgtca gaccccgtag aaaagatcaa aggatcttct tgagatcctt  1860
tttttctgcg cgtaatctgc tgcttgcaaa caaaaaaacc accgctacca gcggtggttt  1920
gtttgccgga tcaagagcta ccaactcttt ttccgaaggt aactggcttc agcagagcgc  1980
agataccaaa tactgttctt ctagtgtagc cgtagttagg ccaccacttc aagaactctg  2040
tagcaccgcc tacatacctc gctctgctaa tcctgttacc agtggctgct gccagtggcg  2100
ataagtcgtg tcttaccggg ttggactcaa gacgatagtt accggataag gcgcagcggt  2160
cgggctgaac ggggggttcg tgcacacagc ccagcttgga gcgaacgacc tacaccgaac  2220
tgagatacct acagcgtgag ctatgagaaa gcgccacgct tcccgaaggg agaaaggcgg  2280
acaggtatcc ggtaagcggc agggtcggaa caggagagcg cacgagggag cttccagggg  2340
gaaacgcctg gtatctttat agtcctgtcg ggtttcgcca cctctgactt gagcgtcgat  2400
ttttgtgatg ctcgtcaggg gggcggagcc tatggaaaaa cgccagcaac gcggcctttt  2460
tacggttcct ggccttttgc tggccttttg ctcacatgtt ctttcctgcg ttatcccctg  2520
attctgtgga taaccgtatt accgcctttg agtgagctga taccgctcgc cgcagccgaa  2580
cgaccgagcg cagcgagtca gtgagcgagg aagcggaaga gcgcccaata cgcaaaccgc  2640
ctctccccgc gcgttggccg attcattaat gcagctggca cgacaggttt cccgactgga  2700
aagcgggcag tgagcgcaac gcaattaatg tgagttagct cactcattag gcaccccagg  2760
ctttacactt tatgcttccg gctcgtatgt tgtgtggaat tgtgagcgga taacaatttc  2820
acacaggaaa cagctatgac catgattacg ccaagctatt taggtgacac tatagaatac  2880
tcaagctatg catccaacgc gttgggagct ctcccatatg gtcgacctgc aggcggccgc  2940
gaattcacta gtgattgttt gaggagcgag gcatttcttc atttcttcgt ggagaagaaa  3000
gggcacacct gcagactaaa cagccaagta agaaaagtta tttatcatca tcacaatatc  3060
ctttctggcc tgtctccaag agaaagaaac ttttaaactt tttaaatttt aacttttgct  3120
tgtgctcgta tgcttacaaa agcttgcaac gaaacacagc ggaagcaagt tcagaacacg  3180
ccaatgacat ctttgctctc caaaattgaa aattgttttg tcaaatttta aaaactgatt  3240
ctgtaagaaa ccttaatttt tgcaaacaat caaaaaatcg ccgttgactg agtgtgattg  3300
aactcactcc aacgaaagcg ttagtccctc ttcctatact ttaccataat aatatccctc  3360
ttagattcca tcccgacctg ttcctactac gagcttataa acccctacgc cccaagccag  3420
gtaagagaga ctagtaaatt cttgacaatc tgactgacta tcctaaacct tctcgactac  3480
tatgcaaagg actagtcgct gtagtcccag ttgtgtgtac tatagcagta aagcgttggt  3540
gtacttaaca gtaaaacagt aaaaccaaag ccccccctaaa ttccccaaac agaatgagtt  3600
gtctcagtcc gaaactttct ttgcaatgaa atacgattgg tttggaaagt tgacagtgag  3660
tgaaaagcct ttcgattgat tgatttgctt cggtcattca ttcactcatt cattcactca  3720
ttcaaattga aatgagcatg aaagtggtcg aagtggagta tctaggcgat ctacatgaac  3780
gacttcaagg agcaagagtg cgagaggtaa aaagtatgtt aaagcgttaa aagctgcaaa  3840
agctgtaaaa gtgaaagccc atctggaaac catagaaacg ttctcaattc ctcgattcct  3900
cgattcctcg tgcagacgca gaagaagact gacaaagcat cggcactggc actgacatgc  3960
gggtacgagt aggtacggac agcgagtgcc cacacagccc caagcccaca cattcattac  4020
attcattcat tgaacacatt gaacgcattg aacaatcaat cactccacat tgtcactgtc  4080
aactgatgtc aactggtaaa cttgtaactt gtattgtatt gacctcgctt ggtgcataga  4140
gtgcgtagag tgcgtagagt gcgtagccgt cgccccggag agacgctgtt gactgacaac  4200
tgtgttaagg tgtcgattac aacaaacaaa caaataaaca aacaaccaaa caaacacctc  4260
ccaacacacg agctttgacg tcctcaccac ccggtttgcc ctcgcagtcg cggtcagttc  4320
agtgccacga gtgccacggg gcgtaaggaa gtttaggaag gcgtgtttcg aatcccttta  4380
cagcgcggcg ctcgcgaact gaagacgcgg agatacgcag tagtgagtgg gtggagcaag  4440
aaaagtagag ggcccccgta cgtcccggag gagagaccga ttgtggattg gactgctgga  4500
```

```
tcgtggaata ggcaagatct agctagaggt cgacggtata cagacatgat aagatacatt  4560
gatgagtttg gacaaaccac aactagaatg cagtgaaaaa aatgctttat ttgtgaaatt  4620
tgtgatgcta ttgctttatt tgtaaccatt ataagctgca ataaacaagt tggggtgggc  4680
gaagaactcc agcatgagat ccccgcgctg gaggatcatc cagccggcgt cccggaaaac  4740
gattccgaag cccaaccttt catagaaggc ggcggtggaa tcgaaatctc gtgatggcag  4800
gttgggcgtc gcttggtcgg tcatttcgcg gatctcaaaa gaactcgtcc aggaggcggt  4860
agaacgcaat cctctggctg tccggggcgg cgatgccgta gagcacgaga aagcggtcgg  4920
cccactcgcc gccaagctcc tcggcgatgt cccgcgtggc gagcgcgatg tcttggtagc  4980
ggtccgccac gcccaggcgc ccgcagtcga taaagcccga gaagcggccg ttctcgacca  5040
tgatgttggg gaggcaggcg tcgccgtgcg tgaccacgag gtcctcgccg tccggcatcc  5100
tagccttaag cctggcgaac agttccgccg gcgcgaggcc ctggtgctcc tcgtcgaggt  5160
cgtcttggtc gacgaggcca gcctccatcc gcgtgcgggc gcgttcgatc ctgtgcttcg  5220
cctggtggtc gaaggggcag gtggcggggt cgagggtgtg caggcggcgc atggcgtcgg  5280
ccatgatgga caccttctca gcgggcgcga ggtggctgct gaggaggtcc tggccgggca  5340
cttccccgag gagcagccag tcgcggccgg cttcggtgac gacgtcgagc acagcggcgc  5400
acggaacccc cgtcgtggca agccagctga ggcgggcagc ttcgtcctgg agctcgttga  5460
gggcgccgct aaggtcggtc ttgacaaaca ggaccggccg gccctgcgcg ctaaggcgga  5520
acacggccgc gtccgagcag ccgatcgtct gctgagccca gtcgtagccg aacagccgtt  5580
ccacccaagc agcgggcgag ccagcgtgaa ggccgtcctg ttcaatcatg ttggctagtg  5640
ttgcttaggt cgcttgctgc tgctggtgtt gcttgttctg cttgtcgttt ggggtctgcc  5700
cgaagtggac gcgtgacaca gcccagcgtt cgcgactttt ccagcaacca gctcgctccg  5760
cgtcagggtc actctctgct cactcccctg tctagttcgg cagaactgga gaggcaaccc  5820
gcgcttccag agggttctcc tccggaatca gttcagaatt cagaattcag aagagggaat  5880
cgcagaaccg gccgcttcgg gagttggttc gctgcaccat agcaggtggg cgatgaggcc  5940
aaccgccctg ctggctggat tctctcgggt tggcacatcg aacgaccggg acccgcgcgc  6000
gagttgtccc tgccagttgc taccagcctg ccagcgtcgg agagttatgc gctgcctgcc  6060
ggccggagag agagcgggcg tggaaagtgg cgtgtggggc gaacgcatgg ccctcccgcg  6120
tggcccgatt tcctatgcat ccgctccgct ctctctctcg gaggcaagaa gagcacacaa  6180
caacgcccgg cgggtgcacc aggcgctgcg gcagatccag atctaacttt ctgaggctct  6240
ccataaaacc ctgcacacga tctttggctt ttggctcatt cgtcaaacga aacaaaatgc  6300
caggcttgtc gttggttcca actacggttg taaagttgta tggcgagtgc actcgttttt  6360
cgtcgaacca gtctggatgc ttctgcatca tggctttctt gaaggcaaca gtttccgtga  6420
aagtagactc cagggctgta taagaacctg gagcaagggt ggtcttcatg ccttgctcca  6480
tcatgtggat gacactgtga ctcacaaaat tgcatccaat ctcagacatg tacatattga  6540
ggttgtagtt ttccgggtcc gtcacgttgg agatggagat tccgctcgcc gaagcatcgc  6600
agcagtacca atgacttgag cgatccgcca cccagtgtag gtatagtcca aatcgtacaa  6660
tctcttcggg gacaggatcc ccgttgataa gtgaataagg tgcgctcgag ttgagatatt  6720
ccccaagctg gcttgccagt actacatccg tcatcttgta gttttcgtta tggtctgggt  6780
cctcgcaggt cccgttgcaa gcgcaagccg gatcacagtt gtagttaacg tattgctcac  6840
ctaacatcat atcgcctccg gcgagaggga ttggaccgct caccaatttg gagatgtgtt  6900
tagaagtgac ggttccgctt ttagggcagg tctcgccagt gaatggagat ccatcagggc  6960
caatgctagt atagcctcca acacaaagca gatccgtctc tccaaaagcc catcgtcgag  7020
cagaagcgag cgcaccctcg taaaagttgt cgtccatatt tggggccagg cccgggcaat  7080
gcgcacggta aaactcatac gactttttga agcgatacct ctgacagtca ccctccttgc  7140
cacccgtgtg ctccttggcg ctctcggtta aaatggagcc attgaagtgt ccgatgtacg  7200
ggattcctaa gtgccgctgt gttcctccca gcttggtgtt tgtacggaga aaacctctca  7260
taggtggagt ccaccactcc aatcccatgt ccgcgccaca gctgtcaatt gcgcggtact  7320
gtacgaaatc aatcgcctga gaatacgcgg ccatgaagta agcgtactct gctttgaggc  7380
cctgtgccac agcaatataa tagatcgcgt aaaagtgaat gaagcctctg caggcggagg  7440
tatcgttgaa cccggttgtc atctgtggga gcagacttgc caggatgcac tttggacgcc  7500
agtcattgta cgagcactaa tcgaattccc gcggccgcca tggcggccgg gagcatgcga  7560
cgtcgggccc aattcgccc                                                7579
```

```
SEQ ID NO: 49          moltype = DNA  length = 20
FEATURE                Location/Qualifiers
misc_feature           1..20
                       note = primer
source                 1..20
                       mol_type = other DNA
                       organism = synthetic construct
SEQUENCE: 49
gtggtcgaag tggagtatct                                              20

SEQ ID NO: 50          moltype = DNA  length = 20
FEATURE                Location/Qualifiers
misc_feature           1..20
                       note = primer
source                 1..20
                       mol_type = other DNA
                       organism = synthetic construct
SEQUENCE: 50
actcgccata caactttaca                                              20

SEQ ID NO: 51          moltype = DNA  length = 25
FEATURE                Location/Qualifiers
misc_feature           1..25
                       note = primer
source                 1..25
                       mol_type = other DNA
```

```
                         organism = synthetic construct
SEQUENCE: 51
cggagctcgg agaacaacat agaag                                        25

SEQ ID NO: 52            moltype = DNA  length = 23
FEATURE                  Location/Qualifiers
misc_feature             1..23
                         note = primer
source                   1..23
                         mol_type = other DNA
                         organism = synthetic construct
SEQUENCE: 52
gtgcaaccag gtggcaagat tgt                                          23

SEQ ID NO: 53            moltype = DNA  length = 21
FEATURE                  Location/Qualifiers
misc_feature             1..21
                         note = primer
misc_feature             6
                         note = n is a, c, g, or t
misc_feature             12
                         note = n is a, c, g, or t
source                   1..21
                         mol_type = other DNA
                         organism = synthetic construct
SEQUENCE: 53
ttyytncayg tntaycayca y                                            21

SEQ ID NO: 54            moltype = DNA  length = 23
FEATURE                  Location/Qualifiers
misc_feature             1..23
                         note = primer
misc_feature             12
                         note = n is a, c, g, or t
misc_feature             18
                         note = n is a, c, g, or t
source                   1..23
                         mol_type = other DNA
                         organism = synthetic construct
SEQUENCE: 54
gcrtgrtgrt anacrtgnar raa                                          23

SEQ ID NO: 55            moltype = DNA  length = 190
FEATURE                  Location/Qualifiers
misc_feature             1..190
                         note = cDNA (DNA fragment contains elo1)
source                   1..190
                         mol_type = other DNA
                         organism = synthetic construct
SEQUENCE: 55
cgccaccatc tttgctatct ggtttatgat cgccaagtac gccccgggcg gcgacgcata  60
ctttagcgtc atcctgaact cgttcgtgca caccgtcatg tacgcgtact acttcttctc  120
gtcgcagggc ttcgggttcg tcaagccgat caagccgtac atcacctcgc tgcagatgac  180
gcagttcatg                                                         190

SEQ ID NO: 56            moltype = DNA  length = 210
FEATURE                  Location/Qualifiers
misc_feature             1..210
                         note = cDNA (DNA fragment contains elo2)
source                   1..210
                         mol_type = other DNA
                         organism = synthetic construct
SEQUENCE: 56
ccgacgacca gcacaccgag tgggtctcgt gcgtgcgctt ctcgccctcg accaccaacc  60
cgctgatcgt gtcgtgcggc tgggacaagc tcgtcaaggt ctggaacctc tcgaactgca  120
agcttcgggc caacctcatc ggccacgacg gctacctcaa ctcggtcacc gtcagcccgg  180
acggctccct gtgcgcttcg ggcggcaagg                                   210

SEQ ID NO: 57            moltype = DNA  length = 200
FEATURE                  Location/Qualifiers
misc_feature             1..200
                         note = cDNA (DNA fragment contains elo3)
source                   1..200
                         mol_type = other DNA
                         organism = synthetic construct
SEQUENCE: 57
aagctaacct gggcgtagtt tttcttgagg atcatcatga acgtgtcgct ccagtcgaga  60
aactttgtca ggaggtgcac gaacacgaaa aactcgatgt tcgagtcgcg cgacttgttg  120
aggccgaaag ggttgccgtt ggccaggtcg acctgcggcc agaggcccca caccatccag  180
```

```
ccgcacaccg cgatttggac                                              200

SEQ ID NO: 58          moltype = DNA  length = 21
FEATURE                Location/Qualifiers
misc_feature           1..21
                       note = primer
source                 1..21
                       mol_type = other DNA
                       organism = synthetic construct
SEQUENCE: 58
tatgatcgcc aagtacgccc c                                            21

SEQ ID NO: 59          moltype = DNA  length = 21
FEATURE                Location/Qualifiers
misc_feature           1..21
                       note = primer
source                 1..21
                       mol_type = other DNA
                       organism = synthetic construct
SEQUENCE: 59
gaactgcgtc atctgcagcg a                                            21

SEQ ID NO: 60          moltype = DNA  length = 20
FEATURE                Location/Qualifiers
misc_feature           1..20
                       note = primer
source                 1..20
                       mol_type = other DNA
                       organism = synthetic construct
SEQUENCE: 60
tctcgccctc gaccaccaac                                              20

SEQ ID NO: 61          moltype = DNA  length = 22
FEATURE                Location/Qualifiers
misc_feature           1..22
                       note = primer
source                 1..22
                       mol_type = other DNA
                       organism = synthetic construct
SEQUENCE: 61
cggtgaccga gttgaggtag cc                                           22

SEQ ID NO: 62          moltype = DNA  length = 22
FEATURE                Location/Qualifiers
misc_feature           1..22
                       note = primer
source                 1..22
                       mol_type = other DNA
                       organism = synthetic construct
SEQUENCE: 62
caaccctttc ggcctcaaca ag                                           22

SEQ ID NO: 63          moltype = DNA  length = 26
FEATURE                Location/Qualifiers
misc_feature           1..26
                       note = primer
source                 1..26
                       mol_type = other DNA
                       organism = synthetic construct
SEQUENCE: 63
ttcttgagga tcatcatgaa cgtgtc                                       26

SEQ ID NO: 64          moltype = DNA  length = 1139
FEATURE                Location/Qualifiers
misc_feature           1..1139
                       note = cDNA (elo1)
source                 1..1139
                       mol_type = other DNA
                       organism = synthetic construct
SEQUENCE: 64
ctaatacgac tcactatagg gcaagcagtg gtaacaacgc agagtacgcg gggaccccaa  60
acgcccgacg acaaccaaga agacagccag ccgaacaatc ggacgaagat gacgagcaac  120
atgagcgcgt ggggcgtcgc cgtcgaccag acgcagcagg tcgtcgacca gatcatgggc  180
ggcgccgagc cgtacaagct gacagaaggg cgcatgacga acgtcgagac gatgctggcg  240
atcgagtgcg gctacgccgc catgctgctg ttcctgaccc cgatcatgaa gcaggccgag  300
aagcccttcg agctcaagtc cttcaagctc gcccacaacc tgttcctgtt cgtcctgtcc  360
gcctacatgt gcctcgagac cgtccgccag gcctaccttg cgggctactc ggtgttcggc  420
aacgacatgg agaagggcag cgagccgcac gcgcacggca tggcccaaat cgtgtggatc  480
ttttacgtgt ccaaggcgta cgagttcgtg gacacgctga tcatgatcct gtgcaaaaag  540
```

```
ttcaaccagg tctccgtcct gcacgtgtac caccacgcca ccatctttgc tatctggttt  600
atgatcgcca agtacgcccc gggcggcgac gcatacttta gcgtcatcct gaactcgttc  660
gtgcacaccg tcatgtacgc gtactacttc ttctcgtcgc agggcttcgg gttcgtcaag  720
ccgatcaagc cgtacatcac ctcgctgcag atgacgcagt tcatggcgat gctcgtgcag  780
tcgctgtacg actaccttta cccgtgcgac tacccgcagg ggctcgtcaa gctcctcggc  840
gtgtacatgc tcaccctgct tgcgctcttc ggcaactttt tcgtgcagag ctacctcaag  900
aagtcgaaca agcccaaggc caagtcggcc taagccgacc cgctcgccgg caaccgagca  960
gcacctaggc gcatctcggc ccggaacctt ttcgacctgc tgtggagcgc gcgacgcgtt  1020
tcgcgaccgt ccgcgcgttc ttgacactct ttgctctgtg tgtttcgcac ttgacaacct  1080
ggaacagaca catacacgat acaaatcatc agaacagaca aaaaacaacc tcaaattat   1139

SEQ ID NO: 65          moltype = DNA  length = 1261
FEATURE                Location/Qualifiers
misc_feature           1..1261
                       note = cDNA (elo3)
source                 1..1261
                       mol_type = other DNA
                       organism = synthetic construct
SEQUENCE: 65
ctaatacgac tcactatagg gcaagcagtg gtatcaacgc agagtacgcg gggaccccga  60
acgtgtttct cccaggacgt gccgctgtcg ctcgctgatc caccccgaagc gcggtcggct  120
ggcacggtcg ctcggctgga agttgagtag tttgctttct gttactgcgc tgctttgtaa  180
acgcgaccat ggcgacgcgc acctcgaaga gcgctccggc ggtttccaag tcggccaagg  240
ttgccgcgcc ggcgaagaag cggtcggtcg acaggagcga cggtttcttc cgcacgttca  300
acctgtgcgc cctgtacggg tctgccctcg cctatgcgta caagcacggc ccggtggaca  360
atgacggcca ggggctgtac tttcacaagt cgcccatgta cgcgttcgcc gtgtcggacg  420
tcatgacctt cggcgcgccg ctgatgtacg tgctcggtgt gatgctgctc agcaggtaca  480
tggcggacaa aaagcccctg actggcttca tcaagaccta catccagccc gtctacaacg  540
tggtccaaat cgcggtgtgc ggctggatgg tgtggggcct ctggccgcag gtcgacctgg  600
ccaacggcaa ccctttcggc ctcaacaagt cgcgcgactc gaacatcgag tttttcgtgt  660
tcgtgcacct cctgacaaag tttctcgact ggagcgacac gttcatgatg atcctcaaga  720
aaaactacgc ccaggttagc tttctgcagg tgttccacca cgcaacgatc ggcatggtgt  780
ggtcgttcct tcttcagcgt ggctggggct cgggcaccgc cgcgtacggt gctttcatca  840
actcggtcac gcacgtgatc atgtactcgc actactttgc cacctcgctc aacatcaaca  900
acccgttcaa gcggtacatc acgagcttcc agctcgccca gtttgcaagc tgcatcgtgc  960
atgccctact ggtgcttgcc ttcgaggagg tgtacccgct cgagtacgct tacctgcaga  1020
tcagctacca catcatcatg ctctacctgt tcggacgccg catgaactgg agccccgagt  1080
ggtgcaccgg tgagatcgac ggccttgacg ccccaagcgc ccccaccaag tccgagtaaa  1140
cctgtttccg gctggctccc gagccatgct taccatgaat gaacctgcaa acagtctgag  1200
gtccttgtgc aaaccgctca gtgggacgtc gacgaagaaa gaaacaatgt gtactcgtcc  1260
c                                                                  1261

SEQ ID NO: 66          moltype = AA  length = 275
FEATURE                Location/Qualifiers
SITE                   275
                       note = misc_feature - Xaa can be any naturally occurring
                        amino acid
source                 1..275
                       mol_type = protein
                       organism = synthetic construct
SEQUENCE: 66
MTSNMSAWGV AVDQTQQVVD QIMGGAEPYK LTEGRMTNVE TMLAIECGYA AMLLFLTPIM  60
KQAEKPFELK SFKLAHNLFL FVLSAYMCLE TVRQAYLAGY SVFGNDMEKG SEPHAHGMAQ  120
IVWIFYVSKA YEFVDTLIMI LCKKFNQVSV LHVYHHATIF AIWFMIAKYA PGGDAYFSVI  180
LNSFVHTVMY AYYFFSSQGF GFVKPIKPYI TSLQMTQFMA MLVQSLYDYL YPCDYPQGLV  240
KLLGVYMLTL LALFGNFFVQ SYLKKSNKPK AKSAX                             275

SEQ ID NO: 67          moltype = DNA  length = 825
FEATURE                Location/Qualifiers
misc_feature           1..825
                       note = cDNA (T. aureum ATCC 34304 elo1)
source                 1..825
                       mol_type = other DNA
                       organism = synthetic construct
SEQUENCE: 67
atgacgagca acatgagcgc gtggggcgtc gccgtcgacc agacgcagca ggtcgtcgac  60
cagatcatgg gcggcgccga gccgtacaag ctgacagaag ggcgcatgac gaacgtcgag  120
acgatgctgg cgatcgagtg cggctacgcc gccatgctgc tgttcctgac cccgatcatg  180
aagcaggccg agaagccctt cgagctcaag tccttcaagc tcgcccacaa cctgttcctg  240
ttcgtcctgt ccgcctacat gtgcctcgag accgtccgcc aggcctacct tgcgggctac  300
tcggtgttcg gcaacgacat ggagaagggc agcgagccgc acgcgcacgg catggcccaa  360
atcgtgtgga tcttttacgt gtccaaggcg tacgagttcg tggacacgct gatcatgatc  420
ctgtgcaaaa agttcaacca ggtctccgtc ctgcacgtgt accaccacgc caccatcttt  480
gctatctggt ttatgatcgc caagtacgcc ccgggcggcg acgcatactt tagcgtcatc  540
ctgaactcgt tcgtgcacac cgtcatgtac gcgtactact tcttctcgtc gcagggcttc  600
gggttcgtca agccgatcaa gccgtacatc acctcgctgc agatgacgca gttcatggcg  660
atgctcgtgc agtcgctgta cgactacctt tacccgtgcg actacccgca ggggctcgtc  720
aagctcctcg gcgtgtacat gctcaccctg cttgcgctct tcggcaactt tttcgtgcag  780
agctacctca agaagtcgaa caagcccaag gccaagtcgg cctaa                  825
```

```
SEQ ID NO: 68          moltype = AA  length = 317
FEATURE                Location/Qualifiers
SITE                   317
                       note = misc_feature - Xaa can be any naturally occurring
                        amino acid
source                 1..317
                       mol_type = protein
                       organism = synthetic construct
SEQUENCE: 68
MATRTSKSAP AVSKSAKVAA PAKKRSVDRS DGFFRTFNLC ALYGSALAYA YKHGPVDNDG  60
QGLYFHKSPM YAFAVSDVMT FGAPLMYVLG VMLLSRYMAD KKPLTGFIKT YIQPVYNVVQ  120
IAVCGWMVWG LWPQVDLANG NPFGLNKSRD SNIEFFVFVH LLTKFLDWSD TFMMILKKNY  180
AQVSFLQVFH HATIGMVWSF LLQRGWGSGT AAYGAFINSV THVIMYSHYF ATSLNINNPF  240
KRYITSFQLA QFASCIVHAL LVLAFEEVYP LEYAYLQISY HIIMLYLFGR RMNWSPEWCT  300
GEIDGLDAPS APTKSEX                                                 317

SEQ ID NO: 69          moltype = DNA  length = 951
FEATURE                Location/Qualifiers
misc_feature           1..951
                       note = cDNA (T. aureum ATCC 34304 elo3)
source                 1..951
                       mol_type = other DNA
                       organism = synthetic construct
SEQUENCE: 69
atggcgacgc gcacctcgaa gagcgctccg gcggtttcca agtcggccaa ggttgccgcg  60
ccggcgaaga agcggtcggt cgacaggagc gacggtttct tccgcacgtt caacctgtgc  120
gccctgtacg ggtctgccct cgcctatgcg tacaagcacg gcccggtgga caatgacggc  180
caggggctgt actttcacaa gtcgcccatg tacgcgttcg ccgtgtcgga cgtcatgacc  240
ttcggcgcgc cgctgatgta cgtgctcggt gtgatgctgc tcagcaggta catggcggac  300
aaaaagcccc tgactggctt catcaagacc tacatccagc ccgtctacaa cgtggtccaa  360
atcgcggtgt gcggctggat ggtgtggggc ctctggccgc aggtcgacct ggccaacggc  420
aacccctttcg gcctcaacaa gtcgcgcgac tcgaacatcg agtttttcgt gttcgtgcac  480
ctcctgacaa agtttctcga ctggagcgac acgttcatga tgatcctcaa gaaaaactac  540
gcccaggtta gctttctgca ggtgttccac cacgcaacga tcggcatggt gtggtcgttc  600
cttcttcagc gtggctgggg ctcgggcacc gccgcgtacg gtgctttcat caactcggtc  660
acgcacgtga tcatgtactc gcactacttt gccacctcgc tcaacatcaa caacccgttc  720
aagcggtaca tcacgagctt ccagctcgcc cagtttgcaa gctgcatcgt gcatgcccta  780
ctggtgcttg ccttcgagga ggtgtacccg ctcgagtacg cttacctgca gatcagctac  840
cacatcatca tgctctacct gttcggacgc cgcatgaact ggagccccga gtggtgcacc  900
ggtgagatcg acggccttga cgccccaagc gcccccacca agtccgagta a           951

SEQ ID NO: 70          moltype = DNA  length = 38
FEATURE                Location/Qualifiers
misc_feature           1..38
                       note = primer
source                 1..38
                       mol_type = other DNA
                       organism = synthetic construct
SEQUENCE: 70
ataagcttaa aatgtctagc aacatgagcg cgtggggc                          38

SEQ ID NO: 71          moltype = DNA  length = 28
FEATURE                Location/Qualifiers
misc_feature           1..28
                       note = primer
source                 1..28
                       mol_type = other DNA
                       organism = synthetic construct
SEQUENCE: 71
tgtctagaac gcgcggacgg tcgcgaaa                                     28

SEQ ID NO: 72          moltype = DNA  length = 40
FEATURE                Location/Qualifiers
misc_feature           1..40
                       note = primer
source                 1..40
                       mol_type = other DNA
                       organism = synthetic construct
SEQUENCE: 72
taaagcttaa aatgtctacg cgcacctcga agagcgctcc                         40

SEQ ID NO: 73          moltype = DNA  length = 31
FEATURE                Location/Qualifiers
misc_feature           1..31
                       note = primer
source                 1..31
                       mol_type = other DNA
                       organism = synthetic construct
```

```
SEQUENCE: 73
catctagact cggacttggt gggggcgctt g                              31

SEQ ID NO: 74           moltype = DNA  length = 949
FEATURE                 Location/Qualifiers
misc_feature            1..949
                        note = cDNA (TaELO1 coding region)
source                  1..949
                        mol_type = other DNA
                        organism = synthetic construct
SEQUENCE: 74
ataagcttaa aatgacgagc aacatgagcg cgtggggcgt cgccgtcgac cagacgcagc  60
aggtcgtcga ccagatcatg ggcggcgccg agccgtacaa gctgacagaa gggcgcatga  120
cgaacgtcga gacgatgctg gcgatcgagt gcggctacgc cgccatgctg ctgttcctga  180
ccccgatcat gaagcaggcc gagaagccct tcgagctcaa gtccttcaag ctcgcccaca  240
acctgttcct gttcgtcctg tccgcctaca tgtgcctcga gaccgtccgc caggcctacc  300
ttgcgggcta ctcggtgttc ggcaacgaca tggagaaggg cagcgagccg cacgcgcacg  360
gcatggccca aatcgtgtgg atcttttacg tgtccaaggc gtacgagttc gtggacacgc  420
tgatcatgat cctgtgcaaa aagttcaacc aggtctccgt cctgcacgtg taccaccacg  480
ccaccatctt tgctatctgg tttatgatcg ccaagtacgc cccgggcggc gacgcatact  540
ttagcgtcat cctgaactcg ttcgtgcaca ccgtcatgta cgcgtactac ttcttctcgt  600
cgcagggctt cgggttcgtc aagccgatca agccgtacat cacctcgctg cagatgacgc  660
agttcatggc gatgctcgtg cagtcgctgt acgactacct ttacccgtgc gactacccgc  720
aggggctcgt caagctcctc ggcgtgtaca tgctcaccct gcttgcgctc ttcggcaact  780
tttcgtgca gagctacctc aagaagtcga acaagcccaa ggccaagtcg gcctaagccg  840
acccgctcgc cggcaaccga gcagcaccta ggcgcatctc ggcccggaac cttttcgacc  900
tgctgtggag cgcgcgacgc gtttcgcgac cgtccgcgcg ttctagaca             949

SEQ ID NO: 75           moltype = DNA  length = 967
FEATURE                 Location/Qualifiers
misc_feature            1..967
                        note = cDNA (TaELO2 coding region)
source                  1..967
                        mol_type = other DNA
                        organism = synthetic construct
SEQUENCE: 75
taaagcttaa aatggcgacg cgcacctcga agagcgctcc ggcggtttcc aagtcggcca  60
aggttgccgc gccggcgaag aagcggtcgg tcgacaggag cgacggtttc ttccgcacgt  120
tcaacctgtg cgccctgtac gggtctgccc tcgcctatgc gtacaagcac ggcccggtgg  180
acaatgacgg ccaggggctg tactttcaca agtcgcccat gtacgcgttc gccgtgtcgg  240
acgtcatgac cttcggcgcg ccgctgatgt acgtgctcgg tgtgatgctg ctcagcaggt  300
acatggcgga caaaaagccc ctgactggct tcatcaagac ctacatccag cccgtctaca  360
acgtggtcca aatcgcggtg tgcggctgga tggtgtgggg cctctggccg caggtcgacc  420
tggccaacgg caacccctttc ggcctcaaca agtcgcgcga ctcgaacatc gagtttttcg  480
tgttcgtgca cctcctgaca aagtttctcg actggagcga cacgttcatg atgatcctca  540
agaaaaacta cgcccaggtt agctttctgc aggtgttcca ccacgcaacg atcggcatgg  600
tgtggtcgtt ccttcttcag cgtggctggg gctcgggcac cgccgcgtac ggtgctttca  660
tcaactcggt cacgcacgtg atcatgtact cgcactactt tgccacctcg ctcaacatca  720
acaacccgtt caagcggtac atcacgagct tccagctcgc ccagtttgca agctgcatcg  780
tgcatgccct actggtgctt gccttcgagg aggtgtaccc gctcgagtac gcttacctgc  840
agatcagcta ccacatcatc atgctctacc tgttcggacg ccgcatgaac tggagccccg  900
agtggtgcac cggtgagatc gacggccttg acgccccaag cgcccccacc aagtccgagt  960
ctagatg                                                         967

SEQ ID NO: 76           moltype = DNA  length = 1122
FEATURE                 Location/Qualifiers
misc_feature            1..1122
                        note = cDNA (TaELO2 ORF upstream region)
source                  1..1122
                        mol_type = other DNA
                        organism = synthetic construct
SEQUENCE: 76
cgttagaacg cgtaatacga ctcactatag ggatatcccc cgcgaggcga tggctgctcc  60
gacgacgtgg gctggcgacg tcgctcgcaa aggcgttccg caaccgcgcg ttccgctgta  120
acgagaccgt tttccctgcg ctgctgggtg gacctagcgc gtgtgtcacc tgccggcccc  180
cgttgcgtgc aaccgaattg atcgataata gaattacata acaaacaact tgctggatga  240
gtacaagacc agcgtagtgt ggctgtggga cgttgaacgg agcgggtcct gtgacggcgc  300
agaaaggaac tccgcccgag gtgaaacccc gatgcgcagg actctgcggc cacagcccct  360
ccgccagtat tccactaaaa atccgccccc tttgacaaag atcgcaaccc cgtcccatca  420
actcctcaca ataggctttc cactggcgga aacgtccccg gcacaggagt gcctcccgcg  480
gttctgcgca tacggctgac cactacgcag cgcgatatcc tccatccgcg tatatatccg  540
taaacaacgg aacattctcc ctctcaacga ggcgtggttt tcgaagccat gcctttcttc  600
cttcctactt gccttccttc tttctttctt tctttccttc ttttgcaagc gtgcgcgaac  660
ttgaaggtac tacttacact tgacagagag agatagagac ggcaattcga ccaagtactt  720
tccacgattt tttttttttt tgttttggtc gctttcgttg gtcgtgcatg atggatggcc  780
gggattttta caattggatg cgccaggctg ccacgcatgc cgtgacgctc gctcgcggcg  840
actcatgatg cttgccagtg gcagtgcatc cagctcttcc ctctgctcgt cgtgtactca  900
ctggcgatgc tctcggcgct cgttcaaggg ccatcgatcg atcgatcgat cgatcgatcg  960
atcaatcacg tttggtggac tcggcagacc ccgaacgtgt ttctcccagg acgtgccgct  1020
```

```
gtcgctcgct gatccacccg aagcgcggtc ggctggcacg gtcgctcggc tggaagttga  1080
gtagtttgct ttctgttgct gcgctgcttt gtaaacgcga cc                    1122

SEQ ID NO: 77           moltype = DNA  length = 1204
FEATURE                 Location/Qualifiers
misc_feature            1..1204
                        note = cDNA (TaELO2 downstream region)
source                  1..1204
                        mol_type = other DNA
                        organism = synthetic construct
SEQUENCE: 77
acctgtttcc ggctggctcc cgagccatgc ttaccatgaa tgaacctgca aacagtctga  60
ggtccttgtg caaaccgctc agtgggacgt cgacgaagaa agaaacaatg tgtactcgtc  120
ttgctctgct cccgcgccgt tttttatcgt tgttgagacc tctcgcgcag ttttgggaat  180
caaccaaaac aagagcccgg cgtcagcgtt tgcttcgccc tcggctgcac tcgctcggca  240
cgcaggtata actgggtgag taccaagccc cgcatttgtc tgtccgcgat ccgcgcacgc  300
tgcgggtcag gacgacatcg cgctgcacgt cacagtgggt cccttttgac gtggctgcgg  360
cgatgaggag gcttggctcg gcttcatggc aaggcaacag actcgcttcc aggacgcgca  420
cgacgagcag cgctgctttg atcgaccttg cctgcgtcac cgcctcggct gctttgatcg  480
atcgttgtca ccggccgagt gaccgcgaac gcattgcccg cacggctcgg ctcggctcgg  540
accggaccgg ctcgccttgg cggcgcggcg cgatggcgac ccagacgcga ccggagccgc  600
gcgcggagga caaggccatg ttcatcttcg ggctcgggta cgttgggagc aggctcgcca  660
accagctggc ggaacagggg tggcgcgtcg cggggtcggt gagggagctc gggcgcgagg  720
acgactttgc cgagttcgaa aagtccaagc tgagcggcaa ggtgcaggtg ttccgactcc  780
cgcttgaggg cgaggacaac acgcccgctc gcgcgcggga gatacttagc gggtaccagc  840
acctgctgtt cacggcgcca gtggaccgcg cccggaactg tgaccccttc ttgggcgacc  900
ccgttctcgg ccccgtgatc gtcgagctag cagaggaggg ccgcatcgac tgggccggct  960
atctctcaac cacttcggtc tacggcaacc acgacggcga gtgggtggac gagaccacgc  1020
cgctcatgcc cacgctcaaa cgcggcgagc agcgcgtcat ggtggagcgc gccttcctgt  1080
acgagtcggg cctcccggcc catatctttc ggctgccagg aatctacggc ccagggcgcg  1140
gcccgatatc acgaattctc tccctatagt gagtcgtatt acgcgttcta acgacaatat  1200
gtac                                                              1204

SEQ ID NO: 78           moltype = DNA  length = 31
FEATURE                 Location/Qualifiers
misc_feature            1..31
                        note = primer
source                  1..31
                        mol_type = other DNA
                        organism = synthetic construct
SEQUENCE: 78
ctcccgggtg gacctagcgc gtgtgtcacc t                                31

SEQ ID NO: 79           moltype = DNA  length = 25
FEATURE                 Location/Qualifiers
misc_feature            1..25
                        note = primer
source                  1..25
                        mol_type = other DNA
                        organism = synthetic construct
SEQUENCE: 79
ggtcgcgttt acaaagcagc gcagc                                       25

SEQ ID NO: 80           moltype = DNA  length = 52
FEATURE                 Location/Qualifiers
misc_feature            1..52
                        note = primer
source                  1..52
                        mol_type = other DNA
                        organism = synthetic construct
SEQUENCE: 80
gctgcgctgc tttgtaaacg cgaccatgat tgaacaggac ggccttcacg ct          52

SEQ ID NO: 81           moltype = DNA  length = 52
FEATURE                 Location/Qualifiers
misc_feature            1..52
                        note = primer
source                  1..52
                        mol_type = other DNA
                        organism = synthetic construct
SEQUENCE: 81
tcgggagcca gccggaaaca ggttcaaaag aactcgtcca ggaggcggta ga          52

SEQ ID NO: 82           moltype = DNA  length = 23
FEATURE                 Location/Qualifiers
misc_feature            1..23
                        note = primer
source                  1..23
                        mol_type = other DNA
```

```
                         organism = synthetic construct
SEQUENCE: 82
acctgtttcc ggctggctcc cga                                              23

SEQ ID NO: 83            moltype = DNA  length = 27
FEATURE                  Location/Qualifiers
misc_feature             1..27
                         note = primer
source                   1..27
                         mol_type = other DNA
                         organism = synthetic construct
SEQUENCE: 83
atcccggggc cgagaacggg gtcgccc                                          27

SEQ ID NO: 84            moltype = DNA  length = 2696
FEATURE                  Location/Qualifiers
misc_feature             1..2696
                         note = cDNA (TaELO2 ORF upstream/Neor/ TaELO2 ORF
                          downstream)
source                   1..2696
                         mol_type = other DNA
                         organism = synthetic construct
SEQUENCE: 84
ctcccgggtg gacctagcgc gtgtgtcacc tgccggcccc cgttgcgtgc aaccgaattg  60
atcgataata gaattacata acaaacaact tgctggatga gtacaagacc agcgtagtgt  120
ggctgtggga cgttgaacgg agcgggtcct gtgatggcgc agaaaggaac tccgcccgag  180
gtgaaacccc gatgcgcagg actctgcggc cacagcccct ccgccagtat tccactaaaa  240
atccgccccc tttgacaaag atcgcaaccc cgtcccatca actcctcaca ataggctttc  300
cactggcgga aacgtccccg gcacaggagt gcctcccgcg gttctgcgca tacggctgac  360
cactacgcag cgcgatatcc tccatccgcg tatatatccg taaacaacgg aacattctcc  420
ctctcaacga ggcgtggttt tcgaagccat gcctttcttc cttcctactt gccttccttc  480
tttctttctt tctttccttc ttttgcaagc gtgcgcgaac ttgaaggtac tacttacact  540
tgacagagag agatagagac ggcaattcga ccaagtactt tccacgattt tttttttttt  600
tgttttggtc gctttcgttg gtcgtgcatg atggatggcc gggattttta caattggatg  660
cgccaggctg ccacgcatgc cgtgacgctt gctcgcggcg actcatgatg cttgccagtg  720
gcagtgcatc cagctcttcc ctctgctcgt cgtgtactca ctggcgatgc tctcggcgct  780
cgttcaaggg ccatcgatcg atcgatcgat cgatcgatcg atcaatcacg tttggtggac  840
tcggcagacc ccgaacgtgt ttctcccagg acgcgccgct gtcgctcgct gatccacccg  900
aagcgcggtc ggctggcacg gtcgctcggc tggaagttga gtagtttgct ttctgttgct  960
gcgctgcttt gtaaacgcga ccatgattga acaggacggc cttcacgctg gctcgcccgc  1020
tgcttgggtg gaacggctgt tcggctacga ctgggctcag cagacgatcg gctgctcgga  1080
cgcggccgtg ttccgcctta gcgcgcaggg ccggccggtc ctgtttgtca agaccgacct  1140
tagcggcgcc ctcaacgagc tccaggacga agctgcccgc ctcagctggc ttgccacgac  1200
gggggttccg tgcgccgctg tgctcgacgt cgtcaccgaa gccggccgcg actggctgct  1260
cctcggggaa gtgcccggcc aggacctcct cagcagccac ctcgcgcccg ctgagaaggt  1320
gtccatcatg gccgacgcca tgcgccgcct gcacaccctc gaccccgcca cctgcccctt  1380
cgaccaccag gcgaagcaca ggatcgaacg cgcccgcacg cggatggagg ctggcctcgt  1440
cgaccaagac gacctcgacg aggagcacca gggcctcgcg ccggcggaac tgttcgccag  1500
gcttaaggct aggatgccgg acggcgagga cctcgtggtc acgcacggcg acgcctgcct  1560
ccccaacatc atggtcgaga acggccgctt ctcgggcttt atcgactgcg ggcgcctggg  1620
cgtggcggac cgctaccaag acatcgcgct cgccacgcgg gacatcgccg aggagcttgg  1680
cggcgagtgg gccgaccgct ttctcgtgct ctacggcatc gccgccccgg acagccagag  1740
gattgcgttc taccgcctcc tggacgagtt cttttgaacc tgtttccggc tggctcccga  1800
gccatgctta ccatgaatga acctgcaaac agtctgaggt ccttgtgcaa accgctcagt  1860
gggacgtcga cgaagaaaga aacaatgtgt actcgtcttg ctctgctccc gcgccgtttt  1920
ttatcgttgt tgagacctct cgcgcagttt tgggaatcaa ccaaaacaag agcccggcgt  1980
cagcgtttgc ttcgccctcg gctgcactcg ctcggcacgc aggtataact gggtgagtac  2040
caagccccgc atttgtctgt ccgcgatccg cgcacgctgc gggtcaggac gacatcgcgc  2100
tgcacgtcac agtgggtccc ttttgacgtg gctgcggcga tgaggaggct tggctcggct  2160
tcatggcaag gcaacagact cgcttccggg acgcgcacga cgagcagcgc tgctttgatc  2220
gaccttgcct gcgtcaccgc ctcggctgct ttgatcgatc gttgtcaccg gccgagtgac  2280
cgcgaacgca ttgcccgcac ggctcggctc ggcccggacc ggaccggctc gccttggcgg  2340
cgcggcgcga tggcgaccca gacgcggccg gagccgcgcg cggaggacaa ggccatgttc  2400
atcttcgggc tcgggtacgt tgggagcagg ctcgccaacc agctggcgga acaggggtgg  2460
cgcgtcgcgg ggtcggtgag ggagctcggg cgcgaggacg actttgccga gttcgaaaag  2520
tccaagctga gcggcaaggt gcaggtgttc cgactcccgc ttgagggcga ggacaacacg  2580
cccgctcgcg cgcgggagat acttagcggg taccagcacc tgctgttcac ggcgccagtg  2640
gaccgcgccc ggaactgtga ccccttcttg ggcgaccccg ttctcggccc cgggat      2696

SEQ ID NO: 85            moltype = DNA  length = 30
FEATURE                  Location/Qualifiers
misc_feature             1..30
                         note = primer
source                   1..30
                         mol_type = other DNA
                         organism = synthetic construct
SEQUENCE: 85
ggatatcccc cgcgaggcga tggctgctcc                                       30
```

```
SEQ ID NO: 86           moltype = DNA  length = 30
FEATURE                 Location/Qualifiers
misc_feature            1..30
                        note = primer
source                  1..30
                        mol_type = other DNA
                        organism = synthetic construct
SEQUENCE: 86
tgatatcggg ccgcgccctg ggccgtagat                                   30

SEQ ID NO: 87           moltype = DNA  length = 25
FEATURE                 Location/Qualifiers
misc_feature            1..25
                        note = primer
source                  1..25
                        mol_type = other DNA
                        organism = synthetic construct
SEQUENCE: 87
gtacgtgctc ggtgtgatgc tgctc                                        25

SEQ ID NO: 88           moltype = DNA  length = 24
FEATURE                 Location/Qualifiers
misc_feature            1..24
                        note = primer
source                  1..24
                        mol_type = other DNA
                        organism = synthetic construct
SEQUENCE: 88
gcggcgtccg aacaggtaga gcat                                         24

SEQ ID NO: 89           moltype = DNA  length = 35
FEATURE                 Location/Qualifiers
misc_feature            1..35
                        note = primer
source                  1..35
                        mol_type = other DNA
                        organism = synthetic construct
SEQUENCE: 89
atccgcgtat atatccgtaa acaacggaac attct                             35

SEQ ID NO: 90           moltype = DNA  length = 26
FEATURE                 Location/Qualifiers
misc_feature            1..26
                        note = primer
source                  1..26
                        mol_type = other DNA
                        organism = synthetic construct
SEQUENCE: 90
cttcgggtgg atcagcgagc gacagc                                       26

SEQ ID NO: 91           moltype = DNA  length = 27
FEATURE                 Location/Qualifiers
misc_feature            1..27
                        note = primer
source                  1..27
                        mol_type = other DNA
                        organism = synthetic construct
SEQUENCE: 91
gccgcagcgc ctggtgcacc cgccggg                                      27

SEQ ID NO: 92           moltype = DNA  length = 59
FEATURE                 Location/Qualifiers
misc_feature            1..59
                        note = primer
source                  1..59
                        mol_type = other DNA
                        organism = synthetic construct
SEQUENCE: 92
tcgcgggtga gttcaggctt tttcatgttg gctagtgttg cttaggtcgc ttgctgctg   59

SEQ ID NO: 93           moltype = DNA  length = 57
FEATURE                 Location/Qualifiers
misc_feature            1..57
                        note = primer
source                  1..57
                        mol_type = other DNA
                        organism = synthetic construct
SEQUENCE: 93
agcgacctaa gcaacactag gccaacatga aaaagcctga actcaccgcg acgtctg     57
```

```
SEQ ID NO: 94          moltype = DNA  length = 29
FEATURE                Location/Qualifiers
misc_feature           1..29
                       note = primer
source                 1..29
                       mol_type = other DNA
                       organism = synthetic construct
SEQUENCE: 94
ctattccttt gccctcggac gagtgctgg                                    29

SEQ ID NO: 95          moltype = DNA  length = 1636
FEATURE                Location/Qualifiers
misc_feature           1..1636
                       note = cDNA (T. aureum ATCC 34304 ubiruitin promoter/ Hygr)
source                 1..1636
                       mol_type = other DNA
                       organism = synthetic construct
SEQUENCE: 95
gctagccgca gcgcctggtg cacccgccgg gcgttggttg tgtgtgctat ttactatgcc  60
taccgagaga gagagcggag cggatgcata ggaaatcggg ccacgcggga gggccatgcg  120
ttcgccccac acgccactta taccacgccc gctctctctc cggccggcag gcagcgcata  180
actataccga cgctggcagg cttggtagca actggcaggg acaactcgcg cgcgggtccc  240
ggtcgttcga tgtgccaacc cgagagaatc cagccagcag ggcggttggc ctcatcgccc  300
acctgctatg gtgcagcgaa ccaactcccg aagcggccgg ttccgcgatt ccctcttctg  360
aattctgaat tctgaactga ttccggagga gaaccctctg gaagcgcggg ttgcctctcc  420
agttctgccg aactagacag gggagtgagc atgatgagtg accctgacgc gtgagctgag  480
ctggttgctg gaatatagtc gctgaacgct gggctgtgtc acgcgtccac ttcgggcaga  540
ccccaaacga caagcagaac aagcaacacc agcagcagca agcgacctaa gcaacactag  600
ccaacatgaa aaagcctgaa ctcaccgcga cgtctgtcga gaagtttctg atcgaaaagt  660
tcgacagcgt ctccgacctg atgcagctct cggagggcga agaatctcgt gctttcagct  720
tcgatgtagg agggcgtgga tatgtcctgc gggtaaatag ctgcgccgat ggtttctaca  780
aagatcgtta tgtttatcgg cactttgcat cggccgcgct cccgattccg gaagtgcttg  840
acattgggga attcagcgag agcctgacct attgcatctc ccgccgtgca cagggtgtca  900
cgttgcaaga cctgcctgaa accgaactgc ccgctgttct gcagccggtc gcggaggcca  960
tggatgcgat cgctgcggcc gatcttagcc agacgagcgg gttcggccca ttcggaccgc  1020
aaggaatcgg tcaatacact acatggcgtg atttcatatg cgcgattgct gatccccatg  1080
tgtatcactg gcaaactgtg atggacgaca ccgtcagtgc gtccgtcgcg caggctctcg  1140
atgagctgat gctttgggcc gaggactgcc ccgaagtccg gcacctcgtg cacgcggatt  1200
tcggctccaa caatgtcctg acggacaatg gccgcataac agcggtcatt gactggagcg  1260
aggcgatgtt cggggattcc caatacgagg tcgccaacat cttcttctgg aggccgtggt  1320
tggcttgtat ggagcagcag acgcgctact tcgagcggag gcatccggag cttgcaggat  1380
cgccgcggct ccgggcgtat atgctccgca ttggtcttga ccaactctat cagagcttgg  1440
ttgacggcaa tttcgatgat gcagcttggg cgcagggtcg atgcgacgca atcgtccgat  1500
ccggagccgg gactgtcggg cgtacacaaa tcgcccgcag aagcgcggcc gtctggaccg  1560
atggctgtgt agaagtactc gccgatagtg gaaaccgacg ccccagcact cgtccgaggg  1620
caaaggaata gtctag                                                  1636

SEQ ID NO: 96          moltype = DNA  length = 33
FEATURE                Location/Qualifiers
misc_feature           1..33
                       note = primer
source                 1..33
                       mol_type = other DNA
                       organism = synthetic construct
SEQUENCE: 96
gtgctagccg cagcgcctgg tgcacccgcc ggg                               33

SEQ ID NO: 97          moltype = DNA  length = 37
FEATURE                Location/Qualifiers
misc_feature           1..37
                       note = primer
source                 1..37
                       mol_type = other DNA
                       organism = synthetic construct
SEQUENCE: 97
gttctagact attcctttgc cctcggacga gtgctgg                           37

SEQ ID NO: 98          moltype = DNA  length = 37
FEATURE                Location/Qualifiers
misc_feature           1..37
                       note = primer
source                 1..37
                       mol_type = other DNA
                       organism = synthetic construct
SEQUENCE: 98
gttctagacc tgtttccggc tggctcccga gccatgc                           37

SEQ ID NO: 99          moltype = DNA  length = 40
```

```
FEATURE                Location/Qualifiers
misc_feature           1..40
                       note = primer
source                 1..40
                       mol_type = other DNA
                       organism = synthetic construct
SEQUENCE: 99
gtgctagcgg tcgcgtttac aaagcagcgc agcaacagaa                       40

SEQ ID NO: 100         moltype = DNA  length = 3537
FEATURE                Location/Qualifiers
misc_feature           1..3537
                       note = cDNA (TaELO2 ORF upstream region/T. aureum ATCC
                        34304 ubiquitin promotor/ Hygr /TaELO2 ORF downstream
                        region)
source                 1..3537
                       mol_type = other DNA
                       organism = synthetic construct
SEQUENCE: 100
ctcccgggtg gacctagcgc gtgtgtcacc tgccggcccc cgttgcgtgc aaccgaattg  60
atcgataata gaattacata acaaacaact tgctggatga gtacaagacc agcgtagtgt  120
ggctgtggga cgttgaacgg agcgggtcct gtgacggcgc agaaaggaac tccgcccgag  180
gtgaaacccc gatgcgcagg actctgcggc cacagcccct ccgccagtat tccactaaaa  240
atccgccccc tttgacaaag atcgcaaccc cgtcccatca actcctcaca ataggctttc  300
cactggcgga aacgtccccg gcacaggagt gcctcccgcg gttctgcgca tacggctgac  360
cactacgcag cgcgatatcc tccatccgcg tatatatccg taaacaacgg aacattctcc  420
ctctcaacga ggcgtggttt tcgaagccat gcctttcttc cttcctactt gccttccttc  480
tttctttctt tctttctttc ttttgtaagc gtgcgcgaac ttgaaggtac tacttacact  540
tgacagagag agatagagac ggcaattcga ccaagtactt tccacgattt tttttttttt  600
tgttttggtc gctttcgttg gtcgtgcatg atggatggcc gggattttta caattggatg  660
cgccaggctg ccacgcatgc cgtgacgctc gctcgcggcg actcatggtg cttgccagtg  720
gcagtgcatc cagctcttcc ctctgctcgt cgtgtactca ctggcgatgc tctcggcgct  780
cgttcaaggg ccatcgatcg atcgatcgat cgatcgatcg atcaatcacg tttggtggac  840
tcggcagacc ccgaacgtgt ttctcccagg acgtgccgct gtcgctcgct gatccacccg  900
aagcgcggtc ggctggcacg gtcgctcggc tggaagttga gtagtttgct ttctgttgct  960
gcgctgcttt gtaaacgcga ccgctagccg cagcgcctgg tgcacccgcc gggcgttggt  1020
tgtgtgtgct atttactatg cctaccgaga gagagagcgg agcggatgca taggaaatcg  1080
ggccacgcgg gagggccatg cgttcgcccc acacgccact tataccacgc ccgctctctc  1140
tccggccggc aggcagcgca taactatacc gacgctggca ggcttggtag caactggcag  1200
ggacaactcg cgcgcgggtc ccggtcgttc gatgtgccaa cccgagagaa tccagccagc  1260
agggcggttg gcctcatcgc ccacctgcta tggtgcagcg aaccaactcc cgaagcggcc  1320
ggttccgcga ttccctcttc tgaattctga attctgaact gattccggag gagaaccctc  1380
tggaagcgcg ggttgcctct ccagttctgc cgaactagac aggggagtga gcatgatgag  1440
tgaccctgac gcgtgagctg agctggttgc tggaatatag tcgctgaacg ctgggctgtg  1500
tcacgcgtcc acttcgggca gaccccaaac gacaagcaga acaagcaaca ccagcagcag  1560
caagcgacct aagcaacact agccaacatg aaaaagcctg aactcaccgc gacgtctgtc  1620
gagaagtttc tgatcgaaaa gttcgacagc gtctccgacc tgatgcagct ctcggagggc  1680
gaagaatctc gtgctttcag cttcgatgta ggagggcgtg gatatgtcct gcgggtaaat  1740
agctgcgccg atggtttcta caaagatcgt tatgtttatc ggcactttgc atcggccgcg  1800
ctcccgattc cggaagtgct tgacattggg gaattcagcg agagcctgac ctattgcatc  1860
tcccgccgtg cacagggtgt cacgttgcaa gacctgcctg aaaccgaact gcccgctgtt  1920
ctgcagccgg tcgcggaggc catggatgcg atcgctgcgg ccgatcttag ccagacgagc  1980
gggttcggcc cattcggacc gcaaggaatc ggtcaataca ctacatggcg tgatttcata  2040
tgcgcgattg ctgatcccca tgtgtatcac tggcaaactg tgatggacga caccgtcagt  2100
gcgtccgtcg cgcaggctct cgatgagctg atgctttggg ccgaggactg ccccgaagtc  2160
cggcacctcg tgcacgcgga tttcggctcc aacaatgtcc tgacggacaa tggccgcata  2220
acagcggtca ttgactggag cgaggcgatg ttcggggatt cccaatacga ggtcgccaac  2280
atcttcttct ggaggccgtg gttggcttgt atggagcagc agacgcgcta cttcgagcgg  2340
aggcatccgg agcttgcagg atcgccgcgg ctccgggcgt atatgctccg cattggtctt  2400
gaccaactct atcagagctt ggttgacggc aatttcgatg atgcagcttg ggcgcagggt  2460
cgatgcgacg caatcgtccg atccggagcc gggactgtcg ggcgtacaca aatcgcccgc  2520
agaagcgcgg ccgtctggac cgatggctgt gtagaagtac tcgccgatag tggaaaccga  2580
cgccccagca ctcgtccgag ggcaaaggaa tagtctagac ctgtttccgg ctggctcccg  2640
agccatgctt accatgaatg aacctgcaaa cagtctgagg tccttgtgca aaccgctcag  2700
tgggacgtcg acgaagaaag aaacaatgtg tactcgtctt gctctgctcc cgcgccgttt  2760
tttatcgttg ttgagacctc tcgcgcagtt ttgggaatca accaaaacaa gagcccggcg  2820
tcagcgtttg cttcgccctc ggctgcactc gctcggcacg caggtataac tgggtgagta  2880
ccaagccccg catttgtctg tccgcgatcc gcgcacgctg cgggtcagga cgacatcgcg  2940
ctgcacgtca cagtgggtcc cttttgacgt ggctgcggcg atgaggaggc ttggctcggc  3000
ttcatggcaa ggcaacagac tcgcttccgg gacgcgcacg acgagcagcg ctgctttgat  3060
cgaccttgcc tgcgtcaccg cctcggctgc tttgatcgat cgttgtcacc ggccgagtga  3120
ccgcgaacgc attgcccgca cggctcggct cggcccggac cggaccggct cgccttggcg  3180
gcgcggcgcg atggcgaccc agacgcggcc ggagccgcgc gcggaggaca aggccatgtt  3240
catcttcggg ctcgggtacg ttgggagcag gctcgccaac cagctggcgg aacaggggtg  3300
gcgcgtcgcg gggtcggtga gggagctcgg gcgcgaggac gactttgccg agttcgaaaa  3360
gtccaagctg agcggcaagg tgcaggtgtt ccgactcccg cttgagggcg aggacaacac  3420
gcccgctcgc gcgcgggaga tacttagcgg gtaccagcac ctgctgttca cggcgccagt  3480
ggaccgcgcc cggaactgtg acccccttctt gggcgacccc gttctcggcc ccgggat     3537
```

```
SEQ ID NO: 101         moltype = DNA  length = 30
FEATURE                Location/Qualifiers
misc_feature           1..30
                       note = primer
source                 1..30
                       mol_type = other DNA
                       organism = synthetic construct
SEQUENCE: 101
atggcgacgc gcacctcgaa gagcgctccg                                   30

SEQ ID NO: 102         moltype = DNA  length = 30
FEATURE                Location/Qualifiers
misc_feature           1..30
                       note = primer
source                 1..30
                       mol_type = other DNA
                       organism = synthetic construct
SEQUENCE: 102
aggatcatca tgaacgtgtc gctccagtcg                                   30

SEQ ID NO: 103         moltype = DNA  length = 23
FEATURE                Location/Qualifiers
misc_feature           1..23
                       note = primer
source                 1..23
                       mol_type = other DNA
                       organism = synthetic construct
SEQUENCE: 103
cgatgaaagg tcacagaaga gtc                                          23

SEQ ID NO: 104         moltype = DNA  length = 3181
FEATURE                Location/Qualifiers
misc_feature           1..3181
                       note = genomic DNA (T. aureum ATCC 34304 OrfA upstream)
source                 1..3181
                       mol_type = other DNA
                       organism = synthetic construct
SEQUENCE: 104
aagcttttgc tctgcggctc tgcttgttcg aagccaacgc gcctcgcgaa gtatctgcaa  60
tctgcactcc tccggagagt aagtacgtaa gtacgtgcgt ggtgcgcgcg gattgcggtg  120
acgaaagaga gggttgggtt ggagatgctg cggcatgccg ggcgactcga gcagcatgtc  180
gccgcgagag gacctggaaa gctttcggtt tggtccgctg ccgaggcgag gctggcagag  240
tactgcgggc ggagctctcg agggaatatg ctcctcaaag acggcgtgcg cgtttgtgcc  300
cccgaatccg aatgcggaga gtcctgcgcg tttcggcccg ccgcgcgtat ccggccacgg  360
gagcgccgct gtgacgacga ggggatcaat ctgggtgcca gagtcaacgc ccagggtcgg  420
ggggatcacg ccgcgctcca ttgcaaggag aaccttgcac attcccgcaa agccggccgc  480
gacgagggtg tgtccgaagt tgcctttcgt ggacccgatc cgggggcttg cgccctcaaa  540
gcaggctttg acggcttgga gctcgacggt gtcgccctgc ggcgtgccgg tggcgtggca  600
ctcgacgtac tggacgtctc ggggcggcac gccgacgagc tcgtaggtgg ctttcaagca  660
ggcctcctcg cttggctggt gcggcttgag aggaagcccg cagcctgcgt tgctcaagct  720
ggccccaaga agcgtcccgt agatgtggtc tccgtcgcgc tcggcgtccg cgaggcgctt  780
gagcaccatc accgagccgc cctcgccggg cgtcagccct tgcgtgtccc gatgaaacgg  840
catcgagaca ccgttctcac cgactggcat cgcgtggaac gtgctaaacc cagtcaggat  900
gaagaagggc tctgggaagc acgtcgctcc gcacagcatc aagtcagcct cgcccgagag  960
gaggtggtcc tgagcgagtc gcagaacgta aagggccgag gcgcaggcgg cgtcgagcga  1020
gtagtgcagc gggccgaggc cgagctgtcc ggcgacgaag gaggctgggt cgcggtgggt  1080
cctcgggtcc ccgggcagcg ggtgaagcgc tctggttcgc gtcgaccagg gcgtttggtc  1140
cgcgaagcaa tgcttgccaa tccgcctctc agcatgggct tggtaaaggt tgagcagctc  1200
gccttgcagg ttgtccatcg ggaaggacag gcagccgctg acaatgccgc agcgcttgag  1260
ctgcgctggg tcgaacttgc cgccgtcgct gcgcctgtcc tgcgcgtctt gaagcgcagc  1320
cgcggcgagg ccgaggagca ggtcgtgctc gttgtcgact ttgggatcga tgcatccgta  1380
cctctcgttg cagaacgtat cggcgtactt tgacctctcg ggcgcatagt gctcttctcg  1440
tcgtgctgac ccgaggcgat cgtctgagat acaggcagag ttgattttgc cgttcatgag  1500
cgtgtcccag aacgcttcct tgccgcggca ccctgcatac tcgaccgcca tgcccacgac  1560
agcgatccgc gtgtcagggc atgggtccgc gcgcgccacc gagacgccct cgtcatttct  1620
cccgccctgg ttcatctctt tctgagcctt gtggcctctt gctttcgatt tcgatcggca  1680
gctccaacgc gcagctcgat ggccgattgc ttgctaaggc ggcgtgcaga caaccgctgc  1740
tcgaggttct gggcaagccg aggttcgccg cagggttcgt ggaggcactg ggatgttgtt  1800
ttgcggcagc tgcagcgctt gcggagcgag cggcgcagga cgacgttttc cgcgttcgcg  1860
cgaagctgcc tctcggctat tgtgacccgc cgccgacgct ggcagagacg tcgccgtcgg  1920
ccaccgcacc tcgagatcaa ttcgcagagg ctggcagagc cggtagcatt gcggcgtggc  1980
attgcgtgtg ccatgtgcat gtgtggcaaa caaatccagc caacctccga gtcgggcaga  2040
ccgaccgtgt gagttctcgc tgttgactga tctcttgatt gagcccaata atgatcacgg  2100
cctgagatcc ttcgcgctga gagatgcatg cgggcgctcg ttcctgggtt ggcgacccaa  2160
cggcgagtca cgtcgcccac tccgccacgc cccacacatg gccgccgatc cctcccgcca  2220
cacgaacggc gggccaagat cgcacgcctc cgtcggacga tgactgactg actgattggc  2280
tgacgacggc cgccctcgtg cgcggcgtcg ggcgtcgtcg caaaccaggc aggcaggcag  2340
gaaggaagga aggaagggcc aggccctggt gcgaaacgct ggcctgctcc gctgcaagcc  2400
aagccgcgct cgcaggtgta cttccgagtc ctcgcgatga ttaggcaagc ctgagcgagc  2460
```

```
acgtaagctg cactgcggct gttcaaccag agagagagtt ggctctcttg cgtcaaggcg  2520
gcgcgcagcc cacttgcgtc gcggctgagg gcccctggag gggaggaagg aggccggcga  2580
gcggcgagtg gcggccctca ctggcaccag gtcgcaggag gccaggcagc ccgccacgga  2640
caggaatcct cagggcgcag cagcgcacta cgtagtgcag agacgcagag cgggccggat  2700
ccgcagtgcg gtcgcgccac cccgccgcgc agctcgctcg cggacggggt ccgtggccgc  2760
gcgaaaacgg acacggtgtg ggagcggaca tgggatcgag aacgccgttc gccctgctcg  2820
cgctgccagc agcaggagcc gtccgaagga cgagcggccg gccgcctgtc ccccctccgc  2880
gcactcgaag cgcgcccggc agcgccccat tgcgtgcgcg gatggcgtct tggctggtcc  2940
ctctcgaggc gcttgctcgt gctcgccacg ccttgtccgc ctcctcgctg agcaagcgat  3000
gagctgagca cggaccgcct gcaagtgcaa gtgttcttgt gctgcagggc gccgaagaat  3060
tggattctgg cccatgatca gtttgattgg gccgagggag ggagggaggc tgggcgagtg  3120
ggcgacacca gcaagccgga ctgcgagagg ggcggggcag gatgtgagcg caggaaagtg  3180
a                                                                  3181

SEQ ID NO: 105         moltype = DNA  length = 3377
FEATURE                Location/Qualifiers
misc_feature           1..3377
                       note = genomic DNA (T. aureum ATCC 34304 OrfA upstream
                        genomic DNA fragment)
source                 1..3377
                       mol_type = other DNA
                       organism = synthetic construct
SEQUENCE: 105
gaattcgatt aatacgactc actataggga gaagcttttg ctctgcggct ctgcttgttc  60
gaagccaacg cgcctcgcga agtatctgca atctgcactc ctccggagag taagtacgta  120
agtacgtgcg tggtgcgcgc ggattgcggt gacgaaagag agggttgggt tggagatgct  180
gcggcatgcc gggcgactcg agcagcatgt cgccgcgaga ggacctggaa agctttcggt  240
ttggtccgct gccgaggcga ggctggcaga gtactgcggg cggagctctc gagggaatat  300
gctcctcaaa gacggcgtgc gcgtttgtgc ccccgaatcc gaatgcggag agtcctgcgc  360
gtttcggccc gccgcgcgta tccggccacg ggagcgccgc tgtgacgacg aggggatcaa  420
tctgggtgcc agagtcaacg cccagggtcg gggggatcac gccgcgctcc attgcaagga  480
gaaccttgca cattcccgca aagccggccg cgacgagggt gtgtccgaag ttgcctttcg  540
tggacccgat ccgggggctt gcgccctcaa agcaggcttt gacggcttgg agctcgacgg  600
tgtcgccctg cggcgtgccg gtggcgtggc actcgacgta ctggacgtct cggggcggca  660
cgccgacgag ctcgtaggtg gctttcaagc aggcctcctc gcttggctgg tgcggcttga  720
gaggaagccc gcagcctgcg ttgctcaagc tggccccaag aagcgtcccg tagatgtggt  780
ctccgtcgcg ctcggcgtcc gcgaggcgct tgagcaccat caccgagccg ccctcgccgg  840
gcgtcagccc ttgcgtgtcc cgatgaaacg gcatcgagac accgttctca ccgactggca  900
tcgcgtggaa cgtgctaaac ccagtcagga tgaagaaggg ctctgggaag cacgtcgctc  960
cgcacagcat caagtcagcc tcgcccgaga ggaggtggtc ctgagcgagt cgcagaacgt  1020
aaagggccga ggcgcaggcg gcgtcgagcg agtagtgcag cgggccgagg ccgagctgtc  1080
cggcgacgaa ggaggctggg tcgcggtggg tcctcgggtc cccgggcagc gggtgaagcg  1140
ctctggttcg cgtcgaccag ggcgtttggt ccgcgaagca atgcttgcca atccgcctct  1200
cagcatgggc ttggtaaagg ttgagcagct cgccttgcag gttgtccatc gggaaggaca  1260
ggcagccgct gacaatgccg cagcgcttga gctgcgctgg gtcgaacttg ccgccgtcgc  1320
tgcgcctgtc ctgcgcgtct tgaagcgcag ccgcggcgag gccgaggagc aggtcgtgct  1380
cgttgtcgac tttgggatcg atgcatccgt acctctcgtt gcagaacgta tcggcgtact  1440
ttgacctctc gggcgcatag tgctcttctc gtcgtgctga cccgaggcga tcgtctgaga  1500
tacaggcaga gttgattttg ccgttcatga gcgtgtccca gaacgcttcc ttgccgcggc  1560
accctgcata ctcgaccgcc atgcccacga cagcgatccg cgtgtcaggg catgggtccg  1620
cgcgcgccac cgagacgccc tcgtcatttc tcccgccctg gttcatctct ttctgagcct  1680
tgtggcctct tgctttcgat ttcgatcggc agctccaacg cgcagctcga tggccgattg  1740
cttgctaagg cggcgtgcag acaaccgctg ctcgaggttc tgggcaagcc gaggttcgcc  1800
gcagggttcg tggaggcact gggatgttgt tttgcggcag ctgcagcgct tgcggagcga  1860
gcggcgcagg acgacgtttt ccgcgttcgc gcgaagctgc ctctcggcta ttgtgacccg  1920
ccgccgacgc tggcagagac gtcgccgtcg gccaccgcac ctcgagatca attcgcagag  1980
gctggcagag ccggtagcat tgcggcgtgg cattgcgtgt gccatgtgca tgtgtggcaa  2040
acaaatccag ccaacctccg agtcgggcag accgaccgtg tgagttctcg ctgttgactg  2100
atctcttgat tgagcccaat aatgatcacg gcctgagatc cttcgcgctg agagatgcat  2160
gcgggcgctc gttcctgggt tggcgaccca acggcgagtc acgtcgccca ctccgccacg  2220
ccccacacat ggccgccgat ccctcccgcc acacgaacgg cgggccaaga tcgcacgcct  2280
ccgtcggacg atgactgact gactgattgg ctgacgacgg ccgccctcgt gcgcggcgtc  2340
gggcgtcgtc gcaaaccagg caggcaggca ggaaggaagg aaggaagggc caggccctgg  2400
tgcgaaacgc tggcctgctc cgctgcaagc caagccgcgc tcgcaggtgt acttccgagt  2460
cctcgcgatg attaggcaag cctgagcgag cacgtaagct gcactgcggc tgttcaacca  2520
gagagagagt tggctctctt gcgtcaaggc ggcgcgcagc ccacttgcgt cgcggctgag  2580
ggcccctgga ggggaggaag gaggccggcg agcggcgagt ggcggccctc actggcacca  2640
ggtcgcagga ggccaggcag cccgccacgg acaggaatcc tcagggcgca gcagcgcact  2700
acgtagtgca gagacgcaga gcgggccgga tccgcagtgc ggtcgcgcca ccccgccgcg  2760
cagctcgctc gcggacgggg tccgtggccg cgcgaaaacg gacacggtgt gggagcggac  2820
atgggatcga gaacgccgtt cgccctgctc gcgctgccag cagcaggagc cgtccgaagg  2880
acgagcggcc ggccgcctgt cccccctccg cgcactcgaa gcgcgcccgg cagcgcccca  2940
ttgcgtgcgc ggatggcgtc ttggctggtc cctctcgagg cgcttgctcg tgctcgccac  3000
gccttgtccg cctcctcgct gagcaagcga tgagctgagc acggaccgcc tgcaagtgca  3060
agtgttcttg tgctgcaggg cgccgaagaa ttggattctg gcccatgatc agtttgattg  3120
ggccgaggga gggagggagg ctgggcgagt gggcgacacc agcaagccgg actgcgagag  3180
gggcggggca ggatgtgagc gcaggaaagt gacgcaagtg catccggcca tcattgggcc  3240
atcattgggc catcattggt gttttgggcc gcgctttgcg gatcgtccgg ccgatcaggt  3300
acgaggccac gaacctacgt cgtttgccgc gctcaggctg gttggttgca cttggactct  3360
```

```
tctgtgacct ttcatcg                                              3377

SEQ ID NO: 106         moltype = DNA  length = 21
FEATURE                Location/Qualifiers
misc_feature           1..21
                       note = primer
source                 1..21
                       mol_type = other DNA
                       organism = synthetic construct
SEQUENCE: 106
cagggcgagc gagtgtggtt c                                         21

SEQ ID NO: 107         moltype = DNA  length = 1160
FEATURE                Location/Qualifiers
misc_feature           1..1160
                       note = genomic DNA (T. aureum ATCC 34304 OrfA downstream)
source                 1..1160
                       mol_type = other DNA
                       organism = synthetic construct
SEQUENCE: 107
tggctctcga ccaaagccga gtagagtact ctactcagta ctcttttcac ataccggcag  60
gcagtgttgc tgtgggattg gtccgggggc tcttctgcac gcggcctccg tcgcgcgcag  120
aaatgccccg tcactggctg cccaggaggc agccgaatcc ctctagctag ctagctaggc  180
tagagcgtct tttccgtagt ttttcacaaa gccagtatca catggataac gaacgaaggt  240
ttcgggctcg cgctcgcagg cgttaggacg aagttgatcg ccccacgtca cttcaaacga  300
gtgaaccaag atcacgttgc atctgctcgc aagatcttct tcttccacgc cgcatcgatg  360
cgatggattt caaactcttt tcagggcttt taggtgagta tggcagcgct gtttgcgtgg  420
cagcgctgtt tgcgtggttg tactctctaa aggtgcttcc acgcatgcgc gcacaaaggg  480
gcatggcatg gttggcggcg cactctggcc ctcatttgaa gcagactatc gaagggtcca  540
gttggtactg cggcaggtcc ggcgagagca agcgcggcgg tcgctcccac tcgtccctgc  600
acagttgctg gactggcgac ggctggcgca cctgactacg agaagactcg agacgcacag  660
aggtagtcag ggacgaccga ccgcaaagca caaaccgctc caaaacggcc gcaccaggca  720
gggcagtaaa ctaaaaacga atgtacctcc atcgcgcgta tctgccgagc ctcctcccac  780
gcttcggctg ggcttgattc accagtgtcc gcaagctgaa ccgaccgtct tcgatgtcat  840
gaagcttggc gcggcattag tcagacgacg cggcacgcca ggattctgtc ggtttctggg  900
aaatgggcat ctatatagct gattccctct gtcatgaggc ggccttgttc tggccctggg  960
ccgccgttcg gatgatctat gatgtcgttg tacgcataaa gcttgtcgaa aacgtcggcc  1020
atgtcttcct cagagatgta accgagcggc gcgtcgtggc gattgatgcc gatgctacaa  1080
aagccgccga gttagctcga atgtcagatg cattgcgggc tggcccgcat ggcgcgggcg  1140
cagcagcgag aggttctaga                                           1160

SEQ ID NO: 108         moltype = DNA  length = 1204
FEATURE                Location/Qualifiers
misc_feature           1..1204
                       note = genomic DNA (T. aureum ATCC 34304 OrfA downstream
                        genomic DNA fragment)
source                 1..1204
                       mol_type = other DNA
                       organism = synthetic construct
SEQUENCE: 108
cagggcgagc gagtgtggtt ctgaacaagg ctctttcgtt ttgatggctc tcgaccaaag  60
ccgagtagag tactctactc agtactcttt tcacataccg gcaggcagtg ttgctgtggg  120
attggtccgg gggctcttct gcacgcggcc tccgtcgcgc gcagaaatgc cccgtcactg  180
gctgcccagg aggcagccga atccctctag ctagctagct aggctagagc gtcttttccg  240
tagtttttca caaagccagt atcacatgga taacgaacga aggtttcggg ctcgcgctcg  300
caggcgttag gacgaagttg atcgccccac gtcacttcaa acgagtgaac caagatcacg  360
ttgcatctgc tcgcaagatc ttcttcttcc acgccgcatc gatgcgatgg atttcaaact  420
cttttcaggg cttttaggtg agtatggcag cgctgtttgc gtggcagcgc tgtttgcgtg  480
gttgtactct ctaaaggtgc ttccacgcat gcgcgcacaa aggggcatgg catggttggc  540
ggcgcactct ggccctcatt tgaagcagac tatcgaaggg tccagttggt actgcggcag  600
gtccggcgag agcaagcgcg gcggtcgctc ccactcgtcc ctgcacagtt gctggactgg  660
cgacggctgg cgcacctgac tacgagaaga ctcgagacgc acagaggtag tcagggacga  720
ccgaccgcaa agcacaaacc gctccaaaac ggccgcacca ggcagggcag taaactaaaa  780
acgaatgtac ctccatcgcg cgtatctgcc gagcctcctc ccacgcttcg gctgggcttg  840
attcaccagt gtccgcaagc tgaaccgacc gtcttcgatg tcatgaagct tggcgcggca  900
ttagtcagac gacgcggcac gccaggattc tgtcggtttc tgggaaatgg gcatctatat  960
agctgattcc ctctgtcatg aggcggcctt gttctggccc tgggccgccg ttcggatgat  1020
ctatgatgtc gttgtacgca taaagcttgt cgaaaacgtc ggccatgtct tcctcagaga  1080
tgtaaccgag cggcgcgtcg tggcgattga tgccgatgct acaaaagccg ccgagttagc  1140
tcgaatgtca gatgcattgc gggctggccc gcatggcgcg ggcgcagcag cgagaggttc  1200
taga                                                            1204

SEQ ID NO: 109         moltype = DNA  length = 20
FEATURE                Location/Qualifiers
misc_feature           1..20
                       note = primer
source                 1..20
                       mol_type = other DNA
                       organism = synthetic construct
```

```
SEQUENCE: 109
tgatgccgat gctacaaaag                                              20

SEQ ID NO: 110          moltype = DNA  length = 1488
FEATURE                 Location/Qualifiers
misc_feature            1..1488
                        note = genomic DNA (T. aureum ATCC 34304 OrfA downstream
                         genomic DNA fragment)
source                  1..1488
                        mol_type = other DNA
                        organism = synthetic construct
SEQUENCE: 110
aagcttgtac ggtgaaaagc cctttggcgc agcccgaaac aagtcttgct tctcctgccc  60
cgtcaaactc gcaaactctg gcagcaactc ccgcacgctc tgtaccacgg cgaacccaag  120
ggcaggcacg cggtgaaacg acttgcatgc ttgcacaaca accccttgc cgacgtcgac  180
gcggtcgcct tcggagagcc caaacacagc gaacgccgga tccgcctgcg cctctgcatg  240
cgcctctgca tgcgcctcga catgcgcctc ggcctccgtg cctgcttgcc gggccggcgg  300
ggcagcagga agtgcgtggc cgaggtccat cgcatcaaag gctcgcttcg cggcgtgaaa  360
ggcctcgagc gcctccgccg gcaagtacac cttggtcttg cacttgagca tgctcctgat  420
ccgcgcgtag aggaagacgg ccgcgcagtg gtccaggtgc ccgtgcgaca agaacacgtg  480
ctccgccctc gccgcggcct tgtccggctc gtccccgagc gacccgcagt cgaactgcaa  540
gcagacccgc gagcccaggt ccacttgcag cgccgtgccg cagccggccc tcgactgccc  600
cgtcacgcgg acgtgcgagg ccatctcccg ccgcgagcct ggagcgccag agcctcctgc  660
tgctgccgtg ccgcctcggg gggcgcgagg agggtctcgc ctgatgcagc gcgcggggcc  720
gacgcagcag cgcgggtgga ggaagactgc gctgtgggcg gcggccctcg ggctgctgct  780
cttgtggctc ctgtccgtgc gctcgttcgt gcacggcgtg gcggacaggg aggcggacgc  840
cgtcgccccg cgcgagggcc ccagggcgcc ggcgccaaag aggactggcg ggaggaatga  900
tatgcccgct gagcctgccg ctggtaggcc cgcgcacagc tcgcctcgag ggacgcccga  960
cggcaacgcg gtcgagtgct ccacgaccaa gggcccgttc cgcgtggtcc tcacgcctag  1020
cctagcgccg aacgggacca agtttttcat cgggctggtg gaagcaggct atttcgacca  1080
aggcatcgcc ttctttcgcg tcaacaaggc catcacgcag ttcgggatca ccaagcgaag  1140
gccacgcgat gaggatccgt tcgtgcagtt cagaggcggg gcccagcgcg acgagaaccc  1200
tttcggtggc gtggaggatg acgaggagag tgtccatcgc aggcacatgc acccgtggcg  1260
gcgcggcacg attgcctcga taggcggctt ccactttgtt gtcacgatcc gcggggacaa  1320
aaagtaagtt cttgaatgtt gtgaagtgcg ccaactcgcg ttcggagcgg acctggaccg  1380
atattcagca atctagaacc tctcgctgct gcgcccgcgc catgcgggcc agcccgcaat  1440
gcatctgaca ttcgagctaa ctcggcggct tttgtagcat cggcatca               1488

SEQ ID NO: 111          moltype = DNA  length = 2551
FEATURE                 Location/Qualifiers
misc_feature            1..2551
                        note = genomic DNA (T. aureum ATCC 34304 OrfA downstream
                         genomic DNA fragment)
source                  1..2551
                        mol_type = other DNA
                        organism = synthetic construct
SEQUENCE: 111
tggctctcga ccaaagccga gtagagtact ctactcagta ctcttttcac ataccggcag  60
gcagtgttgc tgtgggattg gtccgggggc tcttctgcac gcggcctccg tcgcgcgcag  120
aaatgccccg tcactggctg cccaggaggc agccgaatcc ctctagctag ctagctaggc  180
tagagcgtct tttccgtagt ttttcacaaa gccagtatca catggataac gaacgaaggt  240
ttcgggctcg cgctcgcagg cgttaggacg aagttgatcg ccccacgtca cttcaaacga  300
gtgaaccaag atcacgttgc atctgctcgc aagatcttct tcttccacgc cgcatcgatg  360
cgatggattt caaactcttt tcagggcttt taggtgagta tggcagcgct gtttgcgtgg  420
cagcgctgtt tgcgtggttg tactctctaa aggtgcttcc acgcatgcgc gcacaaaggg  480
gcatggcatg gttggcggcg cactctggcc ctcatttgaa gcagactatc gaagggtcca  540
gttggtactg cggcaggtcc ggcgagagca agcgcggcgg tcgctcccac tcgtccctgc  600
acagttgctg gactggcgac ggctggcgca cctgactacg agaagactcg agacgcacag  660
aggtagtcag ggacgaccga ccgcaaagca caaaccgctc caaaacggcc gcaccaggca  720
gggcagtaaa ctaaaaacga atgtacctcc atcgcgcgta tctgccgagc ctcctcccac  780
gcttcggctg ggcttgattc accagtgtcc gcaagctgaa ccgaccgtct tcgatgtcat  840
gaagcttggc gcggcattag tcagacgacg cggcacgcca ggattctgtc ggtttctggg  900
aaatgggcat ctatatagct gattccctct gtcatgaggc ggccttgttc tggccctggg  960
ccgccgttcg gatgatctat gatgtcgttg tacgcataaa gcttgtcgaa aacgtcggcc  1020
atgtcttcct cagagatgta accgagcggc gcgtcgtggc gattgatgcc gatgctacaa  1080
aagccgccga gttagctcga atgtcagatg cattgcgggc tggcccgcat ggcgcgggcg  1140
cagcagcgag aggttctaga ttgctgaata tcggtccagg tccgctccga acgcgagttg  1200
gcgcacttca caacattcaa gaacttactt tttgtccccg cggatcgtga caacaaagtg  1260
gaagccgcct atcgaggcaa tcgtgccgcg ccgccacggg tgcatgtgcc tgcgatggac  1320
actctcctcg tcatcctcca cgccaccgaa agggttctcg tcgcgctggg ccccgcctct  1380
gaactgcacg aacggatcct catcgcgtgg ccttcgcttg gtgatcccga actgcgtgat  1440
ggccttgttg acgcgaaaga aggcgatgcc ttggtcgaaa tagcctgctt ccaccagccc  1500
gatgaaaaac ttggtcccgt tcggcgctag gctaggcgtg aggaccacgc ggaacgggcc  1560
cttggtcgtg gagcactcga ccgcgttgcc gtcgggcgtc cctcgaggcg agctgtgcgc  1620
gggcctacca gcggcaggct cagcgggcat atcattcctc ccgccagtcc tctttggcgc  1680
cggcgccctg gggccctcgc gcggggcgac ggcgtccgcc tccctgtccg ccacgccgtg  1740
cacgaacgag cgcacggaca ggagccacaa gagcagcagc ccgagggccg ccgcccacag  1800
cgcagtcttc ctccacccgc gctgctgcgt cggccccgcg cgctgcatca ggcgagaccc  1860
tcctcgcgcc ccccgaggcg gcacggcagc agcaggaggc tctggcgctc caggctcgcg  1920
```

-continued

```
gcgggagatg gcctcgcacg tccgcgtgac ggggcagtcg agggccggct gcggcacggc  1980
gctgcaagtg gacctgggct cgcgggtctg cttgcagttc gactgcgggt cgctcgggga  2040
cgagccggac aaggccgcgg cgagggcgga gcacgtgttc ttgtcgcacg ggcacctgga  2100
ccactgcgcg gccgtcttcc tctacgcgcg gatcaggagc atgctcaagt gcaagaccaa  2160
ggtgtacttg ccggcggagg cgctcgaggc ctttcacgcc gcgaagcgag cctttgatgc  2220
gatggacctc ggccacgcac ttcctgctgc cccgccggcc cggcaagcag gcacggaggc  2280
cgaggcgcat gtcgaggcgc atgcagaggc gcatgcagag gcgcaggcgg atccggcgtt  2340
cgctgtgttt gggctctccg aaggcgaccg cgtcgacgtc ggcaaggggg ttgttgtgca  2400
agcatgcaag tcgtttcacc gcgtgcctgc ccttgggttc gccgtggtac agagcgtgcg  2460
ggagttgctg ccagagtttg cgagtttgac ggggcaggag aagcaagact tgtttcgggc  2520
tgcgccaaag ggcttttcac cgtacaagct t                                  2551

SEQ ID NO: 112         moltype = DNA  length = 1835
FEATURE                Location/Qualifiers
misc_feature           1..1835
                       note = 18S rDNA (T. aureum ATCC 34304)
source                 1..1835
                       mol_type = other DNA
                       organism = synthetic construct
SEQUENCE: 112
cgaatattcc tggttgatcc tgccagtagt catacgctta tctcaaagat taagccatgc  60
atgtctaagt ataaaggctt atactctgaa actgcgaacg gctcattata tcagttatag  120
tttctttgat agtgtttttt ctacatggat acttgtggca aatctagaaa caatacatgc  180
gtacaggcct gactttgggg gagggctgca tttatttgac ttaagccaat acccctcggg  240
gttgttttgg tgattcagaa taactgagcg aatcgcatag ctttcgggcg gcgatgaatc  300
atttcaagtt tctgccccat cagctgtcga tggtagggta taggcctacc atggctgtca  360
cgggtgacgg agaattaggg ttcgattccg gagagggagc ctgagagacg gctaccacat  420
ccaaggaagg cagcaggcgc gtaaattact caatgttgac tcgacgaagt agtgacgaga  480
attaacaatg cggagcgctc agcgttttgc aattggaatg agagcaatgt aaaagcctca  540
tcgaggatcc attggagggc aagtctggtg ccagcagccg cggtaattcc agctccaata  600
gcgtatacta aagttgttgc agttaaaaag ctcgtagttg aacctctggt agggccgacc  660
ttggcgcgcg gtgaatgccg cgtcgtttag aagcgtcgtg cccggccatc ctcccccggt  720
cttttgggct gggggtcgtt tactgtaaaa aaaatagagt gttccaagca gggggtaata  780
tcccggtata tagtagtatg gaataatgag ataggacttt ggtactattt tgttggtttg  840
catgccaagg taatgattaa gagggacagt tgggggtatt cgtatttaga tgtcagaggt  900
gaaattcttg gatttcgaa agacgaacta ctgcgaaagc atttaccaag gatgttttca  960
ttaatcaaga acgaaagtta ggggatcgaa gatgattaga taccatcgta gtcttaaccg  1020
taaactatgc cgacttgcga ttgtccggcg tcgcttttag atgacctggg cagcagcaca  1080
tgagaaatca aagtctttgg gttccggggg gagtatggtc gcaaggctga aacttaaagg  1140
aattgacgga agggcaccac caggagtgga gcctgcggct taatttgact caacacggga  1200
aaacttacca ggtccggaca taggaaggat tgacagattg agagctcttt cttgattcta  1260
tgggtggtgg tgcatggccg ttcttagttg gtggagtgat ttgtctggtt aattccgtta  1320
acgaacgaga ccacagccta ctaaatagtg gccgttatgg cgacatagcg gtgaacttct  1380
tagagggaca tttcgggtat accggaagga agtttgtggc aataacaggt ctgtgatgcc  1440
cttagatgtt ctgggccgca cgcgcgctac actgatcggt tcaacgagta tttgtttttt  1500
tctcattttg ggagggggca gagtccttgg ccggaaggtc tgggtaatct tttgaatgcc  1560
gatcgtgatg gggctagatt tttgcaatta ttaatctcca acgaggaatt cctagtagac  1620
gcaagtcatc agcttgcatc gattacgtcc ctgccctttg tacacaccgc ccgtcgcacc  1680
taccgattga acgatccggt gagaccttgg gattctgttg tggctgattc attttggctg  1740
cgatgggaga acttgagcaa accttatcgt ttagaggaag gtgaagtcgt aacaaggttt  1800
ccgtagtgaa cctgcaattc aaaaaaagcc gttac                              1835

SEQ ID NO: 113         moltype = DNA  length = 30
FEATURE                Location/Qualifiers
misc_feature           1..30
                       note = primer
source                 1..30
                       mol_type = other DNA
                       organism = synthetic construct
SEQUENCE: 113
cgaatattcc tggttgatcc tgccagtagt                                    30

SEQ ID NO: 114         moltype = DNA  length = 46
FEATURE                Location/Qualifiers
misc_feature           1..46
                       note = primer
source                 1..46
                       mol_type = other DNA
                       organism = synthetic construct
SEQUENCE: 114
gtaacggctt tttttgaatt gcaggttcac tacgcttgtt agaaac                  46

SEQ ID NO: 115         moltype = DNA  length = 661
FEATURE                Location/Qualifiers
misc_feature           1..661
                       note = EF1 alpha promoter (T. aureum ATCC 34304)
source                 1..661
                       mol_type = other DNA
                       organism = synthetic construct
```

```
SEQUENCE: 115
ggtttccgta gtgaacctgc aattcaaaaa aagccgttac tcacatcagg ccgccactca  60
tccgggcgaa agcttcgcgc attcgtcctc gtcacctcgg gtcccctgtg tcgtgacgga  120
aagcgcgacg agacgcggcc gcagcagaga gccccggggg cccgcgtcac ggggggcctg  180
gcggcggtcc tccttaagcc aaaccgaggg ttagggctcc aggctgttcg gcggggtcgc  240
gggcgcggtg gacgcgcggg gccgcctagc acctcctagc gcgcgactac caggatagcc  300
cccgcgagtg cgcagggcgg tccgcggggc ggagggcggc ccagcagcgc ggcgcggcgg  360
gcgggtgcgg ctgcgtaagg tggcggcggg cgcgggcggt tagtgttggt gttaggtcgc  420
ggcggggctg tgttccgggc atccgcctta cggcggtgca tactggttgg ctgggaggcg  480
gtttgcgggg ttagataggc ggccaaggtg agctgcgttg ggcggataaa tccgtggagg  540
cgctcgttga cggcgcggca gagacggaac gcggagcagc acggagtagc aagcaggagt  600
agcaggagta gcaagcagcg gcaaaggaag gctagatgat tgaacaggac ggccttcacg  660
c                                                                  661

SEQ ID NO: 116         moltype = DNA  length = 46
FEATURE                Location/Qualifiers
misc_feature           1..46
                       note = primer
source                 1..46
                       mol_type = other DNA
                       organism = synthetic construct
SEQUENCE: 116
ggtttccgta gtgaacctgc aattcaaaaa aagccgttac tcacat                 46

SEQ ID NO: 117         moltype = DNA  length = 46
FEATURE                Location/Qualifiers
misc_feature           1..46
                       note = primer
source                 1..46
                       mol_type = other DNA
                       organism = synthetic construct
SEQUENCE: 117
gcgtgaaggc cgtcctgttc aatcatctag ccttcctttg ccgctg                 46

SEQ ID NO: 118         moltype = DNA  length = 835
FEATURE                Location/Qualifiers
misc_feature           1..835
                       note = Neomycin resistance gene (Neor)
source                 1..835
                       mol_type = other DNA
                       organism = synthetic construct
SEQUENCE: 118
catcggcaaa ggaaggctag atgattgaac aggacggcct tcacgctggc tcgcccgctg  60
cttgggtgga acggctgttc ggctacgact gggctcagca gacgatcggc tgctcggacg  120
cggccgtgtt ccgccttagc gcgcagggcc ggccggtcct gtttgtcaag accgacctta  180
gcggcgccct caacgagctc caggacgaag ctgcccgcct cagctggctt gccacgacgg  240
gggttccgtg cgccgctgtg ctcgacgtcg tcaccgaagc cggccgcgac tggctgctcc  300
tcggggaagt gcccggccag gacctcctca gcagccacct cgcgcccgct gagaaggtgt  360
ccatcatggc cgacgccatg cgccgcctgc acaccctcga ccccgccacc tgcccttcg  420
accaccaggc gaagcacagg atcgaacgcg cccgcacgcg gatggaggct ggcctcgtcg  480
accaagacga cctcgacgag gagcaccagg gcctcgcgcc ggcggaactg ttcgccaggc  540
ttaaggctag gatgccggac ggcgaggacc tcgtggtcac gcacggcgac gcctgcctcc  600
ccaacatcat ggtcgagaac ggccgcttct cgggctttat cgactgcggg cgcctgggcg  660
tggcggaccg ctaccaagac atcgcgctcg ccacgcggga catcgccgag gagcttggcg  720
gcgagtgggc cgaccgcttt ctcgtgctct acggcatcgc cgccccggac agccagagga  780
ttgcgttcta ccgcctcctg gacgagttct tttgagatcc gcgccggcta tgcgc       835

SEQ ID NO: 119         moltype = DNA  length = 45
FEATURE                Location/Qualifiers
misc_feature           1..45
                       note = primer
source                 1..45
                       mol_type = other DNA
                       organism = synthetic construct
SEQUENCE: 119
catcggcaaa ggaaggctag atgattgaac aggacggcct tcacg                  45

SEQ ID NO: 120         moltype = DNA  length = 46
FEATURE                Location/Qualifiers
misc_feature           1..46
                       note = primer
source                 1..46
                       mol_type = other DNA
                       organism = synthetic construct
SEQUENCE: 120
gcgcatagcc ggcgcggatc tcaaaagaac tcgtccagga ggcggt                 46

SEQ ID NO: 121         moltype = DNA  length = 1249
FEATURE                Location/Qualifiers
```

```
misc_feature           1..1249
                       note = EF1 alpha terminator (T. aureum ATCC 34304)
source                 1..1249
                       mol_type = other DNA
                       organism = synthetic construct
SEQUENCE: 121
tcctggacga gttcttttga gatccgcgcc ggctatgcgc ccgtgctcga ctgccacact  60
gcccacattg cctgcaagtt cgctgagctc cagaacaaga tggaccgccg ctcgggcaag  120
attctcgagg agacccccaa gttcatcaag tcgggtggac tctgccatgg tcaagatgta  180
tcccctccaa gcgcatgtgc gtcgagtcct tcaccgagta cccgccgctc ggccgctttg  240
ccgtgcgcga catgcgcgtc accgtcgctg tcggcgtcat caagtccgtc accaagggcg  300
acaaataaat tctacgaaag attttttttcc tcaagaagcg ccctaaagtt gacccctagc  360
agcgacgact gtgtgtgccg ttgtgagtcg agttgcgatg tcgtgcagcg cccgtcgcgt  420
cccatgctcg cgcgcgactc cgtctctgct tttcatctca agtcaagagt gggaagttcc  480
cttgctttat ctcactattt agaggtcgct cacggctgct ggttcctcgt cgcatgtagc  540
acagcctcgt ccaatcgcag cctgcaccac cccgctcgcc tgggaaaatg cgctcagcgg  600
attcgcactg gcactcctct cctcggacag gtgcgatgtg gaagcggtca catcctcggc  660
gccctcggcc acgccagcat ctgcgcaatc gctctcctcg ttctcagccg caaccgcagg  720
caggccgacg tcgtttacct cggaatccac cgagcatttc gagcccatcg cgctggcgtc  780
cacctcgatc ataccttctc catcgccgtc cgctgcggct tccgattctt ctgctgccgc  840
aaccgcgacg tcggcccccg tctcctccgt tctttccgat gccggcgcag tggccgcgcc  900
ctctgctcga accggctcgt gttcagcgtc agggcctgcg cttgagctcg ggcggctctt  960
ccgagtgatc cggccccgcg aggcaaggaa tcggcggctc tggagtgtcg gggcagccgc  1020
tctcactgcc ggtctttggc tggctgcctg tcctgcctcg cgttggcctt tgcttttgcc  1080
taggctttcg ccttggtgac ggcgtttgcc tgctgcggcg acttggcgcg gccgcggaat  1140
agcgcctcaa agtcctgctc gaggcgcccc agctctgact tgatttgcga ggtcccggtg  1200
gcatgagctc cgctgccctc gtccttacgg cccgtctttc gctgcagtg              1249

SEQ ID NO: 122         moltype = DNA  length = 46
FEATURE                Location/Qualifiers
misc_feature           1..46
                       note = primer
source                 1..46
                       mol_type = other DNA
                       organism = synthetic construct
SEQUENCE: 122
tcctggacga gttcttttga gatccgcgcc ggctatgcgc ccgtgc                 46

SEQ ID NO: 123         moltype = DNA  length = 30
FEATURE                Location/Qualifiers
misc_feature           1..30
                       note = primer
source                 1..30
                       mol_type = other DNA
                       organism = synthetic construct
SEQUENCE: 123
cactgcagcg aaagacgggc cgtaaggacg                                   30

SEQ ID NO: 124         moltype = DNA  length = 4453
FEATURE                Location/Qualifiers
misc_feature           1..4453
                       note = fusion DNA (T. aureum ATCC 34304 18S rDNA/T. aureum
                        ATCC 34304 EF1 alpha promoter/Neor/T. aureum ATCC 34304
                        EF1 alpha terminator)
source                 1..4453
                       mol_type = other DNA
                       organism = synthetic construct
SEQUENCE: 124
cgaatattcc tggttgatcc tgccagtagt catacgctta tctcaaagat taagccatgc  60
atgtctaagt ataaaggctt atactctgaa actgcgaacg gctcattata tcagttatag  120
tttctttgat agtgtttttt ctacatggat acttgtggca aatctagaaa caatacatgc  180
gtacaggcct gactttgggg gagggctgca tttatttgac ttaagccaat acccctcggg  240
gttgttttgg tgattcagaa taactgagcg aatcgcatag ctttcgggcg gcgatgaatc  300
atttcaagtt tctgccccat cagctgtcga tggtagggta taggcctacc atggctgtca  360
cgggtgacgg agaattaggg ttcgattccg gagagggagc ctgagagacg gctaccacat  420
ccaaggaagg cagcaggcgc gtaaattact caatgttgac tcgacgaagt agtgacgaga  480
attaacaatg cggagcgctc agcgttttgc aattggaatg agagcaatgt aaaagcctca  540
tcgaggatcc attggagggc aagtctggtg ccagcagccg cggtaattcc agctccaata  600
gcgtatacta aagttgttgc agttaaaaag ctcgtagttg aacctctggt agggccgacc  660
ttggcgcgcg gtgaatgccg cgtcgtttag aagcgtcgtg cccggccatc ctcccccggt  720
cttttgggct gggggtcgtt tactgtaaaa aaaatagagt gttccaagca gggggtaata  780
tcccggtata tagtagtatg gaataatgag ataggacttt ggtactattt tgttggtttg  840
catgccaagg taatgattaa gagggacagt tgggggtatt cgtatttaga tgtcagaggt  900
gaaattcttg gattttcgaa agacgaacta ctgcgaaagc atttaccaag gatgttttca  960
ttaatcaaga acgaaagtta ggggatcgaa gatgattaga taccatcgta gtcttaaccg  1020
taaactatgc cgacttgcga ttgtccggcg tcgcttttag atgacctggg cagcagcaca  1080
tgagaaatca aagtctttgg gttccggggg gagtatggtc gcaaggctga aacttaaagg  1140
aattgacgga agggcaccac caggagtgga gcctgcggct taatttgact caacacggga  1200
aaacttacca ggtccggaca taggaaggat tgacagattg agagctcttt cttgattcta  1260
```

```
tgggtggtgg tgcatggccg ttcttagttg gtggagtgat ttgtctggtt aattccgtta  1320
acgaacgaga ccacagccta ctaaatagtg gccgttatgg cgacatagcg gtgaacttct  1380
tagagggaca tttcgggtat accggaagga agtttgtggc aataacaggt ctgtgatgcc  1440
cttagatgtt ctgggccgca cgcgcgctac actgatcggt tcaacgagta tttgtttttt  1500
tctcattttg ggagggggca gagtccttgg ccggaaggtc tgggtaatct tttgaatgcc  1560
gatcgtgatg gggctagatt tttgcaatta ttaatctcca acgaggaatt cctagtagac  1620
gcaagtcatc agcttgcatc gattacgtcc ctgccctttg tacacaccgc ccgtcgcacc  1680
taccgattga acgatccggt gagaccttgg gattctgttg tggctgattc attttggctg  1740
cgatgggaga acttgagcaa accttatcgt ttagaggaag gtgaagtcgt aacaaggttt  1800
ccgtagtgaa cctgcaattc aaaaaaagcc gttactcaca tcaggccgcc actcatccgg  1860
gcgaaagctt cgcgcattcg tcctcgtcac ctcgggtccc ctgtgtcgtg acggaaagcg  1920
cgacgagacg cggccgcagc agagagcccc gggggcccgc gtcacggggg gcctggcggc  1980
ggtcctcctt aagccaaacc gagggttagg gctccaggct gttcggcggg gtcgcgggcg  2040
cggtggacgc gcggggccgc ctagcacctc ctagcgcgcg actaccagga tagcccccgc  2100
gagtgcgcag ggcggtccgc ggggcggagg gcggcccagc agcgcggcgc ggcgggcggg  2160
tgcggctgcg taaggtggcg gcgggcgcgg gcggttagtg ttggtgttag gtcgcggcgg  2220
ggctgtgttc cgggcatccg ccttacggcg gtgcatactg gttggctggg aggcggtttg  2280
cggggttaga taggcggcca aggtgagctg cgttgggcgg ataaatccgt ggaggcgctc  2340
gttgacggcg cggcagagac ggaacgcgga gcagcacgga gtagcaagca ggagtagcag  2400
gagtagcaag catggcaaag gaaggctaga tgattgaaca ggacggcctt cacgctggct  2460
cgcccgctgc ttgggtggaa cggctgttcg gctacgactg ggctcagcag acgatcggct  2520
gctcggacgc ggccgtgttc cgccttagcg cgcagggccg gccggtcctg tttgtcaaga  2580
ccgaccttag cggcgccctc aacgagctcc aggacgaagc tgcccgcctc agctggcttg  2640
ccacgacggg ggttccgtgc gccgctgtgc tcgacgtcgt caccgaagcc ggccgcgact  2700
ggctgctcct cggggaagtg cccggccagg acctcctcag cagccacctc gcgcccgctg  2760
agaaggtgtc catcatggcc gacgccatgc gccgcctgca caccctcgac cccgccacct  2820
gccccttcga ccaccaggcg aagcacagga tcgaacgcgc ccgcacgcgg atggaggctg  2880
gcctcgtcga ccaagacgac ctcgacgagg agcaccaggg cctcgcgccg gcggaactgt  2940
tcgccaggct taaggctagg atgccggacg gcgaggacct cgtggtcacg cacggcgacg  3000
cctgcctccc caacatcatg gtcgagaacg gccgcttctc gggctttatc gactgcgggc  3060
gcctgggcgt ggcggaccgc taccaagaca tcgcgctcgc cacgcgggac atcgccgagg  3120
agcttggcgg cgagtgggcc gaccgctttc tcgtgctcta cggcatcgcc gccccggaca  3180
gccagaggat tgcgttctac cgcctcctgg acgagttctt ttgagatccg cgccggctat  3240
gcgcccgtgc tcgactgcca cactgcccac attgcctgca agttcgctga gctccagaac  3300
aagatggacc gccgctcggg caagattctc gaggagaccc ccaagttcat caagtcgggt  3360
ggactctgcc atggtcaaga tgtatcccct ccaagcgcat gtgcgtcgag tccttcaccg  3420
agtacccgcc gctcggccgc tttgccgtgc gcgacatgcg cgtcaccgtc gctgtcggcg  3480
tcatcaagtc cgtcaccaag ggcgacaaat aaattctacg aaagattttt ttcctcaaga  3540
agcgccctaa agttgacccc tagcagcgac gactgtgtgt gccgttgtga gtcgagttgc  3600
gatgtcgtgc agcgcccgtc gcgtcccatg ctcgcgcgcg actccgtctc tgcttttcat  3660
ctcaagtcaa gagtgggaag ttcccttgct ttatctcact atttagaggt cgctcacggc  3720
tgctggttcc tcgtcgcatg tagcacagcc tcgtccaatc gcagcctgca ccaccccgct  3780
cgcctgggaa aatgcgctca gcggattcgc actggcactc ctctcctcgg acaggtgcga  3840
tgtggaagcg gtcacatcct cggcgccctc ggccacgcca gcatctgcgc aatcgctctc  3900
ctcgttctca gccgcaaccg caggcaggcc gacgtcgttt acctcggaat ccaccgagca  3960
tttcgagccc atcgcgctgg cgtccacctc gatcatacct tctccatcgc cgtccgctgc  4020
ggcttccgat tcttctgctg ccgcaaccgc gacgtcggcc cccgtctcct ccgttctttc  4080
cgatgccggc gcagtggccg cgccctctgc tcgaaccggc tcgtgttcag cgtcagggcc  4140
tgcgcttgag ctcgggcggc tcttccgagt gatccggccc cgcgaggcaa ggaatcggcg  4200
gctctggagt gtcggggcag ccgctctcac tgccggtctt tggctggctg cctgtcctgc  4260
ctcgcgttgg cctttgcttt tgcctaggct ttcgccttgg tgacggcgtt tgcctgctgc  4320
ggcgacttgg cgcggccgcg gaatagcgcc tcaaagtcct gctcgaggcg ccccagctct  4380
gacttgattt gcgaggtccc ggtggcatga gctccgctgc cctcgtcctt acggcccgtc  4440
tttcgctgca gtg                                                     4453
```

```
SEQ ID NO: 125          moltype = DNA  length = 1218
FEATURE                 Location/Qualifiers
misc_feature            1..1218
                        note = genomic DNA (T. aureum ATCC 34304 OrfA upstream
                         genomic DNA fragment)
source                  1..1218
                        mol_type = other DNA
                        organism = synthetic construct
SEQUENCE: 125
cccgaattcg gacgatgact gactgactga ttggctgacg acggccgccc tcgtgcgcgg  60
cgtcgggcgt cgtcgcaaac caggcaggca ggcaggaagg aaggaaggaa gggccaggcc  120
ctggtgcgaa acgctggcct gctccgctgc aagccaagcc gcgctcgcag gtgtacttcc  180
gagtcctcgc gatgattagg caagcctgag cgagcacgta agctgcactg cggctgttca  240
accagagaga gagttggctc tcttgcgtca aggcggcgcg cagcccactt gcgtcgcggc  300
tgagggcccc tggaggggag gaaggaggcc ggcgagcggc gagtggcggc cctcactggc  360
accaggtcgc aggaggccag gcagcccgcc acggacagga atcctcaggg cgcagcagcg  420
cactacgtag tgcagagacg cagagcgggc cggatccgca gtgcggtcgc gccaccccgc  480
cgcgcagctc gctcgcggac ggggtccgtg gccgcgcgaa aacggacacg gtgtgggagc  540
ggacatggga tcgagaacgc cgttcgccct gctcgcgctg ccagcagcag gagccgtccg  600
aaggacgagc ggccggccgc ctgtcccccc tccgcgcact cgaagcgcgc ccggcagcgc  660
cccattgcgt gcgcggatgg cgtcttggct ggtccctctc gaggcgcttg ctcgtgctcg  720
ccacgccttg tccgcctcct cgctgagcaa gcgatgagct gagcacggac cgcctgcaag  780
tgcaagtgtt cttgtgctgc agggcgccga agaattggat tctggcccat gatcagtttg  840
attgggccga gggagggagg gaggctgggc gagtgggcga caccagcaag ccggactgcg  900
```

```
agaggggcgg ggcaggatgt gagcgcagga aagtgacgca agtgcatccg gccatcattg  960
ggccatcatt gggccatcat tggtgttttg ggccgcgctt tgcggatcgt ccggccgatc  1020
aggtacgagg ccacgaacct acgtcgtttg ccgcgctcag gctggttggt tgcacttgga  1080
ctcttctgtg acctttcatc gtgtgcaggc aaactcgatt tgcagacccg agacacggcg  1140
aaggatccgt gctgcaaacg caagtggagt gcgtcgagag caccgccgag accaagagcc  1200
gaggcagaca agcttggg                                                1218

SEQ ID NO: 126         moltype = DNA  length = 32
FEATURE                Location/Qualifiers
misc_feature           1..32
                       note = primer
source                 1..32
                       mol_type = other DNA
                       organism = synthetic construct
SEQUENCE: 126
cccgaattcg gacgatgact gactgactga tt                                32

SEQ ID NO: 127         moltype = DNA  length = 28
FEATURE                Location/Qualifiers
misc_feature           1..28
                       note = primer
source                 1..28
                       mol_type = other DNA
                       organism = synthetic construct
SEQUENCE: 127
cccaagcttg tctgcctcgg ctcttggt                                     28

SEQ ID NO: 128         moltype = DNA  length = 1000
FEATURE                Location/Qualifiers
misc_feature           1..1000
                       note = genomic DNA (T. aureum ATCC 34304 OrfA downstream
                        genomic DNA fragment)
source                 1..1000
                       mol_type = other DNA
                       organism = synthetic construct
SEQUENCE: 128
cccccatggt gttgctgtgg gattggtccg ggggctcttc tgcacgcggc ctccgtcgcg  60
cgcagaaatg ccccgtcact ggctgcccag gaggcagccg aatccctcta gctagctagc  120
taggctagag cgtcttttcc gtagtttttc acaaagccag tatcacatgg ataacgaacg  180
aaggtttcgg gctcgcgctc gcaggcgtta ggacgaagtt gatcgcccca cgtcacttca  240
aacgagtgaa ccaagatcac gttgcatctg ctcgcaagat cttcttcttc cacgccgcat  300
cgatgcgatg gatttcaaac tcttttcagg gcttttaggt gagtatggca gcgctgtttg  360
cgtggcagcg ctgtttgcgt ggttgtactc tctaaaggtg cttccacgca tgcgcgcaca  420
aaggggcatg gcatggttgg cggcgcactc tggccctcat ttgaagcaga ctatcgaagg  480
gtccagttgg tactgcggca ggtccggcga gagcaagcgc ggcggtcgct cccactcgtc  540
cctgcacagt tgctggactg gcgacggctg gcgcacctga ctacgagaag actcgagacg  600
cacagaggta gtcagggacg accgaccgca aagcacaaac cgctccaaaa cggccgcacc  660
aggcagggca gtaaactaaa aacgaatgta cctccatcgc gcgtatctgc cgagcctcct  720
cccacgcttc ggctgggctt gattcaccag tgtccgcaag ctgaaccgac cgtcttcgat  780
gtcatgaagc ttggcgcggc attagtcaga cgacgcggca cgccaggatt ctgtcggttt  840
ctgggaaatg ggcatctata tagctgattc cctctgtcat gaggcggcct tgttctggcc  900
ctgggccgcc gttcggatga tctatgatgt cgttgtacgc ataaagcttg tcgaaaacgt  960
cggccatgtc ttcctcagag atgtaaccga gccatggggg                        1000

SEQ ID NO: 129         moltype = DNA  length = 28
FEATURE                Location/Qualifiers
misc_feature           1..28
                       note = primer
source                 1..28
                       mol_type = other DNA
                       organism = synthetic construct
SEQUENCE: 129
cccccatggt gttgctgtgg gattggtc                                     28

SEQ ID NO: 130         moltype = DNA  length = 30
FEATURE                Location/Qualifiers
misc_feature           1..30
                       note = primer
source                 1..30
                       mol_type = other DNA
                       organism = synthetic construct
SEQUENCE: 130
cccccatggc tcggttacat ctctgaggaa                                   30

SEQ ID NO: 131         moltype = DNA  length = 1632
FEATURE                Location/Qualifiers
misc_feature           1..1632
                       note = fusion DNA (T. aureum ATCC 34304 ubiqitin
                        promoter/Hygr)
```

```
source                  1..1632
                        mol_type = other DNA
                        organism = synthetic construct
SEQUENCE: 131
cccaagcttg ccgcagcgcc tggtgcaccc gccgggcgtt gttgtgtgct cttcttgcct  60
ccgagagaga gagcggagcg gatgcatagg aaatcgggcc acgcgggagg gccatgcgtt  120
cgccccacac gccactttcc acgcccgctc tctctccggc cggcaggcag cgcataactc  180
tccgacgctg gcaggctggt agcaactggc agggacaact cgcgcgcggg tcccggtcgt  240
tcgatgtgcc aacccgagag aatccagcca gcagggcggt tggcctcatc gcccacctgc  300
tatggtgcag cgaaccaact cccgaagcgg ccggttctgc gattccctct tctgaattct  360
gaattctgaa ctgattccgg aggagaaccc tctggaagcg cgggttgcct ctccagttct  420
gccgaactag acaggggagt gagcagagag tgaccctgac gcggagcgag ctggttgctg  480
gaaaagtcgc gaacgctggg ctgtgtcacg cgtccacttc gggcagaccc caaacgacaa  540
gcagaacaag caacaccagc agcagcaagc gacctaagca acactagcca acatgaaaaa  600
gcctgaactc accgcgacgt ctgtcgagaa gtttctgatc gaaaagttcg acagcgtctc  660
cgacctgatg cagctctcgg agggcgaaga atctcgtgct ttcagcttcg atgtaggagg  720
gcgtggatat gtcctgcggg taaatagctg cgccgatggt ttctacaaag atcgttatgt  780
ttatcggcac tttgcatcgg ccgcgctccc gattccggaa gtgcttgaca ttggggaatt  840
cagcgagagc ctgacctatt gcatctcccg ccgtgcacag ggtgtcacgt tgcaagacct  900
gcctgaaacc gaactgcccg ctgttctgca gccggtcgcg gaggccatgg atgcgatcgc  960
tgcggccgat cttagccaga cgagcgggtt cggcccattc ggaccgcaag gaatcggtca  1020
atacactaca tggcgtgatt tcatatgcgc gattgctgat ccccatgtgt atcactggca  1080
aactgtgatg gacgacaccg tcagtgcgtc cgtcgcgcag gctctcgatg agctgatgct  1140
ttgggccgag gactgccccg aagtccggca cctcgtgcac gcggatttcg gctccaacaa  1200
tgtcctgacg gacaatggcc gcataacagc ggtcattgac tggagcgagg cgatgttcgg  1260
ggattcccaa tacgaggtcg ccaacatctt cttctggagg ccgtggttgg cttgtatgga  1320
gcagcagacg cgctacttcg agcggaggca tccggagctt gcaggatcgc cgcggctccg  1380
ggcgtatatg ctccgcattg gtcttgacca actctatcag agcttggttg acggcaattt  1440
cgatgatgca gcttgggcgc agggtcgatg cgacgcaatc gtccgatccg gagccgggac  1500
tgtcgggcgt acacaaatcg cccgcagaag cgcggccgtc tggaccgatg gctgtgtaga  1560
agtactcgcc gatagtggaa accgacgccc cagcactcgt ccgagggcaa aggaatagtc  1620
gacgcatgcg gg                                                       1632

SEQ ID NO: 132          moltype = DNA  length = 36
FEATURE                 Location/Qualifiers
misc_feature            1..36
                        note = primer
source                  1..36
                        mol_type = other DNA
                        organism = synthetic construct
SEQUENCE: 132
cccaagcttg ccgcagcgcc tggtgcaccc gccggg                             36

SEQ ID NO: 133          moltype = DNA  length = 43
FEATURE                 Location/Qualifiers
misc_feature            1..43
                        note = primer
source                  1..43
                        mol_type = other DNA
                        organism = synthetic construct
SEQUENCE: 133
cccgcatgcg tcgactattc ctttgccctc ggacgagtgc tgg                     43

SEQ ID NO: 134          moltype = DNA  length = 1000
FEATURE                 Location/Qualifiers
misc_feature            1..1000
                        note = genomic DNA (T. aureum ATCC 34304 OrfA downstream
                         genomic DNA fragment)
source                  1..1000
                        mol_type = other DNA
                        organism = synthetic construct
SEQUENCE: 134
cccgtcgacg tgttgctgtg ggattggtcc gggggctctt ctgcacgcgg cctccgtcgc  60
gcgcagaaat gccccgtcac tggctgccca ggaggcagcc gaatccctct agctagctag  120
ctaggctaga gcgtcttttc cgtagttttt cacaaagcca gtatcacatg gataacgaac  180
gaaggtttcg ggctcgcgct cgcaggcgtt aggacgaagt tgatcgcccc acgtcacttc  240
aaacgagtga accaagatca cgttgcatct gctcgcaaga tcttcttctt ccacgccgca  300
tcgatgcgat ggatttcaaa ctcttttcag ggcttttagg tgagtatggc agcgctgttt  360
gcgtggcagc gctgtttgcg tggttgtact ctctaaaggt gcttccacgc atgcgcgcac  420
aaaggggcat ggcatggttg gcggcgcact ctggccctca tttgaagcag actatcgaag  480
ggtccagttg gtactgcggc aggtccggcg agagcaagcg cggcggtcgc tcccactcgt  540
ccctgcacag ttgctggact ggcgacggct ggcgcacctg actacgagaa gactcgagac  600
gcacagaggt agtcagggac gaccgaccgc aaagcacaaa ccgctccaaa acggccgcac  660
caggcagggc agtaaactaa aaacgaatgt acctccatcg cgcgtatctg ccgagcctcc  720
tcccacgctt cggctgggct tgattcacca gtgtccgcaa gctgaaccga ccgtcttcga  780
tgtcatgaag cttggcgcgg cattagtcag acgacgcggc acgccaggat tctgtcggtt  840
tctgggaaat gggcatctat atagctgatt ccctctgtca tgaggcggcc ttgttctggc  900
cctgggccgc cgttcggatg atctatgatg tcgttgtacg cataaagctt gtcgaaaacg  960
tcggccatgt cttcctcaga gatgtaaccg agtcgacggg                         1000
```

```
SEQ ID NO: 135          moltype = DNA  length = 29
FEATURE                 Location/Qualifiers
misc_feature            1..29
                        note = primer
source                  1..29
                        mol_type = other DNA
                        organism = synthetic construct
SEQUENCE: 135
cccgtcgacg tgttgctgtg ggattggtc                                    29

SEQ ID NO: 136          moltype = DNA  length = 29
FEATURE                 Location/Qualifiers
misc_feature            1..29
                        note = primer
source                  1..29
                        mol_type = other DNA
                        organism = synthetic construct
SEQUENCE: 136
cccgtcgact cggttacatc tctgaggaa                                    29

SEQ ID NO: 137          moltype = DNA  length = 3705
FEATURE                 Location/Qualifiers
misc_feature            1..3705
                        note = fusion DNA (T. aureum OrfA upstream/EF1 alpha
                         promoter/Neor/T. aureum OrfA downstream)
source                  1..3705
                        mol_type = other DNA
                        organism = synthetic construct
SEQUENCE: 137
cccccatggc tcggttacat ctctgaggaa gacatggccg acgttttcga caagctttat  60
gcgtacaacg acatcataga tcatccgaac ggcggcccag ggccagaaca aggccgcctc  120
atgacagagg gaatcagcta tatagatgcc catttcccag aaaccgacag aatcctggcg  180
tgccgcgtcg tctgactaat gccgcgccaa gcttcatgac atcgaagacg gtcggttcag  240
cttgcggaca ctggtgaatc aagcccagcc gaagcgtggg aggaggctcg gcagatacgc  300
gcgatggagg tacattcgtt tttagtttac tgccctgcct ggtgcggccg ttttggagcg  360
gtttgtgctt tgcggtcggt cgtccctgac tacctctgtg cgtctcgagt cttctcgtag  420
tcaggtgcgc cagccgtcgc cagtccagca actgtgcagg gacgagtggg agcgaccgcc  480
gcgcttgctc tcgccggacc tgccgcagta ccaactggac ccttcgatag tctgcttcaa  540
atgagggcca gagtgcgccg ccaaccatgc catgcccctt tgtgcgcgca tgcgtggaag  600
cacctttaga gagtacaacc acgcaaacag cgctgccacg caaacagcgc tgccatactc  660
acctaaaagc cctgaaaaga gtttgaaatc catcgcatcg atgcggcgtg gaagaagaag  720
atcttgcgag cagatgcaac gtgatcttgg ttcactcgtt tgaagtgacg tggggcgatc  780
aacttcgtcc taacgcctgc gagcgcgagc ccgaaacctt cgttcgttat ccatgtgata  840
ctggctttgt gaaaaactac ggaaaagacg ctctagccta gctagctagc tagagggatt  900
cggctgcctc ctgggcagcc agtgacgggg catttctgcg cgcgacggag gccgcgtgca  960
gaagagcccc cggaccaatc ccacagcaac accatggcag agtcgcccga cttgatgaac  1020
ttgggggtct cctcgagaat cttgcccgag cggcggtcca tcttgttctg gagctcagcg  1080
aacttgcagg caatgtgggc agtgtggcgg tcgagcacgg gcgcatagcc ggcgcggatc  1140
tcaaaagaac tcgtccagga ggcggtagaa cgcaatcctc tggctgtccg gggcggcgat  1200
gccgtagagc acgagaaagc ggtcggccca ctcgccgcca agctcctcgg cgatgtcccg  1260
cgtggcgagc gcgatgtctt ggtagcggtc cgccacgccc aggcgcccgc agtcgataaa  1320
gcccgagaag cggccgttct cgaccatgat gttggggagg caggcgtcgc cgtgcgtgac  1380
cacgaggtcc tcgccgtccg gcatcctagc cttaagcctg gcgaacagtt ccgccggcgc  1440
gaggccctgg tgctcctcgt cgaggtcgtc ttggtcgacg aggccagcct ccatccgcgt  1500
gcgggcgcgt tcgatcctgt gcttcgcctg gtggtcgaag gggcaggtgg cggggtcgag  1560
ggtgtgcagg cggcgcatgg cgtcggccat gatggacacc ttctcagcgg gcgcgaggtg  1620
gctgctgagg aggtcctggc cgggcacttc cccgaggagc agccagtcgc ggccggcttc  1680
ggtgacgacg tcgagcacag cggcgcacgg aacccccgtc gtggcaagcc agctgaggcg  1740
ggcagcttcg tcctggagct cgttgagggc gccgctaagg tcggtcttga caaacaggac  1800
cggccggccc tgcgcgctaa ggcggaacac ggccgcgtcc gagcagccga tcgtctgctg  1860
agcccagtcg tagccgaaca gccgttccac ccaagcagcg ggcgagccag cgtgaaggcc  1920
gtcctgttca atcatctagc cttcctttgc cgctgcttgc tactcctgct actcctgctt  1980
gttacttcgt gttgctccgc gttccgtctc tgccgcgccg tccacgagcg cctccacgga  2040
tttatccgcc caacgcggct caccttggcc gcctatctaa ccccgcaaac cgcctcccag  2100
ccaaccattg cgccgccgta aggcggattc ccagaacaca gccccgccgc gacctaaccc  2160
aacctaaccg cccgcgcccg ccgccacctt acgcagccgc acccgcccgc cgcgccgcgc  2220
tgctgggccg ccctcgcccc gcagaccgcc ctgcgcgctc gcgggggcta tcctggtagt  2280
cgcgcgctag gaggtgctag gcggccccgt gcttccacct cgcccgcgac cccgccgaac  2340
agcctggagc cctaaccctc ggtttggctt aaggaggact gccgccaggc cccccgtgac  2400
gcgggccccc ggggctctct gctgcggccg cgtctcgtcg cactttccgt cccgacacag  2460
gggacccgag gtgacgagga cgaatgcgcg aagcttgtct gcctcggctc ttggtctcgg  2520
cggtgctctc gacgcactcc acttgcgttt gcagcacgga tccttcgccg tgtctcgggt  2580
ctgcaaatcg agtttgcctg cacacgatga aaggtcacag aagagtccaa gtgcaaccaa  2640
ccagcctgag cgcggcaaac gacgtaggtt cgtggcctcg tacctgatcg gccggacgat  2700
ccgcaaagcg cggcccaaaa caccaatgat ggcccaatga tggcccaatg atggccggat  2760
gcacttgcgt cactttcctg cgctcacatc ctgccccgcc cctctcgcag tccggcttgc  2820
tggtgtcgcc cactcgccca gcctccctcc ctccctcggc ccaatcaaac tgatcatggg  2880
ccagaatcca attcttcggc gccctgcagc acaagaacac ttgcacttgc aggcggtccg  2940
```

```
tgctcagctc atcgcttgct cagcgaggag gcggacaagg cgtggcgagc acgagcaagc  3000
gcctcgagag ggaccagcca agacgccatc cgcgcacgca atggggcgct gccgggcgcg  3060
cttcgagtgc gcggaggggg gacaggcggc cggccgctcg tccttcggac ggctcctgct  3120
gctggcagcg cgagcagggc gaacggcgtt ctcgatccca tgtccgctcc cacaccgtgt  3180
ccgttttcgc gcggccacgg accccgtccg cgagcgagct gcgcggcggg gtggcgcgac  3240
cgcactgcgg atccggcccg ctctgcgtct ctgcactacg tagtgcgctg ctgcgccctg  3300
aggattcctg tccgtggcgg gctgcctggc ctcctgcgac ctggtgccag tgagggccgc  3360
cactcgccgc tcgccggcct ccttcctccc ctccaggggc cctcagccgc gacgcaagtg  3420
ggctgcgcgc cgccttgacg caagagagcc aactctctct ctggttgaac agccgcagtg  3480
cagcttacgt gctcgctcag gcttgcctaa tcatcgcgag gactcggaag tacacctgcg  3540
agcgcggctt ggcttgcagc ggagcaggcc agcgtttcgc accagggcct ggcccttcct  3600
tccttccttc ctgcctgcct gcctggtttg cgacgacgcc cgacgccgcg cacgagggcg  3660
gccgtcgtca gccaatcagt cagtcagtca tcgtccgaat tcggg                 3705

SEQ ID NO: 138         moltype = DNA  length = 3826
FEATURE                Location/Qualifiers
misc_feature           1..3826
                       note = fusion DNA (T. aureum OrfA upstream/ubiquitin
                        promoter/Hygr/T. aureum OrfA downstream)
source                 1..3826
                       mol_type = other DNA
                       organism = synthetic construct
SEQUENCE: 138
cccccatggc tcggttacat ctctgaggaa gacatggccg acgttttcga caagctttat  60
gcgtacaacg acatcataga tcatccgaac ggcggcccag ggccagaaca aggccgcctc  120
atgacagagg gaatcagcta tatagatgcc catttcccag aaaccgacag aatcctggcg  180
tgccgcgtcg tctgactaat gccgcgccaa gcttcatgac atcgaagacg gtcggttcag  240
cttgcggaca ctggtgaatc aagcccagcc gaagcgtggg aggaggctcg gcagatacgc  300
gcgatggagg tacattcgtt tttagtttac tgccctgcct ggtgcggccg ttttggagtg  360
gtttgtgctt tgcggtcggt cgtccctgac tacctctgtg cgtctcgagt cttctcgtag  420
tcaggtgcgc cagccgtcgc cagtccagca actgtgcagg gacgagtggg agcgaccgcc  480
gcgcttgctc tcgccggacc tgccgcagta ccaactggac ccttcgatag tctgcttcaa  540
atgagggcca gagtgcgccg ccaaccatgc catgcccctt tgtgcgcgca tgcgtggaag  600
cacctttaga gagtacaacc acgcaaacag cgctgccacg caaacagcgc tgccacgcaa  660
acagcgctgc catactcacc taaaagccct gaaaagagtt tgaaatccat cgcgtcgatg  720
cggcgtggaa gaagaagatc ttgcgagcag acgcaacgtg atcttggttc actcgtttga  780
agtgacgcgg gacgatcaac ttcgtcctaa cgcctgcgag cgcgagcccg aaaccttcgt  840
tcgttatcca tgtgatactg gctttgtgaa aaactacgga aaagacgcta gctagaggga  900
ttcggctgcc tccttgggca gccagtgacg gggcatttct gcgcgcgacg gaggccgcgt  960
gcaaaagagc ccccggacca atcccacagc aacacgtcga ctattccttt gccctcggac  1020
gagtgctggg gcgtcggttt ccactatcgg cgagtacttc tacacagcca tcggtccaga  1080
cggccgcgct tctgcgggcg atttgtgtac gcccgacagt cccggctccg gatcggacga  1140
ttgcgtcgca tcgaccctgc gcccaagctg catcatcgaa attgccgtca accaagctct  1200
gatagagttg gtcaagacca atgcggagca tatacgcccg gagccgcggc gatcctgcaa  1260
gctccggatg cctccgctcg aagtagcgcg tctgctgctc catacaagcc aaccacggcc  1320
tccagaagaa gatgttggcg acctcgtatt gggaatcccc gaacatcgcc tcgctccagt  1380
caatgaccgc tgttatgcgg ccattgtccg tcaggacatt gttggagccg aaatccgcgt  1440
gcacgaggtg ccggacttcg gggcagtcct cggcccaaag catcagctca tcgagagcct  1500
gcgcgacgga cgcactgacg gtgtcgtcca tcacagtttg ccagtgatac acatggggat  1560
cagcaatcgc gcatatgaaa tcacgccatg tagtgtattg accgattcct tgcggtccga  1620
atgggccgaa cccgctcgtc tggctaagat cggccgcagc gatcgcatcc atggcctccg  1680
cgaccggctg cagaacagcg ggcagttcgg tttcaggcag gtcttgcaac gtgacaccct  1740
gtgcacggcg ggagatgcaa taggtcaggc tctcgctgaa ttccccaatg tcaagcactt  1800
ccggaatcgg gagcgcggcc gatgcaaagt gccgataaac ataacgatct ttgtagaaac  1860
catcggcgca gctatttacc cgcaggacat atccacgccc tcctacatcg aagctgaaag  1920
cacgagattc ttcgccctcc gagagctgca tcaggtcgga gacgctgtcg aacttttcga  1980
tcagaaactt ctcgacagac gtcgcggtga gttcaggctt tttcatgttg gctagtgttg  2040
cttaggtcgc ttgctgctgc tggtgttgct tgttctgctt gtcgtttggg gtctgcccga  2100
agtggacgcg tgacacagcc cagcgttcgc gacttttcca gcaaccagct cgctcccgcg  2160
tcagggtcac tctctgctca ctcccctgtc tagttcggca gaactggaga ggcaacccgc  2220
gcttccagag ggttctcctc cggaatcagt tcagaattca gaattcagaa gagggaatcg  2280
cagaaccggc cgcttcggga gttggttcgc tgcaccatag caggtgggcg atgaggccaa  2340
ccgccctgct ggctggattc tctcgggttg gcacatcgaa cgaccgggac ccgcgcgcga  2400
gttgtccctg ccagttgcta ccagcctgcc agcgtcggag agttatgcgc tgcctgccgg  2460
ccggagagag agcgggcgtg gaaagtggcg tgtggggcga acgcatggcc ctcccgcgtg  2520
gcccgatttc ctatgcatcc gctccgctct ctctctcgga ggcaagaaga gcacaccaac  2580
aacgcccggc gggtgcacca ggcgctgcgg caagcttgtc tgcctcggct cttggtctcg  2640
gcggtgctct cgacgcactc cacttgcgtt tgcagcacgg atccttcgcc gtgtctcggg  2700
tctgcaaatc gagtttgcct gcacacgatg aaaggtcaca gaagagtcca agtgcaacca  2760
accagcctga gcgcggcaaa cgacgtaggt tcgtggcctc gtacctgatc ggccggacga  2820
tccgcaaagc gcggcccaaa acaccaatga tggcccaatg atggcccaat gatggccgga  2880
tgcacttgcg tcactttcct gcgctcacat cctgccccgc ccctctcgca gtccggcttg  2940
ctggtgtcgc ccactcgccc agcctccctc cctccctcgg cccaatcaaa ctgatcatgg  3000
gccagaatcc aattcttcgg cgccctgcag cacaagaaca cttgcacttg caggcggtcc  3060
gtgctcagct catcgcttgc tcagcgagga ggcggacaag gcgtggcgag cacgagcaag  3120
cgcctcgaga gggaccagcc aagacgccat ccgcgcacgc aatggggcgc tgccgggcgc  3180
gcttcgagtg cgcggagggg ggacaggcgg ccggccgctc gtccttcgga cggctcctgc  3240
tgctggcagc gcgagcaggg cgaacggcgt tctcgatccc atgtccgctc ccacaccgtg  3300
tccgttttcg cgcggccacg gaccccgtcc gcgagcgagc tgcgcggcgg ggtggcgcga  3360
```

```
ccgcactgcg gatccggccc gctctgcgtc tctgcactac gtagtgcgct gctgcgccct  3420
gaggattcct gtccgtggcg ggctgcctgg cctcctgcga cctggtgcca gtgagggccg  3480
ccactcgccg ctcgccggcc tccttcctcc cctccagggg ccctcagccg cgacgcaagt  3540
gggctgcgcg ccgccttgac gcaagagagc caactctctc tctggttgaa cagccgcagt  3600
gcagcttacg tgctcgctca ggcttgccta atcatcgcga ggactcggaa gtacacctgc  3660
gagcgcggct tggcttgcag cggagcaggc cagcgtttcg caccagggcc tggcccttcc  3720
ttccttcctt cctgcctgcc tgcctggttt gcgacgacgc ccgacgccgc gcacgagggc  3780
ggccgtcgtc agccaatcag tcagtcagtc atcgtccgaa ttcggg                3826

SEQ ID NO: 139         moltype = DNA  length = 22
FEATURE                Location/Qualifiers
misc_feature           1..22
                       note = primer
source                 1..22
                       mol_type = other DNA
                       organism = synthetic construct
SEQUENCE: 139
gaagcgtccc gtagatgtgg tc                                           22

SEQ ID NO: 140         moltype = DNA  length = 21
FEATURE                Location/Qualifiers
misc_feature           1..21
                       note = primer
source                 1..21
                       mol_type = other DNA
                       organism = synthetic construct
SEQUENCE: 140
gcccgagagg tcaaagtacg c                                            21

SEQ ID NO: 141         moltype = DNA  length = 20
FEATURE                Location/Qualifiers
misc_feature           1..20
                       note = primer
source                 1..20
                       mol_type = other DNA
                       organism = synthetic construct
SEQUENCE: 141
gcgagcccag gtccacttgc                                              20

SEQ ID NO: 142         moltype = DNA  length = 22
FEATURE                Location/Qualifiers
misc_feature           1..22
                       note = primer
source                 1..22
                       mol_type = other DNA
                       organism = synthetic construct
SEQUENCE: 142
cagcccgatg aaaaacttgg tc                                           22

SEQ ID NO: 143         moltype = DNA  length = 22
FEATURE                Location/Qualifiers
misc_feature           1..22
                       note = primer
source                 1..22
                       mol_type = other DNA
                       organism = synthetic construct
SEQUENCE: 143
gggagcgcag ggaaaacggt ct                                           22

SEQ ID NO: 144         moltype = DNA  length = 20
FEATURE                Location/Qualifiers
misc_feature           1..20
                       note = primer
source                 1..20
                       mol_type = other DNA
                       organism = synthetic construct
SEQUENCE: 144
ccagcccacg tcgtcggagc                                              20

SEQ ID NO: 145         moltype = DNA  length = 2297
FEATURE                Location/Qualifiers
misc_feature           1..2297
                       note = genomic DNA (T. aureum ATCC 34304 C20 elongase
                        upstream genomic DNA fragment)
source                 1..2297
                       mol_type = other DNA
                       organism = synthetic construct
SEQUENCE: 145
ggccggggca gcccgcccag cacgccgctg cgctgctttc ggtcatgcga acctggctcc  60
```

```
ccacagcaat gctgcgcggt cgctgcgcct cttgaggctc ggcgacgttg gcccggtttg  120
gggcaccctg acgttgcacg aacgtccgct gcatctcagg cgcactcgga tcgacaactg  180
tgcaaccggt cagcctttcg cggcagattg ggcacttgcc gcgctcgcgt atccgcgtgg  240
cgcattcttc gcacacgcag gcgtgccggc agggaagcag gagggtgttt atcgtggcgt  300
ccatgtagac cttgcacagc cgcggctcac tttccctcgg cgcagtcccg tgcccaacgt  360
cggggccggg cgccggcgcc ggcgagggcg tcggttctgg gatgggatca ggatccgccg  420
aggctgcaga ttgctgtgcg ggggtgccgg ggcgcggccc attagcaccg tcctgcggaa  480
tatccaggag ggtgctcatc acggaagcca tgtccgggcg ctggctgccg tcttcgtgcg  540
tgcaacgatc caccaggtca aggagcaccc gagccacgtt ttggcgggtg cgaaaagcgg  600
cttggtcaac gcagcgctcc gggtcgaagc cgttgtcgcg catccagtac ggaagcaggt  660
cgaggccgcg gcggcaggga aagcaaggcg gcttgccgga cacaagctcg ccgagcacga  720
cgccaaaggc gtaaacgtcc acggggcgat tgtactcgac atgggtggcg ccctccaggt  780
cggagatctc gggcgccatg tagccaagcg tgcccacttg tgtcatcgtt tgcatggtgt  840
ggagcgtggt actggcggcc accttggaca cgccaaagtc cgtccagcac agccttaggc  900
ccgcgccctt gttcaggttg accagagcgt tgtcgctctt ggatgtctct gtgcagcacg  960
ccagcagcgt gcagcgccct gaggccgtgc gccgcctggt atgccagcgc ctcgcgagcg  1020
ctgccgtcca aaagcggcgc gctccccgaa tcatcgcgga gctggatggc cttcttgagc  1080
gacatttcca tgcggggcat gatgatcgca aacctgccgc cgctctgtgg ctcgagcgcg  1140
gtcgccagga ccgtgagcac gttctcgtgc gttgcgctcg ccatccgcga ggcctcagcg  1200
cgaaagtcat cgaggacgcc gagcgtctgc ccgggccgcg gtaccttgac agcgcagcgc  1260
ccgaacggcg ccacgtccgc ttcaaacacc tcgccaaagg cgccttgtcc gagcagctcg  1320
ccccagccgc agccgcgacc actcgatctc gggcacgcgt gccatcgacc cttgcagcgt  1380
ggccttgcca agtcacagtc cagcgcgcag ttcagtgtct gccgcgccag gtccaccacg  1440
atcaattcat ccgagtcggc tgcgaactgg acaagtgcca tttgggtgcg ggcaacgcgc  1500
aagatcaccc agcactggca tgaagaccat gaatgaatga atgaccgtgc gcgagtgacc  1560
gaccaacacg agtccagccg actccttctt cttctccttc ttcttcttct tcttcttctc  1620
gtagcgggcg tcaacagcat caatcaggca tggcggcatt cactctgcgc gatggatggc  1680
acgagcgctg gaggtgatga acgcactgcc cggattggct ctcggtcact gtcagcacat  1740
gatgcctgtg cttgcgcgga gcgcgctatg tctcgttctg tgtcaagaca caggcgcaac  1800
tcttgatgga ttcttgaagc gcatgtaact gaagtctgac agactcggaa gtccattgtg  1860
aacaatgttg ttccacaatt gctccaattg ttccgattat tccacaattg ttgttccaat  1920
tgttccaatt gttccgatta ttccgattat tccactttag ttgttccagt tgttccgatt  1980
gttccacaat tgttgttccg attattccag ttgttccagt tgttccaatt attccaattg  2040
ttccagttcc ttactcttga catcggggga ataacgggtg tgtatttagg ggttcggcga  2100
aagcagaatg gccgaacgta acagcggaga ggaacctctt tagcggggtt tgcgtatcgg  2160
ggaaaccagg tgttgtgctg gcgaggagga tcccccgcga ggcgatggct gctccgacga  2220
cgtgggctgg cgacgtcgct cgcaaaggcg ttccgcaacc gcgcgttccg ctgtaacgag  2280
accgttttcc ctgcgct                                                 2297
```

```
SEQ ID NO: 146          moltype = DNA  length = 23
FEATURE                 Location/Qualifiers
misc_feature            1..23
                        note = primer
source                  1..23
                        mol_type = other DNA
                        organism = synthetic construct
SEQUENCE: 146
gccgctcatg cccacgctca aac                                          23
```

```
SEQ ID NO: 147          moltype = DNA  length = 23
FEATURE                 Location/Qualifiers
misc_feature            1..23
                        note = primer
source                  1..23
                        mol_type = other DNA
                        organism = synthetic construct
SEQUENCE: 147
ctttcggctg ccaggaatct acg                                          23
```

```
SEQ ID NO: 148          moltype = DNA  length = 2189
FEATURE                 Location/Qualifiers
misc_feature            1..2189
                        note = genomic DNA (T. aureum ATCC 34304 OrfA downstream
                         genomic DNA fragment)
source                  1..2189
                        mol_type = other DNA
                        organism = synthetic construct
SEQUENCE: 148
ctttcggctg ccaggaatct acggcccagg gcgcggcccg atctcacgaa ttcgcaaggg  60
ccaggcccgc agtatcgtca aggagggcca ggtcttctcg cgggcgcacg tcgacgatat  120
caccggtgcg atccgcgctt cgctggccaa cccaaacccg ggccgcgcct acaacgtttg  180
cgacgacgag cctgcaatga accatgtcgt gacagagttt gcctgcgaac tcatggacgt  240
cccgcccccg aagcgcgaag actttgacaa ggtgcgcgag accatgtcaa gcatgtcgct  300
ctccttcttc tcagagagca agcgggtctt caacaagcgg ctcaaggaag agctgcggta  360
cgcgctattg tacccgacct accgcgaagg gatcaaagcc caactggagg aggagcttgc  420
caacggctgg acgctcatcg acgcctcggg tgcttctgct ggaaccgact cccctgcctc  480
gcccaaagcg cccgccccca tcgccgcctc aagtgacgag tcgagcgggc agagcgcgac  540
agcggccgag ccggtgcgcc ggcgcaggcg ccccgagcgc aaggcgctcc cgcctgctgg  600
gccgagtggg ccgtcggtct tgcagagggt ttctcgggca atttatgggc cgttcagttg  660
```

```
gctcctcggt cgcctgtttg ggccactttc gagccgcgct gtcggcttgt ttcgcggctg  720
ggcgcactgg ctgttgcgtc tcgtggggct gcgcgcatcc gcgccgggcg gcggccgtac  780
aacctgcctc cttgttgaca acggctcgct caaaccagag ccttttcgcc agctgcgcgt  840
gcacgcggcg aacctcgaag agtctcttag gagcgacgcg cgtgccccac atcccgtgca  900
ggtggtggcc gtcagcgcga ggtacagcga ccgcatcgac gcctcccttc tggacggcaa  960
gcccggcgtc gccctcgccg ggttcctgag ttccttcaag gccgacgccg agtcgcagcc  1020
agcaaccagc gaggttggcc gcatcatcgc gctcccctac tttctgggcc caagcaagac  1080
ggccacgtcg tatgttgctt cccagctcgc agagcacttt ccaggagccg agcgcaccat  1140
tgccgctccg ctcgtgtcgc gggacggcgc cattgcgcag ctcctcgctg acatggtcca  1200
tgacgtcgct cgggcgcgcg cgctgcaggc cccgtacgcg gtagttctcg tcgaccacgg  1260
gtccccgagc cgagcggtca accgcgttcg gcgggccatc gctgcgcgga tgcgccgccg  1320
ccttggcccg aacgcgcgct gcgttgtcga ctgctccatg gagcgccgcg agggcgacgc  1380
tttcgccttc aacgagcctc tgctagagtc ggttttcacc aagggtggtc tcgactctgg  1440
cgacgtcatt ctcgcgatgg cattttggc gcctggtcgc cacgctggcg agggcggcga  1500
tatcgcggag atccttgacg aggctatcgc aaagtcggct ggcaagctgc gcgttcacca  1560
aacgcggttg attggtgacg tggacaggaa cggtacgcag atttgcgccc tcctcaagaa  1620
caggccgctt gccgcgctgt aacggcaaga gcatccacaa ttcctgacct gagcaaacca  1680
gcccacgcga gagaccgaac acgtcaagcc gatgaggcgc agaaaacaaa gaaaaaaagc  1740
aaaaagaaca aaaacccaag gcaaaatgat ggcaattttc ttggtatgga aagccgatga  1800
tcgccgagtg tcgctggcta tttgctctgg tggggcatcg agctcgatga ccgaaatcca  1860
ccaattatct gcgtgtcaat catttggagc ataagacccg ggaaggcctt gagcaagcga  1920
agaaaccggc gcgtgttcac acgatagtac gagacgtcgc tctctgcgcg gatctcaatc  1980
tgagccttct tgtctccgcg gatgaaagtg ttcatgtccc cgacaagggc gccgcgccca  2040
acccctcgtt tgggctgcgc cgcgctactg gaaatggtga ttccgcgaaa cgtgcccgat  2100
tcgcctttct caacagggct caccgtgaca gaaccctcag cgacaagaac gatgccgtca  2160
atcttttcgc cgggcgaggc tttctgcag                                    2189

SEQ ID NO: 149          moltype = DNA  length = 618
FEATURE                 Location/Qualifiers
misc_feature            1..618
                        note = genomic DNA (T. aureum ATCC 34304 ubiquitin promoter)
source                  1..618
                        mol_type = other DNA
                        organism = synthetic construct
SEQUENCE: 149
cccagatctg ccgcagcgcc tggtgcaccc gccgggcgtt gttggtgtgc tcttcttgcc  60
tccgagagag agagcggagc ggatgcatag gaaatcgggc cacgcgggag ggccatgcgt  120
tcgccccaca cgccactttc cacgcccgct ctctctccgg ccggcaggca gcgcataact  180
ctccgacgct ggcaggctgg tagcaactgg cagggacaac tcgcgcgcgg gtcccggtcg  240
ttcgatgtgc caacccgaga gaatccagcc agcagggcgg ttggcctcat cgcccacctg  300
ctatggtgca gcgaaccaac tcccgaagcg gccggttctg cgattccctc ttctgaattc  360
tgaattctga actgattccg gaggagaacc ctctggaagc gcgggttgcc tctccagttc  420
tgccgaacta gacaggggag tgagcagaga gtgaccctga cgcggagcga gctggttgct  480
ggaaaagtcg cgaacgctgg gctgtgtcac gcgtccactt cggcagtcc ccaaacgaca  540
agcagaacaa gcaacaccag cagcagcaag cgacctaagc aacactagcc aacatggcca  600
agcctttgtc tcaagaag                                                618

SEQ ID NO: 150          moltype = DNA  length = 58
FEATURE                 Location/Qualifiers
misc_feature            1..58
                        note = primer
source                  1..58
                        mol_type = other DNA
                        organism = synthetic construct
SEQUENCE: 150
cttcttgaga caaaggcttg gccatgttgg ctagtgttgc ttaggtcgct tgctgctg    58

SEQ ID NO: 151          moltype = DNA  length = 432
FEATURE                 Location/Qualifiers
misc_feature            1..432
                        note = Blasticidin resistance gene (Blar)
source                  1..432
                        mol_type = other DNA
                        organism = synthetic construct
SEQUENCE: 151
agcgacctaa gcaacactag ccaacatggc caagcctttg tctcaagaag aatccaccct  60
cattgaaaga gcaacggcta caatcaacag catccccatc tctgaagact acagcgtcgc  120
cagcgcagct ctctctagcg acggccgcat cttcactggt gtcaatgtat atcattttac  180
tgggggacct tgtgcagaac tcgtggtgct gggcactgct gctgctgcgg cagctggcaa  240
cctgacttgt atcgtcgcga tcggaaatga gaacaggggc atcttgagcc cctgcggacg  300
gtgccgacag gtgcttctcg atctgcatcc tgggatcaaa gccatagtga aggacagtga  360
tggacagccg acggcagttg ggattcgtga attgctgccc tctggttatg tgtgggaggg  420
ctaagatctg gg                                                      432

SEQ ID NO: 152          moltype = DNA  length = 54
FEATURE                 Location/Qualifiers
misc_feature            1..54
                        note = primer
source                  1..54
```

```
                         mol_type = other DNA
                         organism = synthetic construct
SEQUENCE: 152
agcgacctaa gcaacactag ccaacatggc caagcctttg tctcaagaag aatc        54

SEQ ID NO: 153           moltype = DNA  length = 38
FEATURE                  Location/Qualifiers
misc_feature             1..38
                         note = primer
source                   1..38
                         mol_type = other DNA
                         organism = synthetic construct
SEQUENCE: 153
cccagatctt agccctccca cacataacca gagggcag                          38

SEQ ID NO: 154           moltype = DNA  length = 1000
FEATURE                  Location/Qualifiers
misc_feature             1..1000
                         note = fusion DNA (T. aureum ATCC 34304 ubiquitin
                          promoter/pTracer-CMV/Bsd/lacZ Blar)
source                   1..1000
                         mol_type = other DNA
                         organism = synthetic construct
SEQUENCE: 154
cccagatctg ccgcagcgcc tggtgcaccc gccgggcgtt gttggtgtgc tcttcttgcc  60
tccgagagag agagcggagc ggatgcatag gaaatcgggc cacgcgggag ggccatgcgt  120
tcgccccaca cgccactttc cacgcccgct ctctctccgg ccggcaggca gcgcataact  180
ctccgacgct ggcaggctgg tagcaactgg cagggacaac tcgcgcgcgg gtcccggtcg  240
ttcgatgtgc caacccgaga gaatccagcc agcagggcgg ttggcctcat cgcccacctg  300
ctatggtgca gcgaaccaac tcccgaagcg gccggttctg cgattccctc ttctgaattc  360
tgaattctga actgattccg gaggagaacc ctctggaagc gcgggttgcc tctccagttc  420
tgccgaacta gacaggggag tgagcagaga gtgaccctga cgcggagcga gctggttgct  480
ggaaaagtcg cgaacgctgg gctgtgtcac gcgtccactt cgggcagtcc ccaaacgaca  540
agcagaacaa gcaacaccag cagcagcaag cgacctaagc aacactagcc aacatggcca  600
agcctttgtc tcaagaagaa tccaccctca ttgaaagagc aacggctaca atcaacagca  660
tccccatctc tgaagactac agcgtcgcca gcgcagctct ctctagcgac ggccgcatct  720
tcactggtgt caatgtatat cattttactg gggaccttgg tgcagaactc gtggtgctgg  780
gcactgctgc tgctgcggca gctggcaacc tgacttgtat cgtcgcgatc ggaaatgaga  840
acaggggcat cttgagcccc tgcggacggt gccgacaggt gcttctcgat ctgcatcctg  900
ggatcaaagc catagtgaag gacagtgatg gacagccgac ggcagttggg attcgtgaat  960
tgctgccctc tggttatgtg tgggagggct aagatctggg                        1000

SEQ ID NO: 155           moltype = DNA  length = 812
FEATURE                  Location/Qualifiers
misc_feature             1..812
                         note = cDNA (T.aureum ATCC 34304 ubiquitin promoter)
source                   1..812
                         mol_type = other DNA
                         organism = synthetic construct
SEQUENCE: 155
tcggtacccg ttagaacgcg taatacgact cactataggg agagtcgact gagcacaact  60
ctgctgcgag cgggcctcga gagcgtttgc ttcgagccgc ggagcaaggg ggatggatcg  120
ctcatgcggt cgtgcggccc tcggtcaccc ggtgggtcct gcactgacgc atctgttctg  180
atcagacaca cgaacgaaca aaccgaggag ccgcagcgcc tggtgcaccc gccgggcgtt  240
gttgtgtgct cttcttgcct ccgagagaga gagcggagcg gatgcatagg aaatcgggcc  300
acgcgggagg gccatgcgtt tgccccacac gccactttcc acgcccgctc tctctccggc  360
cggcaggcag cgcataactc tccgacgctg gcaggctggt agcaactggc agggacaact  420
cgcgcgcggg tcccggtcgt tcgatgtgcc aacccgagag aatccagcca gcagggcggt  480
tggcctcatc gcccacctgc tatggtgcag cgaaccaact cccgaagctg ccggttctgc  540
gattccctct tctgaattct gaattctgaa ctgattccgg aggagaaccc tctggaagcg  600
cgggttgcct ctccagttct gccgaactag acaggggagt gagcagagag tgaccctgac  660
gcggagcgag ctggttgctg gaaaagtcgc gaacgctggg ctgtgtcacg cgtccacttc  720
gggcagaccc caaacgacaa gcagaacaag caacaccagc agcagcaagc gatctaagca  780
acactagcca acatggtgag caagggcgag ga                                812

SEQ ID NO: 156           moltype = DNA  length = 29
FEATURE                  Location/Qualifiers
misc_feature             1..29
                         note = primer
source                   1..29
                         mol_type = other DNA
                         organism = synthetic construct
SEQUENCE: 156
tcggtacccg ttagaacgcg taatacgac                                    29

SEQ ID NO: 157           moltype = DNA  length = 41
FEATURE                  Location/Qualifiers
misc_feature             1..41
                         note = primer
```

```
source                  1..41
                        mol_type = other DNA
                        organism = synthetic construct
SEQUENCE: 157
tcctcgccct tgctcaccat gttggctagt gttgcttagg t                    41

SEQ ID NO: 158          moltype = DNA  length = 748
FEATURE                 Location/Qualifiers
misc_feature            1..748
                        note = Enhanced GFP gene (Enhanced GFP DNA fragment)
source                  1..748
                        mol_type = other DNA
                        organism = synthetic construct
SEQUENCE: 158
acctaagcaa cactagccaa catggtgagc aagggcgagg agctgttcac cggggtggtg  60
cccatcctgg tcgagctgga cggcgacgta aacggccaca agttcagcgt gtccggcgag  120
ggcgagggcg atgccaccta cggcaagctg accctgaagt tcatctgcac caccggcaag  180
ctgcccgtgc cctggcccac cctcgtgacc accctgacct acggcgtgca gtgcttcagc  240
cgctaccccg accacatgaa gcagcacgac ttcttcaagt ccgccatgcc cgaaggctac  300
gtccaggagc gcaccatctt cttcaaggac gacggcaact acaagacccg cgccgaggtg  360
aagttcgagg gcgacaccct ggtgaaccgc atcgagctga agggcatcga cttcaaggag  420
gacggcaaca tcctggggca caagctggag tacaactaca acagccacaa cgtctatatc  480
atggccgaca agcagaagaa cggcatcaag gtgaacttca agatccgcca caacatcgag  540
gacggcagcg tgcagctcgc cgaccactac cagcagaaca cccccatcgg cgacggcccc  600
gtgctgctgc ccgacaacca ctacctgagc acccagtccg ccctgagcaa agaccccaac  660
gagaagcgcg atcacatggt cctgctggag ttcgtgaccg ccgccgggat cactctcggc  720
atggacgcca agttgaccag tgccgttc                                   748

SEQ ID NO: 159          moltype = DNA  length = 41
FEATURE                 Location/Qualifiers
misc_feature            1..41
                        note = primer
source                  1..41
                        mol_type = other DNA
                        organism = synthetic construct
SEQUENCE: 159
acctaagcaa cactagccaa catggtgagc aagggcgagg a                    41

SEQ ID NO: 160          moltype = DNA  length = 58
FEATURE                 Location/Qualifiers
misc_feature            1..58
                        note = primer
source                  1..58
                        mol_type = other DNA
                        organism = synthetic construct
SEQUENCE: 160
gaacggcact ggtcaacttg gcgtccatgc cgagagtgat cccggcggcg gtcacgaa    58

SEQ ID NO: 161          moltype = DNA  length = 1519
FEATURE                 Location/Qualifiers
misc_feature            1..1519
                        note = fusion DNA (T. aureum ATCC 34304 ubiquitin promoter/
                         Enhanced GFP)
source                  1..1519
                        mol_type = other DNA
                        organism = synthetic construct
SEQUENCE: 161
tcggtacccg ttagaacgcg taatacgact cactataggg agagtcgact gagcacaact  60
ctgctgcgag cgggcctcga gagcgtttgc ttcgagccgc ggagcaaggg ggatggatcg  120
ctcatgcggt cgtgcggccc tcggtcaccc ggtgggtcct gcactgacgc atctgttctg  180
atcagacaca cgaacgaaca aaccgaggag ccgcagcgcc tggtgcaccc gccgggcgtt  240
gttgtgtgct cttcttgcct ccgagagaga gagcggagcg gatgcatagg aaatcgggcc  300
acgcgggagg gccatgcgtt tgccccacac gccactttcc acgcccgctc tctctccggc  360
cggcaggcag cgcataactc tccgacgctg gcaggctggt agcaactggc agggacaact  420
cgcgcgcggg tcccggtcgt tcgatgtgcc aacccgagag aatccagcca gcagggcggt  480
tggcctcatc gcccacctgc tatggtgcag cgaaccaact cccgaagctg ccggttctgc  540
gattccctct tctgaattct gaattctgaa ctgattccgg aggagaaccc tctggaagcg  600
cgggttgcct ctccagttct gccgaactag acaggggagt gagcagagag tgaccctgac  660
gcggagcgag ctggttgctg gaaaagtcgc gaacgctggg ctgtgtcacg cgtccacttc  720
gggcagaccc caaacgacaa gcagaacaag caacaccagc agcagcaagc gacctaagca  780
acactagcca acatggtgag caagggcgag gagctgttca ccggggtggt gcccatcctg  840
gtcgagctgg acggcgacgt aaacggccac aagttcagcg tgtccggcga gggcgagggc  900
gatgccacct acggcaagct gaccctgaag ttcatctgca ccaccggcaa gctgcccgtg  960
ccctggccca ccctcgtgac caccctgacc tacggcgtgc agtgcttcag ccgctacccc  1020
gaccacatga agcagcacga cttcttcaag tccgccatgc ccgaaggcta cgtccaggag  1080
cgcaccatct tcttcaagga cgacggcaac tacaagaccc gcgccgaggt gaagttcgag  1140
ggcgacaccc tggtgaaccg catcgagctg aagggcatcg acttcaagga ggacggcaac  1200
atcctggggc acaagctgga gtacaactac aacagccaca acgtctatat catggccgac  1260
aagcagaaga acggcatcaa ggtgaacttc aagatccgcc acaacatcga ggacggcagc  1320
```

```
gtgcagctcg ccgaccacta ccagcagaac acccccatcg gcgacggccc cgtgctgctg  1380
cccgacaacc actacctgag cacccagtcc gccctgagca aagaccccaa cgagaagcgc  1440
gatcacatgg tcctgctgga gttcgtgacc gccgccggga tcactctcgg catggacgcc  1500
aagttgacca gtgccgttc                                                1519

SEQ ID NO: 162          moltype = DNA  length = 1319
FEATURE                 Location/Qualifiers
misc_feature            1..1319
                        note = fusion DNA (T. aureum ATCC 34304 ubiquitin promoter/
                         Enhanced GFP)
source                  1..1319
                        mol_type = other DNA
                        organism = synthetic construct
SEQUENCE: 162
cccagatctg ccgcagcgcc tggtgcaccc gccgggcgtt gttgtgtgct cttcttgcct  60
ccgagagaga gagcggagcg gatgcatagg aaatcgggcc acgcgggagg gccatgcgtt  120
tgccccacac gccactttcc acgcccgctc tctctccggc cggcaggcag cgcataactc  180
tccgacgctg gcaggctggt agcaactggc agggacaact cgcgcgcggg tcccggtcgt  240
tcgatgtgcc aacccgagag aatccagcca gcagggcggt tggcctcatc gcccacctgc  300
tatggtgcag cgaaccaact cccgaagctg ccggttctgc gattccctct tctgaattct  360
gaattctgaa ctgattccgg aggagaaccc tctggaagcg cgggttgcct ctccagttct  420
gccgaactag acaggggagt gagcagagag tgaccctgac gcggagcgag ctggttgctg  480
gaaaagtcgc gaacgctggg ctgtgtcacg cgtccacttc gggcagaccc caaacgacaa  540
gcagaacaag caacaccagc agcagcaagc gacctaagca acactagcca acatggtgag  600
caagggcgag gagctgttca ccggggtggt gcccatcctg gtcgagctgg acggcgacgt  660
aaacggccac aagttcagcg tgtccggcga gggcgagggc gatgccacct acggcaagct  720
gaccctgaag ttcatctgca ccaccggcaa gctgcccgtg ccctggccca ccctcgtgac  780
caccctgacc tacggcgtgc agtgcttcag ccgctacccc gaccacatga agcagcacga  840
cttcttcaag tccgccatgc ccgaaggcta cgtccaggag cgcaccatct tcttcaagga  900
cgacggcaac tacaagaccc gcgccgaggt gaagttcgag ggcgacaccc tggtgaaccg  960
catcgagctg aagggcatcg acttcaagga ggacggcaac atcctggggc acaagctgga  1020
gtacaactac aacagccaca acgtctatat catggccgac aagcagaaga acggcatcaa  1080
ggtgaacttc aagatccgcc acaacatcga ggacggcagc gtgcagctcg ccgaccacta  1140
ccagcagaac acccccatcg gcgacggccc cgtgctgctg cccgacaacc actacctgag  1200
cacccagtcc gccctgagca aagaccccaa cgagaagcgc gatcacatgg tcctgctgga  1260
gttcgtgacc gccgccggga tcactctcgg catggacgcc aagttgacca gtgccgttc   1319

SEQ ID NO: 163          moltype = DNA  length = 408
FEATURE                 Location/Qualifiers
misc_feature            1..408
                        note = cDNA (Zeor)
source                  1..408
                        mol_type = other DNA
                        organism = synthetic construct
SEQUENCE: 163
cgccgccggg atcactctcg gcatggacgc caagttgacc agtgccgttc cggtgctcac  60
cgcgcgcgac gtcgccggag cggtcgagtt ctggaccgac cggctcgggt tctcccggga  120
cttcgtggag gacgacttcg ccggtgtggt ccgggacgac gtgaccctgt tcatcagcgc  180
ggtccaggac caggtggtgc cggacaacac cctggcctgg gtgtgggtgc gcggcctgga  240
cgagctgtac gccgagtggt cggaggtcgt gtccacgaac ttccgggacg cctccgggcc  300
ggccatgacc gagatcggcg agcagccgtg ggggcgggag ttcgccctgc gcgacccggc  360
cggcaactgc gtgcacttcg tggccgagga gcaggactga gatctggg              408

SEQ ID NO: 164          moltype = DNA  length = 54
FEATURE                 Location/Qualifiers
misc_feature            1..54
                        note = primer
source                  1..54
                        mol_type = other DNA
                        organism = synthetic construct
SEQUENCE: 164
cgccgccggg atcactctcg gcatggacgc caagttgacc agtgccgttc cggt       54

SEQ ID NO: 165          moltype = DNA  length = 38
FEATURE                 Location/Qualifiers
misc_feature            1..38
                        note = primer
source                  1..38
                        mol_type = other DNA
                        organism = synthetic construct
SEQUENCE: 165
cccagatctc agtcctgctc ctcggccacg aagtgcac                         38

SEQ ID NO: 166          moltype = DNA  length = 1677
FEATURE                 Location/Qualifiers
misc_feature            1..1677
                        note = fusion DNA (T. aureum ATCC 34304 ubiquitin
                         promoter/Enhanced GFP/pcDNA3.1 Zeo(+) Zeor)
source                  1..1677
```

```
                        mol_type = other DNA
                        organism = synthetic construct
SEQUENCE: 166
cccagatctg ccgcagcgcc tggtgcaccc gccgggcgtt gttgtgtgct cttcttgcct  60
ccgagagaga gagcggagcg gatgcatagg aaatcgggcc acgcgggagg gccatgcgtt  120
tgccccacac gccactttcc acgcccgctc tctctccggc cggcaggcag cgcataactc  180
tccgacgctg gcaggctggt agcaactggc agggacaact cgcgcgcggg tcccggtcgt  240
tcgatgtgcc aacccgagag aatccagcca gcagggcggt tggcctcatc gcccacctgc  300
tatggtgcag cgaaccaact cccgaagctg ccggttctgc gattccctct tctgaattct  360
gaattctgaa ctgattccgg aggagaaccc tctggaagcg cgggttgcct ctccagttct  420
gccgaactag acaggggagt gagcagagag tgaccctgac gcggagcgag ctggttgctg  480
gaaaagtcgc gaacgctggg ctgtgtcacg cgtccacttc gggcagaccc caaacgacaa  540
gcagaacaag caacaccagc agcagcaagc gacctaagca acactagcca acatggtgag  600
caagggcgag gagctgttca ccggggtggt gcccatcctg gtcgagctgg acggcgacgt  660
aaacggccac aagttcagcg tgtccggcga gggcgagggc gatgccacct acggcaagct  720
gaccctgaag ttcatctgca ccaccggcaa gctgcccgtg ccctggccca ccctcgtgac  780
caccctgacc tacggcgtgc agtgcttcag ccgctacccc gaccacatga agcagcacga  840
cttcttcaag tccgccatgc ccgaaggcta cgtccaggag cgcaccatct tcttcaagga  900
cgacggcaac tacaagaccc gcgccgaggt gaagttcgag ggcgacaccc tggtgaaccg  960
catcgagctg aagggcatcg acttcaagga ggacggcaac atcctggggc acaagctgga  1020
gtacaactac aacagccaca acgtctatat catggccgac aagcagaaga acggcatcaa  1080
ggtgaacttc aagatccgcc acaacatcga ggacggcagc gtgcagctcg ccgaccacta  1140
ccagcagaac acccccatcg gcgacggccc cgtgctgctg cccgacaacc actacctgag  1200
cacccagtcc gccctgagca aagaccccaa cgagaagcgc gatcacatgg tcctgctgga  1260
gttcgtgacc gccgccggga tcactctcgg catggacgcc aagttgacca gtgccgttcc  1320
ggtgctcacc gcgcgcgacg tcgccggagc ggtcgagttc tggaccgacc ggctcgggtt  1380
ctcccgggac ttcgtggagg acgacttcgc cggtgtggtc cgggacgacg tgaccctgtt  1440
catcagcgcg gtccaggacc aggtggtgcc ggacaacacc ctggcctggg tgtgggtgcg  1500
cggcctggac gagctgtacg ccgagtggtc ggaggtcgtg tccacgaact tccgggacgc  1560
ctccgggccg gccatgaccg agatcggcga gcagccgtgg gggcgggagt tcgccctgcg  1620
cgacccggcc ggcaactgcg tgcacttcgt ggccgaggag caggactgag atctggg     1677

SEQ ID NO: 167          moltype = DNA  length = 2884
FEATURE                 Location/Qualifiers
misc_feature            1..2884
                        note = genomic DNA (T. aureum ATCC 34304 C20 elongase
                         upstream/C20 elongase/C20 elongase downstream)
source                  1..2884
                        mol_type = other DNA
                        organism = synthetic construct
SEQUENCE: 167
cccgaattca ctagtgattc tcccgggtgg acctagcgcg tgtgtcacct gccggccccc  60
gttgcgtgca accgaattga tcgataatag aattacataa caaacaactt gctggatgag  120
tacaagacca gcgtagtgtg gctgtgggac gttgaacgga gcgggtcctg tgatggcgca  180
gaaaggaact ccgcccgagg tgaaaccccg atgcgcagga ctctgcggcc acagcccctc  240
cgccagtatt ccactaaaaa tccgccccct ttgacaaaga tcgcaacccc gtcccatcaa  300
ctcctcacaa taggctttcc actggcggaa acgtccccgg cacaggagtg cctcccgcgg  360
ttctgcgcat acggctgacc actacgcagc gcgatatcct ccatccgcgt atatatccgt  420
aaacaacgga acattctccc tctcaacgag gcgtggtttt cgaagtcatg cctttcttcc  480
ttcctacttt ccttccttct ttctttcttt ctttccttct tttgcaagcg tgcgcgaact  540
tgaaggtact acttacactt gacagagaga gatagagacg gcaattcgac caagtacttt  600
ccacgatttt tttttttttt gttttggtcg ctttcgttgg tcgtgcatga tggatggccg  660
ggatttttac aattggatgc gccaggctgc cacgcatgcc gtgacgcttg ctcgcggcga  720
ctcatgatgc ttgccagtgg cagtgcatcc agctcttccc tctgctcgtc gtgtactcac  780
tggcgatgct ctcggcgctc gttcaagggc catcgatcga tcgatcgatc gatcgatcga  840
tcaatcacgt ttggtggact cggcagaccc cgaacgtgtt tctcccagga cgcgccgctg  900
tcgctcgcta atccacccga agcgcggtcg gctggcacgg tcgctcggct ggaagttgag  960
tagtttgctt tctgttgctg cgctgctttg taaacgcgac catggcgacg cgcacctcga  1020
agagcgctcc ggcggtttcc aagtcggcca aggttgccgc gccggcgaag aagcggtcgg  1080
tcgacaggag cgacggtttc ttccgcacgt tcaacctgtg cgccctgtac gggtctgccc  1140
tcgcctatgc gtacaagcac ggcccggtgg acaatgacgg ccaggggctg tactttcaca  1200
agtcgcccat gtacgcgttc gccgtgtcgg acgtcatgac cttcggcgcg ccgctgatgt  1260
acgtgctcgg tgtgatgctg ctcagcaggt acatggcgga caaaaagccc ctgactggct  1320
tcatcaagac ctacatccag cccgtctaca acgtggtcca aatcgcggtg tgcggctgga  1380
tggtgtgggg cctctggccg caggtcgacc tggccaacgg caacccctttc ggcctcaaca  1440
agtcgcgcga ctcgaacatc gagtttttcg tgttcgtgca cctcctgaca aagtttctcg  1500
actggagcga cacgttcatg atgatcctca agaaaaacta cgcccaggtt agctttctgc  1560
aggtgttcca ccacgcaacg atcggcatgg tgtggtcgtt ccttcttcag cgtggctggg  1620
gctcgggcac cgccgcgtac ggtgctttca tcaactcggt cacgcacgtg atcatgtact  1680
cgcactactt tgccacctcg ctcaacatca acaacccgtt caagcggtac atcacgagct  1740
tccagctcgc ccagtttgca agctgcatcg tgcatgccct actggtgctt gccttcgagg  1800
aggtgtaccc gctcgagtac gcttacctgc agatcagcta ccacatcatc atgctctacc  1860
tgttcggacg ccgcatgaac tggagccccg agtggtgcac cggtgagatc gacggccttg  1920
acgccccaag cgcccccacc aagtccgagt aaacctgttt ccggctggct cccgagccat  1980
gcttaccatg aatgaacctg caaacagtct gaggtccttg tgcaaaccgc tcagtgggac  2040
gtcgacgaag aaagaaacaa tgtgtactcg tcttgctctg ctcccgcgcc gttttttatc  2100
gttgttgaga cctctcgcgc agttttggga atcaaccaaa acaagagccc ggcgtcagcg  2160
tttgcttcgc cctcggctgc actcgctcgg cacgcaggta taactgggtg agtaccaagc  2220
cccgcatttg tctgtccgcg atccgcgcac gctgcgggtc aggacgacat cgcgctgcac  2280
```

-continued

```
gtcacagtgg gtcccttttg acgtggctgc ggcgatgagg aggcttggct cggcttcatg  2340
gcaaggcaac agactcgctt ccgggacgcg cacgacgagc agcgctgctt tgatcgacct  2400
tgcctgcgtc accgcctcgg ctgctttgat cgatcgttgt caccggccga gtgaccgcga  2460
acgcattgcc cgcacggctc ggctcggccc ggaccggacc ggctcgcctt ggcggcgcgg  2520
cgcgatggcg acccagacgc ggccggagcc gcgcgcggag gacaaggcca tgttcatctt  2580
cgggctcggg tacgttggga gcaggctcgc caaccagctg gcggaacagg ggtggcgcgt  2640
cgcggggtcg gtgagggagc tcgggcgcga ggacgacttt gccgagttcg aaaagtccaa  2700
gctgagcggc aaggtgcagg tgttccgact cccgcttgag ggcgaggaca acacgcccgc  2760
tcgcgcgcgg gagatactta gcgggtacca gcacctgctg ttcacggcgc cagtggaccg  2820
cgcccggaac tgtgacccct tcttgggcga ccccgttctc ggccccggga taatcgaatt  2880
cggg                                                              2884

SEQ ID NO: 168         moltype = DNA  length = 50
FEATURE                Location/Qualifiers
misc_feature           1..50
                       note = primer
source                 1..50
                       mol_type = other DNA
                       organism = synthetic construct
SEQUENCE: 168
cccgaattca ctagtgattc tcccgggtgg acctagcgcg tgtgtcacct            50

SEQ ID NO: 169         moltype = DNA  length = 40
FEATURE                Location/Qualifiers
misc_feature           1..40
                       note = primer
source                 1..40
                       mol_type = other DNA
                       organism = synthetic construct
SEQUENCE: 169
cccgaattcg attatcccgg ggccgagaac ggggtcgccc                       40

SEQ ID NO: 170         moltype = DNA  length = 1939
FEATURE                Location/Qualifiers
misc_feature           1..1939
                       note = fusion DNA (T. aureum ATCC 34304 C20 elongase
                        upstream/C20 elongase downstream)
source                 1..1939
                       mol_type = other DNA
                       organism = synthetic construct
SEQUENCE: 170
cccgaattca ctagtgattc tcccgggtgg acctagcgcg tgtgtcacct gccggccccc  60
gttgcgtgca accgaattga tcgataatag aattacataa caaacaactt gctggatgag  120
tacaagacca gcgtagtgtg gctgtgggac gttgaacgga gcgggtcctg tgatggcgca  180
gaaaggaact ccgcccgagg tgaaaccccg atgcgcagga ctctgcggcc acagcccctc  240
cgccagtatt ccactaaaaa tccgccccct ttgacaaaga tcgcaacccc gtcccatcaa  300
ctcctcacaa taggctttcc actggcggaa acgtccccgg cacaggagtg cctcccgcgg  360
ttctgcgcat acggctgacc actacgcagc gcgatatcct ccatccgcgt atatatccgt  420
aaacaacgga acattctccc tctcaacgag gcgtggtttt cgaagtcatg cctttcttcc  480
ttcctacttt ccttccttct ttctttcttt ctttccttct tttgcaagcg tgcgcgaact  540
tgaaggtact acttacactt gacagagaga gatagagacg gcaattcgac caagtacttt  600
ccacgatttt tttttttttt gttttggtcg ctttcgttgg tcgtgcatga tggatggccg  660
ggatttttac aattggatgc gccaggctgc cacgcatgcc gtgacgcttg ctcgcggcga  720
ctcatgatgc ttgccagtgg cagtgcatcc agctcttccc tctgctcgtc gtgtactcac  780
tggcgatgct ctcggcgctc gttcaagggc catcgatcga tcgatcgatc gatcgatcga  840
tcaatcacgt ttggtggact cggcagaccc cgaacgtgtt tctcccagga cgcgccgctg  900
tcgctcgcta atccacccga agcgcggtcg gctggcacgg tcgctcggct ggaagttgag  960
tagtttgctt tctgttgctg cgctgctttg taaacgcgac cagatctacc tgtttccggc  1020
tggctcccga gccatgctta ccatgaatga acctgcaaac agtctgaggt ccttgtgcaa  1080
accgctcagt gggacgtcga cgaagaaaga aacaatgtgt actcgtcttg ctctgctccc  1140
gcgccgtttt ttatcgttgt tgagacctct cgcgcagttt tgggaatcaa ccaaaacaag  1200
agcccggcgt cagcgtttgc ttcgccctcg gctgcactcg ctcggcacgc aggtataact  1260
gggtgagtac caagccccgc atttgtctgt ccgcgatccg cgcacgctgc gggtcaggac  1320
gacatcgcgc tgcacgtcac agtgggtccc ttttgacgtg gctgcggcga tgaggaggct  1380
tggctcggct tcatggcaag gcaacagact cgcttccggg acgcgcacga cgagcagcgc  1440
tgctttgatc gaccttgcct gcgtcaccgc ctcggctgct ttgatcgatc gttgtcaccg  1500
gccgagtgac cgcgaacgca ttgcccgcac ggctcggctc ggcccggacc ggaccggctc  1560
gccttggcgg cgcggcgcga tggcgaccca gacgcggccg gagccgcgcg cggaggacaa  1620
ggccatgttc atcttcgggc tcgggtacgt tgggagcagg ctcgccaacc agctggcgga  1680
acaggggtgg cgcgtcgcgg ggtcggtgag ggagctcggg cgcgaggacg actttgccga  1740
gttcgaaaag tccaagctga gcggcaaggt gcaggtgttc cgactcccgc ttgagggcga  1800
ggacaacacg cccgctcgcg cgcgggagat acttagcggg taccagcacc tgctgttcac  1860
ggcgccagtg gaccgcgccc ggaactgtga ccccttcttg ggcgaccccg ttctcggccc  1920
cgggataatc gaattcggg                                              1939

SEQ ID NO: 171         moltype = DNA  length = 38
FEATURE                Location/Qualifiers
misc_feature           1..38
                       note = primer
```

```
source                  1..38
                        mol_type = other DNA
                        organism = synthetic construct
SEQUENCE: 171
cccagatcta cctgtttccg gctggctccc gagccatg                    38

SEQ ID NO: 172          moltype = DNA  length = 38
FEATURE                 Location/Qualifiers
misc_feature            1..38
                        note = primer
source                  1..38
                        mol_type = other DNA
                        organism = synthetic construct
SEQUENCE: 172
cccagatctg gtcgcgttta caaagcagcg cagcaaca                    38

SEQ ID NO: 173          moltype = DNA  length = 31
FEATURE                 Location/Qualifiers
misc_feature            1..31
                        note = primer
source                  1..31
                        mol_type = other DNA
                        organism = synthetic construct
SEQUENCE: 173
ctcccgggtg gacctagcgc gtgtgtcacc t                           31

SEQ ID NO: 174          moltype = DNA  length = 27
FEATURE                 Location/Qualifiers
misc_feature            1..27
                        note = primer
source                  1..27
                        mol_type = other DNA
                        organism = synthetic construct
SEQUENCE: 174
atcccggggc cgagaacgcc ctcgccc                                27

SEQ ID NO: 175          moltype = DNA  length = 3215
FEATURE                 Location/Qualifiers
misc_feature            1..3215
                        note = fusion DNA (T. aureum C20 elongase
                         upstream/ubiquitin promoter/Blar/SV40 terminator/T. aureum
                         C20 elongase downstream)
source                  1..3215
                        mol_type = other DNA
                        organism = synthetic construct
SEQUENCE: 175
ctcccgggtg gacctagcgc gtgtgtcacc tgccggcccc cgttgcgtgc aaccgaattg  60
atcgataata gaattacata acaaacaact tgctggatga gtacaagacc agcgtagtgt  120
ggctgtggga cgttgaacgg agcgggtcct gtgatggcgc agaaaggaac tccgcccgag  180
gtgaaacccc gatgcgcagg actctgcggc cacagcccct ccgccagtat tccactaaaa  240
atccgccccc tttgacaaag atcgcaaccc cgtcccatca actcctcaca ataggctttc  300
cactggcgga aacgtccccg gcacaggagt gcctcccgcg gttctgcgca tgcggctgac  360
cactacgcag cgcgatatcc tccatccgcg tatatatccg taaacaacgg aacattctcc  420
ctctcaacga ggcgtggttt tcgaagtcat gcctttcttc cttcctactt tccttccttc  480
tttctttctt tctttccttc ttttgcaagc gtgcgcgaac ttgaaggtac tacttacact  540
tgacagagag agatagagac ggcaattcga ccaagtactt tccacgattt ttttttttt  600
tgttttggtc gctttcgttg gtcgtgcatg atggatggcc gggattttta caattggatg  660
cgccaggctg ccacgcatgc cgtgacgctt gctcgcggcg actcatgatg cttgccagtg  720
gcagtgcatc cagctcttcc ctctgctcgt cgtgtactca ctggcgatgc tctcggcgct  780
cgttcaaggg ccatcgatcg atcgatcgat cgatcgatcg atcaatcacg tttggtggac  840
tcggcagacc ccgaacgtgt ttctcccagg acgcgccgct gtcgctcgct aatccacccg  900
aagcgcggtc ggctggcacg gtcgctcggc tggaagttga gtagtttgct ttctgttgct  960
gcgctgcttt gtaaacgcga ccagatctgg atctgccgca gcgcctggtg cacccgccgg  1020
gcgttgttgt gtgctcttct tgcctccgag agagagagcg gagcggatgc ataggaaatc  1080
gggccacgcg ggagggccat gcgttcgccc cacacgccac tttccacgcc cgctctctct  1140
ccggccggca ggcagcgcat aactctccga cgctggcagg ctggtagcaa ctggcaggga  1200
caactcgcgc gcgggtcccg gtcgttcgat gtgccaaccc gagagaatcc agccagcagg  1260
gcggttggcc tcatcgccca cctgctatgg tgcagcgaac caactcccga agcggccggt  1320
tctgcgattc cctcttctga attctgaatt ctgaactgat tccggaggag aaccctctgg  1380
aagcgcgggt tgcctctcca gttctgccga actagacagg ggagtgagca gagagtgacc  1440
ctgacgcgga gcgagctggt tgctggaaaa gtcgcgaacg ctgggctgtg tcacgcgtcc  1500
acttcgggca gtccccaaac gacaagcaga acaagcaaca ccagcagcag caagcgacct  1560
aagcaacact agccaacatg gccaagcctt tgtctcaaga agaatccacc ctcattgaaa  1620
gagcaacggc tacaatcaac agcatcccca tctctgaaga ctacagcgtc gccagcgcag  1680
ctctctctag cgacggccgc atcttcactg gtgtcaatgt atatcatttt actgggggac  1740
cttgtgcaga actcgtggtg ctgggcactg ctgctgctgc ggcagctggc aacctgactt  1800
gtatcgtcgc gatcggaaat gagaacaggg gcatcttgag cccctgcgga cggtgccgac  1860
aggtgcttct cgatctgcat cctgggatca aagccatagt gaaggacagt gatggacagc  1920
cgacggcagt tgggattcgt gaattgctgc cctctggtta tgtgtgggag ggctaagatc  1980
```

```
cgcgaaatga ccgaccaagc gacgcccaac ctgccatcac gagatttcga ttccaccgcc  2040
gccttctatg aaaggttggg cttcggaatc gttttccggg acgccggctg gatgatcctc  2100
cagcgcgggg atctcatgct ggagttcttc gcccacccca acttgtttat tgcagcttat  2160
aatggttaca aataaagcaa tagcatcaca aatttcacaa ataaagcatt tttttcactg  2220
cattctagtt gtggtttgtc caaactcatc aatgtatctt atcatgtctg tataccgtcg  2280
acctctagct agatctacct gtttccggct ggctcccgag ccatgcttac catgaatgaa  2340
cctgcaaaca gtctgaggtc cttgtgcaaa ccgctcagtg ggacgtcgac gaagaaagaa  2400
acaatgtgta ctcgtcttgc tctgctcccg cgccgttttt tatcgttgtt gagacctctc  2460
gcgcagtttt gggaatcaac caaaacaaga gcccggcgtc agcgtttgct tcgccctcgg  2520
ctgcactcgc tcggcacgca ggtataactg ggtgagtacc aagccccgca tttgtctgtc  2580
cgcgatccgc gcacgctgcg ggtcaggacg acatcgcgct gcacgtcaca gtgggtccct  2640
tttgacgtgg ctgcggcgat gaggaggctt ggctcggctt catggcaagg caacagactc  2700
gcttccggga cgcgcacgac gagcagcgct gctttgatcg accttgcctg cgtcaccgcc  2760
tcggctgctt tgatcgatcg ttgtcaccgg ccgagtgacc gcgaacgcat tgcccgcacg  2820
gctcggctcg gcccggaccg gaccggctcg ccttggcggc gcggcgcgat ggcgacccag  2880
acgcggccgg agccgcgcgc ggaggacaag gccatgttca tcttcgggct cgggtacgtt  2940
gggagcaggc tcgccaacca gctggcggaa caggggtggc gcgtcgcggg gtcggtgagg  3000
gagctcgggc gcgaggacga ctttgccgag ttcgaaaagt ccaagctgag cggcaaggtg  3060
caggtgttcc aactcccgct tgagggcgag gacaacacgc ccgctcgcgc gcgggagata  3120
cttagcgggt accagcacct gctgttcacg gcgccagtgg accgcgcccg gaactgtgac  3180
cccttcttgg gcgaccccgt tctcggcccc gggat                             3215
```

```
SEQ ID NO: 176          moltype = DNA  length = 3887
FEATURE                 Location/Qualifiers
misc_feature            1..3887
                        note = fusion DNA (T. aureum C20 elongase
                         upstream/ubiquitin promoter/Enhanced GFP/Zeor/SV40
                         terminator/T. aureum C20 elogase downstream)
source                  1..3887
                        mol_type = other DNA
                        organism = synthetic construct
SEQUENCE: 176
ctcccgggtg gacctagcgc gtgtgtcacc tgccggcccc cgttgcgtgc aaccgaattg  60
atcgataata gaattacata acaaacaact tgctggatga gtacaagacc agcgtagtgt  120
ggctgtggga cgttgaacgg agcgggtcct gtgatggcgc agaaaggaac tccgcccgag  180
gtgaaacccc gatgcgcagg actctgcggc cacagcccct ccgccagtat tccactaaaa  240
atccgccccc tttgacaaag atcgcaaccc cgtcccatca actcctcaca ataggctttc  300
cactggcgga aacgtccccg gcacaggagt gcctcccgcg gttctgcgca tacggctgac  360
cactacgcag cgcgatatcc tccatccgcg tatatatccg taaacaacgg aacattctcc  420
ctctcaacga ggcgtggttt tcgaagtcat gcctttcttc cttcctactt tccttccttc  480
tttctttctt tctttccttc ttttgcaagc gtgcgcgaac ttgaaggtac tacttacact  540
tgacagagag agatagagac ggcaattcga ccaagtactt tccacgattt tttttttttt  600
tgttttggtc gctttcgttg gtcgtgcatg atggatggcc gggatttta caattggatg  660
cgccaggctg ccacgcatgc cgtgacgctt gctcgcggcg actcatgatg cttgccagtg  720
gcagtgcatc cagctcttcc ctctgctcgt cgtgtactca ctggcgatgc tctcggcgct  780
cgttcaaggg ccatcgatcg atcgatcgat cgatcgatcg atcaatcacg tttggtggac  840
tcggcagacc ccgaacgtgt ttctcccagg acgcgccgct gtcgctcgct aatccacccg  900
aagcgcggtc ggctggcacg gtcgctcggc tggaagttga gtagtttgct ttctgttgct  960
gcgctgcttt gtaaacgcga ccagatctgc cgcagcgcct ggtgcacccg ccgggcgttg  1020
ttgtgtgctc ttcttgcctc cgagagagag agcggagcgg atgcatagga aatcgggcca  1080
cgcgggaggg ccatgcgttt gccccacacg ccactttcca cgcccgctct ctctccggcc  1140
ggcaggcagc gcataactct ccgacgctgg caggctggta gcaactggca gggacaactc  1200
gcgcgcgggt cccggtcgtt cgatgtgcca acccgagaga atccagccag cagggcggtt  1260
ggcctcatcg cccacctgct atggtgcagc gaaccaactc ccgaagctgc cggttctgcg  1320
attccctctt ctgaattctg aattctgaac tgattccgga ggagaaccct ctggaagcgc  1380
gggttgcctc tccagttctg ccgaactaga caggggagtg agcagagagt gaccctgacg  1440
cggagcgagc tggttgctgg aaaagtcgcg aacgctgggc tgtgtcacgc gtccacttcg  1500
ggcagacccc aaacgacaag cagaacaagc aacaccagca gcagcaagcg atctaagcaa  1560
cactagccaa catggtgagc aagggcgagg agctgttcac cggggtggtg cccatcctgg  1620
tcgagctgga cggcgacgta aacggccaca agttcagcgt gtccggcgag ggcgagggcg  1680
atgccaccta cggcaagctg accctgaagt tcatctgcac caccggcaag ctgcccgtgc  1740
cctggcccac cctcgtgacc accctgacct acggcgtgca gtgcttcagc cgctaccccg  1800
accacatgaa gcagcacgac ttcttcaagt ccgccatgcc cgaaggctac gtccaggagc  1860
gcaccatctt cttcaaggac gacggcaact acaagacccg cgccgaggtg aagttcgagg  1920
gcgacaccct ggtgaaccgc atcgagctga agggcatcga cttcaaggag gacggcaaca  1980
tcctggggca caagctggag tacaactaca acagccacaa cgtctatatc atggccgaca  2040
agcagaagaa cggcatcaag gtgaacttca agatccgcca caacatcgag gacggcagcg  2100
tgcagctcgc cgaccactac cagcagaaca cccccatcgg cgacggcccc gtgctgctgc  2160
ccgacaacca ctacctgagc acccagtccg ccctgagcaa agaccccaac gagaagcgcg  2220
atcacatggt cctgctggag ttcgtgaccg ccgccgggat cactctcggc atggacgcca  2280
agttgaccag tgccgttccg gtgctcaccg cgcgcgacgt cgccggagcg gtcgagttct  2340
ggaccgaccg gctcgggttc tcccgggact tcgtggagga cgacttcgcc ggtgtggtcc  2400
gggacgacgt gaccctgttc atcagcgcgg tccaggacca ggtggtgccg gacaacaccc  2460
tggcctgggt gtgggtgcgc ggcctggacg agctgtacgc cgagtggtcg gaggtcgtgt  2520
ccacgaactt ccgggacgcc tccgggccgg ccatgaccga gatcggcgag cagccgtggg  2580
ggcgggagtt cgccctgcgc gacccggccg gcaactgcgt gcacttcgtg gccgaggagc  2640
aggactgaga tccgcgaaat gaccgaccaa gcgacgccca acctgccatc acgagatttc  2700
gattccaccg ccgccttcta tgaaaggttg ggcttcggaa tcgttttccg ggacgccggc  2760
tggatgatcc tccagcgcgg ggatctcatg ctggagttct tcgcccaccc caacttgttt  2820
```

```
attgcagctt ataatggtta caaataaagc aatagcatca caaatttcac aaataaagca  2880
ttttttcac tgcattctag ttgtggtttg tccaaactca tcaatgtatc ttatcatgtc  2940
tgtataccgt cgacctctag ctagatctac ctgtttccgg ctggctcccg agccatgctt  3000
accatgaatg aacctgcaaa cagtctgagg tccttgtgca aaccgctcag tgggacgtcg  3060
acgaagaaag aaacaatgtg tactcgtctt gctctgctcc cgcgccgttt tttatcgttg  3120
ttgagacctc tcgcgcagtt ttgggaatca accaaaacaa gagcccggcg tcagcgtttg  3180
cttcgccctc ggctgcactc gctcggcacg caggtataac tgggtgagta ccaagccccg  3240
catttgtctg tccgcgatcc gcgcacgctg cgggtcagga cgacatcgcg ctgcacgtca  3300
cagtgggtcc cttttgacgt ggctgcggcg atgaggaggc ttggctcggc ttcatggcaa  3360
ggcaacagac tcgcttccgg gacgcgcacg acgagcagcg ctgctttgat cgaccttgcc  3420
tgcgtcaccg cctcggctgc tttgatcgat cgttgtcacc ggccgagtga ccgcgaacgc  3480
attgcccgca cggctcggct cggcccggac cggaccggct cgccttggcg gcgcggcgcg  3540
atggcgaccc agacgcggcc ggagccgcgc gcggaggaca aggccatgtt catcttcggg  3600
ctcgggtacg ttgggagcag gctcgccaac cagctggcgg aacaggggtg gcgcgtcgcg  3660
gggtcggtga gggagctcgg gcgcgaggac gactttgccg agttcgaaaa gtccaagctg  3720
agcggcaagg tgcaggtgtt ccgactcccg cttgagggcg aggacaacac gcccgctcgc  3780
gcgcgggaga tacttagcgg gtaccagcac ctgctgttca cggcgccagt ggaccgcgcc  3840
cggaactgtg acccccttctt gggcgacccc gttctcggcc ccgggat              3887

SEQ ID NO: 177         moltype = DNA  length = 21
FEATURE                Location/Qualifiers
misc_feature           1..21
                       note = primer
source                 1..21
                       mol_type = other DNA
                       organism = synthetic construct
SEQUENCE: 177
acgtccgctt caaacacctc g                                          21

SEQ ID NO: 178         moltype = DNA  length = 24
FEATURE                Location/Qualifiers
misc_feature           1..24
                       note = primer
source                 1..24
                       mol_type = other DNA
                       organism = synthetic construct
SEQUENCE: 178
tcggaacaac tggaacaact aaag                                       24

SEQ ID NO: 179         moltype = DNA  length = 22
FEATURE                Location/Qualifiers
misc_feature           1..22
                       note = primer
source                 1..22
                       mol_type = other DNA
                       organism = synthetic construct
SEQUENCE: 179
atgtcgctct ccttcttctc ag                                         22

SEQ ID NO: 180         moltype = DNA  length = 21
FEATURE                Location/Qualifiers
misc_feature           1..21
                       note = primer
source                 1..21
                       mol_type = other DNA
                       organism = synthetic construct
SEQUENCE: 180
tcggctcctg gaaagtgctc t                                          21

SEQ ID NO: 181         moltype = DNA  length = 23
FEATURE                Location/Qualifiers
misc_feature           1..23
                       note = primer
source                 1..23
                       mol_type = other DNA
                       organism = synthetic construct
SEQUENCE: 181
ggcggagcga agtgtgaaag tta                                        23

SEQ ID NO: 182         moltype = DNA  length = 24
FEATURE                Location/Qualifiers
misc_feature           1..24
                       note = primer
source                 1..24
                       mol_type = other DNA
                       organism = synthetic construct
SEQUENCE: 182
gcgacagcat cttgaaatag gcag                                       24
```

```
SEQ ID NO: 183          moltype = DNA  length = 2571
FEATURE                 Location/Qualifiers
source                  1..2571
                        mol_type = genomic DNA
                        organism = Thraustochytrium aureum
SEQUENCE: 183
ggcggagcga agtgtgaaag ttacaaccca gttactgccc attcccggga aaagttgcgc  60
agctcacgcg gttcgctttt ctggtggcct ggcgacgttc gccgcttgcc ggatactccc  120
tcgtgccccc gcgccaggtt tgcccgctgt cgctcgagga gtggactcgc gagtcgcgac  180
agcagcagca ccaaggggga tggatcctcg ttgacagcac caagatgctc tctgcctttc  240
aggtgaaatc gatcgatcaa ttgatcaatc aagatcattg gaagcaaatg ggaagcaaat  300
gcgaaggggg aagaccctcg gtctctgctc gggaacccga cacgaggctg agggcgcgct  360
tctacaggtt gtgcagcggc cgcactgcga gcttgcgccg ggccaaggcg ctcgccagaa  420
ttgctgcgtc tgccgcctcg ggatcagcca ctcggttttt cgtcatcagg gtccaccttc  480
aacctggaag tggactcggc aagtcggcag atccactccg gaattccaag atccccggtc  540
gatcggtgct ggtgcgaatt aggatggacc caggctatgt gagagtcgga gggtggcggt  600
tgtctccacc gtgacagcgc gcgtgtggtg agtaacgcga agcgcgtggt ggagaaatgg  660
ggggagattc gtaggacgcg atgcgctcgt cactgagggt gcgccggtga cgaagcttcg  720
gacccagatt ccgtcggtat ggctcgtgtt cgcacacctt caggaacccg catgacgaga  780
ccactggagt tttcaacgtc acgaagccgc tctgtgtgac gagaattggc ttgcgagtga  840
cgtgaggcgc cgagcatgtc gttggtttgc ctcttcacaa cagaatcaga cgactgggag  900
gctgcacgag gctaaggcca agggcactca ctgactcgga cgtgaagcag aagcagaagc  960
agagcgctcg acggcacgtg gcggcagacc ggcttcggga cgggcaggag acgcaaggcg  1020
cgcaacacta gggggctgga cgtggaccac tggctaagga gcgctggaaa gatgacggtc  1080
gggtttgacg aaacggtgac tatggacacg gtccgcaacc acaacatgcc ggacgacgcc  1140
tggtgcgcga tccacggcac cgtgtacgac atcaccaagt tcagcaaggt gcaccccggc  1200
ggggacatca tcatgctggc cgctggcaag gaggccacca tcctgttcga gacctaccac  1260
atcaagggcg tcccggacgc ggtgctgcgc aagtacaagg tcggcaagct cccccagggc  1320
aagaagggcg aaacgagcca cgtgcccacc gggctcgact cggcctccta ctactcgtgg  1380
gacagcgagt tttacagggt gctccgcgag cgcgtcgcca agaagctggc cgagcccggc  1440
ctcatgcagc gcgcgcgcat ggagctctgg gccaaggcga tcttcctcct ggcaggtttc  1500
tggggctccc tttacgccat gtgcgtgcta gacccgcacg gcggtgccat ggtagccgcc  1560
gttacgctcg gcgtgttcgc tgcctttgtc ggaacttgca tccagcacga cggcagccac  1620
ggcgccttct ccaagtcgcg attcatgaac aaggcggcgg gctggaccct cgacatgatc  1680
ggcgcgagcg cgatgacctg ggagatgcag cacgttcttg gccaccaccc gtacaccaac  1740
ctcatcgaga tggagaacgg tttggccaag gtcaagggcg ccgacgtcga cccgaagaag  1800
gtcgaccagg agagcgaccc ggacgtcttc agtacgtacc cgatgcttcg cctgcacccg  1860
tggcaccgcc agcggtttta ccacaagttc cagcacctgt acgccccgtt tatctttggg  1920
tttatgacga ttaacaaggt gatttcccag gatgtcgggg ttgtgctgcg caagcgcctg  1980
ttccagatcg acgccaactg ccggtatggc agcccctggt acgtggcccg cttctggatc  2040
atgaagctcc tcaccacgct ctacatggtg gcgcttccca tgtacatgca ggggcctgct  2100
cagggcttga agcttttctt catggcccac ttcacctgcg gagaggtcct cgccaccatg  2160
tttattgtca accacatcat cgagggcgtc agctacgctt ccaaggacgc ggtcaagggc  2220
gtcatggctc cgccgcgcac tgtgcacggt gtcaccccga tgcaggtgac gcaaaaggcg  2280
ctcagtgcgg ccgagtcgac caagtcggac gccgacaaga cgaccatgat ccccctcaac  2340
gactgggccg ctgtgcagtg ccagacctct gtgaactggg ctgtcgggtc gtggttttgg  2400
aaccactttt cgggcggcct caaccaccag attgagcacc actgcttccc caaaaccccc  2460
acacggtcaa cgtctacatc tcgggcatcg tcaaggagac ctgcgaagaa tacggcgtgc  2520
cgtaccaggc tgagatcagc ctcttctctg cctatttcaa gatgctgtcg c           2571

SEQ ID NO: 184          moltype = DNA  length = 616
FEATURE                 Location/Qualifiers
source                  1..616
                        mol_type = genomic DNA
                        organism = Thraustochytrium aureum
SEQUENCE: 184
cgcaaggcgc gcaacactag gggggctggac gtggaccact ggctaaggag cgctggaaag  60
atgacggtcg ggtttgacga aacggtgact atggacacgg tccgcaacca caacatgccg  120
gacgacgcct ggtgcgcgat ccacggcacc gtgtacgaca tcaccaagtt cagcaaggtg  180
caccccggcg gggacatcat catgctggcc gctggcaagg aggccaccat cctgttcgag  240
acctaccaca tcaagggcgt cccggacgcg gtgctgcgca agtacaaggt cggcaagctc  300
ccccagggca agaagggcga aacgagccac gtgcccaccg ggctcgactc ggcctcctac  360
tactcgtggg acagcgagtt ttacagggtg ctccgcgagc gcgtcgccaa gaagctggcc  420
gagcccggcc tcatgcagcg cgcgcgcatg gagctctggg ccaaggcgat cttcctcctg  480
gcaggtttct ggggctccct ttacgccatg tgcgtgctag acccgcacgg cggtgccatg  540
gtagccgccg ttacgctcgg cgtgttcgct gcctttgtcg gaacttgcat ccagcacgac  600
ggcagccacg gcgcct                                                  616

SEQ ID NO: 185          moltype = DNA  length = 25
FEATURE                 Location/Qualifiers
misc_feature            1..25
                        note = primer
source                  1..25
                        mol_type = other DNA
                        organism = synthetic construct
SEQUENCE: 185
caggagatct ccaagtcgcg attca                                        25

SEQ ID NO: 186          moltype = DNA  length = 26
```

```
FEATURE                Location/Qualifiers
misc_feature           1..26
                       note = primer
source                 1..26
                       mol_type = other DNA
                       organism = synthetic construct
SEQUENCE: 186
cttggagatc tcctgcccgt cccgaa                                        26

SEQ ID NO: 187         moltype = DNA  length = 3264
FEATURE                Location/Qualifiers
misc_feature           1..3264
                       note = fusion DNA (T. aureum delta 4 desaturase
                        upstream/SV40 terminator/BlaR/ubiquitin promoter/T. aureum
                        delta 4 desaturase)
source                 1..3264
                       mol_type = other DNA
                       organism = synthetic construct
SEQUENCE: 187
ggcggagcga agtgtgaaag ttacaaccca gttactgccc attcccggga aaagttgcgc  60
agctcacgcg gttcgctttt ctggtggcct ggcgacgttc gccgcttgcc ggatactccc  120
tcgtgccccc gcgccaggtt tgcccgctgt cgctcgagga gtggactcgc gagtcgcgac  180
agcagcagca ccaaggggga tggatcctcg ttgacagcac caagatgctc tctgcctttc  240
aggtgaaatc gatcgatcaa ttgatcaatc aagatcattg gaagcaaatg ggaagcaaat  300
gcgaaggggg aagaccctcg gtctctgctc gggaacccga cacgaggctg agggcgcgct  360
tctacaggtt gtgcagcggc cgcactgcga gcttgcgccg ggccaaggcg ctcgccagaa  420
ttgctgcgtc tgccgcctcg ggatcagcca ctcggttttt cgtcatcagg gtccaccttc  480
aacctggaag tggactcggc aagtcggcag atccactccg gaattccaag atccccggtc  540
gatcggtgct ggtgcgaatt aggatggacc caggctatgt gagagtcgga gggtggcggt  600
tgtctccacc gtgacagcgc gcgtgtggtg agtaacgcga agcgcgtggt ggagaaatgg  660
ggggagattc gtaggacgcg atgcgctcgt cactgagggt gcgccggtga cgaagcttcg  720
gacccagatt ccgtcggtat ggctcgtgtt cgcacacctt caggaacccg catgacgaga  780
ccactggagt tttcaacgtc acgaagccgc tctgtgtgac gagaattggc ttgcgagtga  840
cgtgaggcgc cgagcatgtc gttggtttgc ctcttcacaa cagaatcaga cgactgggag  900
gctgcacgag gctaaggcca agggcactca ctgactcgga cgtgaagcag aagcagaagc  960
agagcgctcg acggcacgtg gcggcagacc ggcttcggga cgggcaggag atctagctag  1020
aggtcgacgg tatacagaca tgataagata cattgatgag tttggacaaa ccacaactag  1080
aatgcagtga aaaaaatgct ttatttgtga aatttgtgat gctattgctt tatttgtaac  1140
cattataagc tgcaataaac aagttggggt gggcgaagaa ctccagcatg agatccccgc  1200
gctggaggat catccagccg gcgtcccgga aaacgattcc gaagcccaac ctttcataga  1260
aggcggcggt ggaatcgaaa tctcgtgatg gcaggttggg cgtcgcttgg tcggtcattt  1320
cgcggatctt agccctccca cacataacca gagggcagca attcacgaat cccaactgcc  1380
gtcggctgtc catcactgtc cttcactatg gctttgatcc caggatgcag atcgagaagc  1440
acctgtcggc accgtccgca ggggctcaag atgcccctgt tctcatttcc gatcgcgacg  1500
atacaagtca ggttgccagc tgccgcagca gcagcagtgc ccagcaccac gagttctgca  1560
caaggtcccc cagtaaaatg atatacattg acaccagtga agatgcggcc gtcgctagag  1620
agagctgcgc tggcgacgct gtagtcttca gagatgggga tgctgttgat tgtagccgtt  1680
gctctttcaa tgagggtgga ttcttcttga gacaaaggct tggccatgtt ggctagtgtt  1740
gcttaggtcg cttgctgctg ctggtgttgc ttgttctgct tgtcgtttgg ggactgcccg  1800
aagtggacgc gtgacacagc ccagcgttcg cgacttttcc agcaaccagc tcgctccgcg  1860
tcagggtcac tctctgctca ctcccctgtc tagttcggca gaactggaga ggcaaccccgc  1920
gcttccagag ggttctcctc cggaatcagt tcagaattca gaattcagaa gagggaatcg  1980
cagaaccggc cgcttcggga gttggttcgc tgcaccatag caggtgggcg atgaggccaa  2040
ccgccctgct ggctggattc tctcgggttg gcacatcgaa cgaccgggac ccgcgcgcga  2100
gttgtccctg ccagttgcta ccagcctgcc agcgtcggag agttatgcgc tgcctgccgg  2160
ccggagagag agcgggcgtg gaaagtggcg tgtggggcga acgcatggcc ctcccgcgtg  2220
gcccgatttc ctatgcatcc gctccgctct ctctctcgga ggcaagaaga gcacaccaac  2280
aacgcccggc gggtgcacca ggcgctgcgg cagatccaga tctccaagtc gcgattcatg  2340
aacaaggcgg cgggctggac cctcgacatg atcggcgcga gcgcgatgac ctgggagatg  2400
cagcacgttc ttggccacca cccgtacacc aacctcatcg agatggagaa cggtttggcc  2460
aaggtcaagg gcgccgacgt cgacccgaag aaggtcgacc aggagagcga cccggacgtc  2520
ttcagtacgt acccgatgct tcgcctgcac ccgtggcacc gccagcggtt ttaccacaag  2580
ttccagcacc tgtacgcccc gtttatcttt gggtttatga cgattaacaa ggtgatttcc  2640
caggatgtcg gggttgtgct gcgcaagcgc ctgttccaga tcgacgccaa ctgccggtat  2700
ggcagcccct ggtacgtggc ccgcttctgg atcatgaagc tcctcaccac gctctacatg  2760
gtggcgcttc ccatgtacat gcaggggcct gctcagggct tgaagctttt cttcatggcc  2820
cacttcacct gcggagaggt cctcgccacc atgtttattg tcaaccacat catcgagggc  2880
gtcagctacg cttccaagga cgcggtcaag ggcgtcatgg ctccgccgcg cactgtgcac  2940
ggtgtcaccc cgatgcaggt gacgcaaaag gcgctcagtg cggccgagtc gaccaagtcg  3000
gacgccgaca agacgaccat gatccccctc aacgactggg ccgctgtgca gtgccagacc  3060
tctgtgaact gggctgtcgg gtcgtggttt tggaaccact tttcgggcgg cctcaaccac  3120
cagattgagc accactgctt ccccaaaacc cccacacggt caacgtctac atctcgggca  3180
tcgtcaagga gacctgcgaa gaatacggcg tgccgtacca ggctgagatc agcctcttct  3240
ctgcctattt caagatgctg tcgc                                          3264

SEQ ID NO: 188         moltype = DNA  length = 3935
FEATURE                Location/Qualifiers
misc_feature           1..3935
                       note = fusion DNA (T. aureum delta 4 desaturase
```

```
                         upstream/SV40 terminator /ZeoR/Enhanced GFP/ubiquitin
                         promoter/T. aureum delta 4 desaturase)
source                  1..3935
                        mol_type = other DNA
                        organism = synthetic construct
SEQUENCE: 188
ggcggagcga agtgtgaaag ttacaaccca gttactgccc attcccggga aaagttgcgc  60
agctcacgcg gttcgctttt ctggtggcct ggcgacgttc gccgcttgcc ggatactccc  120
tcgtgccccc gcgccaggtt tgcccgctgt cgctcgagga gtggactcgc gagtcgcgac  180
agcagcagca ccaaggggga tggatcctcg ttgacagcac caagatgctc tctgcctttc  240
aggtgaaatc gatcgatcaa ttgatcaatc aagatcattg gaagcaaatg ggaagcaaat  300
gcgaaggggg aagaccctcg gtctctgctc gggaacccga cacgaggctg agggcgcgct  360
tctacaggtt gtgcagcggc cgcactgcga gcttgcgccg ggccaaggcg ctcgccagaa  420
ttgctgcgtc tgccgcctcg ggatcagcca ctcggttttt cgtcatcagg gtccaccttc  480
aacctggaag tggactcggc aagtcggcag atccactccg gaattccaag atccccggtc  540
gatcggtgct ggtgcgaatt aggatggacc caggctatgt gagagtcgga gggtggcggt  600
tgtctccacc gtgacagcgc gcgtgtggtg agtaacgcga agcgcgtggt ggagaaatgg  660
ggggagattc gtaggacgcg atgcgctcgt cactgagggt gcgccggtga cgaagcttcg  720
gacccagatt ccgtcggtat ggctcgtgtt cgcacacctt caggaacccg catgacgaga  780
ccactggagt tttcaacgtc acgaagccgc tctgtgtgac gagaattggc ttgcgagtga  840
cgtgaggcgc cgagcatgtc gttggtttgc ctcttcacaa cagaatcaga cgactgggag  900
gctgcacgag gctaaggcca agggcactca ctgactcgga cgtgaagcag aagcagaagc  960
agagcgctcg acggcacgtg gcggcagacc ggcttcggga cgggcaggag atctagctag  1020
aggtcgacgg tatacagaca tgataagata cattgatgag tttggacaaa ccacaactag  1080
aatgcagtga aaaaaatgct ttatttgtga aatttgtgat gctattgctt tatttgtaac  1140
cattataagc tgcaataaac aagttggggt gggcgaagaa ctccagcatg agatccccgc  1200
gctggaggat catccagccg gcgtcccgga aaacgattcc gaagcccaac ctttcataga  1260
aggcggcggt ggaatcgaaa tctcgtgatg gcaggttggg cgtcgcttgg tcggtcattt  1320
cgcggatctc agtcctgctc ctcggccacg aagtgcacgc agttgccggc cgggtcgcgc  1380
agggcgaact cccgcccca cggctgctcg ccgatctcgg tcatggccgg cccggaggcg  1440
tcccggaagt tcgtggacac gacctccgac cactcggcgt acagctcgtc caggccgcgc  1500
acccacaccc aggccagggt gttgtccggc accacctggt cctggaccgc gctgatgaac  1560
agggtcacgt cgtcccggac cacaccggcg aagtcgtcct ccacgaagtc ccgggagaac  1620
ccgagccggt cggtccagaa ctcgaccgct ccggcgacgt cgcgcgcggt gagcaccgga  1680
acggcactgg tcaacttggc gtccatgccg agagtgatcc cggcggcggt cacgaactcc  1740
agcaggacca tgtgatcgcg cttctcgttg gggtctttgc tcagggcgga ctgggtgctc  1800
aggtagtggt tgtcgggcag cagcacgggg ccgtcgccga tgggggtgtt ctgctggtag  1860
tggtcggcga gctgcacgct gccgtcctcg atgttgtggc ggatcttgaa gttcaccttg  1920
atgccgttct tctgcttgtc ggccatgata tagacgttgt ggctgttgta gttgtactcc  1980
agcttgtgcc ccaggatgtt gccgtcctcc ttgaagtcga tgcccttcag ctcgatgcgg  2040
ttcaccaggg tgtcgccctc gaacttcacc tcggcgcggg tcttgtagtt gccgtcgtcc  2100
ttgaagaaga tggtgcgctc ctggacgtag ccttcgggca tggcggactt gaagaagtcg  2160
tgctgcttca tgtggtcggg gtagcggctg aagcactgca cgccgtaggt cagggtggtc  2220
acgagggtgg gccagggcac gggcagcttg ccggtggtgc agatgaactt cagggtcagc  2280
ttgccgtagg tggcatcgcc ctcgccctcg ccggacacgc tgaacttgtg gccgtttacg  2340
tcgccgtcca gctcgaccag gatgggcacc accccggtga acagctcctc gcccttgctc  2400
accatgttgg ctagtgttgc ttagatcgct tgctgctgct ggtgttgctt gttctgcttg  2460
tcgtttgggg tctgcccgaa gtggacgcgt gacacagccc agcgttcgcg acttttccag  2520
caaccagctc gctccgcgtc agggtcactc tctgctcact cccctgtcta gttcggcaga  2580
actggagagg caacccgcgc ttccagaggg ttctcctccg gaatcagttc agaattcaga  2640
attcagaaga gggaatcgca gaaccggcag cttcgggagt tggttcgctg caccatagca  2700
ggtgggcgat gaggccaacc gccctgctgg ctggattctc tcgggttggc acatcgaacg  2760
accgggaccc gcgcgcgagt tgtccctgcc agttgctacc agcctgccag cgtcggagag  2820
ttatgcgctg cctgccggcc ggagagagag cgggcgtgga aagtggcgtg tggggcaaac  2880
gcatggccct cccgcgtggc ccgatttcct atgcatccgc tccgctctct ctctcggagg  2940
caagaagagc acacaacaac gcccggcggg tgcaccaggc gctgcggcag atctccaagt  3000
cgcgattcat gaacaaggcg gcgggctgga ccctcgacat gatcggcgcg agcgcgatga  3060
cctgggagat gcagcacgtt cttggccacc acccgtacac caacctcatc gagatggaga  3120
acggtttggc caaggtcaag ggcgccgacg tcgacccgaa gaaggtcgac caggagagcg  3180
acccggacgt cttcagtacg tacccgatgc ttcgcctgca cccgtggcac cgccagcggt  3240
tttaccacaa gttccagcac ctgtacgccc cgtttatctt tgggtttatg acgattaaca  3300
aggtgatttc ccaggatgtc ggggttgtgc tgcgcaagcg cctgttccag atcgacgcca  3360
actgccggta tggcagcccc tggtacgtgg cccgcttctg gatcatgaag ctcctcacca  3420
cgctctacat ggtggcgctt cccatgtaca tgcaggggcc tgctcagggc ttgaagcttt  3480
tcttcatggc ccacttcacc tgcggagagg tcctcgccac catgtttatt gtcaaccaca  3540
tcatcgaggg cgtcagctac gcttccaagg acgcggtcaa gggcgtcatg gctccgccgc  3600
gcactgtgca cggtgtcacc ccgatgcagg tgacgcaaaa ggcgctcagt gcggccgagt  3660
cgaccaagtc ggacgccgac aagacgacca tgatcccccct caacgactgg gccgctgtgc  3720
agtgccagac ctctgtgaac tgggctgtcg ggtcgtggtt ttggaaccac ttttcgggcg  3780
gcctcaacca ccagattgag caccactgct tccccaaaac cccccacacgg tcaacgtcta  3840
catctcgggc atcgtcaagg agacctgcga agaatacggc gtgccgtacc aggctgagat  3900
cagcctcttc tctgcctatt tcaagatgct gtcgc                           3935

SEQ ID NO: 189          moltype = DNA  length = 23
FEATURE                 Location/Qualifiers
misc_feature            1..23
                        note = primer
source                  1..23
                        mol_type = other DNA
```

-continued

```
                      organism = synthetic construct
SEQUENCE: 189
aaaagaacaa gccctctcct gga                                       23

SEQ ID NO: 190        moltype = DNA  length = 23
FEATURE               Location/Qualifiers
misc_feature          1..23
                      note = primer
source                1..23
                      mol_type = other DNA
                      organism = synthetic construct
SEQUENCE: 190
gaggtttgta tgttcggcgg ttt                                       23

SEQ ID NO: 191        moltype = DNA  length = 26
FEATURE               Location/Qualifiers
misc_feature          1..26
                      note = primer
source                1..26
                      mol_type = other DNA
                      organism = synthetic construct
SEQUENCE: 191
tgggggacct tgtgcagaac tcgtgg                                    26

SEQ ID NO: 192        moltype = DNA  length = 22
FEATURE               Location/Qualifiers
misc_feature          1..22
                      note = primer
source                1..22
                      mol_type = other DNA
                      organism = synthetic construct
SEQUENCE: 192
gacctacggc gtgcagtgct tc                                        22
```

METHOD FOR PRODUCING MICROBIAL OIL FROM LABYRINTHULID MICROORGANISM CAPABLE OF PRODUCING SAID MICROBIAL OIL

CROSS-REFERENCE OF RELATED APPLICATIONS

This application is a Divisional of application Ser. No. 17/401,894, filed Aug. 13, 2021 which is a Divisional of application Ser. No. 15/740,969, filed Apr. 10, 2018, which is a 371 of International Application No. PCT/JP2016/069825, filed Jul. 4, 2016, which claims priority of Japanese Patent Application No. 2015-134715, filed Jul. 3, 2015, the entire contents of which are incorporated herein by reference.

The sequence listing that is contained in the file named "P171406US02_rep_seq_listing.xml", which is 362 KB and was created on Apr. 29, 2024, is incorporated herein by reference in its entirety.

TECHNICAL FIELD

The present invention relates to microbial oil obtained from a labyrinthulid, a labyrinthulid capable of producing microbial oil, a method for producing the microbial oil and the labyrinthulid, and a use of the microbial oil and the labyrinthulid.

More specifically, the present invention relates to polyunsaturated fatty acids (PUFAs) and the production thereof, and relates to a labyrinthulid genetically modified such that the fatty acid composition is modified, preferably a labyrinthulid that produces PUFAs only via the elongase-desaturase pathway, a method for producing PUFAs using the same, lipids (microbial oils) containing PUFAs produced using the same, and uses thereof.

BACKGROUND ART

Labyrinthulids are eukaryotic microorganisms belonging to the class Labyrinthulomycetes, which includes the order Labyrinthulales and the order Thraustochytriales Labyrinthulids are known to be universally present in oceans. Microorganisms belonging to the order Thraustochytriales are also generically called thraustochytrids.

Labyrinthulids have drawn attention as industrial oil-producing microorganisms. DHA produced by labyrinthulids has been productized as DHA-containing lipid raw materials, high DHA-containing animal feeds, and the like (Non-patent Document 1). Specific examples include breeding techniques for the genus *Thraustochytrium* and genus *Schizochytrium* (Patent Document 1), and techniques for using thraustochytrids and ω-3 HUFAs (highly unsaturated fatty acids) extracted from thraustochytrids (Patent Document 2).

It is generally known that PUFAs are biosynthesized via the elongase-desaturase pathway (also called the standard pathway), but it has also been shown that certain labyrinthulids produce PUFAs via a different pathway, namely a metabolic pathway using polyketide synthase (PKS) (Non-patent Document 2). In the present invention, this pathway will hereinafter be called the PUFA-PKS pathway or the PKS pathway. The compositions of PUFAs produced via this pathway are mostly DHA and n-6 DPA.

There are some scientists who think that labyrinthulids (particularly thraustochytrids) have only the PUFA-PKS pathway as a PUFA biosynthesis pathway, and do not have the general elongase-desaturase pathway found in other organisms (Non-patent Document 3). Actually, it has been reported that by gene-isruption of the PUFA-PKS pathway, some labyrinthulids are rendered lethal and such labyrinthulids cannot be grown unless PUFAs are added to the culture medium (Non-patent Document 3). This result means that since PUFAs are required for growth of these labyrinthulids and the gene of the PUFA-PKS pathway, which is the sole PUFA biosynthesis pathway, has been disrupted, the nature of the labyrinthulids has changed into exogenous PUFAs requirement for growth.

However, contrary to common knowledge of persons skilled in the art, some labyrinthulids having both the PUFA-PKS pathway and the elongase-desaturase pathway as PUFA biosynthesis pathways have been found through our examinations. These are specifically described in the specification of Patent Document 3 and in Non-patent Document 5.

Citing *Thraustochytrium aureum* ATCC 34304 as an example, it has been found that this strain has a Δ12 desaturase gene, which is an entry enzyme of the elongase-desaturase pathway. Furthermore, it has been found that a strain in which this gene was disrupted by homologous recombination accumulates predominantly oleic acid, which is the substrate of Δ12 desaturase, compared to the wild-type strain, and that decreases in both linoleic acid of the product and PUFAs located downstream of the biosynthesis system thereof were observed. Additionally, it has been found that because this strain is capable of producing PUFAs via the elongase-desaturase pathway, by disruption of the PUFA-PKS pathway gene it is not rendered lethal. This report was the first to show that the elongase-desaturase pathway also functions as a PUFA biosynthesis pathway in labyrinthulids, and was discussed in Non-patent Document 6 as well.

At the start, Non-patent Document 6 states that labyrinthulids that produce DHA as the main fatty acid are widely used industrially. In contrast, the creation of labyrinthulids containing desired PUFAs other than DHA as the main fatty acid was first enabled by the discovery of labyrinthulids having both the PUFA-PKS pathway and the elongase-desaturase pathway and by application of transformation techniques to these labyrinthulids (Patent Document 3, Non-patent Document 7). That is, it is possible to create strains containing certain PUFAs other than DHA as the main fatty acid by first disrupting the genes of the PUFA-PKS pathway with homologous recombination technique, and then disrupting or overexpressing the genes of the enzymes constituting the elongase-desaturase pathway appropriately. Example 12 of Patent Document 3 is cited as a specific example. In this example, the PUFA-PKS pathway genes of *Thraustochytrium aureum* ATCC 34304 were disrupted, and then the C20 elongase gene was disrupted. An (>3 desaturase gene derived from Saprolegnia diclina was then transformed, thereby successfully creating a strain in which arachidonic acid increased approximately 6-fold, EPA increased approximately 10-fold, and DHA decreased approximately 1/16 in comparisonwith the wild-type strain.

CITATION LIST

Patent Documents

Patent Document 1: JP 3127161 B
Patent Document 2: JP 3669372 B
Patent Document 3: WO 2012/043826
Patent Document 4: US 2005/0,014,231 A

Non-Patent Documents

Non-patent Document 1: Zvi Cohen et al. editors, "Single Cell Oils Microbial and Algal Oils 2nd edition", (U.S.), AOCS Press, 2010, p. 88
Non-patent Document 2: Metz J G, Roessler P, Faccioti D, et al. Production of polyunsaturated fatty acids by polyketide synthesis in both prokaryotes and eukaryotes. Science 2001; 293: 290-293
Non-patent Document 3: Ratledge C. Omega-3 biotechnology: Errors and omissions, Biotechnology Advances 30 (2012) 1746-1747
Non-patent Document 4: Lippmeier J. C. et al., Lipids, 44 (7), 621-630 (2009)
Non-patent Document 5: Matsuda T, Sakaguchi K, Hamaguchi R, Kobayashi T, Abe E, HamaY, Hayashi M, Honda D, OkitaY, Sugimoto S, Okino N, Ito M. The analysis of delta12 fatty acid desaturase function revealed that two distinct pathways are active for the synthesis of polyunsaturated fatty acids in *Thraustochytrium aureum* ATCC 34304. J. Lipid Res. 53 (6): 1210-1222 (2012)
Non-patent Document 6: ASBMB Today, June 2012, p. 30
Non-patent Document 7: Sakaguchi K, et al., Versatile Transformation System That Is Applicable to both Multiple Transgene Expression and Gene Targeting for Thraustochytrids. Appl. Environ. Microbiol. 78 (9): 3193-3202 (2012)
Non-patent Document 8: Yazawa K., Lipids, 31, Supple. 297-300 (1996)
Non-patent Document 9: Journal of the Japan Society for Bioscience, Biotechnology and Agrochem, 77, 2, 150-153 (2003)
Non-patent Document 10: "Illustrated Bio Experiments Vol. 2 Fundamentals of Gene Analysis", p. 63-68, Shujunsha, published 1995
Non-patent Document 11: Sanger, F. et al., Proc. Natl. Acad. Sci., 74, 5463 (1997)
Non-patent Document 12: Cigan and Donahue, 1987; Romanos et al., 1992
Non-patent Document 13: Ausubel F. M. et al., Current Protocols in Molecular Biology, Unit 13 (1994)
Non-patent Document 14: Guthrie C., Fink G. et al., Methods in Enzymology: Guide to Yeast Genetics and Molecular Biology, Volume 194 (1991)
Non-patent Document 15: Qiu, X. et al. J. Biol. Chem., 276, 31561-6 (2001)
Non-patent Document 16: Abe E., et al., J. Biochem., 140, 247-253 (2006)
Non-patent Document 17: "Illustrated Bio Experiments Vol. 2 Fundamentals of Gene Analysis", p. 117-128, Shujunsha, published 1995
Non-patent Document 18: DIG Manual (Japanese Edition) 8th, Roche Applied Science

SUMMARY OF THE INVENTION

Problem that the Invention is to Solve

The present invention is directed to provide a labyrinthulid genetically modified such that the fatty acid composition is modified, preferably a labyrinthulid that produces PUFAs only via the elongase-desaturase pathway. the invention provides a method for producing PUFAs using the labyrinthulid thereof, lipids (microbial oils) containing PUFAs produced using the method thereof, and uses thereof.

To create a strain containing certain PUFAs other than DHA as the main fatty acids using labyrinthulids having both the PUFA-PKS pathway and the elongase-desaturase pathway, first of all, DHA production via the PUFA-PKS pathway needs to be stopped or inhibited by any means. Specifically, methods such as disrupting PUFA-PKS pathway gene with homologous recombination technique, acquisition of a spontaneous mutant by UV irradiation, drug treatment, or the like, and silencing of PUFA-PKS genes by RNAi (RNA interference), and the like may be considered.

Among these methods, gene-disruption with homologous recombination technique previously described has been technically established. However, the number of drug resistance genes that can be used as markers is generally limited, and there is the problem that when a marker is used in PUFA-PKS pathway gene disruption, the number of markers that can be used in further gene disruption or gene transfer will decrease. This means a decrease in the number of times that gene-disruption and gene-transfer can be implemented after PUFA-PKS pathway gene is disrupted, and thus it becomes an obstacle to create higher-performance strains.

Furthermore, spontaneous mutation and silencing by RNAi are methods with a track record in other organisms but it is unknown whether a desired strain in labyrinthulids can be acquired by these methods.

The present invention is directed to provide a labyrinthulid having very weak or no PUFA-producing activity via the endogenous PUFA-PKS pathway and having PUFA producing activity via the endogenous elongase-desaturase pathway, a method for producing lipids containing PUFAs produced using the labyrinthulid thereof, and lipids containing PUFAs produced using the labyrinthulid thereof.

Means for Solving the Problems

The present inventors conducted a diligent research, and discovered the existence of labyrinthulids having very weak or no PUFA producting activity via the endogenous PUFA-PKS pathway and having PUFA-producing activity via the endogenous elongase-desaturase pathway. And the present invention was accomplished pertaining to microbial oil obtained from labyrinthulids thereof, microbial oil-producing labyrinthulids, methods for producing microbial oil thereof, and uses of microbial oils.

In one aspect of the present invention, a method for producing a microbial oil includes the steps of genetically modifying a labyrinthulid by disrupting and/or silencing a gene, or by transforming another gene in addition to the disruption and/or gene silencing of the gene, and culturing the labyrinthulid, such that a fatty acid composition accumulated in the labyrinthulid comprises an increased EPA content; and collecting the microbial oil having the increased EPA content from the labyrinthulid. The labyrinthulid before the modification is selected from the group consisting of (A) and (B): (A) a labyrinthulid belonging to the genus *Parietichytrium* or genus *Schizochytrium* as disclosed below in detail, and having very weak or no activity of producing PUFAs via a PUFA-PKS pathway; and (B) a labyrinthulid belonging to the genus *Thraustochytrium* as disclosed below in detail, in which a host PUFA-PKS gene is disrupted or silenced to a very weak level. The disrupted and/or silenced gene is a fatty acid elongase gene and/or a fatty acid desaturase gene. The transformed another gene is a fatty acid elongase gene and/or a fatty acid desaturase gene. Typically, the increased EPA content is not less than 11.5% of a total fatty acid composition in labyrinthulid. The fatty acid elongase gene is a C20 elongase gene, and/or wherein the fatty acid desaturase gene is a Δ4 desaturase gene and/or an ω3 desaturase gene. The step of disrupting or transforming the gene of a labyrinthulid may utilize electroporation, a gene gun method, or gene editing, and/or wherein the step of silencing the gene utilizes an antisense method or RNA. The present invention can provide microbial oil produced by the method according to claim 1, wherein the microbial oil satisfies not less than one condition selected from the group consisting of (a) to (d):

(a) ARA is not less than 13.2% of the total fatty acid composition;

(b) The total of ARA and EPA is not less than 36.8% of the total fatty acid composition;

(c) DHA is not greater than 1.3% of the total fatty acid composition; and (d) the total of DHA and n-6 DPA is not greater than 2.9% of the total fatty acid composition.

Further, the microbial oil may satisfy not less than one condition selected from the group consisting of (e) to (h):

(e) ARA is not less than 21.3% of the total fatty acid composition;

(f) EPA is not less than 23.8% of the total fatty acid composition;

(g) DHA is not greater than 0.5% of the total fatty acid composition; and (h) The total of DHA and n-6 DPA is not greater than 0.7% of the total fatty acid composition.

Preferably, the microbial oil satisfies a condition that a GC area ratio of ARA after modification is not less than 4 times greater than before modification, the GC area is a peak area in a GC chart obtained by gas chromatography analysis. The microbial oil satisfies a condition that a GC area ratio of EPA after modification is not less than 8 times greater than before modification, the GC area is a peak area in a GC chart obtained by gas chromatography analysis.

In another aspect of the present invention, a labyrinthulid has been genetically modified by disrupting and/or silencing a gene, or by transforming another gene in addition to the disruption and/or gene silencing of the gene such that a fatty acid composition accumulated in the labyrinthulid comprises an increased EPA content. The labyrinthulid before the modification is selected from the group consisting of (A) and (B): (A) a labyrinthulid belonging to the genus *Parietichytrium* or genus *Schizochytrium* and having very weak or no activity of producing PUFAs via a PUFA-PKS pathway; and (B) a labyrinthulid belonging to the genus *Thraustochytrium* in which a host PUFA-PKS gene is disrupted or silenced to a very weak level. The disrupted and/or silenced gene is a fatty acid elongase gene and/or a fatty acid desaturase gene. The transformed another gene is a fatty acid elongase gene and/or a fatty acid desaturase gene. The increased EPA content is not less than 11.5% of a total fatty acid composition. The fatty acid composition may satisfy not less than one condition selected from the group consisting of (a) to (d):

(a) ARA is not less than 13.2% of the total fatty acid composition;

(b) The total of ARA and EPA is not less than 36.8% of the total fatty acid composition;

(c) DHA is not greater than 1.3% of the total fatty acid composition; and (d) the total of DHA and n-6 DPA is not greater than 2.9% of the total fatty acid composition.

Further, the fatty acid composition satisfies not less than one condition selected from the group consisting of (e) to (h):

(e) ARA is not less than 21.3% of the total fatty acid composition;

(f) EPA is not less than 23.8% of the total fatty acid composition;

(g) DHA is not greater than 0.5% of the total fatty acid composition; and (h) The total of DHA and n-6 DPA is not greater than 0.7% of the total fatty acid composition.

In yet another aspect, the present disclosure includes the following microbial oils (1) to (28).

(1) Microbial oil satisfying at least one condition selected from the group consisting of (a) to (g) below.

(a) ARA is not less than 5% of the total fatty acid composition.

(b) DGLA is not less than 2.5% of the total fatty acid composition.

(c) ETA is not less than 0.35% of the total fatty acid composition.

(d) EPA is not less than 4% of the total fatty acid composition.

(e) n-6 DPA is not greater than 0.20% of the total fatty acid composition.

(f) DHA is not greater than 0.50% of the total fatty acid composition.

(g) The total of DHA and n-6 DPA is not greater than 0.7% of the total fatty acid composition.

(2) The microbial oil according to (1), wherein the microbial oil satisfies at least one condition selected from the group consisting of (h) to (1) below.

(h) The value of LA/DHA by GC area is not less than 0.6 and not greater than 10.

(i) The value of GLA/DHA by GC area is not less than 0.35 and not greater than 10.

(j) The value of DGLA/DHA by GC area is not less than 0.35 and not greater than 10.

(k) The value of ARA/DHA by GC area is not less than 0.7 and not greater than 50.

(l) The value of EPA/DHA by GC area is not less than 0.35 and not greater than 50.

(3) The microbial oil according to (1) or (2), wherein the microbial oil satisfies at least one condition selected from the group consisting of (in) to (o) below.

(m) The value of LA/EPA by GC area is not less than 0.06 and not greater than 0.17.

(n) The value of GLA/EPA by GC area is not less than 0.04 and not greater than 0.12.

(o) The value of DTA/EPA by GC area is not less than 0.01 and not greater than 0.4.

(4) The microbial oil according to any one of (1) to (3), wherein the microbial oil satisfies the condition that the value of DTA/ARA by GC area is not less than 0.01 and not greater than 0.45.

(5) The microbial oil according to any one of (1) to (4), wherein the microbial oil satisfies the condition that the value of DTA/DGLA by GC area is not less than 0.01 and not greater than 1.45.

(6) The microbial oil according to any one of (1) to (5), wherein the microbial oil satisfies at least one condition selected from the group consisting of (p) to (t) below.

(p) The value of LA/n-6 DPA by GC area is not less than 0.4 and not greater than 20.

(q) The value of GLA/n-6 DPA by GC area is not less than 0.2 and not greater than 10.

(r) The value of DGLA/n-6 DPA by GC area is not less than 0.35 and not greater than 30.

(s) The value of ARA/n-6 DPA by GC area is not less than 0.7 and not greater than 60.

(t) The value of EPA/n-6 DPA by GC area is not less than 1.0 and not greater than 70.

(7) The microbial oil according to any one of (1) to (6), wherein the microbial oil satisfies at least one condition selected from the group consisting of (u) to (x) below.

(u) The value of DGLA/LA by GC area is not less than 1.4 and not greater than 10.

(v) The value of ARA/LA by GC area is not less than 5.1 and not greater than 20.

(w) The value of EPA/LA by GC area is not less than 5.5 and not greater than 30.

(x) The value of DTA/LA by GC area is not less than 0.01 and not greate than 0.4.

(8) The microbial oil according to any one of (1) to (7), wherein the microbial oil satisfies at least one condition selected from the group consisting of (y) and (z) below.

(y) The value of DGLA/GLA by GC area is not less than 4.5 and not greater than 20.

(z) The value of ARA/GLA by GC area is not less than 9 and not greater than 30.

(9) The microbial oil according to any one of (1) to (8), wherein the microbial oil satisfies the condition that the value of n-6 DPA/DTA by GC area is not greater than 1.5.

(10) The microbial oil according to any one of (1) to (9), wherein the microbial oil satisfies the condition that the value of DHA/n-3 DPA by GC area is not greater than 4.

(11) The microbial oil according to any one of (1) to (10), wherein the microbial oil satisfies the condition that the value of C20 PUFA/C22 PUFA by GC area is not less than 0.5 and not greater than 50.

(12) The microbial oil according to any one of (1) to (11), wherein the microbial oil satisfies the condition that the value of n-6 PUFA/n-3 PUFA by GC area is not less than 1.8.

(13) A microbial oil obtained from a labyrinthulid genetically modified such that the fatty acid composition is modified, the labyrinthulid being selected from the group consisting of (A) and (B) below.

(A) A labyrinthulid in which the fatty acid composition is modified by disruption and/or gene silencing.

(B) A labyrinthulid in which the fatty acid composition is modified by transforming a gene in addition to disruption and/or gene silencing.

(14) The microbial oil according to (13), wherein the disrupted and/or silenced gene is a PKS gene, a fatty acid elongase gene, and/or a fatty acid desaturase gene.

(15) The microbial oil according to (13) or (14), wherein the transformed gene is a fatty acid elongase gene and/or a fatty acid desaturase gene.

(16) The microbial oil according to (14) or (15), wherein the fatty acid elongase gene is the C20 elongase gene.

(17) The microbial oil according to any one of (13) to (16), wherein the fatty acid desaturase gene is the A4 desaturase gene and/or the (>3 desaturase gene.

(18) The microbial oil according to any one of (13) to (17), wherein the method for disrupting or transforming a gene of a labyrinthulid is electroporation, a gene gun method, or gene editing.

(19) The microbial oil according to any one of (13) to (18), wherein the method for gene silencing of a labyrinthulid is an antisense method or RNA interference.

(20) A microbial oil obtained from a labyrinthulid selected from the group consisting of (C) and (D) below.

(C) A labyrinthulid having very weak or no activity of producing PUFAs via the PUFA-PKS pathway.

(D) A labyrinthulid in which the host PUFA-PKS gene is disrupted or silenced to a very weak level.

(21) The microbial oil according to (20), wherein the labyrinthulid having very weak or no activity of producing PUFAs via the PUFA-PKS pathway is a labyrinthulid belonging to the genus *Parietichytrium* or genus *Schizochytrium.*

(22) The microbial oil according to (21), wherein the labyrinthulid belonging to the genus Parietichytriumis a labyrinthulid belonging to *Parietichytrium sarkarianum.*

(23) The microbial oil according to (21), wherein the labyrinthulid belonging to the genus *Schizochytrium* is a labyrinthulid belonging to *Schizochytrium aggregatum.*

(24) The microbial oil according to (22), wherein the microorganism belonging to *Parietichytrium sarkarianum* is *Parietichytrium* sp. SEK358 (FERM BP-11405), *Parietichytrium sarkarianum* SEK364 (FERM BP-11298), or *Parietichytrium* sp. SEK517 (FERM BP-11406).

(25) The microbial oil according to (23), wherein the microorganism belonging to *Schizochytrium aggregatum* is *Schizochytrium aggregatum* ATCC 28209.

(26) The microbial oil according to (20), wherein the labyrinthulid in which the host PUFA-PKS is disrupted or silenced to a very weak level belongs to the genus *Thraustochytrium.*

(27) The microbial oil according to (26), wherein the labyrinthulid belonging to the genus *Thraustochytrium* is *Thraustochytrium aureum.*

(28) A microbial oil that satisfies at least one condition selected from the group consisting of (E) to (H) below.

(E) A GC area ratio of ARA after modification is not less than 3 times greater than before modification.

(F) A GC area ratio of DGLA after modification is not less than 4 times greater than before modification.

(G) A GC area ratio of ETA after modification is not less than 7 times greater than before modification.

(H) A GC area ratio of EPA after modification is not less than 7 times greater than before modification.

The gist of the present invention includes the following methods for producing microbial oil (29) to (56).

(29) A method for producing microbial oil satisfying at least one condition selected from the group consisting of (a) to (g) below.

(a) ARA is not less than 5% of the total fatty acid composition.

(b) DGLA is not less than 2.5% of the total fatty acid composition.

(c) ETA is not less than 0.35% of the total fatty acid composition.

(d) EPA is not less than 4% of the total fatty acid composition.

(e) n-6 DPA is not greater than 0.20% of the total fatty acid composition.

(f) DHA is not greater than 0.50% of the total fatty acid composition.

(g) The total of DHA and n-6 DPA is not greater than 0.7% of the total fatty acid composition.

(30) The method for producing microbial oil according to (29), wherein the microbial oil satisfies at least one condition selected from the group consisting of (h) to (l) below.

(h) The value of LA/DHA by GC area is not less than 0.6 and not greater than 10.

(i) The value of GLA/DHA by GC area is not less than 0.35 and not greater than 10.

(j) The value of DGLA/DHA by GC area is not less than 0.35 and not greater than 10.

(k) The value of ARA/DHA by GC area is not less than 0.7 and not greater than 50.

(l) The value of EPA/DHA by GC area is not less than 0.35 and not greater than 50.

(31) The method for producing microbial oil according to (29) or (30), wherein the microbial oil satisfies at least one condition selected from the group consisting of (m) to (o) below.

(m) The value of LA/EPA by GC area is not less than 0.06 and not greater than 0.17.

(n) The value of GLA/EPA by GC area is not less than 0.04 and not greater than 0.12.

(o) The value of DTA/EPA by GC area is not less than 0.01 and not greater than 0.4.

(32) The method for producing microbial oil according to any one of (29) to (31), wherein the microbial oil satisfies the condition that the value of DTA/ARA by GC area is not less than 0.01 and not greater than 0.45.

(33) The method for producing microbial oil according to any one of (29) to (32), wherein the microbial oil satisfies the condition that the value of DTA/DGLA by GC area is not less than 0.01 and not greater than 1.8.

(34) The method for producing microbial oil according to any one of (29) to (33), wherein the microbial oil satisfies at least one condition selected from the group consisting of (p) to (t) below.

(p) The value of LA/n-6 DPA by GC area is not less than 0.4 and not greater than 20.

(q) The value of GLA/n-6 DPA by GC area is not less than 0.2 and not greater than 10.

(r) The value of DGLA/n-6 DPA by GC area is not less than 0.35 and not greater than 30.

(s) The value of ARA/n-6 DPA by GC area is not less than 0.7 and not greater than 60.

(t) The value of EPA/n-6 DPA by GC area is not less than 0.4 and not greater than 70.

(35) The method for producing microbial oil according to any one of (29) to (34), wherein the microbial oil satisfies at least one condition selected from the group consisting of (u) to (x) below.

(u) The value of DGLA/LA by GC area is not less than 1.4 and not greater than 10.

(v) The value of ARA/LA by GC area is not less than 5.1 and not greater than 20.

(w) The value of EPA/LA by GC area is not less than 5.5 and not greater than 30.

(x) The value of DTA/LA by GC area is not less than 0.01 and not greater than 0.4.

(36) The method for producing microbial oil according to any one of (29) to (35), wherein the microbial oil satisfies at least one condition selected from the group consisting of (y) and (z) below.

(y) The value of DGLA/GLA by GC area is not less than 4.5 and not greater than 20.

(z) The value of ARA/GLA by GC area is not less than 9 and not greater than 30.

(37) The method for producing microbial oil according to any one of (29) to (36), wherein the microbial oil has a value of n-6 DPA/DTA by GC area of not greater than 1.5.

(38) The method for producing microbial oil according to any one of (29) to (37), wherein the microbial oil has a value of DHA/n-3 DPA by GC area of not greater than 4.

(39) The method for producing microbial oil according to any one of (29) to (38), wherein the microbial oil satisfies the condition that the value of C20 PUFA/C22 PUFA by GC area is not less than 0.5 and not greater than 50.

(40) The method for producing microbial oil according to any one of (29) to (39), wherein the microbial oil satisfies the condition that the value of n-6 PUFA/n-3 PUFA by GC area is not less than 1.8.

(41) A method for producing microbial oil whereby microbial oil is caused to be produced in a labyrinthulid genetically modified such that the fatty acid composition is modified, the labyrinthulid being selected from the group consisting of (A) and (B) below.

(A) A labyrinthulid in which the fatty acid composition is modified by gene-disruption and/or gene silencing.

(B) A labyrinthulid in which the fatty acid composition is modified by transforming a gene in addition to disruption and/or gene silencing.

(42) The method for producing microbial oil according to (41), wherein the disrupted and/or silenced gene is a PKS gene, a fatty acid elongase gene, and/or a fatty acid desaturase gene.

(43) The method for producing microbial oil according to (41) or (42), wherein the transformed gene is a fatty acid elongase gene and/or a fatty acid desaturase gene.

(44) The method for producing microbial oil according to (42) or (43), wherein the fatty acid elongase gene is the C20 elongase gene.

(45) The method for producing microbial oil according to any one of claims 41 to 44, wherein the fatty acid desaturase gene is the A4 desaturase gene and/or the >3 desaturase gene.

(46) The method for producing microbial oil according to any one of (41) to (45), wherein the method for disrupting or transforming a gene of a labyrinthulid is electroporation, a gene gun method, or gene editing.

(47) The method for producing microbial oil according to any one of (41) to (46), wherein the method for gene silencing of a labyrinthulid is an antisense method or RNA interference.

(48) A method for producing microbial oil, wherein microbial oil is caused to be produced in a labyrinthulid selected from the group consisting of (C) and (D) below.

(C) A labyrinthulid having very weak or no activity of producing PUFAs via the PUFA-PKS pathway.

(D) A labyrinthulid in which the host PUFA-PKS gene is disrupted or silenced to a very weak level.

(49) The method for producing microbial oil according to (48), wherein the labyrinthulid having very weak or no activity of producing PUFAs via the PUFA-PKS pathway is a labyrinthulid belonging to the genus *Parietichytrium* or genus *Schizochytrium*.

(50) The method for producing microbial oil according to (49), wherein the labyrinthulid belonging to the genus *Parietichytrium* is a labyrinthulid belonging to *Parietichytrium sarkarianum.*

(51) The method for producing microbial oil according to (50), wherein the labyrinthulid belonging to the genus *Schizochytrium* is a labyrinthulid belonging to *Schizochytrium aggregatum.*

(52) The method for producing microbial oil according to (50), wherein the microorganism belonging to *Parietichytrium sarkarianum* is *Parietichytrium* sp. SEK358 (FERM BP-11405), *Parietichytrium sarkarianum* SEK364 (FERM BP-11298), or *Parietichytrium* sp. SEK517 (FERM BP-11406).

(53) The method for producing microbial oil according to (51), wherein the microorganism belonging to *Schizochytrium aggregatum* is *Schizochytrium aggregatum* ATCC 28209.

(54) The method for producing microbial oil according to (48), wherein the labyrinthulid in which the host PUFA-PKS gene is disrupted or silenced to a very weak level belongs to the genus *Thraustochytrium.*

(55) The method for producing microbial oil according to (54), wherein the labyrinthulid belonging to the genus *Thraustochytrium* is *Thraustochytrium aureum.*

(56) A method for producing microbial oil satisfying at least one condition selected from the group consisting of (E) to (H) below.

(E) The GC area ratio of ARA after modification is not less than 3 times greater than before modification.

(F) The GC area ratio of DGLA after modification is not less than 4 times greater than before modification.

(G) The GC area ratio of ETA after modification is not less than 7 times greater than before modification.

(H) The GC area ratio of EPA after modification is not less than 7 times greater than before modification.

Furthermore, the gist of the present invention includes the following food, animal feed, medication, or industrial product (57), the following genetically modified labyrinthulid (58), and the following method for creating the genetically modified labyrinthulid (59).

(57) A food, animal feed, medication, or industrial product including the microbial oil described in any one of (1) to (28) as a lipid composition.

(58) A labyrinthulid genetically modified such that a produced fatty acid composition is modified, the labyrinthulid producing the microbial oil described in any one of (1) to (28).

(59) A method for creating the labyrinthulid genetically modified such that the produced fatty acid composition described in (58) is modified.

BRIEF DESCRIPTION OF DRAWINGS

FIG. 13 lists the fatty acid proportions of the C20 elongase gene disruption strain when the *Parietichytrium sarkarianum* SEK364 wild-type strain is taken as 100%.

FIG. 22 shows a comparison of the fatty acid compositions of the *Parietichytrium sarkarianum* SEK364 wild-type strain and the Δ4 desaturase gene disruption strain thereof. This table is a quantification of the chart of FIG. 20. In the table, the less-than sign (<) indicates less than or equal to the number following it.

FIG. 34 lists the fatty acid proportions of the C20 elongase gene disruption strain derived from the *Parietichytrium* sp. SEK571 strain when the *Parietichytrium* sp. SEK571 wild-type strain is taken as 100%.

FIG. 35 illustrates results of RACE in which an elongase gene derived from *T. aureum* ATCC 34304 is amplified in Comparative Example 1-2. (Brief description of symbols) 1: 5'-RACE using synthetic adapter-specific oligonucleotide and degenerate oligonucleotide elo-R; 2: 3'-RACE using synthetic adapter-specific oligonucleotide and degenerate oligonucleotide elo-F; 3: 5'-RACE using only elo-R (negative control); 4: 3'-RACE using only elo-F (negative control); 5: 5'-RACE using only synthetic adapter-specific oligonucleotide (negative control); 6: 3'-RACE using only synthetic adapter-specific oligonucleotide (negative control)

FIGS. 36A and 36B illustrate an evaluation of a transformant into which KONeor was transformed in Comparative Example 1-7. FIG. 36A illustrates the oligonucleotide primer pair used in evaluation of the transformant by PCR using genome DNA as a template. (Brief description of symbols) (1) Neor detection primers (SNeoF and SNeoR); (2) KO confirmation 1 (KO Pro F SmaI and KO Term R SmaI); (3) KO confirmation 2 (E2 KO ProF EcoRV and SNeoR); (4) KO confirmation 3 (SNeoF and E2 KO Term R EcoRV); (5) TaELO2 detection (E2 HindIII and E2 XbaI). FIG. 36B illustrates the agarose electrophoresis diagram in evaluation of the transformant by PCR using genome DNA as a template. (Brief description of symbols) 1, 5, 9, 13, 17: Transformant; 2, 6, 10, 14, 18: Wild-type strain; 3, 7, 11, 15, 19: Using KONeor as a template; 4, 8, 12, 16: No template. Furthermore, the used oligonucleotide primer pairs (1) to (5) are the lane numbers.

FIG. 37 illustrates the results of confirmation of TaELO2 copy number by southern blotting in Comparative Example 1-8. (Brief description of symbols) 1: Genome DNA (2.5 μg), BamHI treatment; 2: BglII treatment; 3: EcoRI treatment; 4: EcoRV treatment; 5: HindIII treatment; 6: KpnI treatment; 7: SmaI treatment; 8: XbaI treatment; 9: Positive control (PCR product amplified with 1 ng of E2 KO Pro F EcoRV and E2 KO Term R EcoRV. Including TaELO2.)

FIG. 38A is a schematic diagram of southern blotting to detect a wild-type allele or mutant allele by TKONeor transfer. FIG. 38B illustrates the results of southern blotting. (Brief description of symbols) 1*: T. aureum* wild-type strain (2.5 μg of genome DNA); 2, 3: TKONeor transfer transformant (2.5 μg of genome DNA); 4: Positive control (PCR product amplified with 50 ng of E2 KO ProF EcoRV and E2 KO Term R EcoRV. Includes TaELO2.) FIG. 39A illustrates the oligonucleotide primer pair used. (Brief description of symbols) (1) TaELO2 ORF detection (SNeoF and SNeoR); (2) KO confirmation (E2 KO Pro F EcoRV and ubi-hygro R)

FIG. 39B illustrates the agarose electrophoresis diagram of PCR using oligonucleotide primer pair (1) of KO confirmation. The arrows indicate the transformant of which specific product amplification was confirmed and which was estimated to be TaELO2 deletion homozygote.

FIG. 39C illustrates the agarose electrophoresis diagram of PCR using oligonucleotide primer pair (2) of TaELO2 ORF detection in a transformant identified as a TaELO2 deletion homozygote. (Brief description of symbols) 1: Using KOub600Hygr as a template; 2: Wild-type strain FIGS. 40A and 40B illustrate an evaluation by southern blotting of a transformant obtained by retransfer of KOub600Hygr in Comparative Example 1-11. FIG. 40A is a schematic diagram of southern blotting to detect a wild-type allele, a mutant allele by KONeor transfer, and a mutant allele by KOub600Hygr transfer. FIG. 40B illustrates the results of southern blotting. (Brief description of symbols) 1, 9: Wild-type strain; 2 to 8 and 10 to 16: TaELO2 deletion homozygote FIG. 41 illustrates the results of southern blotting to detect TaELO2 in Comparative Example 1-11. (Brief description of symbols) 1: Wild-type strain; 2 to 5: T TaELO2 deletion homozygote

FIG. 52 lists the fatty acid proportions of the PKS pathway associated gene orfA disruption strain when the *Thraustochytrium aureum* ATCC 34304 wild-type strain is taken as 100%.

FIG. 64 lists the fatty acid proportions of the PKS pathway (orfA gene) and C20 elongase gene double disruption strain when *Thraustochytrium aureum* ATCC 34304 wild-type strain is taken as 100%.

FIG. 71 lists the fatty acid proportions of the PKS pathway (orfA gene) and Δ4 desaturase gene double disruption strain when the *Thraustochytrium aureum* ATCC 34304 wild-type strain is taken as 100%.

MODE FOR CARRYING OUT THE INVENTION

Figure 1:
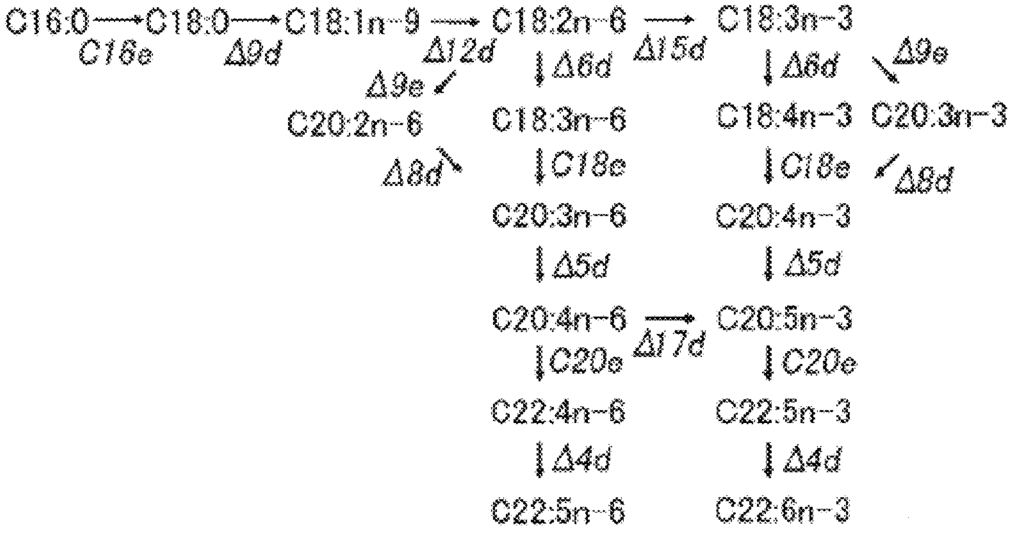
FIG. 1 illustrates the elongase-desaturase pathway and enzymes related to this biosynthesis pathway. (Brief description of symbols) C16:0: Palmitic acid; C18:0: Stearic acid; C18:1n-9: Oleic acid; C18:2n-6: Linoleic acid (LA); C18:3n-3: α-Linolenic acid (ALA); C18:3n-6: γ-Linolenic acid (GLA); C18:4n-3: Stearidonic acid (STA); C20:2n-6: Eicosadienoic acid (EDA); C20:3n-3: Eicosatrienoic acid (ETrA); C20:3n-6: Dihomo-γ-linolenic acid (DGLA); C20:4n-3: Eicosatetraenoic acid (ETA); C20:4n-6: Arachidonic acid (ARA); 20:5n-3: Eicosapentaenoic acid (EPA); C22:4n-6: Docosatetraenoic acid (DTA); C22:5n-3: n-3 Docosapentaenoic acid (n-3 DPA); C22:5n-6: n-6 Docosapentaenoic acid (n-6 DPA); C22:6n-3: Docosahexaenoic acid (DHA); C16e:C16 elongase; Δ9d: Δ9 desaturase; Δ12d: Δ12 desaturase; Δ15d: Δ15 desaturase; Δ9e: Δ9 elongase; Δ6d: Δ6 desaturase; Δ8d: Δ8 desaturase; C18e: C18 elongase; Δ5d: Δ5 desaturase; C20e: C20 elongase; Δ17d: Δ17 desaturase; Δ4d: Δ4 desaturase. Δ15 desaturase and Δ17 desaturase are each sometimes called ω3 desaturase.

The opportunity for the present invention came about due to the discovery of a new pattern of biosynthesis pathway of polyunsaturated fatty acids (PUFAs) in microorganisms called labyrinthulids. Specifically, it is known that PUFAs are generally biosynthesized via the elongase-desaturase pathway, but in some organisms. PUFAs are also biosynthesized via another pathway called the PUFA-PKS pathway. In the past, two types of labyrinthulids were found to exist, namely (I) the type that produces only via the PUFA-PKS pathway and (II) the type that produces via the elongase-desaturase pathway and PUFA-PKS pathway. This time, a third type, (III) a type that produces only via the elongase-desaturase pathway, was newly discovered. In short, a new "pattern" of PUFA biosynthesis pathway was discovered.

Examples are as follows. (1) Labyrinthulids having very weak or no PUFA-producing activity via the endogenous PUFA-PKS pathway and having PUFA-producing activity via the endogenous elongase-desaturase pathway. The present invention relates to labyrinthulids of the above (III) type that produces only via the elongase-desaturase pathway. These labyrinthulids encompass labyrinthulids of type (III) produced by isolating, culturing, and amplifying a wild-type strain having a PUFA biosynthesis pathway, and labyrinthulids having "very weak or no" PUFA-producing activity via the PUFA-PKS pathway.

(2) The labyrinthulids according to (1) above that do not have the endogenous PUFA-PKS pathway. The present invention is limited to (1) above, which are labyrinthulids having no genes or enzymes themselves that constitute the PUFA-PKS pathway.

(3) The labyrinthulids according to (1) above that have very weak or no endogenous PUFA-PKS pathway activity. The present invention is limited to (1) above that have information related to genes of enzymes constituting the PUFA-PKS pathway on the genome but do not express them (and therefore have no activity), or that express them only very weakly or not at all.

(4) The labyrinthulids according to any of (1) to (3) above, wherein DHA and/or n-6 DPA production activity has been lost or the produced quantity of DHA and/or n-6 DPA has been markedly decreased by endogenous Δ4 desaturase gene disruption.

Labyrinthulids of type (III) which produce PUFAs only via the elongase-desaturase pathway differ from those of type (I) which produce only via the PUFA-PKS pathway and those of type (II) which produce via the elongase-desaturase pathway and PUFA-PKS pathway in that they have no PUFA-PKS pathway. Based on this viewpoint, the present invention defines labyrinthulids of the type that produces only via the elongase-desaturase pathway. In other words, the above endogenous Δ4 desaturase gene disruption can be considered a method for determining whether a labyrinthulid is of the type that produces only via the elongase-desaturase pathway.

(5) The labyrinthulids according to (1) to (3) above, wherein DHA and/or n-6 DPA production activity has been lost or the produced quantity of DHA and/or n-6 DPA has been markedly decreased through endogenous C20 elongase gene disruption.

Labyrinthulids of type (III) which produce only via the elongase-desaturase pathway differ from those of type (I) which produce only via the PUFA-PKS pathway and those of type (II) which produce via the elongase-desaturase pathway and PUFA-PKS pathway in that they have no PUFA-PKS pathway. Based on this viewpoint, the present invention defines labyrinthulids of the type that produces only via the elongase-desaturase pathway. In other words, the above endogenous C20 elongase gene disruption can be considered a method for determining whether a labyrinthulid is of the type that produces only via the elongase-desaturase pathway.

(6) The labyrinthulids according to (1) to (5) above that is a microorganism belonging to either the genus *Parietichytrium* or the genus *Schizochytrium.*

Labyrinthulids belonging to the genus *Parietichytrium* or the genus *Schizochytrium* were known before the filing date of the present application, but it was not known that they are labyrinthulids of type (III) which produce PUFAs only via the elongase-desaturase pathway.

(7) The labyrinthulids according to (6) above, wherein the microorganism is *Parietichytrium* sp. SEK358 (FERM BP-11405), *Parietichytrium sarkarianum* SEK364 (FERM BP-11298), *Parietichytrium* sp. SEK517 (FERM BP-11406), or *Schizochytrium aggregatum* ATCC 28209.

(8) A method for producing lipids containing PUFAs, the method including culturing the labyrinthulids described in any of (1) to (7) above in a culture medium and collecting the lipids from the culture.

(9) A method for producing lipids containing PUFAs, the method including culturing labyrinthulids, that were transformed using the labyrinthulids described in any of (1) to (7) above as hosts with the objective of modifying the fatty acid composition and/or highy accumulating fatty acids, in a culture medium and collecting the lipids from the culture.

(10) Lipids containing PUFAs, the lipids being produced by the method of (8) or (9) above.

The present invention can provide labyrinthulea that produce PUFAs via only the elongase-desaturase pathway.

The creation of labyrinthulids equivalent to type (III) which produce only via the elongase-desaturase pathway is also possible, by spontaneous mutation or genetic recombination from type (II) which produce via the elongase-desaturase pathway and PUFA-PKS pathway. Examples of these include microorganisms belonging to the genus *Thraustochytrium*. By using these microorganisms, it is possible to obtain the same polyunsaturated fatty acids as by labyrinthulids of type (III).

[Microorganisms]

Labyrinthulids having very weak or no activity of producing PUFAs via the PUFA-PKS pathway includes labyrinthulids that produce PUFAs only via the elongase-desaturase pathway. A labyrinthulid having very weak PUFA-producing activity means a labyrinthulid in which the elongase-desaturase pathway gene has been disrupted, and which cannot produce PUFAs, and cannot be cultured without supplementing the culture medium with PUFAs. It means that not greater than 1/100 of the DHA synthesized in the organism is DHA synthesized via the PUFA-PKS pathway. The labyrinthulid that has very weak or no activity of producing PUFAs via the endogenous PUFA-PKS pathway and is capable of producing PUFAs via the endogenous elongase-desaturase pathway is not particularly limited, but particularly preferred examples are labyrinthulids belonging to the genus *Parietichytrium* or the genus *Schizochytrium*. Particularly preferred among these are *Parietichytrium* sp. SEK358 (FERM BP-11405), *Parietichytrium sarkarianum* SEK364 (FERM BP-11298), *Parietichytrium* sp. SEK517 (FERM BP-11406), or *Schizochytrium aggregatum* ATCC 28209.

*Parietichytrium* sp. SEK358 was obtained by the method described below. First, 10 mL of surface water collected in the Ishigakijima-Miyaragawa estuary region was placed in a test tube. Pine pollen was added, and the test tube was left to stand at room temperature. After 7 days, a sterilized agar culture medium (2 g of glucose, 1 g of peptone, 0.5 g of yeast extract, 0.2 g of chloramphenicol, 15 g of agar, 100 mL of distilled water, 900 mL of sea water) was swabed with this pine pollen, and colonies that emerged after 5 days were separated and cultured. This was repeated several times, and cells were separated. This strain was internationally deposited on Aug. 11, 2011 as accession number FERM BP-11405 at the International Patent Organism Depositary, National Institute of Advanced Industrial Science and Technology (Tsukuba Central 6, 1-1-1 Higashi, Tsukuba City, Ibaraki Prefecture), and can be procured therefrom.

*Parietichytrium sarkarianum* SEK364 was obtained by culturing a sea water sample collected in the Ishigakijima-Fukidogawa estuary region and separating cells in the same manner as above. This strain was internationally deposited on Sep. 24, 2010 as accession number FERM BP-11298 at the International Patent Organism Depositary, National Institute of Advanced Industrial Science and Technology (Tsukuba Central 6, 1-1-1 Higashi, Tsukuba City, Ibaraki Prefecture), and can be procured therefrom.

*Parietichytrium* sp. SEK571 was obtained by culturing a sea water sample collected in the Iriomotejima-Shiiragawa estuary region and separating cells in the same manner as above. This strain was internationally deposited on Aug. 11, 2011 as accession number FERM BP-11406 at the International Patent Organism Depositary, National Institute of Advanced Industrial Science and Technology (Tsukuba Central 6, 1-1-1 Higashi, Tsukuba City, Ibaraki Prefecture), and can be procured therefrom.

*Schizochytrium aggregatum* ATCC 28209 has been deposited at ATCC, and can be procured therefrom. Labyrinthulids in which PUFA-PKS has been disrupted or expression has been inhibited to a very weak level include labyrinthulids that produce PUFAs via the elongase-desaturase pathway and PUFA-PKS pathway. The PUFA-PKS pathway is required to exist in labyrinthulids that produce PUFAs only via the PUFA-PKS pathway, and when disrupted, there is a requirement for PUFAs. Labyrinthulids that produce PUFAs via the elongase-desaturase pathway and PUFA-PKS pathway, even in a case where the PUFA-PKS pathway has been disrupted, differ in that there is no requirement for PUFAs.

Disruption of the Δ4-desaturase gene using the present invention can dramatically reduce the produced quantities of DHA and n-6 DPA while maintaining the produced quantity of PUFAs overall.

The properties of the microorganisms obtained by the present invention may be combined as desired.

[Microbial Oil]

The present invention relates to microbial oil containing the fatty acid profile of the present invention. The microorganism of the present invention contains not less than 15 wt. %, preferably not less than 30 wt. %, more preferably not less than 50 wt. %, and even more preferably not less than 70 wt. % of lipid components per gram of cells. The lipid components contain not less than 30 wt. %, preferably not less than 50 wt. %, and more preferably not less than 70 wt. % of fatty acid components. The fatty acid components accumulate as not less than 70 wt. %, preferably not less than 80 wt. %, and more preferably not less than 90 wt. % of triglycerides. The microbial oil of the present invention is "crude oil" or "refined oil" containing at least approximately 35 wt. % of triacylglycerol fraction. "Crude oil" is oil extracted from microbial biomass which has not undergone further treatment. "Refined oil" is oil obtained by treating crude oil by standard purification, decoloration, and/or deodorizing processes. The microbial oil further contains "final oil", which is refined oil diluted with vegetable oil. The "microorganisms" are not limited, but include classifications taxonomically associated with any "microalgae", "labyrinthulids", and the deposited microorganisms described in the present specification. The terms "labyrinthulid", "genus *Parietichytrium*", "genus *Schizochytrium*", and "genus *Thraustochytrium*" when used in association with any microbial oils of a deposited microorganism described herein are based on current taxonomic classification including phylogenetically usable information, and are not intended to be limiting if the taxonomic classification is revised after the filing date of the present application. Lipids In the present invention, lipids are lipids produced by labyrinthulids, and are mainly triglycerides, diglycerides, monoglycerides, phospholipids, free fatty acids, sterols, carotenoids, hydrocarbons, and the like.

[Lipids]

In the present invention, lipids are lipids produced by labyrinthulids, and are mainly triglycerides, diglycerides, monoglycerides, phospholipids, free fatty acids, sterols, carotenoids, hydrocarbons, and the like.

[Polyunsaturated Fatty Acids]

In the present invention, a polyunsaturated fatty acid (PUFA) is a fatty acid having not less than 18 carbon atoms and not less than three double bonds, and more preferably a fatty acid having not less than 20 carbon atoms and not less than three double bonds. Specific examples include linoleic acid (LA, 18:2n-6), α-linolenic acid (ALA, 18:3n-3), γ-linolenic acid (GLA, 18:3n-6), stearidonic acid (STA, 18:4n-3), dihomo-γ-linolenic acid (DGLA, 20:3n-6), eicosatetraenoic acid (ETA, 20:4n-3), arachidonic acid (ARA, 20:4n-6), eicosapentaenoic acid (EPA, 20:5n-3), docosatetraenoic acid (DTA, 22:4n-6), n-3 docosapentaenoic acid (n-3 DPA, 22:5n-3), n-6 docosapentaenoic acid (n-6 DPA, 22:5n-6), and docosahexaenoic acid (DHA, 22:6n-3). In the present specification, arachidonic acid is also expressed as ARA. The total fatty acid composition means the composition of fatty acids detected after a microorganism is cultured and freeze dried and the fatty acids are then methyl-esterified and analyzed by GC. Specifically, the total fatty acid composition is the composition of fatty acids having from 14 to 22 carbon chains. In the present invention, GC area means the peak area of the GC chart. A proportion relative to the total fatty acid composition means the proportion of the peak area of the targeting fatty acid relative to the total of peak areas of the entire fatty acid composition, and is expressed as a percentage. In the present invention, C20 PUFA/C22 PUFA means the value obtained by dividing the total of GC peak areas of polyunsaturated fatty acids having 20 carbon chains by the total of GC peak areas of polyunsaturated fatty acids having 22 carbon chains. In the present invention, n-6 PUFA/n-3 PUFA means the value obtained by dividing the total of peak areas of the GC chart of ω6 fatty acids having not less than 20 carbon chains by the total of peak areas of the GC chart of ω3 fatty acids having not less than 20 carbon chains.

[PUFA Biosynthesis Pathways]

Two different pathways associated with PUFA biosynthesis are known. One is a pathway that produces polyunsaturated fatty acids (PUFAs) using polyketide synthase (PKS). In the present invention, this metabolic pathway will be called the PUFA-PKS pathway or the PKS pathway. In the present invention, a PKS gene means a gene that encodes a protein that constitutes polyketide synthase. Polyketide synthase is an enzyme that catalyzes a reaction in which a long-chain substrate such as malonyl-CoA is condensed multiple times in a starter substrate such as acetyl-CoA. Polyketide synthase has generally been known as an enzyme involved in biosynthesis of secondary metabolites of plants, fungi, and the like, but it has also been reported to be involved in PUFA biosynthesis in certain organisms. For example, the marine bacillus *Shewanella* produces eicosapentaenoic acid (EPA) using this enzyme (Non-patent Document 8). Polyketide synthase is known to be similarly involved in PUFA biosynthesis in certain labyrinthulids as well.

The other is a pathway in which, starting from a fatty acid such as palmitic acid, desaturation by desaturase and chain elongation by elongase are repeated to produce PUFAs such as EPA and DHA. In the present invention, this is called the elongase-desaturase pathway. Examples of the enzymes that constitute this system include fatty acid synthesis associated enzymes such as C20 elongase and Δ4 desaturase.

[PUFA Biosynthesis Pathway Differentiation Method]

A method for differentiating between PUFA biosynthesis pathways of labyrinthulids will be described below. However, this is only one example, and needless to say, differentiation does not have to be performed by this method.

As stated above, two PUFA biosynthesis pathways in labyrinthulids are known. One is the PUFA-PKS pathway, by which DHA and n-6 DPA are produced. In this pathway, no PUFAs other than DHA and n-6 DPA are substantially produced such configuration differs greatly from the elongase-desaturase pathway, which is the other PUFA biosynthesis pathway.

The other pathway, namely the elongase-desaturase pathway, is illustrated in FIG. 1. Among the enzymes constituting this pathway, Δ4 desaturase is an enzyme involved in converting n-3 DPA to DHA. This enzyme is also involved in converting DTA to n-6 DPA. Thus, since these conversions do not take place when the gene of this enzyme is disrupted, n-3 DPA and DTA, which are substrates of this enzyme, accumulate, and conversely, DHA and n-6 DPA, which are products of this enzyme, decrease. In a labyrinthulid in which this Δ4 desaturase gene has been disrupted, in a case where the products DHA and/or n-6 DPA are completely undetected or markedly decreased, it is judged that the labyrinthulid has very weak or no PUFA (particularly DHA and/or n-6 DPA) production activity via the endogenous PUFA-PKS pathway.

It is also possible to select C20 elongase rather than Δ4 desaturase and disruption the gene of that enzyme instead. Specifically, C20 elongase is an enzyme involved in converting EPA to n-3 DPA. This enzyme is also involved in converting ARA to DTA. Thus, since these conversions do not take place when the gene of this enzyme is disrupted, EPA and ARA, which are substrates of this enzyme, accumulate, and conversely, n-3 DPA and DTA, which are products of this enzyme, decrease. As a result, DHA and n-6 DPA, which have n-3 DPA and DTA as substrates, also decrease. In a labyrinthulid in which this C20 elongase gene has been disrupted, when the products DHA and/or n-6 DPA are completely undetected or markedly decreased, it is judged that the labyrinthulid has very weak or no PUFA (particularly DHA and/or n-6 DPA) production activity via the endogenous PUFA-PKS pathway.

Gene disruption is performed by transforming something designed such that gene products do not produce activity using an antibiotic resistance gene or the like in all or a portion of the target gene, into a target cell by a method such as a gene gun, electroporation, or gene editing. Gene silencing is performed by transforming an antisense gene designed such that expression of the target gene is inhibited or a gene in which RNAi is expressed, into a cell by a method such as a gene gun, electroporation, or gene editing. Gene disruption and silencing are not limited to these methods provided that expression of the target gene is hindered. When disruption or silencing is performed with a PKS gene as the target, the target is not limited provided that enzyme activity can be eliminated or inhibited, but OrfA is preferably used as the target.

The present invention provides labyrinthulids having very weak or no PUFAproducing activity via the endogenous PUFA-PKS pathway and having PUFA-producing activity via the endogenous elongase-desaturase pathway.

Furthermore, the present invention also includes changing the fatty acid composition produced by a labyrinthulid by manipulating the genes of enzymes constituting the elongase-desaturase pathway of the labyrinthulid. In particular, the fatty acid composition produced by a labyrinthulid can be modified by: (1) disruption and/or silencing of a fatty acid elongase gene, (2) disruption and/or silencing of a fatty acid desaturase gene, (3) transfer of a fatty acid elongase gene, (4) transfer of a fatty acid desaturase gene, and (5) a combination of the above. For example, when stearidonic acid (STA) is desired, a fatty acid elongase gene involved in conversion of stearidonic acid to eicosatetraenoic acid (ETA), specifically the C18 elongase gene, may be disrupted and/or silenced. Furthermore, for example, when eicosapentaenoic acid (EPA) is desired, a fatty acid elongase gene involved in conversion of eicosatetraenoic acid to docosapentaenoic acid (DPA), specifically the C20 elongase gene, may be disrupted and/or silenced. As another example, when eicosapentaenoic acid is desired, a fatty acid desaturase gene that converts arachidonic acid (ARA) to eicosapentaenoic acid, specifically the ω3 desaturase gene, may be transformed. For a labyrinthulid that produces via the elongase-desaturase pathway and PUFA-PKS pathway, the fatty acid composition produced by the labyrinthulid can be modified by: (1) disruption and/or silencing of a fatty acid elongase gene, (2) disruption and/or silencing of a fatty acid desaturase gene, (3) transfer of a fatty acid elongase gene, (4) transfer of a fatty acid desaturase gene, and (5) a combination of the above, using a microorganism in which the PUFA-PKS pathway has been disrupted or silenced. For example, when stearidonic acid (STA) is desired, a fatty acid elongase gene involved in conversion of stearidonic acid to eicosatetraenoic acid (ETA), specifically the C18 elongase gene, may be disrupted and/or silenced. Furthermore, for example, when eicosapentaenoic acid (EPA) is desired, a fatty acid elongase gene involved in conversion of eicosatetraenoic acid to docosapentaenoic acid (DPA), specifically the C20 elongase gene, may be disrupted and/or silenced. As another example, when eicosapentaenoic acid is desired, a fatty acid desaturase gene that converts arachidonic acid (ARA) to eicosapentaenoic acid, specifically the ω3 desaturase gene, may be transformed.

A labyrinthulid (microorganism) in which the produced fatty acid composition has been modified is obtained by transformation of the labyrinthulid. A labyrinthulid in which a fatty acid biosynthesis associated gene has been transformed and/or disrupted can be used in, for example, production of unsaturated fatty acids. In production of unsaturated fatty acids, the conditions of other steps, production equipment and instruments and the like are not particularly limited provided that the labyrinthulid that is used has very weak or no PUFA production activity via the endogenous PUFA-PKS pathway and has PUFA production activity via the endogenous elongase-desaturase pathway, or is a labyrinthulid in which the produced fatty acid composition has been modified as described above. Production of unsaturated fatty acids includes a step of culturing a labyrinthulid that has very weak or no PUFA production activity via the endogenous PUFA-PKS pathway and has PUFA production activity via the endogenous elongase-desaturase pathway, or a labyrinthulid in which the produced fatty acid composition has been modified as described above. Unsaturated fatty acids are produced using these microorganisms and their culture medium.

The above cell culturing conditions (culture medium, culture temperature, ventilation status, and the like) may be set as appropriate according to the type of cell, the targeted type and quantity of unsaturated fatty acids, and the like. Furthermore, an unsaturated fatty acid in the present invention means a substance containing an unsaturated fatty acid, without limitation on its content, purity, shape, composition, and the like. In other words, in the present invention, cells in which the fatty acid composition has been modified or their culture media are themselves considered to be unsaturated fatty acids. Additionally, a step of purifying the unsaturated fatty acids from these cells or culture media may be further included. As the method of purifying the unsaturated fatty acids, a method known as a purification method for lipids (including complex lipids) such as unsaturated fatty acids may be applied.

[Method for Highly Accumulating Unsaturated Fatty Acids in Labyrinthulids]

Accumulation of unsaturated fatty acids in a labyrinthulid is achieved by culturing a labyrinthulid having very weak or no PUFA production activity via the endogenous PUFA-PKS pathway and having PUFA production activity via the endogenous elongase-desaturase pathway, or a transformant thereof. The labyrinthulid may be cultured in, for example, a solid culture medium, liquid culture medium, or the like. The culture medium used at this time is not particularly limited provided that it is a medium commonly used for culturing labyrinthulids and appropriately combines, for example, glucose, fructose, saccharose, starch, glycerin, or the like as a carbon source, yeast extract, corn steep liquor, polypeptone, sodium glutamate, urea, ammonium acetate, ammonium sulfate, ammonium nitrate, ammonium chloride, sodium nitrate, or the like as a nitrogen source, potassium phosphate or the like as an inorganic salt, and other necessary components. However, yeast extract-glucose medium (GY medium) is particularly preferably used. After preparation of the culture medium, the pH is adjusted to within the range of 3.0 to 8.0, and then the culture medium is sterilized by autoclave or the like. Culturing may be performed by aerated and agitated culturing, shake culturing, or static culturing at 10 to 40° C., preferably 15 to 35° C., for 1 to 14 days.

To collect the produced unsaturated fatty acids, the labyrinthulids are grown in a culture medium and the microorganism cells obtained from that culture medium are treated, the lipids (polyunsaturated fatty acids or oil- and fat-containing matter containing polyunsaturated fatty acids) inside the cells are released and collected. Specifically, lipids containing PUFAs can be obtained by collecting the labyrinthulids cultured in this manner by centrifugation or the like, performing treatment such as drying and cell crushing as necessary, and performing extraction using an appropriate organic solvent or supercritical carbon dioxide, liquefied dimethylether, or the like according to conventional methods.

The microbial oil obtained in the present invention is that which satisfies any of the following conditions. The microbial oil obtained in the present invention contains ARA in a proportion of not less than 5%, not less than 7%, not less than 10%, or not less than 15% of the total fatty acid composition. Oils and fats with high ARA obtained in this manner may be used in applications such as nutritional supplements for infants and health foods and medications for adults. ARA may be not greater than 80%, not greater than 70%, not greater than 60%, or not greater than 50% of the total fatty acid composition. The microbial oil obtained in the present invention contains DGLA in a proportion of not less than 2.5%, not less than 5%, or not less than 10% of the total fatty acid composition. Microbial oil with high DGLA obtained in this manner may be used in medicinal applications such as anti-inflammatory agents. DGLA may be not greater than 80%, not greater than 70%, not greater than 60%, or not greater than 50% of the total fatty acid composition. The microbial oil obtained in the present invention contains ETA in a proportion of not less than 0.35%, not less than 0.5%, not less than 0.75%, or not less than 1% of the total fatty acid composition. Microbial oil with high ETA obtained in this manner may be used in medicinal applications such as arthritis treatment. ETA may be not greater than 50%, not greater than 40%, not greater than 30%, or not greater than 20% of the total fatty acid composition. The microbial oil obtained in the present invention contains EPA in a proportion of not less than 4%, not less than 6%, not less than 8%, not less than 10%, or not less than 12% of the total fatty acid composition. Microbial oil with high EPA obtained in this manner may be used in nutritional supplement applications and medicinal applications. EPA may be not greater than 80%, not greater than 70%, not greater than 60%, or not greater than 50% of the total fatty acid composition. The microbial oil obtained in the present invention contains n-6 DPA in a proportion of not greater than 0.20%, not greater than 0.15%, not greater than 0.1%, or not greater than 0.05% of the total fatty acid composition. The microbial oil with low n-6 DPA obtained in this manner does not tend to hinder the functions of other fatty acids. Furthermore, it is advantageous in cases where removal of n-6 DPA by refinement is desired. n-6 DPA may be not less than 0.001%, not less than 0.005%, or not less than 0.01% of the total fatty acid composition. The microbial oil obtained in the present invention contains DHA in a proportion of not greater than 0.50%, not greater than 0.3%, not greater than 0.2%, or not greater than 0.1% of the total fatty acid composition. The microbial oil with low DHA obtained in this manner does not tend to hinder the functions of other fatty acids. Furthermore, it is advantageous in cases where removal of DHA by refinement is desired. DHA may be not less than 0.005%, not less than 0.01%, or not less than 0.05% of the total fatty acid composition. The microbial oil obtained in the present invention contains a total of DHA and n-6 DPA in a proportion of not greater than 0.7%, not greater than 0.8%, not greater than 0.9%, or not greater than 1.0% of the total fatty acid composition. The microbial oil with low DHA and n-6 DPA obtained in this manner does not tend to hinder the functions of other fatty acids and is stable against oxidation. Furthermore, it is advantageous in cases where removal of DHA and n-6 DPA by refinement is desired. The total of DHA and n-6 DPA may be not less than 0.05%, not less than 0.1%, or not less than 0.5% of the total fatty acid composition. The desired concentrations of each of these fatty acids may be combined as desired, limited to a total of 100%.

In another aspect, the microbial oil obtained in the present invention is that which satisfies any of the following conditions. In the microbial oil obtained in the present invention, the value of LA/DHA by GC area is not less than 0.6, not less than 0.7, not less than 0.8, or not less than 0.9, and not greater than 10, not greater than 9, not greater than 8, not greater than 7, or not greater than 6. The microbial oil with a high LA/DHA value obtained in this manner is stable against oxidation, and the functions of LA do not tend to be hindered by DHA. In the microbial oil obtained in the present invention, the value of GLA/DHA by GC area is not less than 0.35, not less than 0.4, not less than 0.5, not less than 0.6, or not less than 0.7, and not greater than 10, not greater than 9, not greater than 8, or not greater than 7. The microbial oil with a high GLA/DHA value obtained in this manner is stable against oxidation, and the functions of GLA do not tend to be hindered by DHA.

In the microbial oil obtained in the present invention, the value of DGLA/DHA by GC area is not less than 0.35, not less than 0.4, not less than 0.5, not less than 0.6, or not less than 0.7, and not greater than 10, not greater than 9, not greater than 8, not greater than 7, or not greater than 6. Microbial oil with a high DGLA/DHA value obtained in this manner may be used in medications having an anti-inflammatory action. In the microbial oil obtained in the present invention, the value of ARA/DHA by GC area is not less than 0.7, not less than 0.8, not less than 0.9, or not less than 1.0, and not greater than 50, not greater than 45, not greater than 40, not greater than 35, or not greater than 30. Microbial oil with a high ARA/DHA value obtained in this manner may be used in modified milk for infants. The value of EPA/DHA by GC area is not less than 0.35, not less than 0.4, not less than 0.5, not less than 0.6, or not less than 0.7, and not greater than 50, not greater than 45, not greater than 40, not greater than 35, or not greater than 30. EPA used in typical medications and the like are mainly esters containing DHA, but the microbial oil with a high EPA/DHA value obtained in this manner contains EPA with a high degree of purity, and can be used in health foods, medications, and the like.

The desired ratios of each of these fatty acids may be combined as desired. In the microbial oil obtained in the present invention, the value of LA/EPA by GC area is not less than 0.06, not less than 0.07, not less than 0.08, or not less than 0.09, and not greater than 0.12, not greater than 0.1, not greater than 0.08, or not greater than 0.06. Microbial oil with a low LA/EPA value obtained in this manner may be used in infusion fluids with a low anti-inflammatory action and the like. In the microbial oil obtained in the present invention, the value of GLA/EPA by GC area is not less than 0.04 or not less than 0.45, and not greater than 0.12, not greater than 0.1, or not greater than 0.8. Microbial oil with a low GLA/EPA value obtained in this manner may be used in infusion fluids with a low anti-inflammatory action and the like. In the microbial oil obtained in the present invention, the value of DTA/EPA by GC area is not less than 0.01, not less than 0.02, not less than 0.03, not less than 0.04, or not less than 0.05, and not greater than 0.4, not greater than 0.35, or not greater than 0.3. The microbial oil with a low DTA/EPA value obtained in this manner is useful for separating high-purity EPA since DTA and EPA are close to each other in GC. The desired ratios of each of these fatty acids may be combined as desired.

In the microbial oil obtained in the present invention, the value of DTA/ARA by GC area is not less than 0.01, not less than 0.03, not less than 0.05, not less than 0.07, or not less than 0.1, and not greater than 0.45, not greater than 0.4, not greater than 0.35, or not greater than 0.3. Microbial oil with a low DTA/ARA value obtained in this manner may be used in formulated milk for infants. In the microbial oil obtained in the present invention, the value of DTA/DGLA by GC area is not less than 0.01, not less than 0.05, not less than 0.1, not less than 0.15, or not less than 0.2, and not greater than 1.45, not greater than 1.4, not greater than 1.3, not greater than 1.2, or not greater than 1.1. Microbial oil with a low DTA/DGLA value obtained in this manner may be used in medications having an anti-inflammatory action and the like. In the microbial oil obtained in the present invention, the value of LA/n-6 DPA by GC area is not less than 0.4, not less than 0.5, not less than 0.6, not less than 0.7, or not less than 0.8, and not greater than 20, not greater than 18, not greater than 16, not greater than 14, or not greater than 12. Microbial oil with a high LA/n-6 DPA value obtained in this manner may be used in edible oils. In the microbial oil obtained in the present invention, the value of GLA/n-6 DPA by GC area is not less than 0.2, not less than 0.4, not less than 0.6, or not less than 0.8, and not greater than 10, not greater than 8, not greater than 6, or not greater than 4. Microbial oil with a high GLA/n-6 DPA value obtained in this manner may be used in health foods and supplements. In the microbial oil obtained in the present invention, the value of DGLA/n-6 DPA by GC area is not less than 0.35, not less than 0.5, not less than 0.75, or not less than 1.0, and not greater than 30, not greater than 27, not greater than 25, not greater than 22, or not greater than 20. Microbial oil with a high DGLA/n-6 DPA value obtained in this manner may be used in medications having an anti-inflammatory action. In the microbial oil obtained in the present invention, the value of ARA/n-6 DPA by GC area is not less than 0.7, not less than 1.0, not less than 2.0, or not less than 3.0, and not greater than 60, not greater than 50, not greater than 40, or not greater than 30. Microbial oil with a high LA/n-6 DPA value obtained in this manner may be used in formulated milk for infants. In the microbial oil obtained in the present invention, the value of EPA/n-6 DPA by GC area is not less than 0.4, not less than 0.6, not less than 0.8, not less than 1, not less than 2, or not less than 5, and not greater than 70, not greater than 60, not greater than 50, not greater than 40, or not greater than 30. Microbial oil with a high EPA/n-6 DPA value obtained in this manner may be used in health foods, supplements, and the like. The desired ratios of each of these fatty acids may be combined as desired.

In the microbial oil obtained in the present invention, the value of DGLA/LA by GC area is not less than 1.4, not less than 2, or not less than 3, and not greater than 10, not greater than 9, not greater than 8, or not greater than 7. The microbial oil obtained in this manner may be used in foods and supplements having an anti-inflammatory action. In the microbial oil obtained in the present invention, the value of ARA/LA by GC area is not less than 5.1, not less than 7, not less than 9, or not less than 11, and not greater than 20, not greater than 17, not greater than 15, or not greater than 12. Microbial oil with a high ARA/LA value obtained in this manner may be used in animal feed and formulated milk for infants. In the microbial oil obtained in the present invention, the value of EPA/LA by GC area is not less than 5.5, not less than 7, not less than 9, not less than 11, or not less than 13, and not greater than 30, not greater than 25, not greater than 22, or not greater than 20. Microbial oil with a high EPA/LA value obtained in this manner may be used in medications and health foods. In the microbial oil obtained in the present invention, the value of DTA/LA by GC area is not less than 0.01, not less than 0.05, not less than 0.07, or not less than 0.1, and not greater than 0.4, not greater than 0.35, not greater than 0.33, not greater than 0.3, or not greater than 0.28. Microbial oil with a low DTA/LA value obtained in this manner may be used in animal feed and foods. The desired ratios of each of these fatty acids may be combined as desired.

In the microbial oil obtained in the present invention, the value of DGLA/GLA by GC area is not less than 4.5, not less than 5, not less than 6, or not less than 7, and not greater than 20, not greater than 17, not greater than 15, or not greater than 12. Microbial oil with a high DGLA/GLA value obtained in this manner may be used in medications having an anti-inflammatory action and the like. In the microbial oil obtained in the present invention, the value of ARA/GLA by GC area is not less than 9, not less than 10, not less than 12, not less than 13, or not less than 14, and not greater than 30, not greater than 28, not greater than 26, not greater than 24, or not greater than 22. Microbial oil with a high ARA/GLA value obtained in this manner may be used in formulated milk for infants. The desired ratios of each of these fatty acids may be combined as desired.

In the microbial oil obtained in the present invention, the value of n-6 DPA/DTA by GC area is not less than 0.001, not less than 0.01, or not less than 0.02, and not greater than 1.5, not greater than 1.4, not greater than 1.3, not greater than 1.2, or not greater than 1.1. The microbial oil obtained in this manner may be used in foods that prevent arteriosclerosis and the like. In the microbial oil obtained in the present invention, the value of DHA/n-3 DPA by GC area is not less than 0.001, not less than 0.01, or not less than 0.02, and not greater than 4, not greater than 4.5, not greater than 4, or not greater than 3.5. The microbial oil obtained in this manner may be used in animal feed or health foods. In the microbial oil obtained in the present invention, the value of C20 PUFA/C22 PUFA by GC area is not less than 0.5, not less than 0.7, not less than 1, or not less than 1.2, and not greater than 50, not greater than 45, not greater than 40, or not greater than 35. Microbial oil with a high C20 PUFA/C22 PUFA value obtained in this manner may be used in health foods and supplements. In the microbial oil obtained in the present invention, the value of n-6 PUFA/n-3 PUFA by GC area is not less than 1.8, not less than 2, not less than 2.5, or not less than 3, and not greater than 100, not greater than 80, not greater than 70, not greater than 60, or not greater than 50. Microbial oil with a high n-6 PUFA/n-3 PUFA value obtained in this manner may be used in edible oils and animal feed. The desired ratios of each of these fatty acids may be combined as desired.

The desired ratios of each of these fatty acids may be combined as desired. The desired concentrations of each of these fatty acids may be combined as desired, limited to a total of 100%.

The unsaturated fatty acids of the present invention also include various medications, foods, animal feeds, and industrial products, and the fields of use thereof are not particularly limited. The foods containing the unsaturated fatty acid-containing oils and fats of the present invention also include health foods such as supplements and food additives and the like. Examples of the industrial products include animal feed for organisms other than humans, films, biodegradable plastics, functional fibers, lubricating oils, and detergents.

Next, the present invention will be specifically described based on examples. Furthermore, in the present specification, the features of each invention described in embodiments related to each aspect of the invention may be combined as desired to form new embodiments, and it is to be understood that such new embodiments may be included in each of the aspects of the present invention.

Example 1

[Labyrinthulids and Culturing Method/Storage Method Thereof]

(1) Strains Used in the Present Invention

*Parietichytrium* sp. SEK358 (FERM BP-11405), *Parietichytrium sarkarianum* SEK364 (FERM BP-11298), and *Parietichytrium* sp. SEK571 (FERM BP-11406) were shared from the Department of Engineering at Konan University. *Thraustochytrium aureum* ATCC 34304 was shared from ATCC.

(2) Culture Medium Composition i. Agar Plate Culture Medium Composition

PDA Agar Plate Culture Medium 0.78% (w/v) of potato dextrose agar medium (available from Nissui Pharmaceutical Co., Ltd.), 1.75% (w/v) of Sealife (available from Marintec Co., Ltd.), and 1.21% (w/v) of agar powder (available from Nacalai Tesque, Inc.) were mixed and then sterilized by autoclave for 20 min at 121° C. After sufficient cooling, ampicillin sodium salt (available from Nacalai Tesque, Inc.) was added so as to result in a final concentration of 100 μg/mL. This was dispensed into a Petri dish and left to stand at a level location to solidify.

ii. Liquid Culture Medium Composition

Gy Liquid Culture Medium 3.18% (w/v) of glucose (available from Nacalai Tesque, Inc.), 1.06% (w/v) of dry yeast extract (available from Nacalai Tesque, Inc.), and 1.75% (w/v) of Sealife (available from Marintec Co., Ltd.) were mixed and then sterilized by autoclave for 20 min at 121° C. Ampicillin sodium salt (available from Nacalai Tesque, Inc.) was then added so as to result in a final concentration of 100 μg/mL.

Pd Liquid Culture Medium 0.48% (w/v) of potato dextrose (available from Difco Laboratories Inc.) and 1.75% (w/v) of Sealife (available from Marintec Co., Ltd.) were mixed and then sterilized by autoclave for 20 min at 121° C. Ampicillin sodium salt (available from Nacalai Tesque, Inc.) was then added so as to result in a final concentration of 100 μg/mL.

(3) Culturing Method i. Agar Plate Culturing

Labyrinthulea cells were inoculated using a platinum loop or a spreader and then static cultured at 25° C., thereby causing emergence of colonies. Subculturing was performed by extracting colonies using a platinum loop and suspending them in sterilized physiological saline solution, and then spreading this suspension using a platinum loop or a spreader. Furthermore, as necessary, it was transformed to a liquid culture by inoculating cells in a liquid culture medium on a flat plate.

ii. Liquid Culturing

Labyrinthulea cells were inoculated, and suspension culturing was performed with stirring at 150 rpm at 25° C. using an Erlenmeyer flask or a test tube. Subculturing was performed by adding a culture solution in which growth was confirmed from the logarithmic growth phase to the stationary phase, in a volume ratio of 1/200 to 1/10 to a fresh GY or PD liquid culture medium. Furthermore, as necessary, it was transformed to an agar plate culture by spreading the cell culture solution on a PDA agar plate culture medium.

(4) Preservation/Storage Method of Labyrinthulids

In addition to subculturing, cryopreservation was performed by producing glycerol stock. Specifically, glycerol (available from Nacalai Tesque, Inc.) was added to a cell suspension that used a GY liquid culture medium from the logarithmic growth phase to the stationary phase, so as to result in a final concentration of 15% (v/v), and this was stored in a deep freezer at −80° C.

Example 2

[Measurement of Fatty Acid Composition of Lipids Produced by C20 Elongase Gene Disruption and Transformation Strain of *Parietichytrium sarkarianum* SEK364]

[Example 2-1]: Subcloning of SV40 Terminator Sequence

An SV40 terminator sequence was amplified with PrimeSTAR HS DNA Polymerase (available from Takara Bio Inc.) using a pcDNA 3.1 myc-His vector (available from Invitrogen Corp.) as a template. The PCR primers used were as shown below. RHO58 was set on the SV40 terminator sequence, and includes BglII and BamHI linker sequences. RHO52 was set on the SV40 terminator sequence, and includes a BglII sequence. [RHO58: 34mer: 5'-CAG ATC TGG ATC CGC GAA ATG ACC GAC CAA GCG A-3' (SEQ ID NO: 1), RHO52: 24mer: 5'-ACG CAA TTA ATG TGA GAT CTA GCT-3' (SEQ ID NO: 2)]. After amplification under the following conditions, it was cloned in pGEM-T Easy Vector (available from Promega Corporation). [PCR cycles: 98° C. 2 min/98° C. 30 sec, 60° C. 30 sec, 72° C. 1 min, 30 cycles/72° C. 1 min]. After amplification with *E. coli*, the sequence was confirmed using a Dye Terminator Cycle Sequencing Kit (available from Beckman Coulter Inc.). This was named pRH27.

Figure 2:
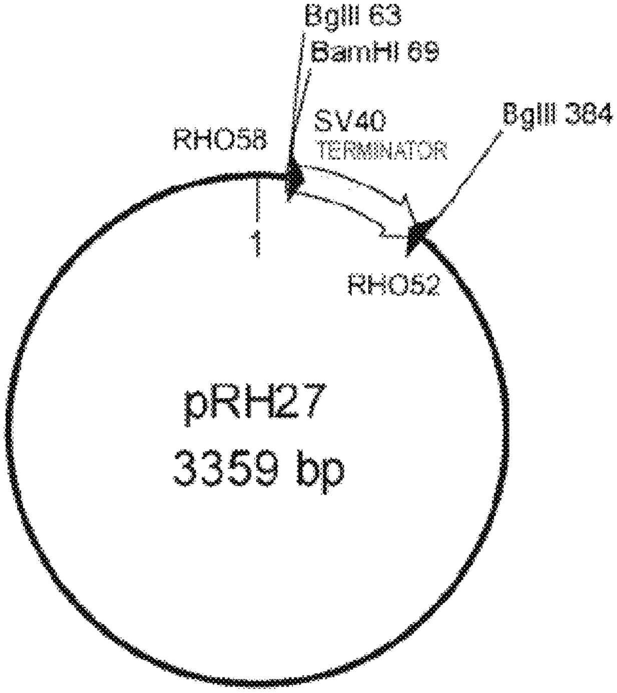
FIG. 2 illustrates a plasmid containing an SV40 terminator sequence derived from a subcloned pcDNA 3.1 Myc-His vector.

The plasmid (pRH27) containing the subcloned SV40 terminator sequence (342 bp, SEQ ID NO: 3) is illustrated in FIG. 2.

[Example 2-2]: Production of Artificially Synthesized Neomycin Resistance Gene Cassette

*Thraustochytrium aureum* ATCC 34304 strain was cultured in a GY culture medium, and cells of the latter logarithmic growth phase were centrifuged for 5 min at 4° C. at 3500×g to form pellets, and the pellets were frozen with liquid nitrogen and then crushed. After phenol extraction of the crushed cell liquid, ethanol precipitation was performed and the precipitate was dissolved in a TE solution. The nucleic acids dissolved in the TE solution were treated with RNase for 30 min at 37° C., and after further phenol extraction, ethanol precipitation was performed and the precipitate was dissolved in a TE solution. A260/280 was measured and the DNA concentration was calculated.

Using this as a template, an ubiquitin promoter sequence (619 bp, SEQ ID NO: 4) was amplified with PrimeSTAR HS DNA Polymerase with GC Buffer (available from Takara Bio Inc.). The PCR primers used were as shown below. RHO53 was set on the ubiquitin promoter sequence, and includes a BglII linker sequence. TKO1 includes the ubiquitin promoter sequence and an artificially synthesized neomycin resistance gene sequence. [RHO53: 36mer: 5'-CCC AGA TCT GCC GCA GCG CCT GGT GCA CCC GCC GGG-3' (SEQ ID NO: 5), TKO1: 58mer: 5'-CGT GAA GGC CGT CCT GTT CAA TCA TGT TGG CTA GTG TTG CTT AGG TCG CTT GCT GCT G-3' (SEQ ID NO: 6)]. [PCR cycles: 98° C. 2 min/98° C. 10 sec, 68° 1 min, 30 cycles/68° C. 1 min].

Using the artificially synthesized neomycin resistance gene sequence as a template, an artificially synthesized neomycin resistance gene sequence (826 bp, SEQ ID NO: 7) was amplified with PrimeSTAR HS DNA Polymerase with GC Buffer (available from Takara Bio Inc.). The PCR primers used were as shown below. TK02 includes the ubiquitin promoter sequence and the artificially synthesized neomycin resistance gene sequence. RHO57 includes the artificially synthesized neomycin resistance gene sequence and has a BglII linker sequence. [TK02: 54mer: 5'-AGC GAC CTA AGC AAC ACT AGC CAA CAT GAT TGA ACA GGA CGG CCT TCA CGC TGG-3' (SEQ ID NO: 8), RHO57: 26mer: 5'-CAG ATC TCA AAA GAA CTC GTC CAG GA-3' (SEQ ID NO: 9)][PCR cycles: 98° C. 2 min/98° C. 10 sec, 68° 1 min, 30 cycles/68° C. 1 min].

Figure 3:
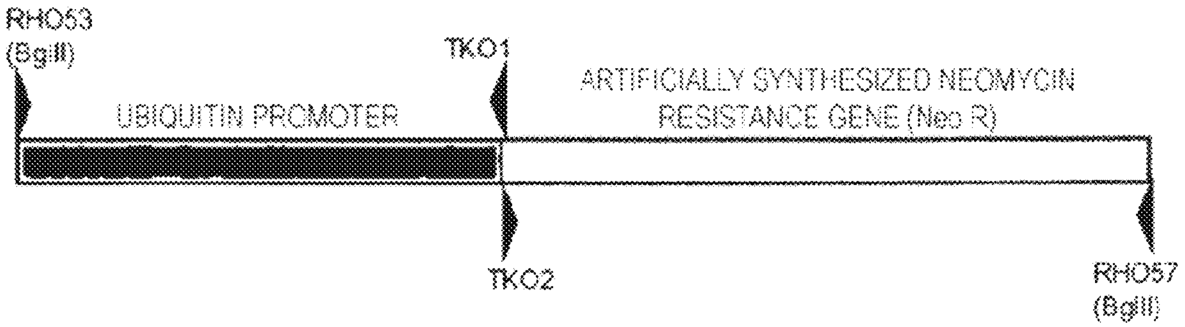
FIG. 3 is a schematic diagram of the primers used in fusion PCR and the products. The final product is a fused sequence of a ubiquitin promoter derived from *Thraustochytrium aureum* ATCC 34304 and an artificially synthesized neomycin resistance gene.

Using SEQ ID NO: 4 and SEQ ID NO: 7 as templates, fusion PCR was performed using RHO53 (SEQ ID NO: 5) and RHO57 (SEQ ID NO: 9) according to the method described in Non-patent Document 9. Amplification was performed using LA Taq Hot Start Version (available from Takara Bio Inc.) as the enzyme with PCR cycles under conditions below: 94° C. 2 min/94° C. 20 sec, 55° C. 30 sec, 68° C. 1 min, 30 cycles/68° C. 1 min (1° C./10 sec from 55° C. to 68° C.), and then the amplified product was digested with BglII. (FIG. 3).

The *Thraustochytrium aureum* ATCC 34304-derived ubiquitin promoter-artificially synthesized neomycin resistance gene sequence (1395 bp, SEQ ID NO: 10) fused as described above was digested with BglII, and the resultant was bound to the BamHI site of pRH27 described in Example 2-1. After amplification of the produced plasmid with *E. coli*, the sequence was confirmed using a Dye Terminator Cycle Sequencing Kit (available from Beckman Coulter Inc.). This was named pRH31.

Figure 4:
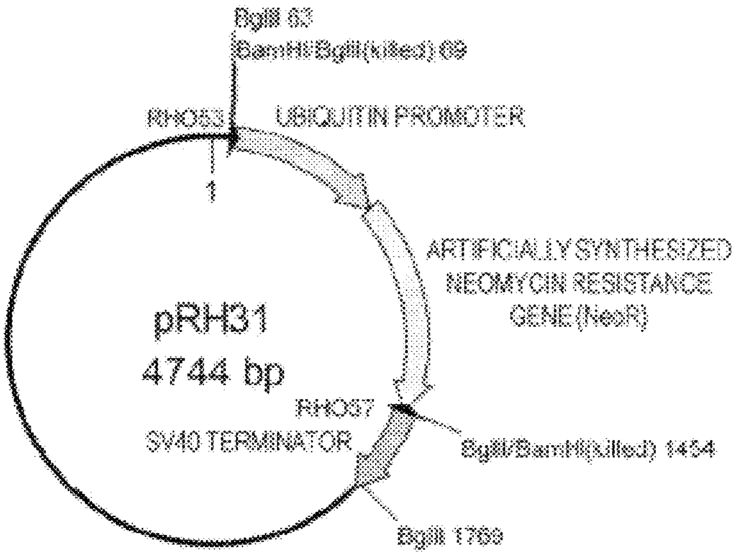
FIG. 4 illustrates the BglII cassette of the produced artificially synthesized neomycin resistance gene.

The produced artificially synthesized neomycin resistance gene cassette (pRH31) is illustrated in FIG. 4.

[Example 2-3]: Production of Hygromycin Resistance Gene Cassette

Using *Thraustochytrium aureum* ATCC 34304 genome DNA as a template, a ubiquitin promoter sequence (617 bp, SEQ ID NO: 11) was amplified with PrimeSTAR HS DNA Polymerase with GC Buffer (available from Takara Bio Inc.). The PCR primers used were as shown below. RHO53 was set on the ubiquitin promoter sequence, and includes a BglII linker sequence. KS08 includes the ubiquitin promoter sequence and a hygromycin resistance gene sequence. [RHO53: 36mer: 5'-CCC AGA TCT GCC GCA GCG CCT GGT GCA CCC GCC GGG-3' (described in Example 2-2, SEQ ID NO: 5), KS08: 58mer: 5'-TCG CGG TGA GTT CAG GCT TTT TCA TGT TGG CTA GTG TTG CTT AGG TCG CTT GCT GCT G-3' (SEQ ID NO: 12)][PCR cycles: 98° C. 2 min/98° C. 30 sec, 68° 2 min, 30 cycles/68° C. 2 min]

Using pcDNA 3.1/Hygro (available from Invitrogen Corp.) as a template, a hygromycin resistance gene (1058 bp, SEQ ID NO: 13) was amplified with PrimeSTAR HS DNA Polymerase with GC Buffer (available from Takara Bio Inc.). The PCR primers used were as shown below. KS07 includes the ubiquitin promoter sequence and the hygromycin resistance gene sequence. RHO56 includes the hygromycin resistance gene sequence and has a BglII linker sequence. [KS07: 56mer: 5'-AGC GAC CTA AGC AAC ACT AGC CAA CAT GAA AAA GCC TGA ACT CAC CGC GAC GTC TG-3' (SEQ ID NO: 14), RHO56: 36mer: 5'-CAG ATC TCT ATT CCT TTG CCC TCG GAC GAG TGC TGG-3' (SEQ ID NO: 15)]. [PCR cycles: 98° C. 2 min/98° C. 30 sec, 68° 2 min, 30 cycles/68° C. 2 min]

Figure 5:
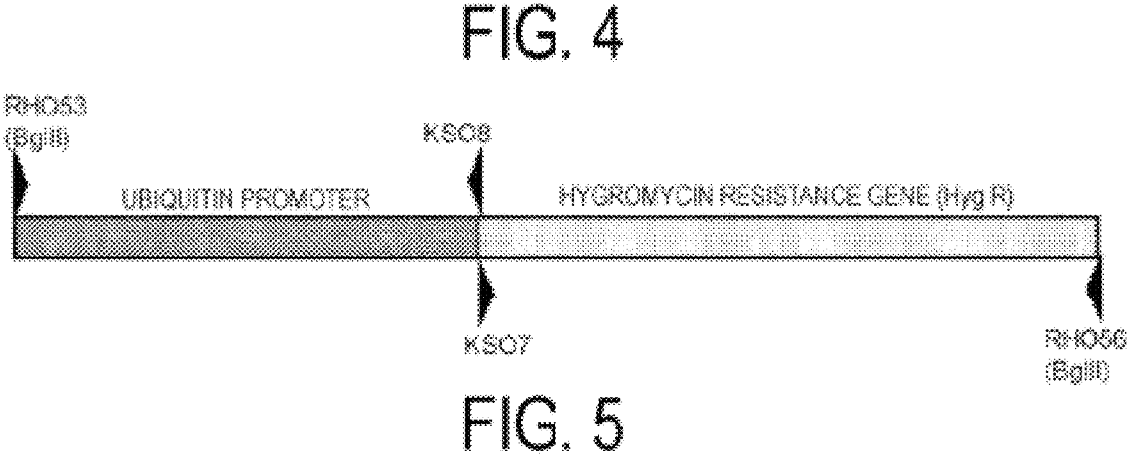
FIG. 5 is a schematic diagram of the primers used in fusion PCR and the products. The final product is a fused sequence of a ubiquitin promoter derived from *Thraustochytrium aureum* ATCC 34304 and a hygromycin resistance gene derived from pcDNA 3.1/Hygro.

Using SEQ ID NO: 11 and SEQ ID NO: 13 as templates, fusion PCR was performed using RHO53 (described in Example 2-2, SEQ ID NO: 5) and RHO56 (SEQ ID NO: 15) according to the method described in Non-patent Document 9. Amplification was performed using LA Taq Hot Start Version (available from Takara Bio Inc.) as the enzyme under the following conditions, and then the amplified product was digested with BglII. [PCR cycles: 94° C. 2 min/94° C. 20 sec, 55° C. 30 sec, 68° C. 1 min, 30 cycles/68° C. 1 min (1° C./10 sec from 55° C. to 68° C.)](FIG. 5).

The *Thraustochytrium aureum* ATCC 34304-derived ubiquitin promoter -pcDNA 3.1/Hygro (available from Invitrogen Corp.)-derived hygromycin resistance gene (1625 bp, SEQ ID NO: 16) fused as described above was digested with BglII, and the resultant was bound to the BamHI site of pRH27 described in Example 2-1, FIG. 2. After amplification of the produced plasmid with *E. coli*, the sequence was confirmed using a Dye Terminator Cycle Sequencing Kit (available from Beckman Coulter Inc.). This was named pRH32.

Figure 6:
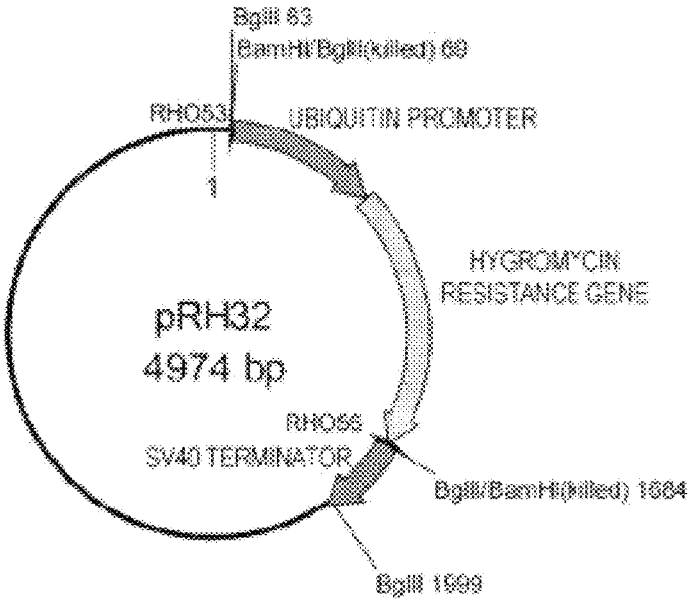
FIG. 6 illustrates the BglII cassette of the produced hygromycin resistance gene derived from pcDNA 3.1/Hygro.

The produced hygromycin resistance gene cassette (pRH32) is illustrated in FIG. 6.

[Example 2-4]: Cloning of Genus *Parietichytrium* C20 Elongase Gene

Genome DNA of *Parietichytrium sarkarianum* SEK364 was extracted by the method described in Example 2-2, and the genome was read.

With the region conserved in the C20 elongase gene as a target, a forward oligonucleotide (PsTaELO2 F1; 5'-CCT TCG GCG CTC CTC TTA TGT ATG T-3') (SEQ ID NO: 17) and a reverse oligonucleotide (PsTaELO2 R2; 5'-CAA TGC AAG AGG CGA ACT GGG AGA G-3') (SEQ ID NO: 18) were synthesized. Next, using the *Parietichytrium sarkarianum* SEK364 genome DNA prepared by the method described in Example 2-2 as a template, PCR was performed using the oligonucleotides PsTaELO2 F1 and PsTaELO2 R2 using LA Taq Hot Start Version (available from Takara Bio Inc.). [PCR cycles: 98° C. 1 min/98° C. 10 sec, 60° C. 30 sec, 72° C. 1 min, 30 cycles/72° C. 7 min/4° C.∞]. The obtained specific amplification product underwent gel purification, and when the base sequence thereof was analyzed by direct sequencing, it exhibited significant homology to a known C20 elongase gene sequence. This shows that it was a partial sequence of the C20 elongase gene derived from *Parietichytrium sarkarianum* SEK364.

Then, the C20 elongase gene derived from *Parietichytrium sarkarianum* SEK364 was cloned by 3'- and 5'-RACE in the same manner as Comparative Example 1-2 to be described later. First, forward oligonucleotide primers (PsRACE F1; 5'-TGG GGC TCT GGA ACC GCT GCT TAC G-3') (SEQ ID NO: 19) and (PsRACE F2; 5'-CTT CCA GCT CTC CCA GTT CGC CTC T-3') (SEQ ID NO: 20), and reverse oligonucleotide primers (PsRACE R1; 5'-CGG GTT GTT GAT GTT GAG CGA GGT G-3') (SEQ ID NO: 21) and (PsRACE R2; 5'-CCC ACG CCA TCC ACG AGC ACA CCA C-3') (SEQ ID NO: 22) were designed. Next, using a cDNA library produced by SMART RACE cDNA Amplification Kit (trade name; available from Clontech Laboratories, Inc.) as a template, 3'- and 5'-RACE were performed using a synthetic adapter-specific oligonucleotide and the above oligonucleotide PsRACE F1 or PsRACE R1. [PCR cycles: 94° C. 30 sec 5 cycles/94° C. 30 sec, 70° C. 30 sec, 72° C. 3 min, 5 cycles/94° C. 30 sec, 68° C. 30 sec, 72° C. 3 min, 25 cycles/4° C.∞]. Then, using the two obtained RACE products as templates, nested PCR was performed using a synthetic adapter-specific oligonucleotide and the above oligonucleotide PsRACE F2 or PsRACE R2. [PCR cycles: 94° C. 1 min/94° C. 30 sec, 68° C. 30 sec, 72° C. 3 min, 25 cycles/72° C. 10 min/4° C.∞]. The obtained specific amplification product underwent gel purification, and when the base sequence thereof was analyzed after TA cloning using pGEM-Easy Vector (available from Promega Corporation), it was confirmed to be the C20 elongase gene derived from *Parietichytrium sarkarianum* SEK364.

Additionally, using the genus *Parietichytrium* genome DNA extracted by the method described in Example 2-2 as a template, a sequence containing a C20 elongase gene sequence (957 bp, SEQ ID NO: 23) was amplified with LA Taq Hot Start Version (available from Takara Bio Inc.). The PCR primers used were as shown below. RHO153 includes a start codon, and has a BamHI site as a linker sequence.

RHO154 includes a stop codon, and has a BamHI site as a linker sequence. [RHO153: 32mer: 5'-CCC GGA TCC ATG GCA GCT CGC GTG GAG AAA CA-3' (SEQ ID NO: 24), RHO154: 33mer: 5'-CCC GGA TCC TTA CTG AGC CTT CTT GGA GGT CTC-3' (SEQ ID NO: 25)]. [PCR cycles: 98° C. 2 min/98° C. 10 sec, 68° 1 min, 30 cycles/68° C. 2 min].

The obtained DNA fragment was cloned in pGEM-T Easy Vector, and after amplification with *E. coli*, the sequence was confirmed using a Dye Terminator Cycle Sequencing Kit (available from Beckman Coulter Inc.).

Figure 7:
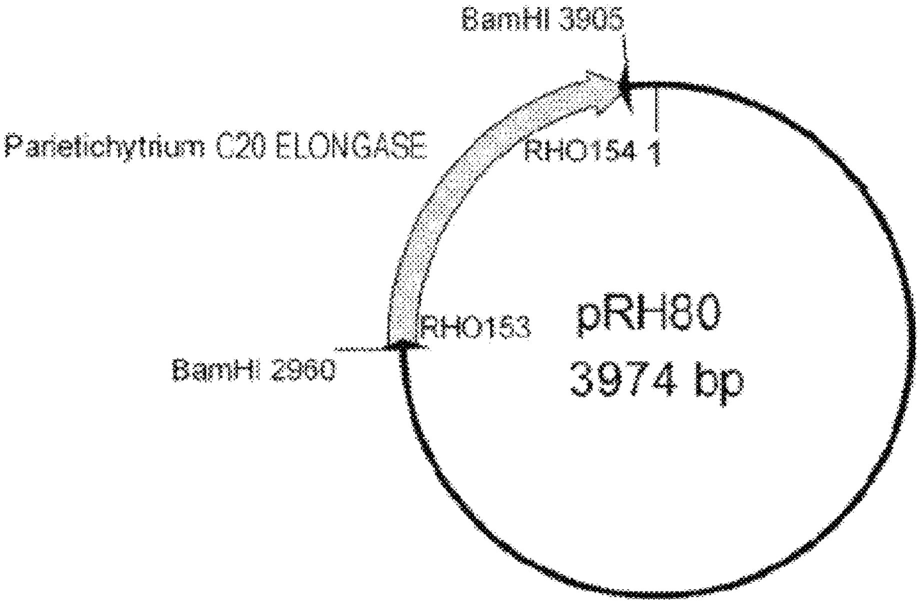
FIG. 7 illustrates a plasmid containing a C20 elongase sequence of cloned genus of *Parietichytrium.*

The genus *Parietichytrium* C20 elongase gene (936 bp, SEQ ID NO: 26) was cloned. This was named pRH80 (FIG. 7). The amino acid sequence is shown SEQ ID NO: 27.

[Example 2-5]: Production of Base Plasmid for Production of Genus *Parietichytrium* C20 Elongase Gene Targeting Vector A primer set that was set up in the reverse direction so as to insert a BglII site into the core portion of the C20 elongase gene sequence was prepared using pRH80 (FIG. 7) produced in Example 2-4 as a template, and the resultant was amplified with PrimeSTAR Max DNA Polymerase (available from Takara Bio Inc.). The PCR primers used were as shown below and have a BglII linker sequence. [RHO155: 26mer: 5'-ACA AAG ATC TCG ACT GGA CCG ACA CC-3' (SEQ ID NO: 28), RHO156: 27mer: 5'-AGT CGA GAT CTT TGT CAG GAG GTG GAC-3' (SEQ ID NO: 29)]. [PCR cycles: 98° C. 2 min/98° C. 10 sec, 56° C. 15 sec, 72° C. 1 min, 30 cycles/72° C. 1 min]. After amplification under the above conditions, it was digested with BglII and then self-ligated. After the ligated sample was amplified with *E. coli*, the sequence was confirmed using a Dye Terminator Cycle Sequencing Kit (available from Beckman Coulter Inc.). This was named pRH83. The C20 elongase gene sequence (935 bp) in which a BglII site was inserted is shown in SEQ ID NO: 30.

Figure 8:
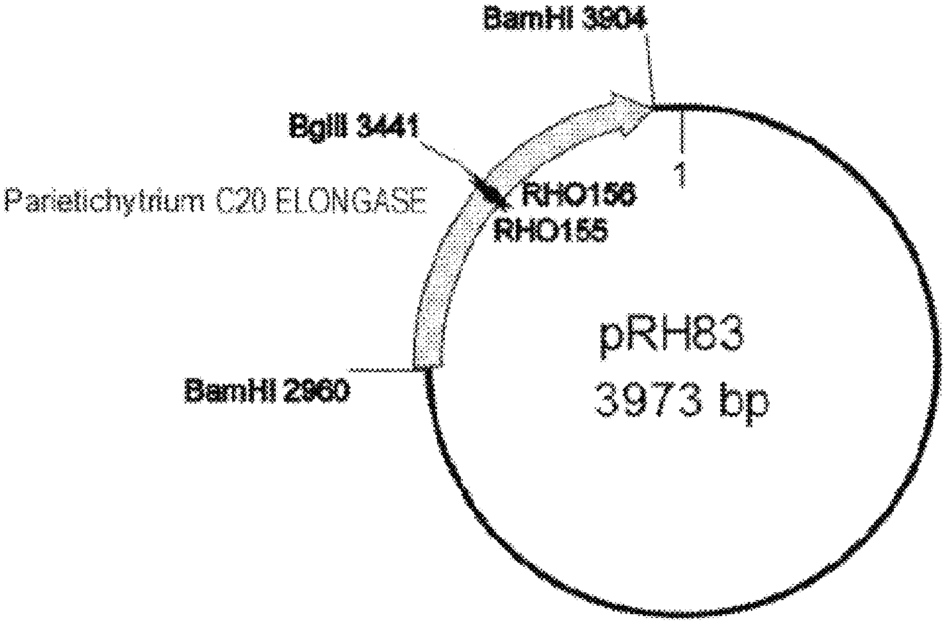
FIG. 8 illustrates a plasmid in which a BglII site has been inserted in a C20 elongase sequence of genus of *Parietichytrium* of the plasmid illustrated in FIG. 7.

FIG. 8 illustrates the produced base plasmid (pRH83) for producing a genus *Parietichytrium* C20 elongase gene targeting vector.

[Example 2-6]: Production of Targeting Vectors (Artificially Synthesized Neomycin Gene and Hygromycin Resistance Gene)

pRH31 (FIG. 4) described in Example 2-2 was digested with BglII, and a DNA fragment containing an artificially synthesized neomycin resistance gene cassette was bound to the BglII site of pRH83 (FIG. 8) described in Example 2-5. This was named pRH85.

pRH32 (FIG. 6) described in Example 2-3 was digested with BglII, and a DNA fragment containing a hygromycin resistance gene cassette was bound to the BglII site of pRH83 (FIG. 8) described in Example 2-5. This was named pRH86.

Figure 9:
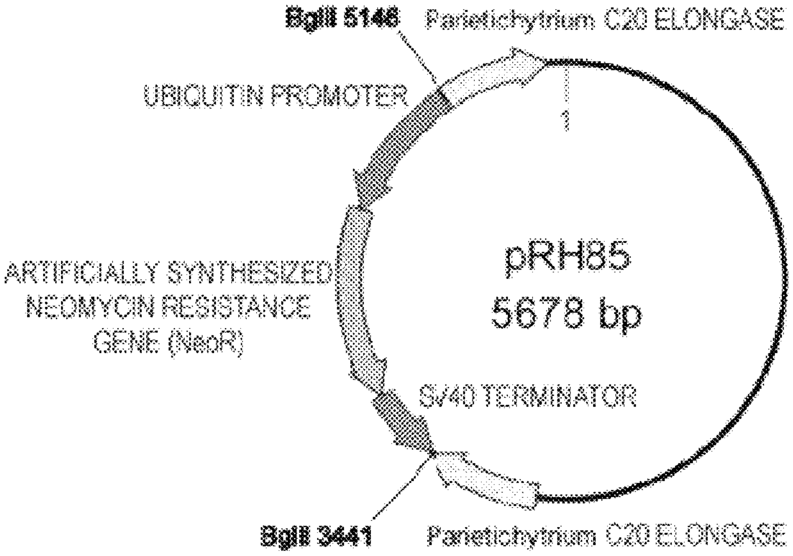
FIG. 9 illustrates the produced genus of *Parietichytrium* C20 elongase gene targeting vectors (two types). As a drug resistance marker, the vectors have a neomycin resistance gene (pRH85) or a hygromycin resistance gene (pRH86).
Figure 9:
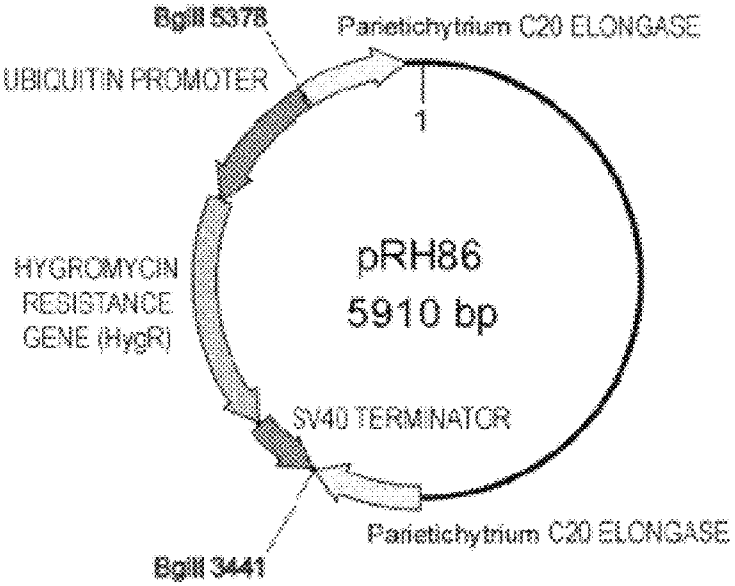

The two produced targeting vectors (pRH85 and 86) are illustrated in FIG. 9.

[Example 2-7]: C20 Elongase Gene Targeting Vector Transfer

Using the two targeting vectors produced in Example 2-6 as templates, the genes were amplified with PrimeSTAR Max DNA Polymerase (available from Takara Bio Inc.) using RHO153 (described in Example 2-4, SEQ ID NO: 24) and RHO154 (described in Example 2-4, SEQ ID NO: 25) as primers. [PCR cycles: 98° C. 2 min/98° C. 30 sec, 68° 2 min, 30 cycles/68° C. 2 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH85 (FIG. 9) described in Example 2-6 was used as a template was 2661 bp, and resulted in a sequence composed of genus *Parietichytrium* C20 elongase gene front half—SV40 terminator sequence—artificially synthesized neomycin resistance gene sequence—ubiquitin promoter sequence—genus *Parietichytrium* C20 elongase gene back half (SEQ ID NO: 31). The transfer fragment obtained when pRH86 (FIG. 9) described in Example 2-6 was used as a template was 2892 bp, and resulted in a sequence composed of genus ParietichytriumC20 elongase gene front half—SV40 terminator sequence—hygromycin resistance gene sequence—ubiquitin promoter sequence—genus *Parietichytrium* C20 elongase gene back half (SEQ ID NO: 32).

The *Parietichytrium sarkarianum* SEK364 strain was cultured for 4 days in a GY culture medium, and cells in the logarithmic growth phase were used for gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 1550 psi). After a recovery time of 24 hr, the transgenic cells were spread on a PDA agar plate culture medium (containing 2 mg/mL of G418 or containing 2 mg/mL of hygromycin). As a result, from 10 to 20 cells of drug resistant strain per shot were obtained.

Figure 10:
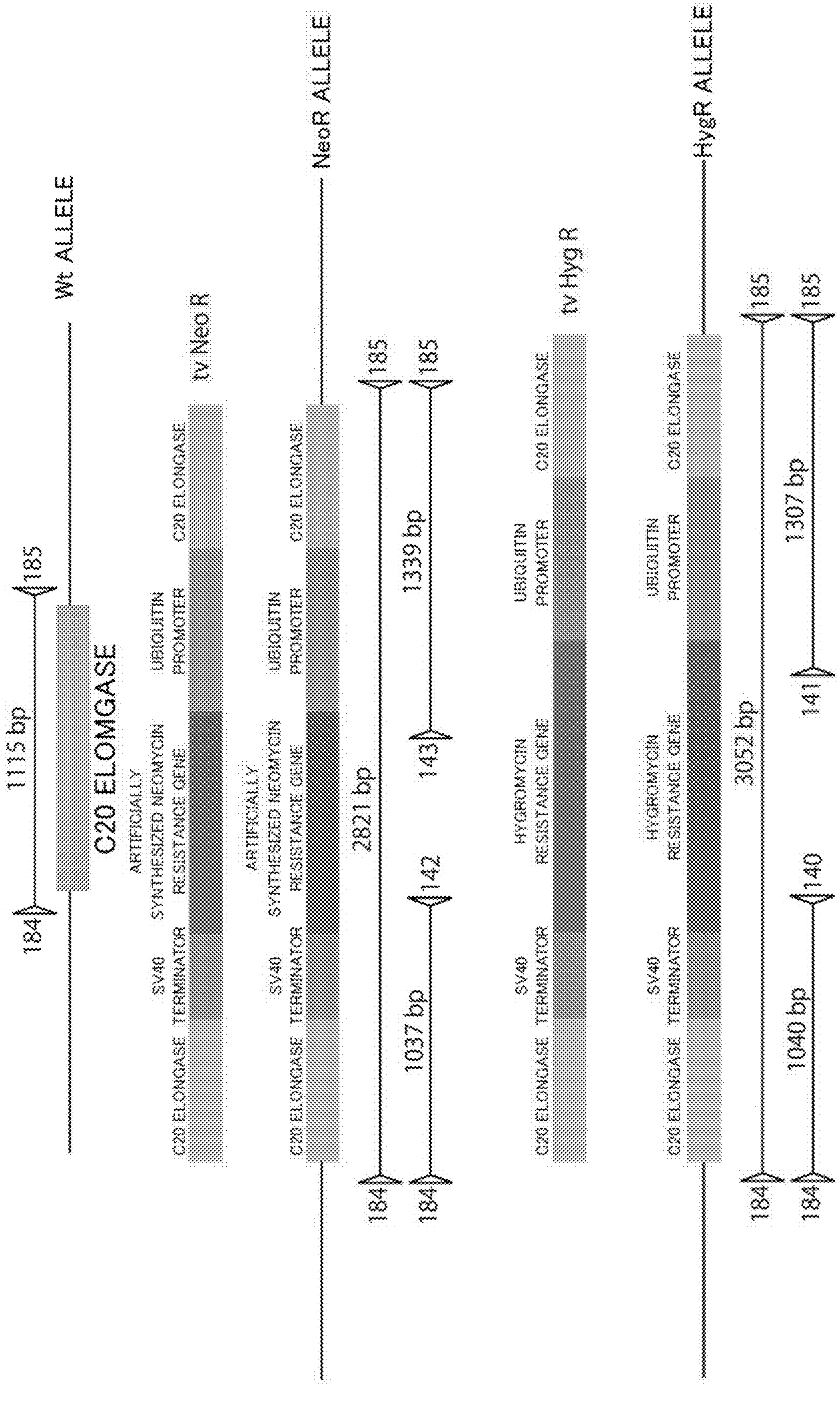
FIG. 10 is a schematic diagram illustrating the positions of the PCR primers used in identification of a C20 elongase gene disruption strain of *Parietichytrium sarkarianum* SEK364, and the expected product.

[Example 2-8]: Identification of C20 Elongase Gene Targeting Homologous Recombinant Genome DNA of the *Parietichytrium sarkarianum* SEK364 strain, a C20 elongase gene hetero homologous recombinant, and a C20 elongase gene homo homologous recombinant (gene disruption strain) were extracted by the method described in Example 2-2, and then A260/280 was measured and the DNA concentration was calculated. Using the genome DNA as templates, PCR for genome structure confirmation was performed using LA Taq Hot Start Version (available from Takara Bio Inc.). The positions of the primers used, the combinations used in amplification, and the expected sizes of the amplification products are illustrated in FIG. 10. RHO184 was set upstream of C20 elongase; RHO185 was set downstream; RHO142 and RHO143 were set on the artificially synthesized neomycin resistance gene; and RHO140 and RHO141 were set on the hygromycin resistance gene. [RHO140: 20mer: 5'-GGT TGA CGG CAA TTT CGA TG-3' (SEQ ID NO: 33), RHO141: 22mer: 5'-CCT CCT ACA TCG AAG CTG AAA G-3' (SEQ ID NO: 34), RHO142: 21mer: 5'-CTT CTC GGG CTT TAT CGA CTG-3' (SEQ ID NO: 35), RHO143: 22mer: 5'-TAA GGT CGG TCT TGA CAA ACA G-3' (SEQ ID NO: 36), RHO184: 24mer: 5'-AGT AGT CCC CGA TTT GGT AGT TGA-3' (SEQ ID NO: 37), RHO185: 22mer: 5'-GGC AGA GAG CAA AAA CAC GAG C-3' (SEQ ID NO: 38)]. [PCR cycles: 98° C. 2 min/98° C. 10 sec, 68° 4 min, 30 cycles/68° C. 7 min].

Figure 11:
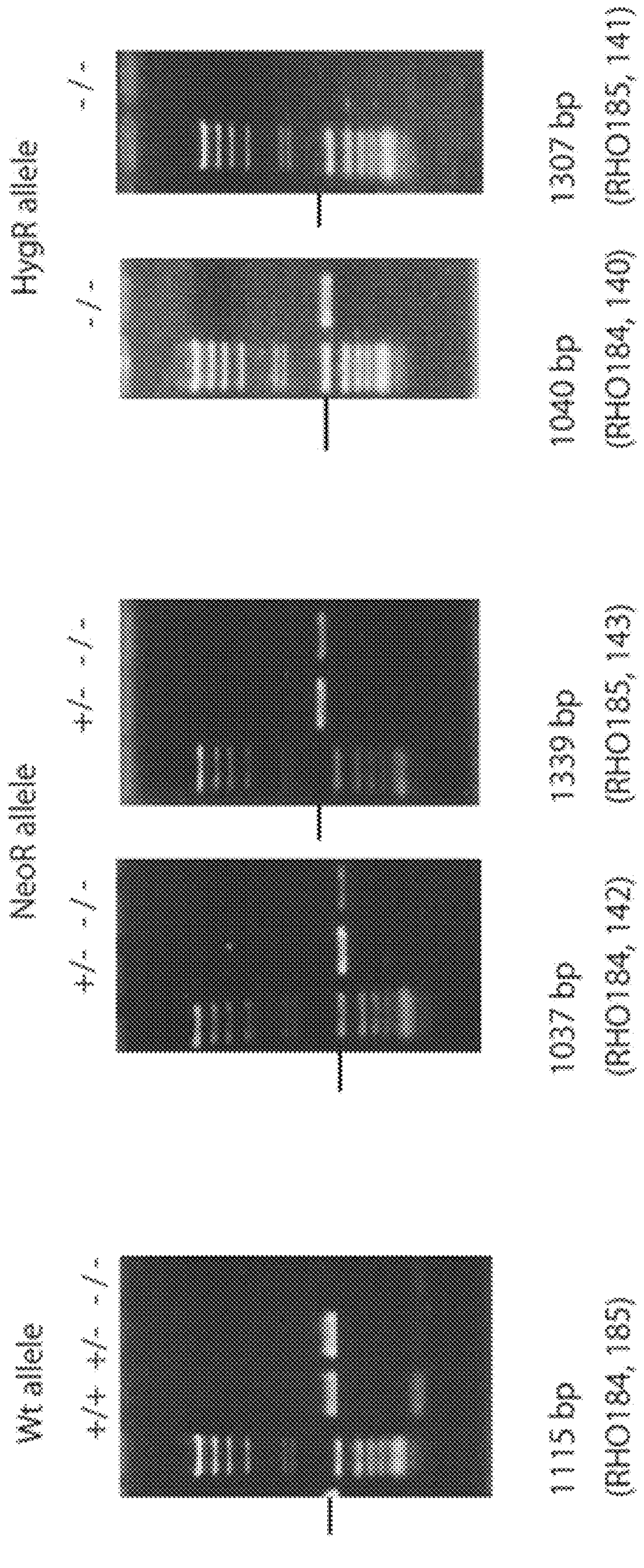
FIG. 11 illustrates an evaluation of C20 elongase gene disruption by PCR using *Parietichytrium sarkarianum* SEK364 genome DNA as a template. (Description of symbols)+/+: *Parietichytrium sarkarianum* SEK364 wild-type strain; +/−: C20 elongase gene first allele homologous recombinant derived from *Parietichytrium sarkarianum* SEK364; −/−: C20 elongase disruption strain derived from *Parietichytrium sarkarianum* SEK364

A C20 elongase gene disruption strain in which there is no amplification in the wild-type allele (Wt allele) and there is amplification in the artificially synthesized neomycin resistance gene allele (NeoR allele) and the hygromycin resistance gene allele (HygR allele) was obtained (FIG. 11).

Example 2-9: Change in Fatty Acid Composition by C20 Elongase Gene Disruption

The *Parietichytrium sarkarianum* SEK364 wild-type strain and the gene disruption strain thereof (C20 elongase gene disruption strain, C20 −/−) were cultured in a GY culture medium. The cells of the latter phase of the logarithmic growth phase were centrifuged for 10 min at 4° C. at 3000 rpm to form pellets, and the obtained pellets were suspended in 0.9% NaCl and washed. Then, the resultant was centrifuged for 10 min at 4° C. at 3000 rpm, and the pellets were suspended in sterilized water and washed. The resultant was further centrifuged for 10 min at 3000 rpm, the supernatant was removed and the precipitate was freeze-dried.

To the freeze-dried cells, 2 mL of methanolic KOH (7.5% KOH in 95% methanol) was added, and after vortexing, the cells were crushed by ultrasound (80° C., 30 min). Then, 500 μL of sterilized water was added and vortexing was performed, and then 2 mL of n-hexane was added and vortexing was performed. The resultant was then centrifuged for 10 min at 3000 rpm, and the top layer was discarded. Another 2 mL of n-hexane was added and vortexing was performed. The resultant was centrifuged for 10 min at 3000 rpm, and the top layer was discarded. One mL of 6 N HCl was added to the remaining bottom layer and vortexing was performed, and then 2 mL of n-hexane was added and vortexing was performed. The resultant was then centrifuged for 10 min at 3000 rpm, and the top layer was collected. Another 2 mL of n-hexane was added and vortexing was performed. The resultant was centrifuged for 10 min at 3000 rpm, and the top layer was collected. The collected top layer was concentrated and dried with nitrogen gas. Two mL of 3 N methanolic HCl was added to the concentrated and dried sample, and the resultant was incubated overnight at 80° C.

The sample was cooled to room temperature, and 1 mL of 0.9% NaCl was added. Then, 2 mL of n-hexane was added and vortexing was performed. The resultant was centrifuged for 10 min at 3000 rpm, and the top layer was collected. Another 2 mL of n-hexane was added and vortexing was performed. The resultant was centrifuged for 10 min at 3000 rpm, and the top layer was collected. A small amount of anhydrous sodium sulfate was added to the collected top layer and then vortexing was performed. The resultant was centrifuged for 10 min at 3000 rpm, and the top layer was collected. The collected top layer was concentrated and dried with nitrogen gas. The concentrated and dried sample was dissolved in 0.5 mL of n-hexane, and 1 μL of the resultant was subjected to GC analysis. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 12:
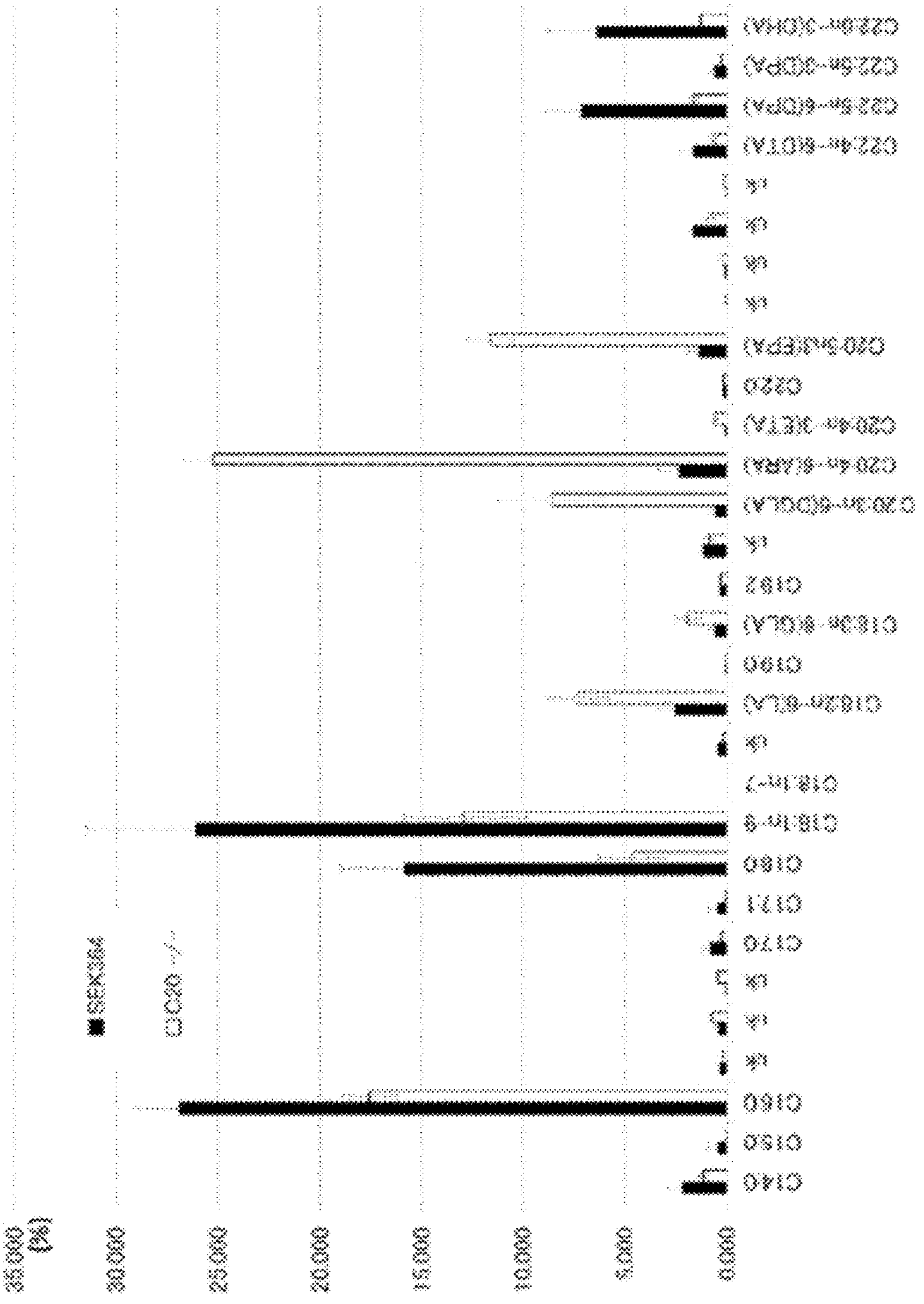
FIG. 12 illustrates a comparison of fatty acid compositions of the *Parietichytrium sarkarianum* SEK364 wild-type strain and the C20 elongase gene disruption strain. The black bars and white bars represent the fatty acid composition of the wild-type strain and the gene disruption strain, respectively. The values are mean±standard deviation.

As a result, when the C20 elongase gene was disrupted in *Parietichytrium sarkarianum* SEK364, fatty acids having not less than 22 carbon chains decreased while fatty acids having 20 carbon chains increased (FIG. 12). FIG. 13 shows the proportion when the wild-type strain is taken as 100%. FIG. 13 shows that, of the total fatty acid composition, ARA is 25.22%, DGLA is 8.62%, ETA is 0.56%, EPA is 11.58%, n-6 DPA is 1.64%, and DHA is 1.28%. FIG. 13 shows that, by GC area, LA/DHA is 5.8, GLA/DHA is 1.5, DGLA/DHA is 6.7, ARA/DHA is 19.7, EPA/DHA is 9.0, LA/EPA is 0.64, GLA/EPA is 0.16, DTA/EPA is 0.06, DTA/ARA is 0.03, DTA/DGLA is 0.08, LA/n-6 DPA is 4.5, GLA/n-6 DPA is 1.2, DGLA/n-6 DPA is 5.3, ARA/n-6 DPA is 15.4, EPA/n-6 DPA is 7.1, DGLA/LA is 1.2, ARA/LA is 3.4, EPA/LA is 1.6, DTA/LA is 0.09, DGLA/GLA is 4.5, ARA/GLA is 13.2, n-6 DPA/DTA is 2.4, DHA/n-3 DPA is 4.9, C20 PUFA/C22 PUFA is 11.94, and n-6 PUFA/n-3 PUFA is 2.67.

In these results, arachidonic acid increased approximately 10-fold, EPA approximately 8-fold, and DGLA approximately 16-fold, while DPA decreased to approximately ¼ and DHA to approximately ⅕.

By selecting the labyrinthulid *Parietichytrium sarkarianum* SEK364 having no PUFA-PKS pathway in this manner, a strain that accumulates PUFAs other than DHA and n-6 DPA can be produced without PUFA-PKS pathway gene disruption. This strain may also be used as a strain that produces EPA and/or ARA, and further disruption or transforming elongase or desaturase genes can create strains that produce desired PUFAs.

Example 3

[Measurement of Fatty Acid Composition of Lipids Produced by Δ4 Desaturase Gene Disruption and Transformation Strain of *Parietichytrium sarkarianum* SEK364]

[Example 3-1]: Cloning of Genus *Parietichytrium* Δ4 Desaturase Gene

Genome DNA of *Parietichytrium* sp. SEK571 was extracted by the method described in Example 2-2. Using the extracted genome DNA as a template, a sequence containing the Δ4 desaturase gene sequence (5003 bp, SEQ ID NO: 39) was amplified with LA Taq Hot Start Version (available from Takara Bio Inc.). The PCR primers used were as shown below. [RHO241: 23mer: 5'-GTT TGA GGA GCG AGG CAT TTC TT-3' (SEQ ID NO: 40), RHO242: 23mer: 5'-AGT GCT CGT ACA ATG ACT GGC GT-3' (SEQ ID NO: 41)].

The obtained DNA fragment was cloned in pGEM-T Easy Vector, and after amplification with *E. coli*, the sequence was confirmed using a Dye Terminator Cycle Sequencing Kit (available from Beckman Coulter Inc.). This was named pRH112 (SEQ ID NO: 42).

Figure 14:
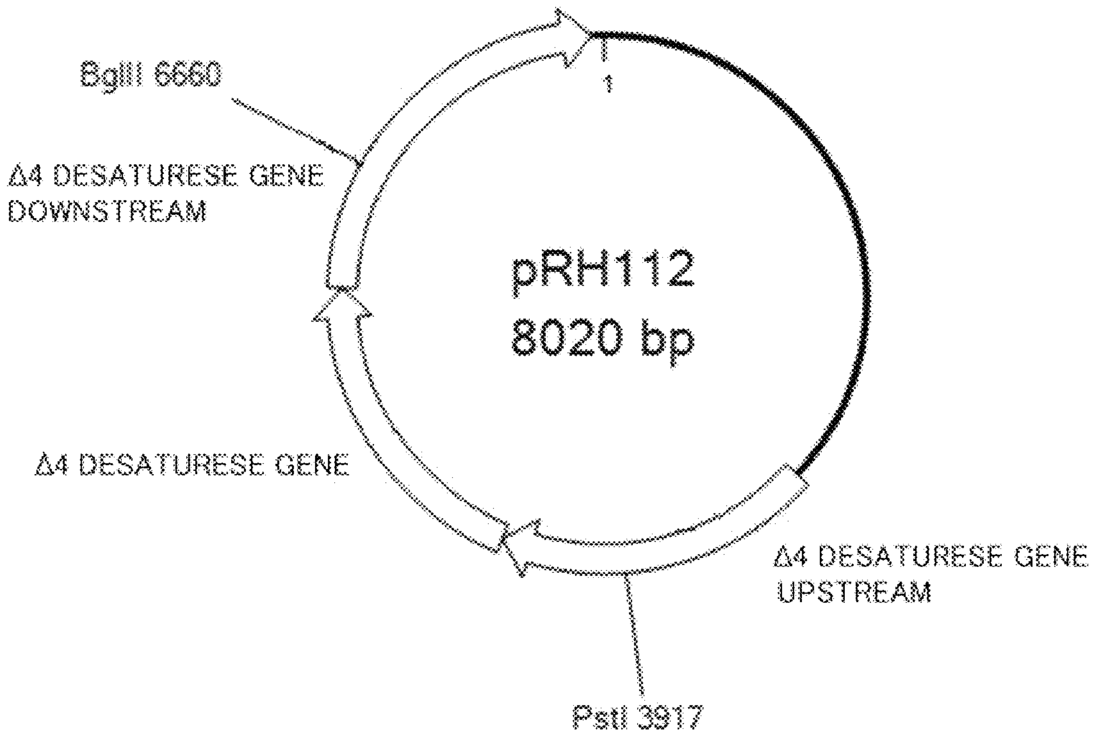
FIG. 14 illustrates a plasmid containing a cloned *Parietichytrium* sp. SEK571 Δ4 desaturase gene sequence and the peripheral sequence.

The plasmid (pRH112) containing the genus of *Parietichytrium* Δ4 desaturase gene sequence (1542 bp, SEQ ID NO: 43) is illustrated in FIG. 14.

[Example 3-2]: Production of Plasmid Serving as Base for Production of Δ4 Desaturase Gene Targeting Vector Using pRH112 (FIG. 14) produced in Example 3-1 as a template, a primer set designed so as to delete the Δ4 desaturase gene and 600 bp downstream of the Δ4 desaturase gene and to produce a BglII site in the deleted portion was prepared. [RHO243: 26mer: 5'-GGC AAG ATC TAA CTT TCT GAG GCT CT-3' (SEQ ID NO: 44), RHO244: 26mer: 5'-AAG TTA GAT CTT GCC TAT TCC ACG AT-3' (SEQ ID NO: 45)]. PrimeSTAR Max DNA Polymerase (available from Takara Bio Inc.) was used in amplification. After the amplified sample was digested with BglII, the resultant was self-ligated. After the ligated sample was amplified with *E. coli*, the sequence was confirmed using a Dye Terminator Cycle Sequencing Kit (available from Beckman Coulter Inc.). This was named pRH117.

Figure 15:
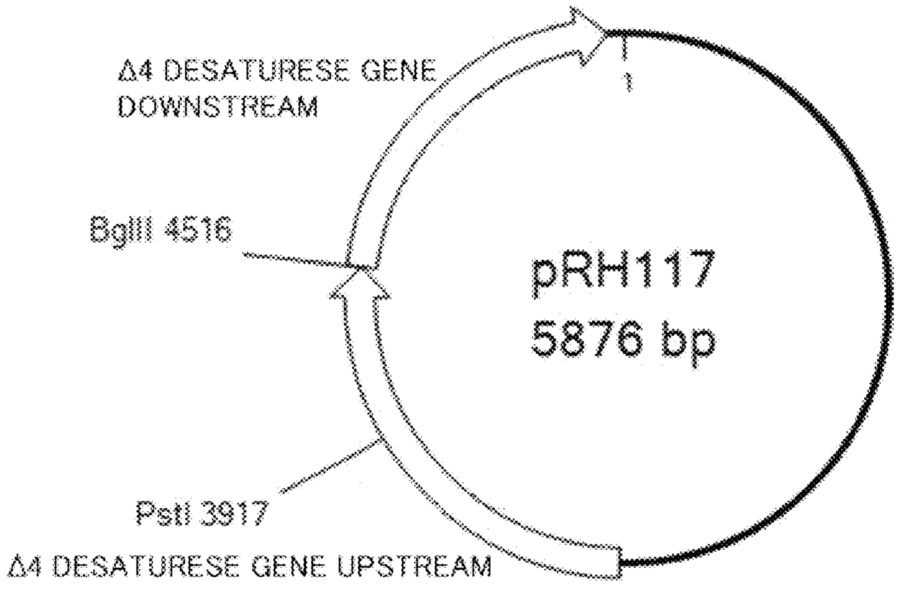
FIG. 15 illustrates a plasmid in which the *Parietichytrium* sp. SEK571 Δ4 desaturase gene sequence and a 600 bp downstream of the Δ4 desaturase gene sequence have been deleted from the plasmid illustrated in FIG. 14 and a BglII site has been inserted.

The produced plasmid (pRH117) serving as a base for production of a Δ4 desaturase gene targeting vector is illustrated in FIG. 15.

Figure 16:
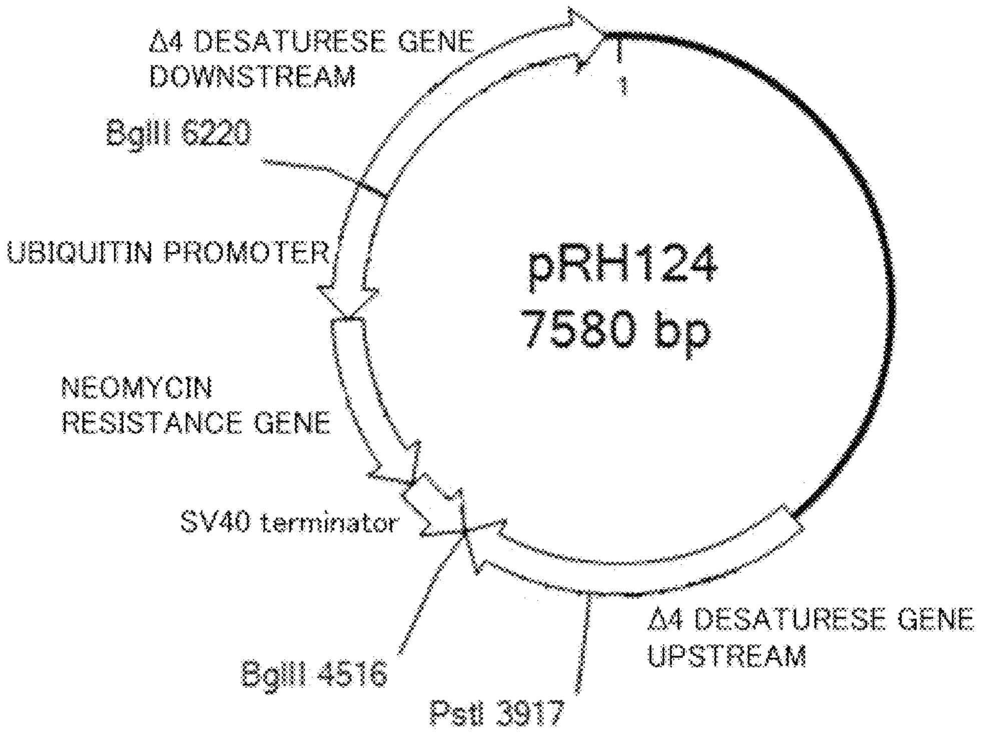
FIG. 16 illustrates a plasmid in which a DNA fragment containing an artificially synthesized neomycin resistance gene cassette has been bound at the BglII site of the plasmid illustrated in FIG. 15.

[Example 3-3]: Production of Δ4 Desaturase Gene Targeting Vector pRH31 (FIG. 4) described in Example 2-2 was digested with BglII, and a DNA fragment containing an artificially synthesized neomycin resistance gene cassette was bound to the BglII site of pRH117 (FIG. 15) described in Example 3-2. This was named pRH124 (FIG. 16). Using this pRH124 as a template, a primer set that was set up so as to delete PstI was prepared. [RHO261: 26mer: 5'-GTG CAG ACG CAG AAG AAG ACT GAC AA-3' (SEQ ID NO: 46), RHO262: 25mer: 5'-CTT CTG CGT CTG CAC GAG GAA TCG A-3' (SEQ ID NO: 47)]. PrimeSTAR Max DNA Polymerase (available from Takara Bio Inc.) was used in amplification. After transforming the PCR product into *E. coli* and amplifying, the sequence was confirmed using a Dye Terminator Cycle Sequencing Kit (available from Beckman Coulter Inc.). This was named pRH126 (SEQ ID NO: 48).

Figure 17:
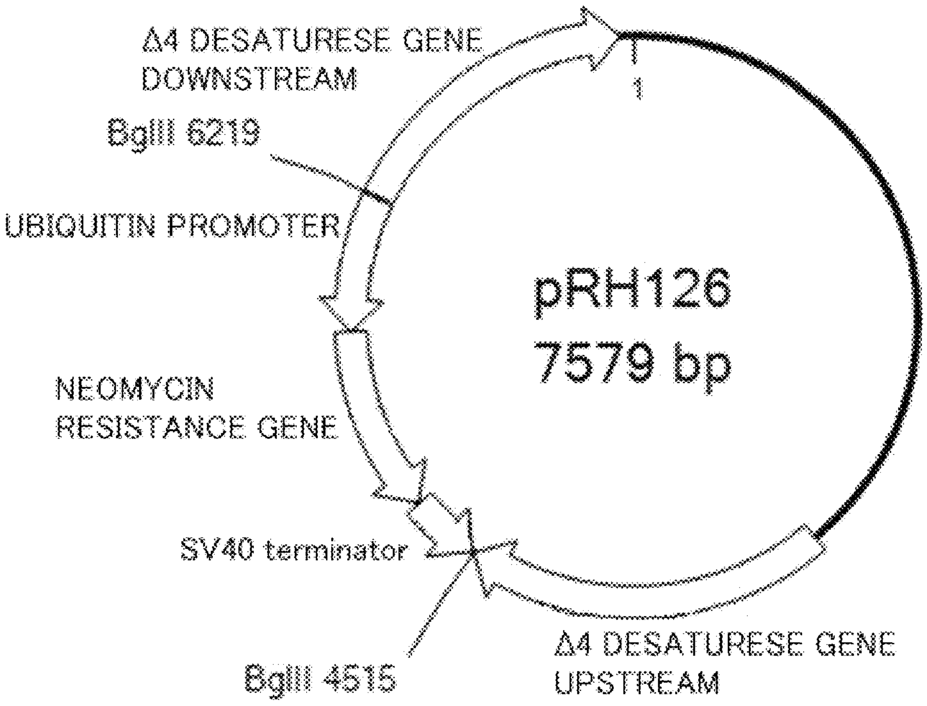
FIG. 17 illustrates the produced genus of *Parietichytrium* Δ4 desaturase gene targeting vector. As a drug resistance marker, the vector has a neomycin resistance gene.

The produced Δ4 desaturase gene targeting vector (pRH126) is illustrated in FIG. 17.

[Example 3-4]: Transfer of Δ4 Desaturase Gene Targeting Vector to *Parietichytrium sarkarianum* SEK364

Using the targeting vector pRH126 (FIG. 17) produced in Example 3-3 as a template, the gene was amplified with PrimeSTAR Max DNA Polymerase (available from Takara Bio Inc.) using RHO241 (described in Example 3-1, SEQ ID NO: 40) and RHO242 (described in Example 3-1, SEQ ID NO: 41) as primers. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH126 (FIG. 17) described in Example 3-3 was used as a template was 4562 bp.

The *Parietichytrium sarkarianum* SEK364 strain was cultured for 1 to 2 days in a GY culture medium, and cells in the logarithmic growth phase were used for gene transfer. To cells corresponding to OD600=1 to 2, 0.625 μg of DNA fragment was transformed by the gene gun method (microcarrier: 0.6 micron gold particles, target distance: 6 cm, chamber vacuum: 26 mmHg, rupture disk: 1550 psi). After a recovery time of 24 hr, the transgenic cells were spread on a PDA agar plate culture medium containing 1 mg/mL of G418. As a result, from 0 to 2 cells of drug resistant strain per shot were obtained.

Figure 18:
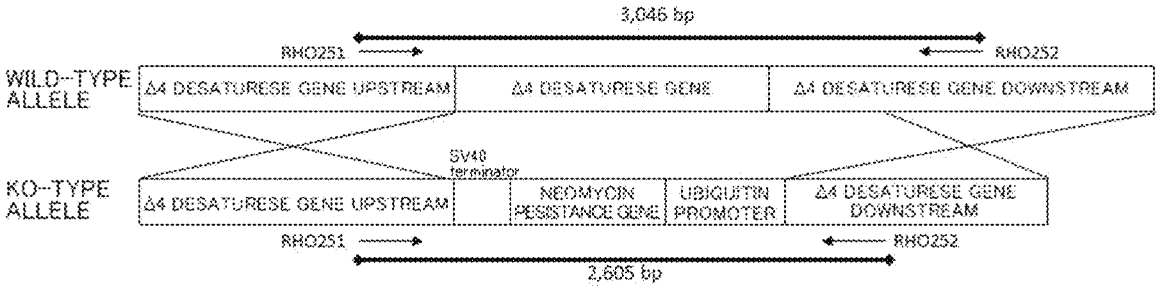
FIG. 18 is a schematic diagram illustrating the positions of the PCR primers used in identification of a Δ4 desaturase gene disruption strain of a genus of *Parietichytrium* labyrinthulid, and the expected product (primers are set within the homologous recombination region).

[Example 3-5]: Identification of Δ4 Desaturase Gene Targeting Homologous Recombinant Genome DNA of the *Parietichytrium sarkarianum* SEK364 strain and the Δ4 desaturase gene disruption strain were extracted by the method described in Example 2-2, and then A260/280 was measured and the DNA concentration was calculated. Using the genome DNA as templates, PCR for genome structure confirmation was performed using PrimeSTAR GXL DNA Polymerase (available from Takara Bio Inc.). The positions of the primers used, the combinations used in amplification, and the expected sizes of the amplification products are illustrated in FIG. 18 (within homologous region). In the primer set designed within the homologous recombination region, 3046 bp was amplified in the *Parietichytrium sarkarianum* SEK364 strain, and 2605 bp was amplified in the Δ4 desaturase gene disruption strain. [RHO251: 20mer: 5'-GTG GTC GAA GTG GAG TAT CT-3' (SEQ ID NO: 49), RHO252: 20mer: 5'-ACT CGC CAT ACA ACT TTA CA-3' (SEQ ID NO: 50)].

Figure 19:
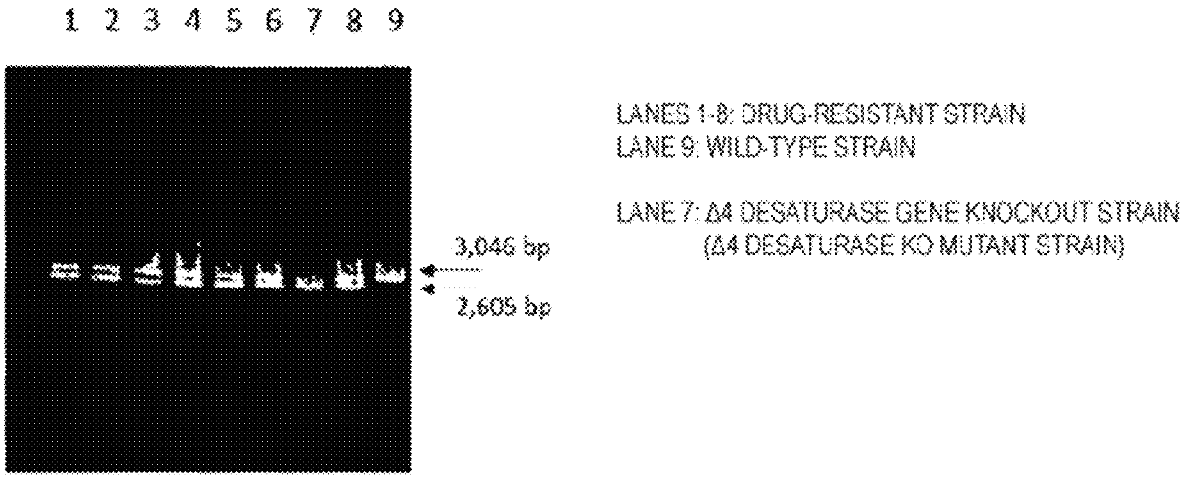
FIG. 19 illustrates evaluation results of Δ4 desaturase gene disruption by PCR using *Parietichytrium sarkarianum* SEK364 genome DNA as a template.

As a result, a Δ4 desaturase gene disruption strain in which there is no amplification derived from the wild-type allele (Wt allele) and there is amplification derived from the Δ4 desaturase gene KO allele (NeoR allele) was obtained (FIG. 19 lane 7: Δ4 desaturase KO mutant strain).

Example 3-6: Change in Fatty Acid Composition by Δ4 Desaturase Gene Disruption

The *Parietichytrium sarkarianum* SEK364 wild-type strain and the Δ4 desaturase gene disruption strain thereof were cultured according to the method described in Example 2-9, and after freeze drying, the fatty acids were methyl-esterified and analyzed using GC. In culturing, the GY liquid culture medium described in Example 1 supplemented with 0.1% of a vitamin solution (vitamin $B_1$ 200 mg, vitamin $B_2$ 1 mg, and vitamin $B_{12}$ 1 mg are dissolved in 100 mL of distilled water) and 0.2% of a trace element solution (EDTA disodium salt 30.0 g, $FeCl_3 \cdot 6H_2O$ 1.45 g, $H_2BO_3$ 34.2 g, $MnCl_2 \cdot 4H_2O$ 4.3 g, $ZnCl_2$ 1.335 g, $CoCl_2 \cdot 6H_2O$ 0.13 g, $NiSO_4 \cdot 6H_2O$ 0.26 g, $CuSO_4$ $5H_2O$ 0.01 g, and $NaMoO_4 \cdot 2H_2O$ 0.025 g are dissolved in 1 L of distilled water) was used. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(2° C./min)→220° C. (10 min); carrier gas: He (1.3 mL/min).

Figure 20:
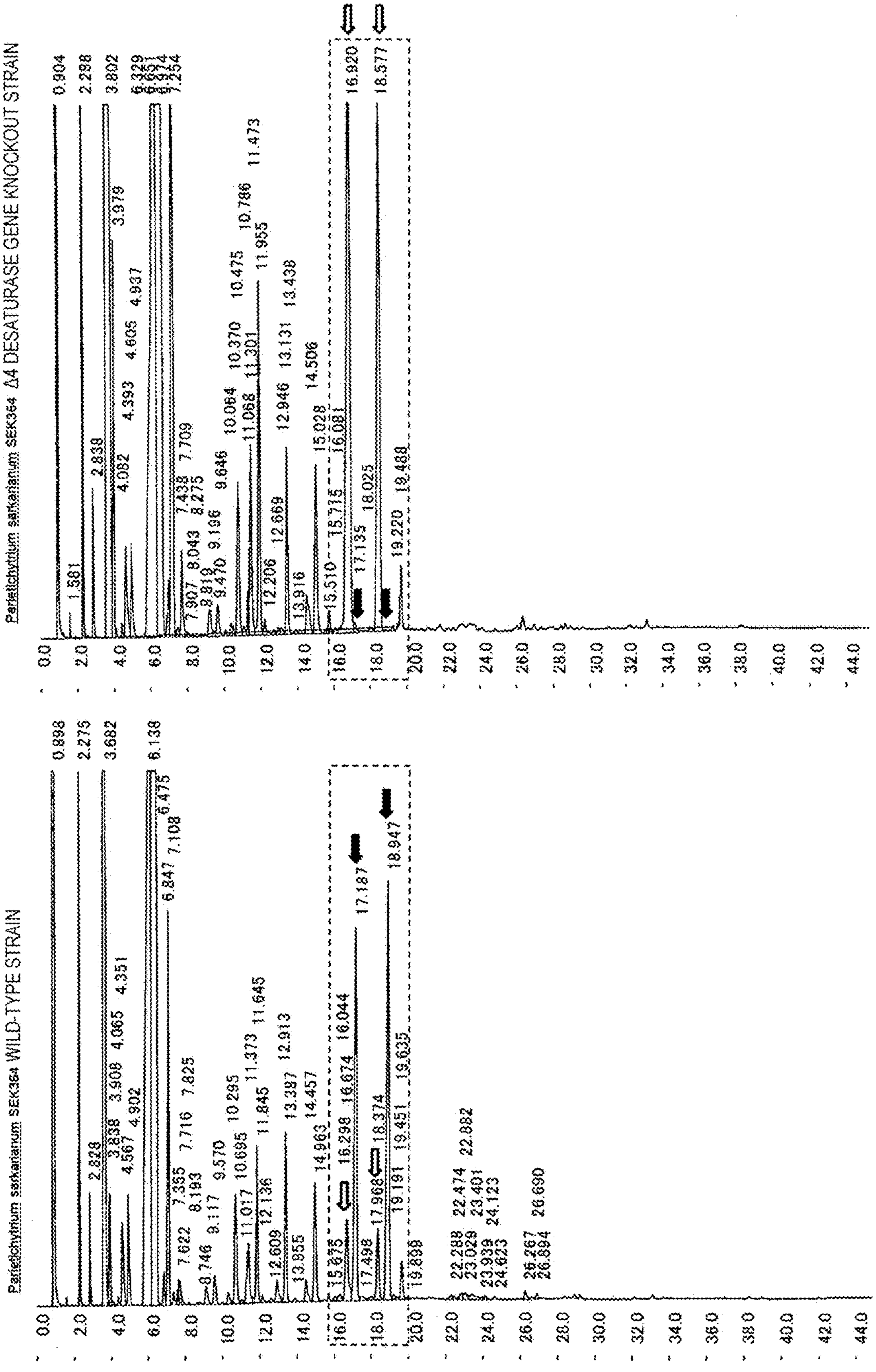
FIG. 20 is a gas chromatograph analysis chart of the fatty acid compositions of the *Parietichytrium sarkarianum* SEK364 wild-type strain and the Δ4 desaturase gene disruption strain thereof.
Figure 21:
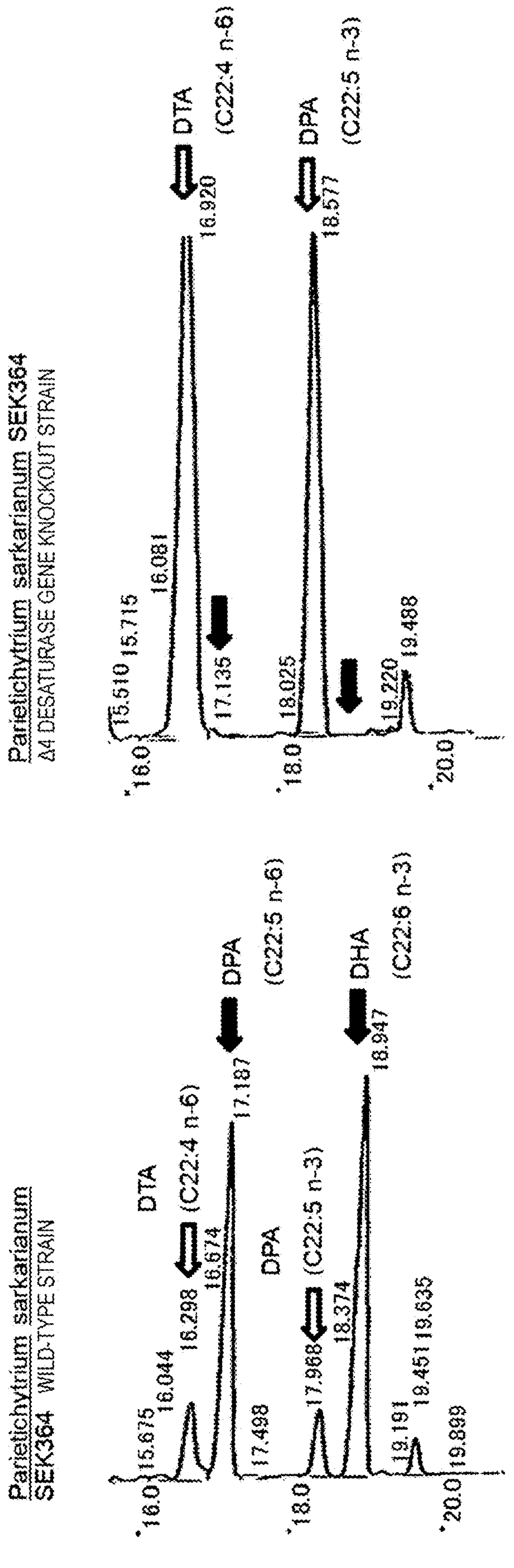
FIG. 21 is a partial enlarged diagram of FIG. 20.

The analysis results chart is shown in FIG. 20, and a partial enlarged diagram thereof is shown in FIG. 21. FIG. 22 shows a quantification of the chart of FIG. 20. This table shows a comparison of the fatty acid compositions of the *Parietichytrium sarkarianum* SEK364 wild-type strain and the Δ4 desaturase gene disruption strain thereof. This table is the quantification of the chart of FIG. 20. The table shows that, of the total fatty acid composition, ARA is 1.59%, DGLA is 0.98%, ETA is 0.05%, EPA is 0.79%, n-6 DPA is 0.00%, and DHA is 0.00%. The table shows that, by GC area, LA/EPA is 5.09, GLA/EPA is 0.48, DTA/EPA is 7.44, DTA/ARA is 3.73, DTA/DGLA is 6.06, DGLA/LA is 0.24, ARA/LA is 0.39, EPA/LA is 0.20, DTA/LA is 1.46, DGLA/GLA is 2.57, ARA/GLA is 4.19, and n-6 DPA/DTA is 0.00.

These results show that when the Δ4 desaturase gene is disrupted in the *Parietichytrium sarkarianum* SEK364 strain, DHA and DPA n-6 cannot be substantially biosynthesized, and conversely, DPA n-3 and DTA, which are substrates thereof, increase.

By selecting the labyrinthulid *Parietichytrium sarkarianum* SEK364 having no PUFA-PKS pathway in this manner, a strain that accumulates PUFAs other than DHA and DPA n-6 can be produced without PUFA-PKS pathway gene disruption. This strain may also be used as a strain that produces n-3 DPA and/or DTA, and further disruption or transforming elongase or desaturase genes can create strains that produce desired PUFAs.

Example 4

[Measurement of Fatty Acid Composition of Lipids Produced by C20 Elongase Gene Disruption and Transformation Strain of *Parietichytrium* sp. SEK358]

[Example 4-1]: Transfer of C20 Elongase Gene Targeting Vector to *Parietichytrium* sp. SEK358 Strain Using the targeting vector produced with pRH85 (FIG. 9) described in Example 2-6 as a template, the gene was amplified with PrimeSTAR Max DNA Polymerase (available from Takara Bio Inc.) using RHO153 (described in Example 2-4, SEQ ID NO: 24) and RHO154 (described in Example 2-4, SEQ ID NO: 25) as primers. [PCR cycles: 98° C. 2 min/98° C. 30 sec, 68° 2 min, 30 cycles/68° C. 2 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH85 (FIG. 9) described in Example 2-6 was used as a template was 2661 bp, and resulted in a sequence composed of genus *Parietichytrium* C20 elongase gene front half—SV40 terminator sequence—artificially synthesized neomycin resistance gene sequence—ubiquitin promoter sequence—genus *Parietichytrium* C20 elongase gene back half (described in Example 2-7, SEQ ID NO: 31).

The *Parietichytrium* sp. SEK358 strain was cultured for 3 days in a GY culture medium, and cells in the logarithmic growth phase were used for gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 900 psi). After a recovery time of 24 hr, the transgenic cells were spread on a PDA agar plate culture medium containing 0.5 mg/mL of G418. As a result, from 10 to 30 cells of drug resistant strain per shot were obtained.

[Example 4-2]: Identification of C20 Elongase Gene Targeting Homologous Recombinant Genome DNA of the *Parietichytrium* sp. SEK358 strain and the C20 elongase gene disruption strain were extracted by the method described in Example 2-2, and then A260/280 was measured and the DNA concentration was calculated. Using the genome DNA as templates, PCR for genome structure confirmation was performed using Mighty Amp DNA Polymerase (available from Takara Bio Inc.). The positions of the primers used, the combinations used in amplification, and the expected sizes of the amplification products are illustrated in FIG. 10 described in Example 2-8.

RHO184 (described in Example 2-8, SEQ ID NO: 37) was set upstream of C20 elongase; RHO185 (described in Example 2-8, SEQ ID NO: 38) was set downstream; RHO142 (described in Example 2-8, SEQ ID NO: 35) and RHO143 (described in Example 2-8, SEQ ID NO: 36) were set on the artificially synthesized neomycin resistance gene. [PCR cycles: 98° C. 2 min/98° C. 10 sec, 68° 2 min, 30 cycles/68° C. 7 min].

Figure 23:
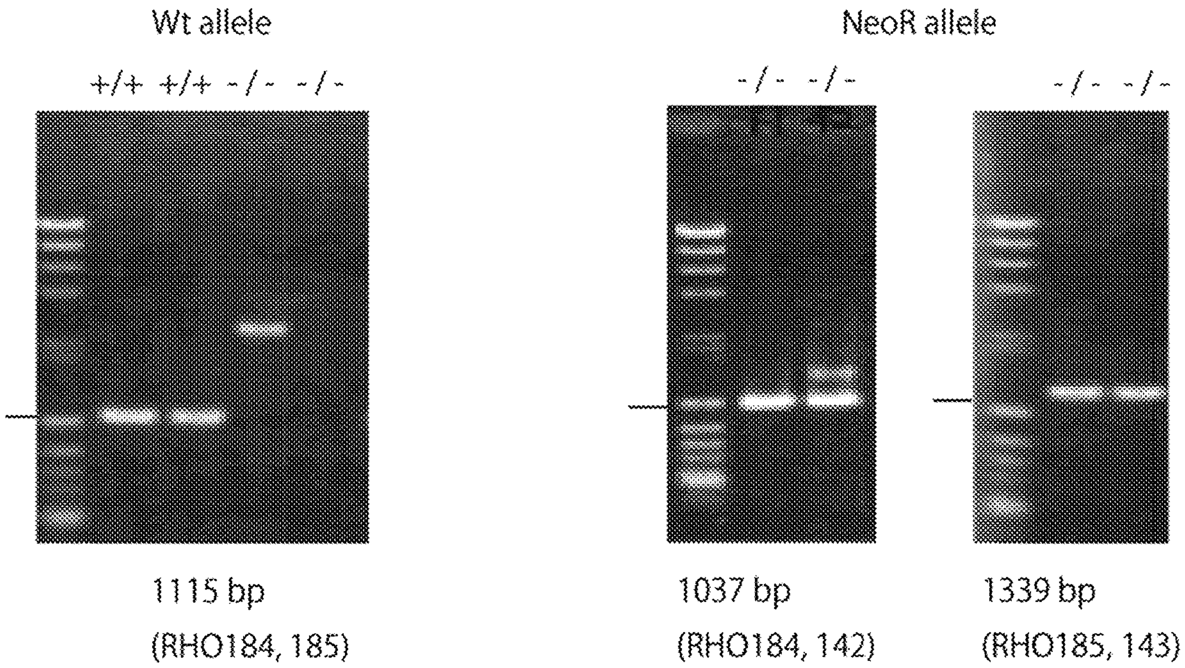
FIG. 23 illustrates an evaluation of C20 elongase gene disruption by PCR using *Parietichytrium* sp. SEK358 strain genome DNA as a template. (Description of symbols) +/+: *Parietichytrium* sp. SEK358 wild-type strain; −/−: C20 elongase gene disruption strain derived from *Parietichytrium* sp. SEK358 strain

A C20 elongase gene disruption strain in which there is no amplification in the wild-type allele (Wt allele) and there is amplification in the artificially synthesized neomycin resistance gene allele (NeoR allele) was obtained (FIG. 23).

[Example 4-3]: Change in Fatty Acid Composition by C20 Elongase Gene Disruption

Figure 24:
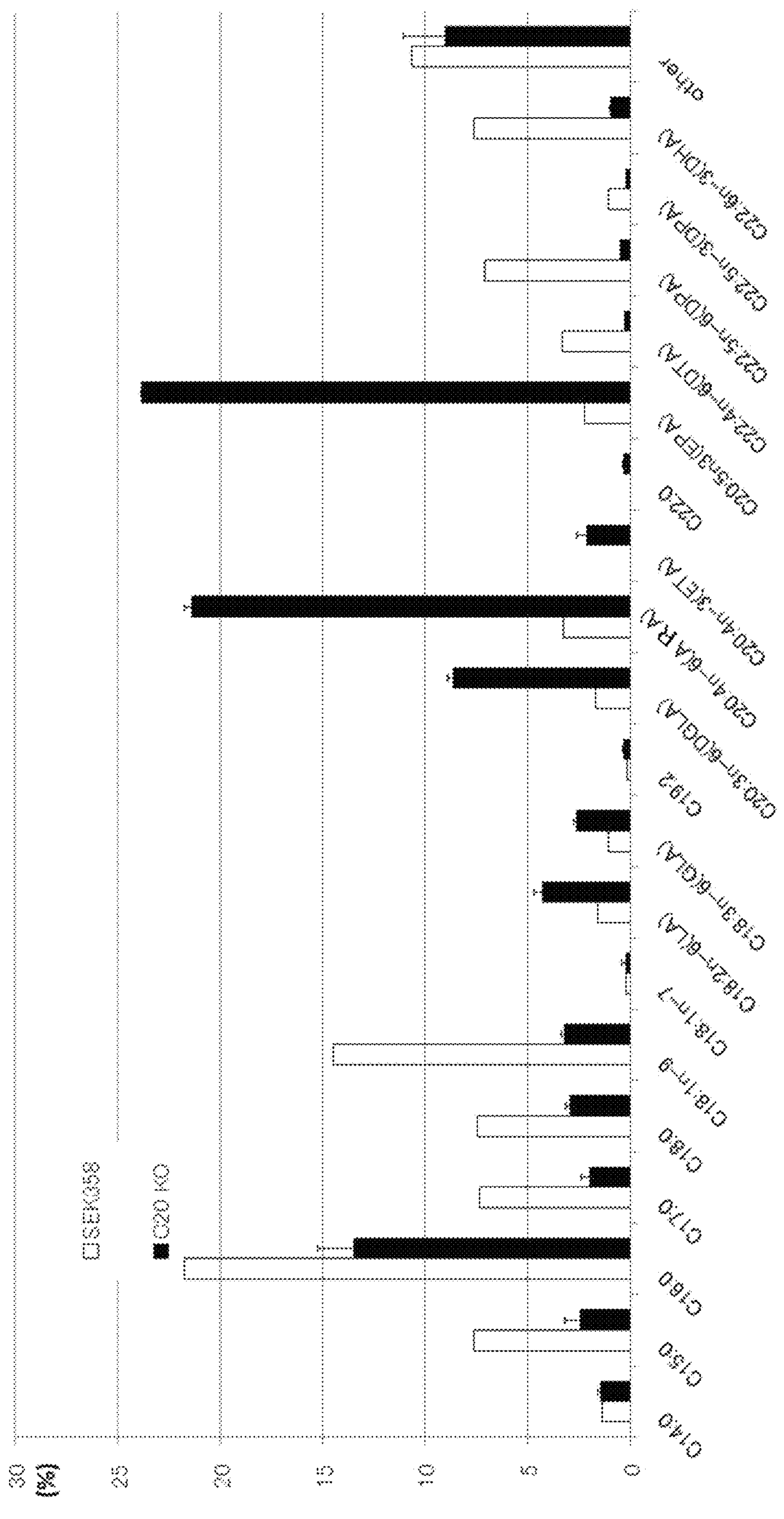
FIG. 24 illustrates a comparison of fatty acid compositions of the *Parietichytrium* sp. SEK358 wild-type strain and the C20 elongase gene disruption strain derived from *Parietichytrium* sp. SEK358 strain. The white bars and black bars represent the fatty acid composition of the wild-type strain and the gene disruption strain, respectively.

The *Parietichytrium* sp. SEK358 wild-type strain and the gene disruption strain thereof (C20 elongase gene disruption strain, C20 KO) were cultured according to the method described in Example 2-9, and after freeze drying, the fatty acids were methyl-esterified and analyzed using GC. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min). The changes in the fatty acid composition are shown in FIG. 24. Furthermore, FIG. 25 shows the proportion when the wild-type strain is taken as 100%.

Figures 25, 26:
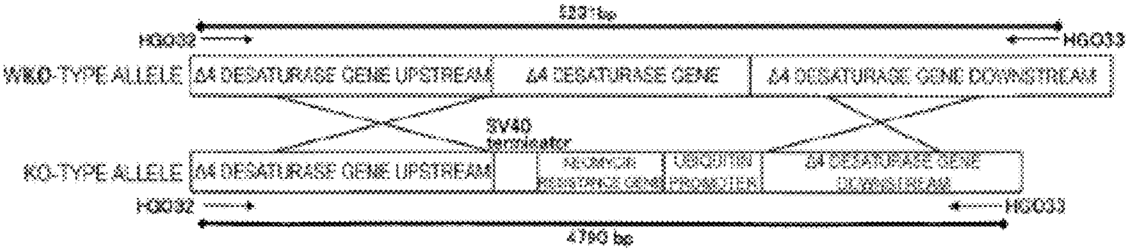
FIG. 25 lists the fatty acid proportions of the C20 elongase gene disruption strain derived from the *Parietichytrium* sp. SEK358 strain when the *Parietichytrium* sp. SEK358 wild-type strain is taken as 100%. In the *Parietichytrium* sp. SEK358 wild-type strain, cases where the relevant fatty acid is below the detection limit are indicated by a diagonal line.
FIG. 26 is a schematic diagram illustrating the positions of the PCR primers used in identification of a Δ4 desaturase gene disruption strain of a genus of *Parietichytrium* labyrinthulid, and the expected product (primers are set outside the homologous recombination region).

FIG. 25 shows that, of the total fatty acid composition, ARA is 21.35%, DGLA is 8.64%, ETA is 2.14%, EPA is 23.83%, n-6 DPA is 0.46%, and DHA is 0.94%. FIG. 25 shows that, by GC area, LA/DHA is 4.6, GLA/DHA is 2.8, DGLA/DHA is 9.19, ARA/DHA is 22.7, EPA/DHA is 25.4, LA/EPA is 0.18, GLA/EPA is 0.11, DTA/EPA is 0.01, DTA/ARA is 0.01, DTA/DGLA is 0.03, LA/n-6 DPA is 9.3, GLA/n-6 DPA is 5.7, DGLA/n-6 DPA is 18.8, R/n-6 DPA is 46.4, EPA/n-6 DPA is 51.8, DGLA/LA is 2.0, ARA/LA is 5.0, EPA/LA is 5.6, DTA/LA is 0.06, DGLA/GLA is 3.3, ARA/GLA is 8.2, n-6 DPA/DTA is 1.8, DHA/n-3 DPA is 4.1, C20 PUFA/C22 PUFA is 29.61, and n-6 PUFA/n-3 PUFA is 1.1.

As a result, when the C20 elongase gene was disrupted in the *Parietichytrium* sp. SEK358 strain, fatty acids having not less than 22 carbon chains decreased while fatty acids having 20 carbon chains increased. Specifically, arachidonic acid increased approximately 7-fold and EPA increased approximately 11-fold, while DPA decreased to approximately 1/15 and DHA decreased to approximately 1/8.

By selecting the labyrinthulid *Parietichytrium* sp. SEK358 having no PUFA-PKS pathway in this manner, a strain that accumulates PUFAs other than DHA and DPA n-6 can be produced without PUFA-PKS pathway gene disruption. This strain may also be used as a strain that produces EPA and/or ARA, and further disruption or transforming elongase or desaturase genes can create strains that produce desired PUFAs.

Example 5

[Measurement of Fatty Acid Composition of Lipids Produced by Δ4 Desaturase Gene Disruption and Transformation Strain of *Parietichytrium* sp. SEK358]

[Example 5-1]: Transfer of Δ4 Desaturase Gene Targeting Vector to *Parietichytrium* sp. SEK358 Strain Using the targeting vector produced with pRH126 (FIG. 17) described in Example 3-3 as a template, the gene was amplified with PrimeSTAR Max DNA Polymerase (available from Takara Bio Inc.) using RHO241 (described in Example 3-1, SEQ ID NO: 40) and RHO242 (described in Example 3-1, SEQ ID NO: 41) as primers. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH126 (FIG. 17) described in Example 3-3 was used as a template was 4562 bp.

The *Parietichytrium* sp. SEK358 strain was cultured for 1 to 2 days in a GY culture medium, and cells in the logarithmic growth phase were used in gene transfer. To cells corresponding to OD600=1 to 2, 0.625 μg of DNA fragment was transformed by the gene gun method (microcarrier: 0.6 micron gold particles, target distance: 6 cm, chamber vacuum: 26 mmHg, rupture disk: 1550 psi). After a recovery time of 24 hr, the transgenic cells were spread on a PDA agar plate culture medium containing 1 mg/mL of G418. As a result, from 0 to 2 cells of drug resistant strain per shot were obtained.

[Example 5-2]: Identification of Δ4 Desaturase Gene Targeting Homologous Recombinant Genome DNA from the *Parietichytrium* sp. SEK358 strain and the Δ4 desaturase gene disruption strain were extracted by the method described in Example 2-2, and then A260/280 was measured and the DNA concentration was calculated. Using the genome DNA as templates, PCR for genome structure confirmation was performed using PrimeSTAR GXL DNA Polymerase (available from Takara Bio Inc.). The positions of the primers used, the combinations used in amplification, and the expected sizes of the amplification products are illustrated in FIG. 18 (within homologous region) and FIG. 26 (outside homologous region). In the primer set designed within the homologous recombination region, 3046 bp was amplified in the *Parietichytrium* sp. SEK358 strain, and 2605 bp was amplified in the Δ4 desaturase gene disruption strain. [RHO251: 20mer: 5'-GTG GTC GAA GTG GAG TAT CT-3' (SEQ ID NO: 49), RHO252: 20mer: 5'-ACT CGC CAT ACA ACT TTA CA-3' (SEQ ID NO: 50)]. In the primer set designed outside the homologous recombination region, 5231 bp was amplified in the *Parietichytrium* sp. SEK358 strain, and 4790 bp was amplified in the Δ4 desaturase gene disruption strain. [HG032: 25mer: 5'-CGG AGC TCG GAG AAC AAC ATA GAA G-3' (SEQ ID NO: 51), HG033: 23mer: 5'-GTG CAA CCA GGT GGC AAG ATT GT-3' (SEQ ID NO: 52)].

Figure 27:
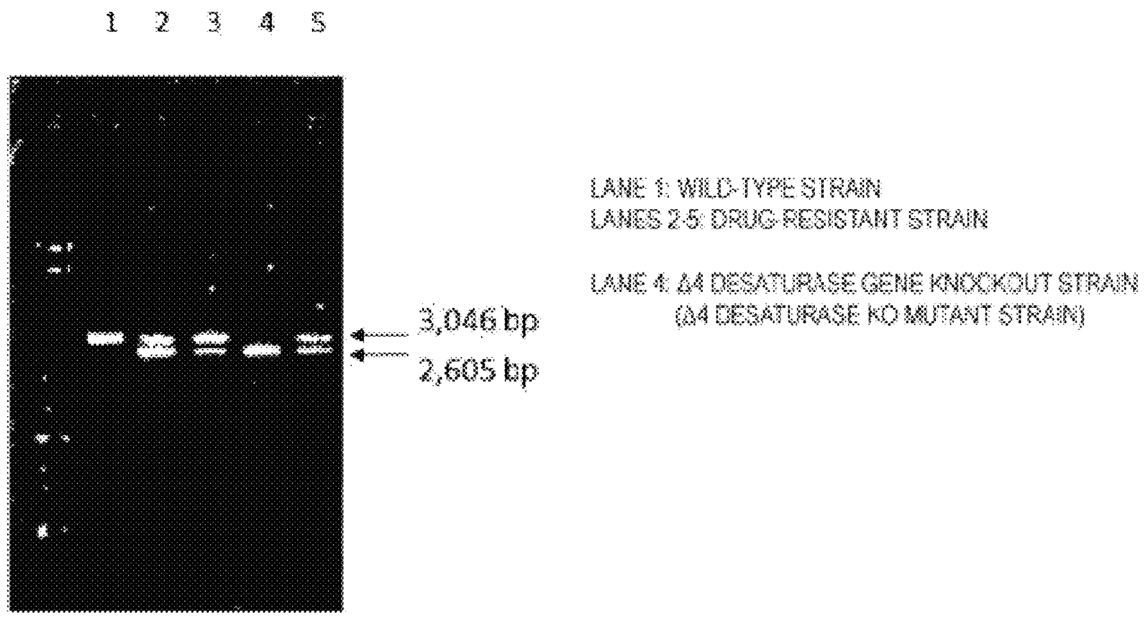
FIG. 27 illustrates evaluation results of Δ4 desaturase gene disruption by PCR using *Parietichytrium* sp. SEK358 genome DNA as a template in the case where the primers are set within the homologous recombination region.
Figure 28:
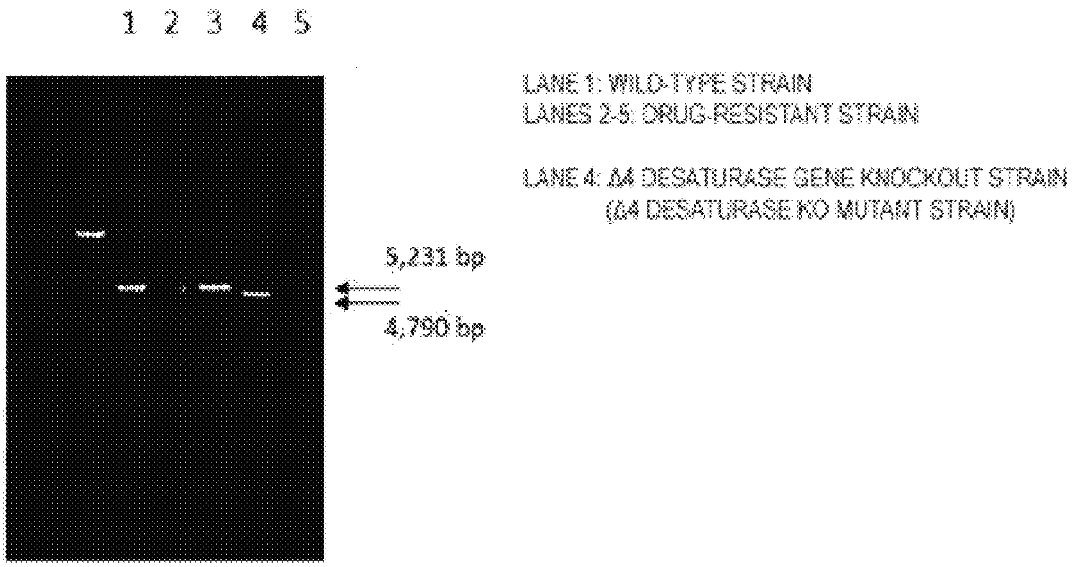
FIG. 28 illustrates evaluation results of Δ4 desaturase gene disruption by PCR using *Parietichytrium* sp. SEK358 genome DNA as a template in the case where the primers are set outside the homologous recombination region.

As a result, a Δ4 desaturase gene disruption strain in which there is no amplification derived from the wild-type allele (Wt allele) and there is amplification derived from the Δ4 desaturase gene KO allele (NeoR allele) was obtained (FIG. 27 lane 4, FIG. 28 lane 4: Δ4 desaturase KO mutant strain).

[Example 5-3]: Change in Fatty Acid Composition by Δ4 Desaturase Gene Disruption The *Parietichytrium* sp. SEK358 wild-type strain and the Δ4 desaturase gene disruption strain thereof (SEK358 delta4 des. KO mutant strain) were cultured according to the method described in Example 2-9, and after freeze drying, the fatty acids were methyl-esterified and analyzed using GC. In culturing, the GY liquid culture medium described in Example 1 supplemented with 0.1% of a vitamin solution (vitamin $B_1$ 200 mg, vitamin $B_2$ 1 mg, and vitamin $B_{12}$ 1 mg are dissolved in 100 mL of distilled water) and 0.2% of a trace element solution (EDTA disodium salt 30.0 g, $FeCl_3$ $6H_2O$ 1.45 g, $H_2BO_3$ 34.2 g, $MnCl_2{\cdot}4H_2O$ 4.3 g, $ZnCl_2$ 1.335 g, $CoCl_2{\cdot}6H_2O$ 0.13 g, $NiSO_4$ $6H_2O$ 0.26 g, $CuSO_4{\cdot}5H_2O$ 0.01 g, and $NaMoO_4{\cdot}2H_2O$ 0.025 g are dissolved in 1 L of distilled water) was used. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(2° C./min)→220° C. (10 min); carrier gas: He (1.3 mL/min).

Figure 29:
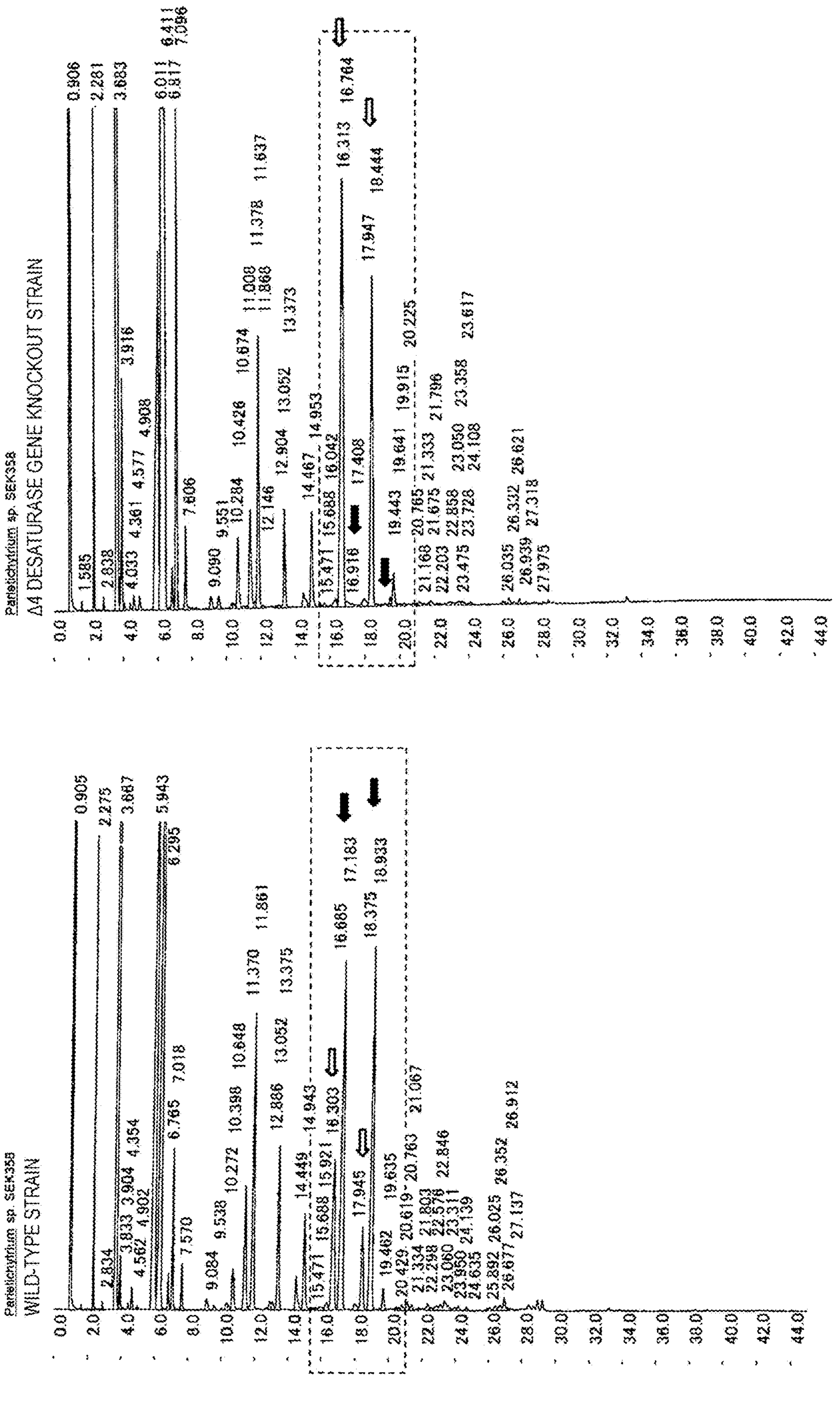
FIG. 29 is a gas chromatograph analysis chart of the fatty acid compositions of the *Parietichytrium* sp. SEK358 wild-type strain and the Δ4 desaturase gene disruption strain thereof.
Figure 30:
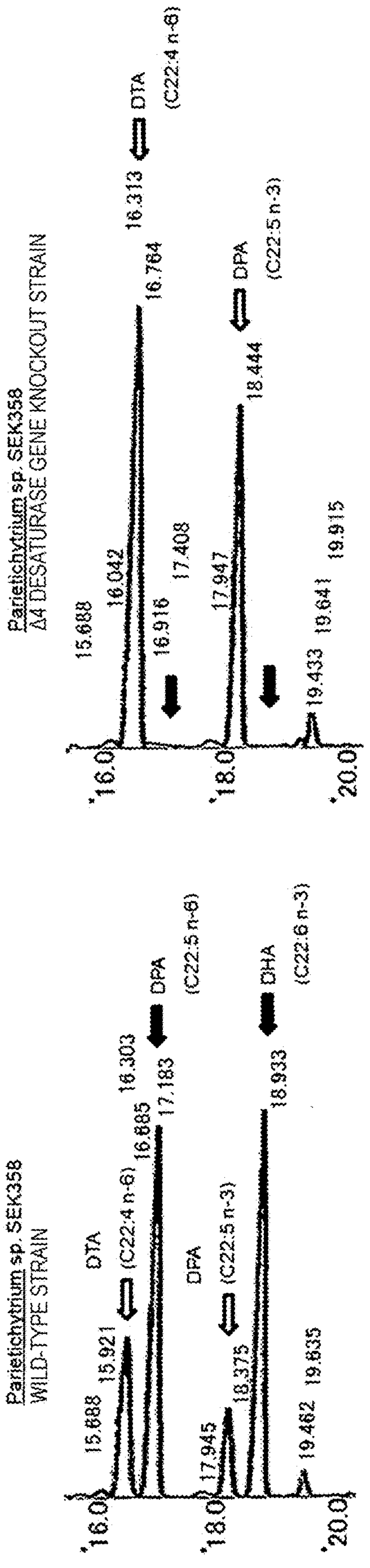
FIG. 30 is a partial enlarged diagram of FIG. 29.
Figures 31, 32:
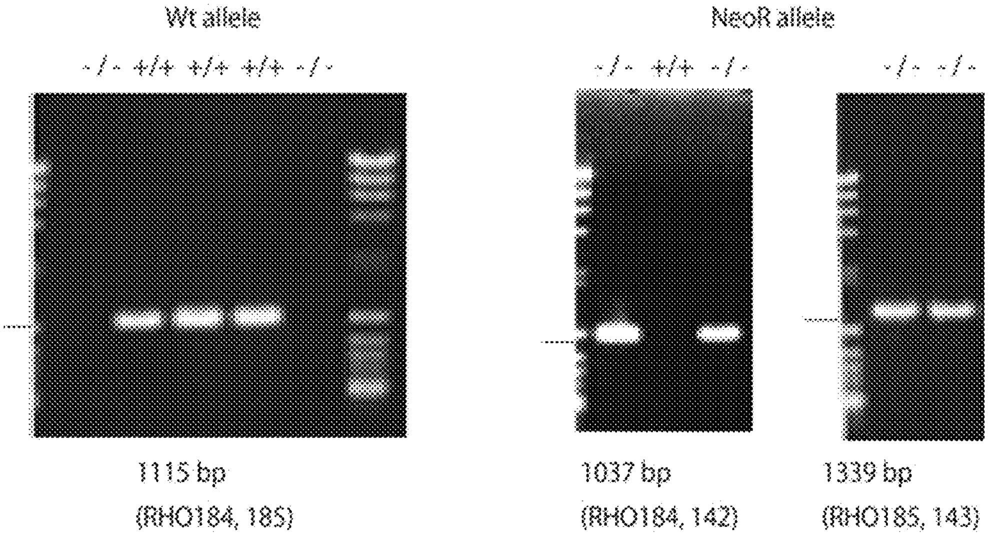
FIG. 31 shows a comparison of the fatty acid compositions of the *Parietichytrium* sp. SEK358 wild-type strain and the Δ4 desaturase gene disruption strain thereof. This table is a quantification of the chart of FIG. 29. In the table, the less-than sign (<) indicates less than or equal to the number following it.
FIG. 32 illustrates an evaluation of C20 elongase gene disruption by PCR using *Parietichytrium* sp. SEK571 strain genome DNA as a template. (Description of symbols)+/+: *Parietichytrium* sp. SEK571 wild-type strain; −/−: C20 elongase gene disruption strain derived from *Parietichytrium* sp. SEK571 strain

The analysis results chart is shown in FIG. 29, and a partial enlarged diagram of the chart is shown in FIG. 30. The table in FIG. 31 shows a quantification of the chart of FIG. 29. This table shows a comparison of the fatty acid compositions of the *Parietichytrium* sp. SEK358 wild-type strain and the Δ4 desaturase gene disruption strain thereof. The table shows that, of the total fatty acid composition, ARA is 3.03%, DGLA is 1.35%, ETA is 0.03%, EPA is 1.10%, n-6 DPA is 0.00%, and DHA is 0.00%. FIG. 31 shows that, by GC area, LA/EPA is 4.2, GLA/EPA is 0.71, DTA/EPA is 7.19, DTA/ARA is 2.60, DTA/DGLA is 5.85, DGLA/LA is 0.29, ARA/LA is 0.66, EPA/LA is 0.24, DTA/LA is 1.71, DGLA/GLA is 1.72, ARA/GLA is 3.87, C20 PUFA/C22 PUFA is 0.42, and n-6 PUFA/n-3 PUFA is 2.0.

The results showed that when the Δ4 desaturase gene was disrupted in the *Parietichytrium* sp. SEK358 strain, DHA and DPA n-6 cannot be substantially biosynthesized, and conversely, n-3 DPA and DTA, which are substrates thereof, increase.

By selecting the labyrinthulid *Parietichytrium* sp. SEK358 having no PUFA-PKS pathway in this manner, a strain that accumulates PUFAs other than DHA and n-6 DPAcan be produced without PUFA-PKS pathway gene disruption. This strain may also be used as a strain that produces n-3 DPA and/or DTA, and further disruption or transforming elongase or desaturase genes can create strains that produce desired PUFAs.

Example 6

[Measurement of Fatty Acid Composition of Lipids Produced by C20 Elongase Gene Disruption and Transformation Strain of *Parietichytrium* sp. SEK571]

[Example 6-1]: Transfer of C20 Elongase Gene Targeting Vector to *Parietichytrium* sp. SEK571 Strain Using the targeting vector produced with pRH85 (FIG. 9) described in Example 2-6 as a template, the gene was amplified with PrimeSTAR Max DNA Polymerase (available from Takara Bio Inc.) using RHO153 (described in Example 2-4, SEQ ID NO: 24) and RHO154 (described in Example 2-4, SEQ ID NO: 25) as primers. [PCR cycles: 98° C. 2 min/98° C. 30 sec, 68° C. 2 min, 30 cycles/68° C. 2 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH85 (FIG. 9) described in Example 2-6 was used as a template was 2661 bp, and resulted in a sequence including genus *Parietichytrium* C20 elongase gene front half—SV40 terminator sequence—artificially synthesized neomycin resistance gene sequence—ubiquitin promoter sequence—genus *Parietichytrium* C20 elongase gene back half (described in Example 2-7, SEQ ID NO: 31).

The *Parietichytrium* sp. SEK571 strain was cultured for 3 days in a GY culture medium, and cells in the logarithmic growth phase were used in gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 1550 psi). After a recovery time of 24 hr, the transgenic cells were spread on a PDA agar plate culture medium containing 0.5 mg/mL of G418. As a result, from 5 to 15 cells of drug resistant strain per shot were obtained.

[Example 6-2]: Identification of C20 Elongase Gene Targeting Homologous Recombinant Genome DNA of the *Parietichytrium* sp. SEK571 strain and the C20 elongase gene disruption strain were extracted by the method described in Example 2-2, and then A260/280 was measured and the DNA concentration was calculated. Using the genome DNA as templates, PCR for genome structure confirmation was performed using Mighty Amp DNA Polymerase (available from Takara Bio Inc.). The positions of the primers used, the combinations used in amplification, and the expected sizes of the amplification products are illustrated in FIG. 10 described in Example 2-8.

RHO184 (described in Example 2-8, SEQ ID NO: 37) was set upstream of C20 elongase; RHO185 (described in Example 2-8, SEQ ID NO: 38) was set downstream; RHO142 (described in Example 2-8, SEQ ID NO: 35) and RHO143 (described in Example 2-8, SEQ ID NO: 36) were set on the artificially synthesized neomycin resistance gene. [PCR cycles: 98° C. 2 min/98° C. 10 sec, 68° 2 min, 30 cycles/68° C. 7 min].

A C20 elongase gene disruption strain in which there is no amplification in the wild-type allele (Wt allele) and there is amplification in the artificially synthesized neomycin resistance gene allele (NeoR allele) was obtained (FIG. 32).

[Example 6-3]: Change in Fatty Acid Composition by C20 Elongase Gene Disruption

The *Parietichytrium* sp. SEK571 strain and the gene disruption strain thereof (C20 elongase gene disruption strain, C20 KO) were cultured according to the method described in Example 2-9, and after freeze drying, the fatty acids were methyl-esterified and analyzed using GC. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 33:
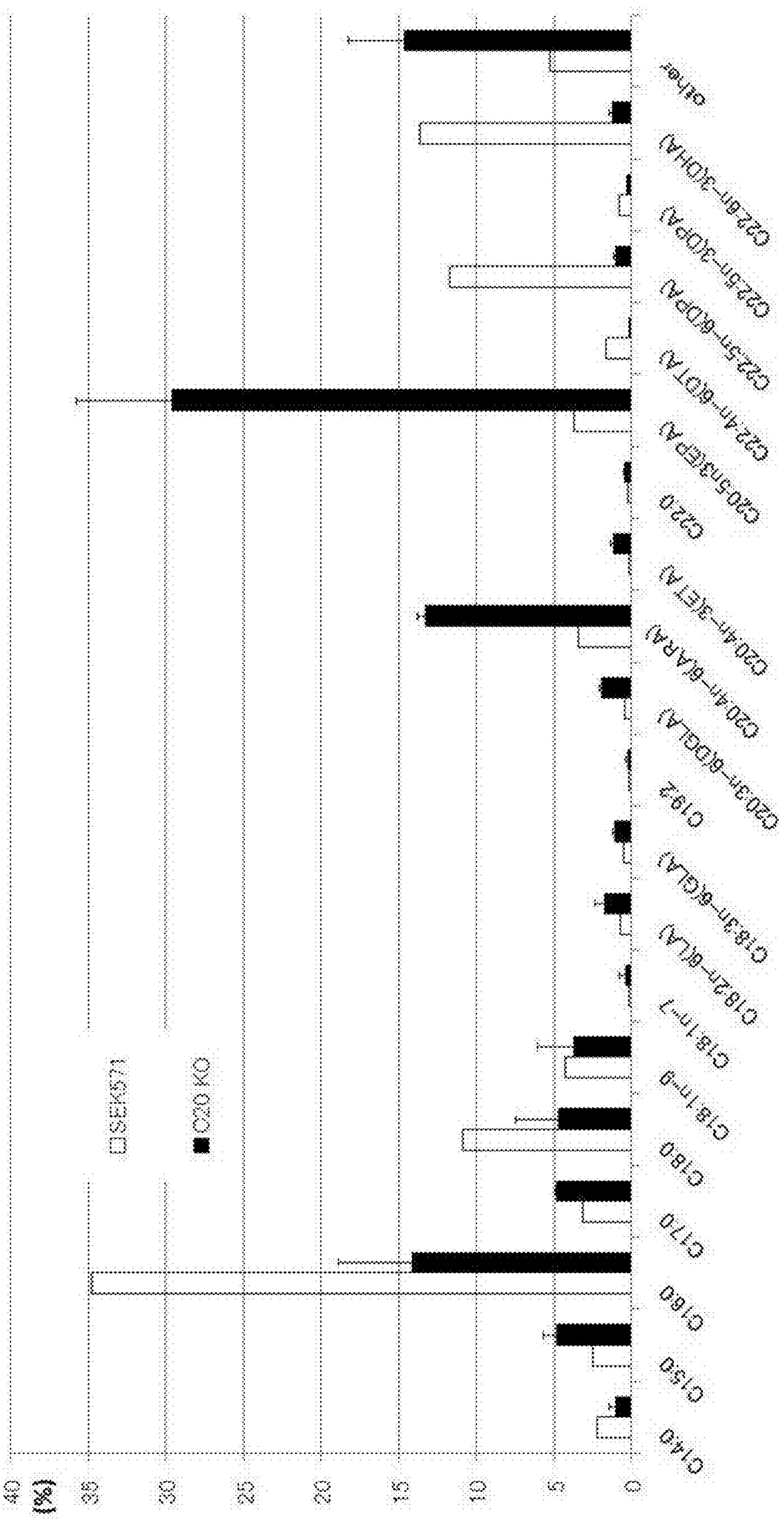
FIG. 33 illustrates a comparison of fatty acid compositions of the *Parietichytrium* sp. SEK571 wild-type strain and the C20 elongase gene disruption strain derived from *Parietichytrium* sp. SEK571 strain. The white bars and black bars represent the fatty acid composition of the wild-type strain and the gene disruption strain, respectively.

The changes in the fatty acid composition are shown in FIG. 33. Furthermore, FIG. 34 shows the proportion when the wild-type strain is taken as 100%.

FIG. 34 shows that, of the total fatty acid composition, ARA is 13.24%, DGLA is 1.93%, ETA is 1.14%, EPA is 29.58%, n-6 DPA is 0.96%, and DHA is 1.17%. FIG. 34 shows that, by GC area, LA/DHA is 1.5, GLA/DHA is 0.9, DGLA/DHA is 1.65, ARA/DHA is 11.3, EPA/DHA is 25.3, LA/EPA is 0.06, GLA/EPA is 0.04, DTA/EPA is 0.01, DTA/ARA is 0.01, DTA/DGLA is 0.08, LA/n-6 DPA is 1.8, GLA/n-6 DPA is 1.1, DGLA/n-6 DPA is 2.0, ARA/n-6 DPA is 13.8, EPA/n-6 DPA is 30.8, DGLA/LA is 1.1, ARA/LA is 7.8, EPA/LA is 17.4, DTA/LA is 0.09, DGLA/GLA is 1.8, ARA/GLA is 12.4, n-6 DPA/DTA is 6.4, DHA/n-3 DPA is 4.7, C20 PUFA/C22 PUFA is 18.1, and n-6 PUFA/n-3 PUFA is 0.51.

As a result, when the C20 elongase gene was disrupted in the *Parietichytrium* sp. SEK571 strain, fatty acids having not less than 22 carbon chains decreased while fatty acids having 20 carbon chains increased. Specifically, arachidonic acid increased approximately 4-fold and EPA increased approximately 8-fold, while DPA decreased to approximately 1/12 and DHA decreased to approximately 1/12.

The results show that *Parietichytrium* sp. SEK571 has very weak or no PUFA production activity via the PUFA-PKS pathway, and by selecting the labyrinthulid *Parietichytrium* sp. SEK571, a strain that accumulates PUFAs other than DHA and n-6 DPA can be produced without PUFA-PKS pathway gene disruption. This strain may also be used as a strain that produces EPA and/or ARA, and further disruption or transforming elongase or desaturase genes can create strains that produce desired PUFAs.

Comparative Example 1

[Measurement of Fatty Acid Composition of Lipids Produced by C20 Elongase Gene Disruption and Transformation Strain of *Thraustochytrium aureum* ATCC 34304]

[Comparative Example 1-1]: Extraction of Total RNA Derived from *T. Aureum* ATCC 34304, and mRNA Purification A *T. aureum* ATCC 34304 culture solution on the third day of culturing using a GY liquid culture medium was centrifuged for 15 min at 3500×g, and the cells were collected. The obtained cells were washed by suspending in a sterilized physiological saline solution and then centrifuging again, and were then rapidly frozen with liquid nitrogen, and then ground into powder form in a mortar. Total RNA was extracted from the obtained crushed cell solution using Sepasol-RNA I Super (available from Nacalai Tesque, Inc.). Then, mRNA was purified from the total RNA according to manufacturer's instructions using Oligotex-dT30<Super> mRNA Purification Kit (trade name; available from Takara Bio Inc.). The obtained total RNA and mRNA were dissolved in an appropriate amount of TE, and then subjected to electrophoresis using formalin-modified gel (1% agarose/MOPS buffer). The result showed that total RNA extraction was successful, that mRNA was purified from the total RNA, and that the RNA was not decomposed by RNase. Furthermore, to proactively avoid RNA decomposition, rubber gloves, a mask, and the like were donned through the experimental operation, and the instruments used were completely RNase-free or the RNase used was inactivated by treatment with diethylpyrocarbonate (available from Nacalai Tesque, Inc.). Furthermore, when decomposing RNA, a solution obtained by adding the recombinant RNase inhibitor RNaseOUT (trade name; available from Invitrogen Corp.) to sterilized MilliQ water treated with diethylpyrocarbonate was used.

[Comparative Example 1-2]: Isolation of *T. Aureum* ATCC 34304-Derived Elongase Gene by RACE Using a histidine box (His box) in which the elongase gene was conserved to a high degree as a target, forward (elo-F; 5'-TTY YTN CAY GTN TAY CAY CAY-3') (SEQ ID NO: 53) and reverse (elo-R; 5'-GCR TGR TGR TAN ACR TGN ARR AA-3') (SEQ ID NO: 54) degenerate oligonucleotides were synthesized. The oligonucleotides were synthesized using a DNA synthesizer (available from Applied Biosystems Corp.). Next, 3'- and 5'-RACE cDNA libraries in which synthetic adapters were appended to the 3' and 5' terminals were produced according to manufacturer's instructions using SMART RACE cDNA Amplification Kit (trade name; available from Clontech Laboratories, Inc.).

Using these as templates, 3'- and 5'-RACE were performed using the synthetic adapter-specific oligonucleotides and the above degenerate oligonucleotides elo-F and elo-R. [PCR cycles: 94° C. 1 min/94° C. 30 sec, 60° C. 30 sec, 72° C. 3 min, 30 cycles/72° C. 10 min/4° C.∞]. As a result, bands of specifically amplified 3'- and 5'-RACE products were confirmed (FIG. 35). Next, the entire amounts of the RACE products were subjected to electrophoresis using 1% agarose gel, the separated DNA fragments were cut with a clean cutter or the like, and DNA fragments were extracted according to the method described in Non-patent Document 10. Then, TA cloning of the DNA fragments was performed using pGEM-T Easy Vector (available from Promega Corporation), and the base sequences thereof were determined according to the method of Sanger et al. (Non-patent Document 11). Specifically, using BigDye (trade name) Terminator v3.1 Cycle Sequencing Kit and 3130 Genetic Analyzer (available from Applied Biosystems Corp.), the base sequence was determined by the dye terminator method according to manufacturer's instructions.

As a result, two respective sequences of 190 bp and 210 bp named elo1 (SEQ ID NO: 55) and elo2 (SEQ ID NO: 56) were successfully identified in the 3'-RACE product, and one 200 bp sequence named elo3 (SEQ ID NO: 57) was successfully identified in the 5'-RACE product. The fact that these elo1, elo2, and elo3 sequences exhibited significant homology to various elongase gene sequences shows that these sequences are partial sequences of elongase genes derived from *T. aureum* ATCC 34304. Additionally, respective oligonucleotide primers were again designed for elo1, elo2, and elo3, and acquisition of cDNA sequences was attempted by RACE. The produced oligonucleotide primers are shown below. elo1 forward oligonucleotide primer (elo1-F1; 5'-TAT GAT CGC CAA GTA CGC CCC-3') (SEQ ID NO: 58) and reverse oligonucleotide primer (elo1-R1; 5'-GAA CTG CGT CAT CTG CAG CGA-3') (SEQ ID NO: 59), elo2 forward oligonucleotide primer (elo2-F1; 5'-TCT CGC CCT CGA CCA CCA AC-3') (SEQ ID NO: 60) and reverse oligonucleotide primer (elo2-R1: 5'-CGG TGA CCG AGT TGA GGT AGC C-3') (SEQ ID NO: 61), elo3 forward oligonucleotide primer (elo3-F1; 5'-CAA CCC TTT CGG CCT CAA CAA G-3') (SEQ ID NO: 62) and reverse oligonucleotide primer (elo3-R1; 5'-TTC TTG AGG ATC ATC ATG AAC GTG TC-3') (SEQ ID NO: 63).

Using the produced forward and reverse oligonucleotide primers, RACE and base sequence analysis of the amplified products were performed by the same methods as described above. As a result, for elo1, specifically amplified 3'- and 5'-RACE products were obtained, and since the duplicate portions thereof matched completely, they were proved to be an 1139 bp elo1 cDNA sequence (SEQ ID NO: 64). Similarly, for elo3, specifically amplified 3'- and 5'-RACE products were obtained, and since the duplicate portions thereof matched completely, they were proved to be a 1261 bp elo3 cDNA sequence (SEQ ID NO: 65).

As a result of sequence analysis, it was found that elo1 is composed of an 825 bp translation sequence (SEQ ID NO: 67) that encodes 275 amino acid residues (SEQ ID NO: 66), and as a result of a BLAST search, it was found not only that elo1 exhibited significant homology to various elongase genes, but also that elo1 completely matches a known presumed A5 elongase gene sequence derived from *T. aureum* (NCBI accession no. CS486301). On the other hand, elo3 was estimated to constituted of a 951 bp translation region (SEQ ID NO: 69) that encodes 317 amino acid residues (SEQ ID NO: 68), and as a result of a BLAST search, elo3 was found to exhibit significant homology to various elongase genes, and thus was confirmed to be a presumed elongase gene derived from *T. aureum* ATCC 34304. Furthermore, a His box in which the elongase gene was conserved to a high degree was found within the presumed amino acid sequences of the two genes. From the above results, the elo1 and elo3 gene were considered to be presumed elongase genes derived from *T. aureum* ATCC 34304 and were designated as TaELO1 and TaELO2, respectively.

[Comparative Example 1-3]: Expression of TaELO1 and TaELO2 with Brewer's Yeast *Saccharomyces cerevisiae* as Host, and Analysis of Fatty Acid Composition of Transgenic Strains Respective expression vectors were constructed in order to cause expression of TaELO1 and TaELO2 using brewer's yeast *S. cerevisiae* as a host. An outline thereof is given below. A pair of oligonucleotide primers (E1 HindIII; 5'-ATA AGC TTA AAA TGT CTA GCA ACA TGA GCG CGT GGG GC-3') (SEQ ID NO: 70) and (E1 XbaI; 5'-TGT CTA GAA CGC GCG GAC GGT CGC GAA A-3') (SEQ ID NO: 71) were produced based on the sequence of the TaELO1 translation region. E1 HindIII is a forward oligonucleotide primer and has a restriction enzyme HindIII site (AAGCTT) at the 5' terminal. Furthermore, the sequence near the start codon of TaELO1 has been modified in reference to the yeast consensus sequence ((A/Y) A (A/U) A AUG UCU; underlined portion is start codon) (Non-patent Document 12). E1 XbaI is a reverse oligonucleotide primer, and has an XbaI site (TCTAGA) at the 5' terminal.

Similarly, a pair of oligonucleotide primers (E2 HindIII; 5'-TAAAGC TTA AAA TGT CTA CGC GCA CCT CGA AGA GCG CTC C-3') (SEQ ID NO: 72) and (E2 XbaI; 5'-CAT CTA GAC TCG GAC TTG GTG GGG GCG CTT G-3') (SEQ ID NO: 73) were produced based on the sequence of the TaELO2 translation region. E2 HindIII is a forward oligonucleotide primer and has a restriction enzyme HindIII site at the 5' terminal. Furthermore, the sequence near the start codon of TaELO2 has been modified in reference to the yeast consensus sequence. E2 XbaI is a reverse oligonucleotide primer, and has an XbaI site at the 5' terminal.

With the 5'-RACE cDNA library described in Comparative Example 1-2 as a template, PCR was performed using the above two oligonucleotide primer pairs. A 949 bp TaELO1 translation region (SEQ ID NO: 74) and a 967 bp TaELO2 translation region (SEQ ID NO: 75), in which the vicinity of the start codon was modified to the consensus sequence and having the restriction enzyme HindII at the 5' terminal and the restriction enzyme XbaI site at the 3' terminal, were amplified. Furthermore, to avoid elongation mistakes, PrimeSTAR DNA Polymerase (trade name; available from Takara Bio Inc.) having high correction activity was used. [PCR cycles: 98° C. 2 min/98° C. 5 sec, 60° C. 5 sec, 72° C. 1.5 min, 30 cycles/72° C. 7 min/4° C.∞].

Next, the amplified PCR products were separated with 1% agarose gel, and then DNA fragments were cut and extracted from the agarose gel. Additionally, after treatment with restriction enzymes HindIII and XbaI, the DNG fragments were again purified using agarose gel, and a cyclized vector was constructed by ligation using DNA Ligation Kit "Mighty Mix" (available from Takara Bio Inc.) to a brewer's yeast expression vector pYES2/CT (available from Invitrogen Corp.) which was made into a straight chain by treatment with restriction enzymes HindIII and XbaI. Furthermore, by analyzing the base sequence, it was confirmed that mutations due to PCR elongation mistakes had not been introduced into the sequences of the TaELO1 and TaELO2 translation regions transformed into pYES2/CT. From the above result, a TaELO1 expression vector pYEELOT and a TaELO2 expression vector pYEELO2 were successfully constructed.

Transformants in which the two constructed expression vectors and pYES2/CT had been transformed into brewer's yeast *S. cerevisiae* by the lithium acetate method were selected according to the methods described in Non-patent Document 13 and Non-patent Document 14. Next, the obtained transformants (pYEELOT transgenic strain, pYEELO2 transgenic strain, and mock transgenic strain) were cultured according to the method of Qiu et al. (Non-patent Document 15), and cell-derived fatty acid extraction and methyl-esterification were performed. However, culturing was carried out after adding 0.02 mM each of the following acids in respective final concentrations: α-linolenic acid (ALA, C18:3Δ9, 12, 15) and linoleic acid (LA, C18:2Δ9, 12) as Δ9 elongase substrates; stearidonic acid (STA, C18:4Δ6, 9, 12, 15) and γ-linolenic acid (GLA, C18:3Δ6, 9, 12) as Δ6 elongase substrates; eicosapentaenoic acid (EPA, C20:5Δ5, 8, 11, 14, 17) and arachidonic acid (AA, C20:4Δ5, 8, 11, 14) as Δ5 elongase substrates. Then, gas chromatography (GC) analysis of the methyl-esterified fatty acids was performed according to the method of Abe et al. (Non-patent Document 16). In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

As a result, the pYEELO1 transgenic strain exhibited Δ6 elongase activity, by which stearidonic acid (STA) is converted to eicosatetraenoic acid (ETA, 20:4Δ8, 11, 14, 17) and γ-linolenic acid (GLA) is converted to dihomo-γ-linolenic acid (DGLA, C20:3Δ8, 11, 14), which was not seen in the host (mock transgenic strain). On the other hand, the pYEELO1 transgenic strain exhibited Δ9 elongase activity, by which α-linolenic acid (ALA) is converted to eicosatrienoic acid (ETrA, C20:3Δ11, 14, 17) and linoleic acid (LA) is converted to eicosadienoic acid (EDA, C20:3Δ11, 14), as well as Δ5 elongase (=C20 elongase) activity, by which eicosapentaenoic acid (EPA) is converted to ω3 docosapentaenoic acid (o3 DPA, C22:5Δ7, 10, 13, 16, 19) and arachidonic acid (ARA) is converted to docosatetraenoic acid (DTA, C22: 4Δ7, 10, 13, 16) (Table 1).

Furthermore, the pYEELO2 transgenic strain exhibited Δ5 elongase (C20 elongase) activity by which EPA is converted to ω3 DPA (C22: 5Δ7, 10, 13, 16, 19) and ARA is converted to DTA, which was not seen in the host. On the other hand, the pYEELO2 transgenic strain exhibited slight Δ6 elongase activity, by which STA is converted to ETA and GLA is converted to DGLA (Table 1). The above result shows that TaELO1 is Δ6/Δ9/Δ5 elongase, and TaELO2 is Δ5/Δ6 elongase.

TABLE 1

| | mock | TaELO1 | TaELO2 | | mock | TaELO1 | TaELO2 |
|---|---|---|---|---|---|---|---|
| LA supplemented (0.2 mM) | | | | ALA supplemented (0.2 mM) | | | |
| LA | 30.5 | 23.5 | 36.3 | ALA | 49.1 | 25.8 | 47.1 |
| EDA | 0.2 | 8.9 | 0.2 | ETrA | 0.2 | 17.9 | 0.3 |
| Conversion efficiency (%) | | 27.4 | | Conversion efficiency (%) | | 41 | |
| GLA supplemented (0.2 mM) | | | | STA supplemented (0.2 mM) | | | |
| GLA | 44.0 | 7.6 | 43.6 | STA | 46.2 | 8.3 | 40.5 |
| DGLA | 0.2 | 29.0 | 0.8 | ETA | 0.3 | 28.1 | 1.7 |
| Conversion efficiency (%) | | 79.3 | 1.9 | Conversion efficiency (%) | | 77.2 | 4.0 |
| ARA supplemented (0.2 mM) | | | | EPA supplemented (0.2 mM) | | | |
| ARA | 30.9 | 23.2 | 8.9 | EPA | 42.0 | 31.2 | 13.1 |
| ADA | — | 5.8 | 13.6 | DPA | 0.1 | 10.6 | 24.5 |
| Conversion efficiency (%) | | 20.1 | 60.3 | Conversion efficiency (%) | | 25.3 | 65.1 |

Conversion efficiency (%) = 100 × product (area)/substrate (area) + product (area)
(n = 1)

[Comparative Example 1-4]: Acquisition of TaELO2 ORF Upstream and Downstream Regions by PCR Genome Walking In the targeting vector for TaELO2 disruption, the regions upstream and downstream of TaELO2 ORF serving as homologous recombination sites were acquired by PCR genome walking. An overview is given below.

Cells of the *T. aureum* ATCC 34304 strain on the third day of culturing in a GY liquid culture medium were rapidly frozen with liquid nitrogen, and then ground into powder form in a mortar. After genome DNA was extracted according to the method described in Non-patent Document 17, and was dissolved in an appropriate quantity of TE. The quantity and purity of the genome DNA were tested by O.D. 260 and O.D. 280 measurement. Next, a genome DNA library was constructed, wherein a cassette sequence having restriction enzyme sites was appended to genome DNA cut with various restriction enzymes according to the manufacturer's protocol using TaKaRa LA PCR (trade name) in vitro Cloning Kit (available from Takara Bio Inc.). Then, using the produced genome DNA library as a template, nested PCR was performed according to the manufacturer's protocol using forward oligonucleotide primers E2 XbaI (described in Comparative Example 1-3, SEQ ID NO: 73) produced based on the sequence of TaELO2 and elo3-F1 (described in Comparative Example 1-2, SEQ ID NO: 62), or the reverse oligonucleotide primers E2 HindIII (described in Comparative Example 1-3, SEQ ID NO: 72) and elo3-R1 (described in Comparative Example 1-2, SEQ ID NO: 63), together with oligonucleotide primers complementary to the sequences of cassettes included in the kit. As a result, an 1122 bp TaELO2 ORF upstream sequence (SEQ ID NO: 76) and a 1204 bp TaELO2 ORF downstream sequence (SEQ ID NO: 77) were successfully acquired.

[Comparative Example 1-5]: Construction of TaELO2 Targeting Vector with Neor as Selection Marker A DNA fragment in which TaELO2 ORF upstream sequence/artificially synthesized Neor/TaELO2 ORF downstream sequence were ligated and produced by fusion PCR. The oligonucleotide primers used were as shown below.

KO Pro F SmaI (SEQ ID NO: 78)
(31mer: 5'-CTC CCG GGT GGA CCT AGC GCG TGT GTC ACC T-3')

(SEQ ID NO: 79)
Pro R (25mer: 5'-GGT CGC GTT TAC AAA GCA GCG CAG C-3')

(SEQ ID NO: 80)
SNeo F (52mer: 5'-GCT GCG CTG CTT TGT AAA CGC GAC CAT GAT TGA ACA GGA CGG CCT TCA CGC T-3')

(SEQ ID NO: 81)
SNeo R (52mer: 5'-TCG GGA GCC AGC CGG AAA CAG GTT CAA AAG AAC TCG TCC AGG AGG CGG TAG A-3')

(SEQ ID NO: 82)
Term F (23mer: 5'-ACC TGT TTC CGG CTG GCT CCC GA-3')

(SEQ ID NO: 83)
KO Term R SmaI (27mer: 5'-ATC CCG GGG CCG AGA ACG GGG TCG CCC-3')

Of these oligonucleotide primers, KO Pro F SmaI/Pro R were used in amplification of the TaELO2 ORF upstream sequence using the *T. aureum* ATCC 34304 genome DNA described in Comparative Example 1-4 as a template, SNeo F/SNeo R were used in amplification of artificially synthesized Neor using artificially synthesized Neor as a template, and Term F/KO Term R SmaI were used in amplification of the TaELO2 ORF downstream sequence using the *T. aureum* ATCC 34304 genome DNA described in Comparative Example 1-4 as a template. As PCR conditions, denaturation was performed at 98° C. for 10 sec, and annealing and the elongation reaction were performed while adjusting as appropriate according to Tm of the primers and the lengths of the amplification products.

As a result, a 2696 bp (SEQ ID NO: 84) TaELO2 ORF upstream sequence/artificially synthesized Neor/TaELO2 ORF downstream sequence was successfully ligated. The result of TA cloning of this sequence using pGEM-T Easy Vector (available from Promega Corporation) was used as a disruption vector, and was named pTKONeor.

[Comparative Example 1-6]: Transfer of TKONeor into *T. Aureum* ATCC 34304

Using, as a template, pTKONeor, which is the TaELO2 targeting vector with the artificially synthesized Neor as a selection marker produced in Comparative Example 1-5, TaELO2 ORF upstream sequence/artificially synthesized Neor/TaELO2 ORF downstream sequence was amplified using a pair of oligonucleotide primers KO Pro F SmaI (Comparative Example 1-5, SEQ ID NO: 78)/KO Term R SmaI (Comparative Example 1-5, SEQ ID NO: 83) and using PrimeSTAR (trade name) HS DNA Polymerase (available from Takara Bio Inc.). [PCR cycles: 98° C. 2 min/98° C. 10 sec, 68° C. 3 min, 30 cycles/68° C. 10 min/4° C.∞]. After electrophoresis using 1% agarose gel, the DNA fragments were extracted, and after ethanol precipitation, the extracted DNA were dissolved in an appropriate quantity of TE. The quantity and purity of the DNA fragments were tested by O.D. 260 and O.D. 280 measurement. The obtained DNA fragment is called TKONeor hereinafter.

Next, the introduction of DNA was performed by the gene gun method. Specifically, the *T. aureum* ATCC 34304 strain was cultured at 25° C. at 150 rpm using a GY liquid culture medium, and cells of the middle to latter logarithmic growth phase were centrifuged for 10 min at 4° C. at 3500×g, and the supernatant was removed. Then, the obtained cells were resuspended in a GY liquid culture medium so as to result in 100 times the concentration of the original culture solution. 20 μL of this cell suspension was thinly spread uniformly and dried in a diameter of approximately 3 cm on PDA agar plate culture medium 5 cm in diameter containing 1 mg/mL of G418 (available from Nacalai Tesque, Inc.). Using a PDS-1000/He System (available from Bio-Rad Laboratories, Inc.), implantation was performed on under the conditions of target distance: 6 cm, vacuum: 26 inches Hg, microcarrier size: 0.6 μm, rupture disk (implantation pressure): 1100 psi. After that, 100 μL of PD liquid culture medium was added drop-wise to the PDA agar plate culture medium, and the cells were spread out again and static culturing was performed. As a result, transformants conferred with G418 resistance were obtained with efficiency of $4.7\times10^1$ cfu/μg DNA.

[Comparative Example 1-7]: PCR Using Genome DNA of Transformant in which TKONeor was Transformed as a Template Seven colonies of transformants were extracted with a toothpick, and were then inoculated in a GY liquid culture medium containing 0.5 mg/mL of G418 (available from Nacalai Tesque, Inc.). After subculturing multiple times, genome DNA was extracted from the cells by the method described in Comparative Example 1-4, and after ethanol precipitation, the extracted genome DNA was dissolved in an appropriate amount of TE. The quantity and purity of the extracted genome DNA were tested by O.D. 260 and O.D. 280 measurement. Then, with the obtained genome DNA of the obtained transformant and the wild-type as templates, PCR was performed using various oligonucleotide primer pairs. The used oligonucleotide primer pairs were as follows:

(1) Neor detection—Sneo F (described in Comparative Example 1-5, SEQ ID NO: 80) and SNeo R (described in Comparative Example 1-5, SEQ ID NO: 81);

(2) KO confirmation 1—KO Pro F SmaI (described in Comparative Example 1-5, SEQ ID NO: 78) and KO Term R SmaI (described in Comparative Example 1-5, SEQ ID NO: 83);

(3) KO confirmation 2—E2 KO ProF EcoRV (30mer: 5'-GGA TAT CCC CCG CGA GGC GAT GGC TGC TCC-3') (SEQ ID NO: 85) and SNeo R (described in Comparative Example 1-5, SEQ ID NO: 81);

(4) KO confirmation 3—Sneo F (described in Comparative Example 1-5, SEQ ID NO: 80) and E2 KO Term R EcoRV (30mer: 5'-TGA TAT CGG GCC GCG CCC TGG GCC GTA GAT-3') (SEQ ID NO: 86);

(5) TaELO2 amplification—E2 HindIII (described in Comparative Example 1-3, SEQ ID NO: 72) and E2 XbaI (described in Comparative Example 1-3, SEQ ID NO: 73) (FIG. 36A).

As a result, it was confirmed that six of the seven analyzed clones were transformants by random integration, but in one clone, TaELO2 ORF was substituted for Neor by homologous recombination (FIG. 36B, lanes 9, 13). At the same time, however, it was found that TaELO2 ORF was amplified (FIG. 36B, lane 17). This suggests the possibility that *T. aureum* ATCC 34304 is at least diploid or TaELO2 is a multicopy gene.

[Comparative Example 1-8]: Confirmation of TaELO2 Copy Number by Southern Blotting The following experiment was conducted in accordance with the method described in "DIG Manual [Japanese Edition]8th, Roche Applied Science" (Non-patent Document 18). Specifically, wild-type genome DNA was cut with various restriction enzymes and then subjected to electrophoresis using 2.5 μg of 0.7% SeaKem (trade name) GTG (trade name) agarose (available from Takara Bio Inc.) per lane. This was transformed to a nylon membrane (Hybond (trade name)-N+, available from GE Healthcare Inc.), and hybridized at 48° C. for 16 hr with a DIG labeled probe produced using PCR DIG Probe Synthesis Kit (available from Roche Applied Science, Inc.). The pair of oligonucleotide primers used in producing the DIG labeled probe were TaELO2 det F (25mer: 5'-GTA CGT GCT CGG TGT GAT GCT GCT C-3') (SEQ ID NO: 87) and TaELO2 det R (24mer: 5'-GCG GCG TCC GAA CAG GTA GAG CAT-3') (SEQ ID NO: 88). [PCR cycles: 98° C. 2 min/98° C. 30 sec, 65° C. 30 sec, 72° C. 1 min, 30 cycles/72° C. 7 min/4° C.∞]. The hybridized probes were detected using the color development method (NBT/BCIP solution).

The results demonstrated that TaELO2 is a single copy gene from the fact that single bands were detected in all lanes treated with the various restriction enzymes (FIG. 37). This suggests that *T. aureum* ATCC 34304 is at least diploid.

Figure 38A:
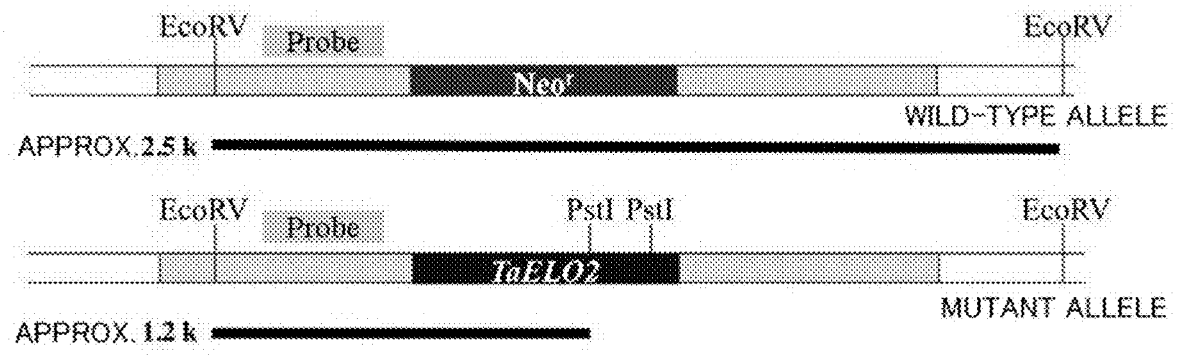
FIGS. 38A and 38B illustrate an evaluation by southern blotting of a transformant into which TKONeor was transformed in Comparative Example 1-9.
Figure 38B:
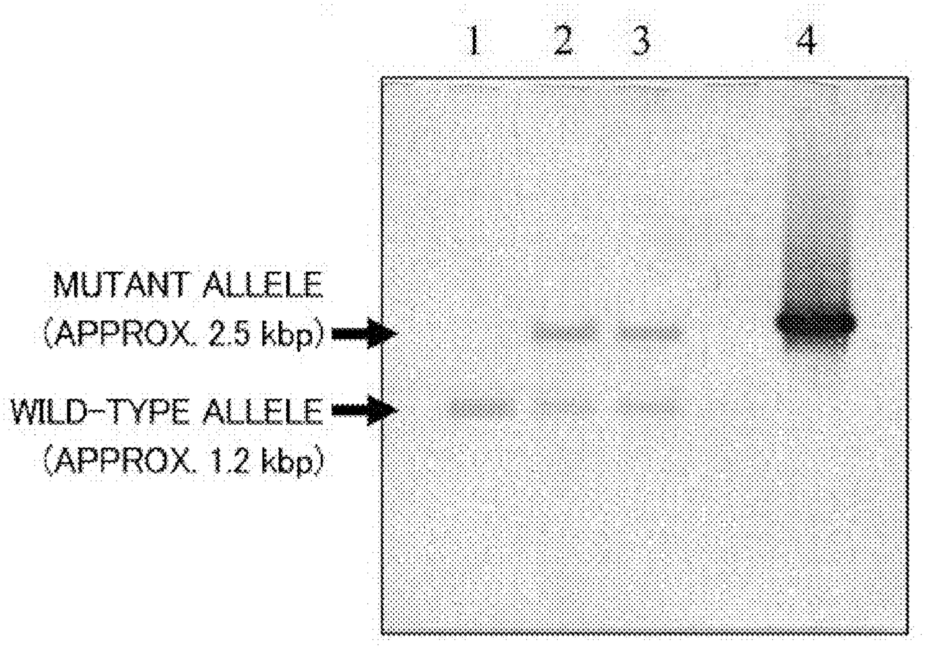

[Comparative Example 1-9]: Evaluation by Southern Blotting of Transformant in which TKONeor was Transformed Southern blotting was performed by the method described in Comparative Example 1-8. Specifically, southern blotting was performed using the color development method (NBT/BCIP solution) relative to genome DNA of the transformant and a wild-type strain digested with EcoRV and PstI, using a DIG labeled probe amplified using the pair of oligonucleotide primers uprobe F (35mer: 5'-ATC CGC GTA TAT ATC CGT AAA CAA CGG AAC ATT CT-3') (SEQ ID NO: 89) and uprobe R (26mer: 5'-CTT CGG GTG GAT CAG CGA GCG ACA GC-3') (SEQ ID NO: 90). [PCR cycles: 98° C. 2 min/98° C. 30 sec, 65° C. 30 sec, 72° C. 1 min, 30 cycles/72° C. 7 min/4° C.∞]. In this case, in the wild-type allele, a DNA fragment of approximately 1.2 kbp was detected, but in the mutant allele in which TaELO2 ORF was substituted for Neor by homologous recombination, a DNA fragment of approximately 2.5 kbp was detected (FIG. 38A).

The result of analysis shows that *T. aureum* ATCC 34304 is at least diploid, since the wild-type allele band was also detected at the same time as the mutant allele.

[Comparative Example 1-10]: Construction of TaELO2 Targeting Vector with Hygr as Selection Marker To disruption the remaining wild-type allele, a TaELO2 targeting vector with Hygr as a selection marker was constructed.

First, a ubiquitin promoter sequence derived from *T. aureum* ATCC 34304 and Hygr were ligated by fusion PCR. The oligonucleotide primers used were as shown below.

```
ubi-600p F
                                        (SEQ ID NO: 91)
(27mer: 5'-GCC GCA GCG CCT GGT GCA CCC GCC GGG-3')

ubi-hygro R
                                        (SEQ ID NO: 92)
(59mer: 5'-TCG CGGG TGA GTT CAG GCT TTT TCA TGT

TGG CTA GTG TTG CTT AGG TCG CTT GCT GCT G-3')

ubi-hygro F
                                        (SEQ ID NO: 93)
(57mer: 5'-AGC GAC CTA AGC AAC ACT AGGC CAA CAT

GAA AAA GCC TGA ACT CAC CGC GAC GTC TG-3')

hygro R
                                        (SEQ ID NO: 94)
(29mer: 5'-CTA TTC CTT TGC CCT CGG ACG AGT GCT

GG-3')
```

Of these oligonucleotide primers, ubi-600p F/ubi-hygro R were used in amplification of the *T. aureum* ATCC 34304-derived ubiquitin promoter sequence using the *T. aureum* ATCC 34304 genome DNA described in Comparative Example 1-4 as a template. Ubi-hygro F/hygro R were used in amplification of artificially synthesized Hygr using pcDNA 3.1 Zeo (available from Invitrogen Corp.) as a template. As PCR conditions, denaturation was performed at 98° C. for 10 sec, and annealing and the elongation reaction were performed while adjusting as appropriate according to Tm of the primers and the lengths of the amplification products.

As a result, 1636 bp (SEQ ID NO: 95) of *T. aureum* ATCC 34304-derived ubiquitin promoter sequence/Hygr was successfully ligated. The result of TA cloning of this sequence using pGEM-T Easy Vector (available from Promega Corporation) was named pTub600Hygr.

Then, using pTub600Hygr as a template, PCR was performed using a pair of oligonucleotide primers ubi-600p F NheI (33mer: 5'-GTG CTA GCC GCA GCG CCT GGT GCA CCC GCC GGG-3') (SEQ ID NO: 96) and hygro R XbaI (37mer: 5'-GTT CTA GAC TAT TCC TTT GCC CTC GGA CGA GTG CTG G-3') (SEQ ID NO: 97) and using PrimeSTAR HS DNA Polymerase (available from Takara Bio Inc.). [PCR cycles: 98° C. 2 min/98° C. 10 sec, 68° C. 3 min, 30 cycles/68° C. 10 min/4° C.∞]. As a result, a *T. aureum* ATCC 34304-derived ubiquitin promoter sequence/Hygr DNA fragment with NheI appended at the 5' terminal and an XbaI site appended at the 3' terminal was prepared. Furthermore, using pTKONeor described in Comparative Example 1-5 as a template, PCR was performed using a pair of oligonucleotide primers KO vec F XbaI (37mer: 5'-GTT CTA GAC CTG TTT CCG GCT GGC TCC CGA GCC ATG C-3') (SEQ ID NO: 98) and KO vec R NheI (40mer: 5'-GTG CTA GCG GTC GCG TTT ACA AAG CAG CGC AGC AAC AGA A-3') (SEQ ID NO: 99) and using PrimeSTAR HS DNA Polymerase (available from Takara Bio Inc.). [PCR cycles: 98° C. 2 min/98° C. 10 sec, 68° C. 3 min, 30 cycles/68° C. 10 min/4° C. ∞]. As a result, a linear vector in which Neor of pTKONeor described in Comparative Example 1-5 was removed and having NheI appended at the 3' terminal and an XbaI site appended at the 5' terminal was prepared. After the two DNA fragments were digested with NheI and XbaI, the DNA fragments were purified using agarose gel, and cyclic vectors were constructed using Ligation Convenience Kit (available from Nippon Gene Co., Ltd.).

The constructed TaELO2 targeting vector having Hygr as a selection marker includes pGEM-T Easy Vector (available from Promega Corporation) as a basic framework, and as an insertion sequence, had a 3537 bp (SEQ ID NO: 100) TaELO2 ORF upstream sequence/*T. aureum* ATCC 34304-derived ubiquitin promoter sequence/Hygr/TaELO2 ORF downstream sequence. This was named pTKOub600Hygr.

[Comparative Example 1-11]: Evaluation of Transformant by PCR Using KOub600Hygr Retransfer and Genome DNA as Templates, Southern Blotting, and RT-PCR Using, as a template, pTKOub600Hygr (described in Comparative Example 1-10), which is the constructed TaELO2 targeting vector with Hygr as a selection marker, TaELO2 ORF upstream sequence/*T. aureum* ATCC 34304-derived ubiquitin promoter sequence/Hygr/TaELO2 ORF downstream sequence was amplified using a pair of oligonucleotide primers KO Pro F SmaI (Comparative Example 1-5, SEQ ID NO: 78)/KO Term R SmaI (Comparative Example 1-5, SEQ ID NO: 83) and using PrimeSTAR HS DNA Polymerase (available from Takara Bio Inc.). [PCR cycles: 98° C. 2 min/98° C. 10 sec, 68° C. 3.5 min, 30 cycles/68° C. 10 min/4° C.∞]. The obtained DNA fragment was named KOub600Hygr. This was transformed into the transformant obtained in Comparative Example 1-7 by the same technique, and after static culturing for 24 hr on PDA agar plate culture medium containing 1 mg/mL of G418 (available from Nacalai Tesque, Inc.), the cells were collected. The static culturing was continued on PDA agar plate culture medium containing 1 mg/mL of G418 (available from Nacalai Tesque, Inc.) and 2 mg/mL of hygromycin B (available from Wako Pure Chemical Industries, Ltd.) to obtain numerous transformants (transfer efficiency: $1.02\times10^3$ cfu/μg DNA).

Figure 39A:
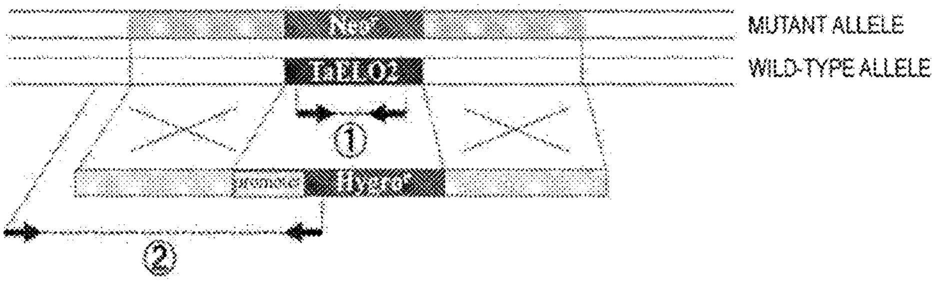
FIGS. 39A to 39C illustrate an evaluation by PCR using as a template genome DNA of a transformant obtained by retransfer of KOub600Hygr in Comparative Example 1-11.

Among them, 50 clones were extracted, and after subculturing multiple times in a GY liquid culture medium containing 1 mg/mL of G418 (available from Nacalai Tesque, Inc.) and 2 mg/mL of hygromycin B (available from Wako Pure Chemical Industries, Ltd.), genome DNA was extracted by the same technique as described in Comparative Example 1-4, and after ethanol precipitation, the extracted genome DNA was dissolved in an appropriate quantity of TE. The quantity and purity of the extracted genome DNA were tested by OD260 and OD280 measurement. Then, with the obtained transformant and wild-type genome DNA as templates, PCR was performed using various oligonucleotide primer pairs. [PCR cycles: 98° C. 2 min/98° C. 10 sec, 68° C. 1 min, 30 cycles/68° C. 10 min/4° C.∞]. The used oligonucleotide primer pairs were as follows:

(1) TaELO2 ORF detection—Sneo F (described in Comparative Example 1-5, SEQ ID NO: 80) and SNeo R (described in Comparative Example 1-5, SEQ ID NO: 81);

(2) KO confirmation—E2 KO Pro F EcoRV (described in Comparative Example 1-7, SEQ ID NO: 85) and ubi-hygro R (described in Comparative Example 1-10, SEQ ID NO: 92) (FIG. 39A).

Figure 39B:
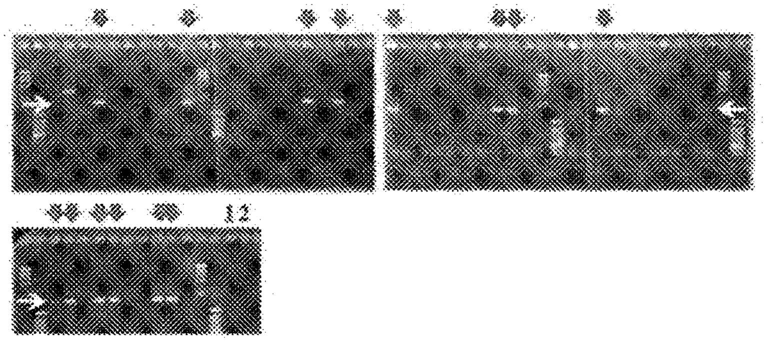
Figure 39C:
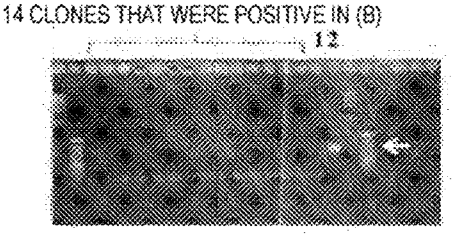

The results showed that of the 50 analyzed clones, 14 clones were transformants which caused homologous recombination in the form of substituting TaELO2 ORF (FIG. 39B, arrows). For these clones, it was confirmed that TaELO2 ORF was not amplified (FIG. 39C).

Then, southern blotting was performed using the technique described in Comparative Example 1-9. Specifically, southern blotting was performed by the color development method (NBT/BCIP solution) relative to genome DNA of the transformant and a wild-type strain digested with EcoRV and PstI, using a DIG labeled probe prepared using the pair of oligonucleotide primers uprobe F (SEQ ID NO: 89) and uprobe R (SEQ ID NO: 90). In this case, in the wild-type allele, a DNA fragment of approximately 1.2 kbp was detected; in the mutant allele in which TaELO2 ORF was substituted for Neor by homologous recombination, a DNA fragment of approximately 2.5 kbp was detected; in the mutant allele in which TaELO2 ORF was substituted for Hygr, a DNA fragment of approximately 1.9 kbp was detected (FIG. 40A).

As a result of analysis, a band of the wild-type allele of approximately 2.5 kbp was disappeared, and instead, a band of the mutant allele of approximately 1.9 kbp in which TaELO2 ORF was substituted for Hygr was detected (FIG. 40B).

Similarly, a DIG labeled probe that detects TaELO2 was prepared by PCR using the pair of oligonucleotide primers TaELO2 probe F (30mer: 5'-ATG GCG ACG CGC ACC TCG AAG AGC GCT CCG-3') (SEQ ID NO: 101) and TaELO2 probe R (30mer: 5'-AGG ATC ATC ATG AAC GTG TCG CTC CAG TCG-3') (SEQ ID NO: 102). [PCR cycles: 98° C. 2 min/98° C. 30 sec, 65° C. 30 sec, 72° C. 1 min, 30 cycles/72° C. 7 min/4° C.∞]. Southern blotting was performed by the color development method (NBT/BCIP solution) relative to genome DNA of transformants (clones 1, 8, 9, 10) and a wild-type strain digested with EcoRV. In this case, TaELO2 was detected as a DNA fragment of approximately 2.5 kbp (FIG. 38A).

The result of analysis showed that TaELO2 was detected in the wild-type strain (FIG. 41, lane 1), whereas in the transformant, TaELO2 was not detected at all (FIG. 41, lanes 2 to 5).

Furthermore, to verify TaELO2 disruption at an mRNA level, TaELO2 mRNA was detected by RT-PCR. From the cells of the transformant (clones 1, 8, 9, 10) and the wild-type strain on the third day of culturing using a GY liquid culture medium, total RNA was extracted using Sepasol-RNA I Super (available from Nacalai Tesque, Inc.) in the same manner as Comparative Example 1-1. Then, 50 μg of total RNA cleaned up using RNeasy Mini Kit (available from QIAGEN N.V.) according to the manufacturer's protocol was treated for 1 hr at 37° C. using 50 U of Recombinant DNase I (available from Takara Bio Inc.), and contaminated genome DNA was decomposed and removed. Then, using the obtained total RNA as a template, a single-strand cDNA library was prepared according to manufacturer's instructions using oligo (dT) primer (available from Novagen Corp.) and PrimeScript Reverse Transcriptase (available from Takara Bio Inc.). Additionally, using the obtained single-strand cDNA library as a template, TaELO2 ORF was amplified using a pair of oligonucleotide primers E2 HindIII (described in Comparative Example 1-3, SEQ ID NO: 72) and E2 XbaI (described in Comparative Example 1-3, SEQ ID NO: 73) and using LA Taq Hot Start Version (available from Takara Bio Inc.). [PCR cycles: 98° C. 2 min/98° C. 10 sec, 68° C. 1 min, 30 cycles/68° C. 10 min/4° C.∞].

Figure 42:
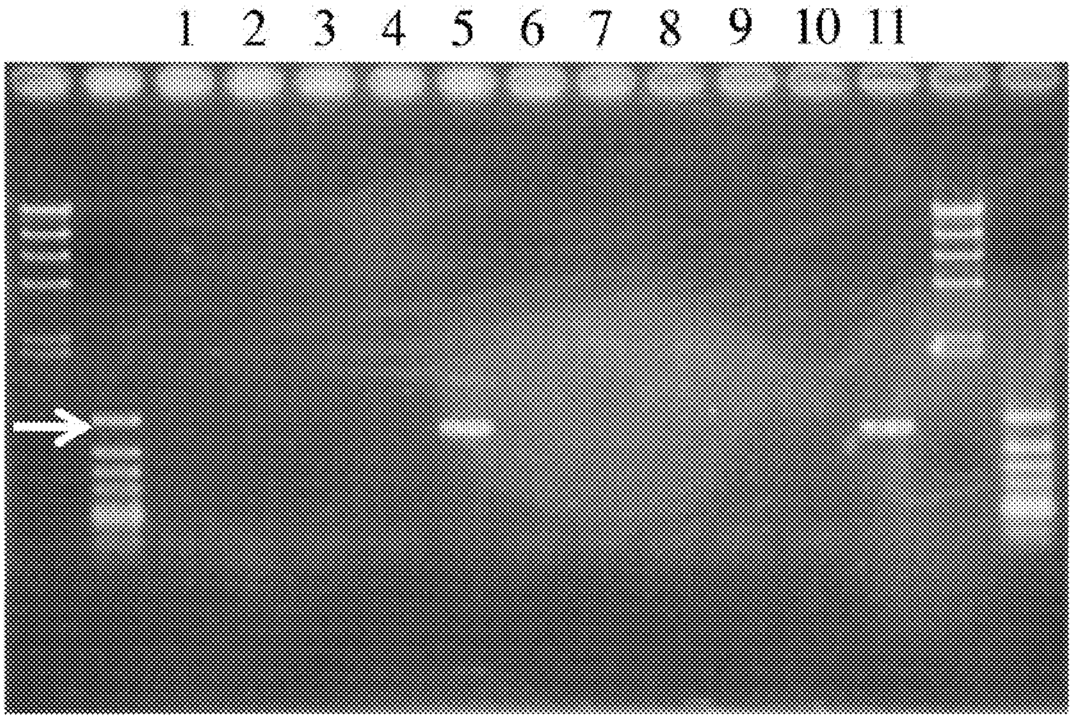
FIG. 42 illustrates the results of agarose electrophoresis of RT-PCR to detect TaELO2 mRNA in Comparative Example 1-11. (Brief description of symbols) 1 to 4: TaELO2 deletion homozygote; 5: Wild-type strain; 6 to 9: TaELO2 deletion homozygote, using total RNA as a template (negative control); 10: Wild-type strain, using total RNA as a template (negative control); 11: Using wild-type genome DNA as a template (positive control)

The result showed that TaELO2 mRNA was detected in the wild-type strain (FIG. 42, lane 5), whereas TaELO2 mRNA was not detected at all in the transformant (clones 1, 8, 9, 10) (FIG. 42, lanes 1 to 4).

The above results showed that a TaELO2 deletion homozygote in which TaELO2 had been completely disrupted was successfully obtained. The above results demonstrate that *T. aureum* ATCC 34304 is diploid.

[Comparative Example 1-12]: Comparison of Fatty Acid Compositions of Wild-Type Strain and TaELO2 Deletion Homozygote The fatty acid compositions of the TaELO2 deletion homozygote obtained in Comparative Example 1-11 and the wild-type strain were compared by GC analysis of the methyl-esterified fatty acids. Specifically, the cells of the wild-type strain and the TaELO2 deletion homozygote after 5 days of culturing in a GY liquid culture medium were collected. The fungus body-derived fatty acids were extracted and methyl-esterified by the method described in Comparative Example 1-3, and GC analysis was performed. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 43:
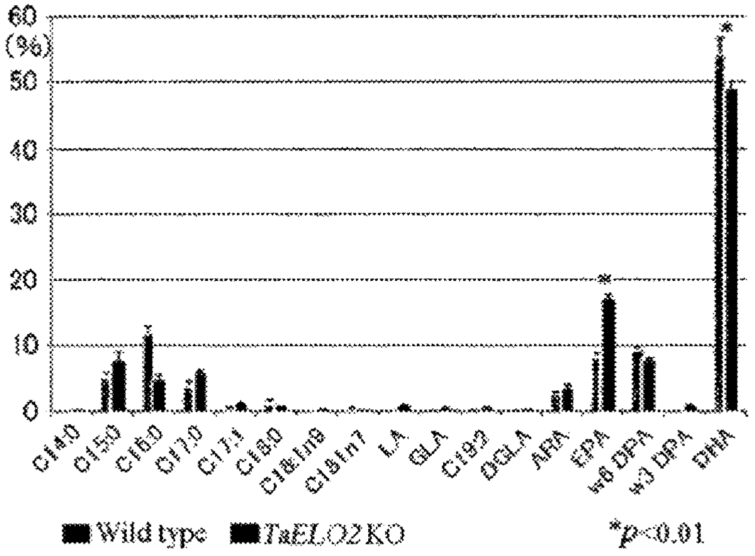
FIG. 43 illustrates the results of a fatty acid composition comparison of the wild-type strain and TaELO2 deletion homozygote in Comparative Example 1-12.

As a result, the quantity of EPA serving as a substrate of TaELO2 increased up to approximately 2-fold in the TaELO2 deletion homozygote (TaELO2 KO) compared to the wild-type strain (Wild type), and a decrease in the amount of the downstream metabolite DHA was observed (FIG. 43).

As described above, it was confirmed that due to C20 elongase gene disruption in *T. aureum* ATCC 34304, similar to genus *Parietichytrium* labyrinthulids, the quantity of the C20 elongase substrate EPA increased compared to the wild-type strain, and conversely, the downstream metabolite DHA and the like decreased. However, unlike the genus *Parietichytrium* labyrinthulids, the proportion of DHA did not really decrease in *T. aureum* ATCC 34304 even when the C20 elongase gene was disrupted. Specifically, the proportion of DHA in the wild-type strain was 54.38%, whereas the proportion of DHA was 48.77%, which is only slightly less in the C20 elongase gene KO strain. A similar trend was seen for n-6 DPA as well.

As described in Comparative Example 1-2, in *T. aureum* ATCC 34304, TaELO1 is present in addition to TaELO2, which was disrupted this time. In Comparative Example 1-3, it was shown that both have Δ5 elongase activity (═C20 elongase activity). However, it was also clear that the Δ5 elongase activity of TaELO1 is considerably lower than the Δ5 elongase activity of TaELO2, and the reason that DHA and n-6 DPA did not really decrease in the TaELO2 deletion homozygote (TaELO2 KO) is difficult to explain by the Δ5 elongase activity (═C20 elongase activity) of TaELO1. This suggests the possibility that in *Thraustochytrium aureum* ATCC 34304, DHA and n-6 DPA are produced via another biosynthesis pathway in addition to the elongase-desaturase pathway.

When such a labyrinthulid is selected, unlike Examples 2, 4, and 6, it is not possible to create a strain which accumulates PUFAs other than DHA and n-6 DPA even by disruption the C20 elongase gene. Therefore, creating such a strain requires disruption of a gene associated with a DHA and n-6 DPA biosynthesis pathway other than the elongase-desaturase pathway.

Comparative Example 2

[Measurement of Fatty Acid Composition of Lipids Produced by PUFA-PKS Gene Disruption and Transformation Strain of *Thraustochytrium aureum* ATCC 34304]

[Comparative Example 2-1]: PUFA-PKS Pathway Associated Gene: OrfA Upstream Sequence Cloning After genome DNA was extracted from *Thraustochytrium aureum* ATCC 34304 by the method described in Example 2-2, A260/280 was measured and the DNA concentration was calculated. Using this extracted genome DNA, a genome cassette library was produced using LA PCR (trade name) in vitro Cloning Kit (available from Takara Bio Inc.). A PCR lower primer [RHO20: 23mer: 5'-CGA TGA AAG GTC ACA GAA GAG TC-3' (SEQ ID NO: 103)] was set on the PUFA-PKS pathway associated gene: OrfA described in Patent Document 4, and DNA was amplified by combining with the cassette primers contained in the above kit. [1st PCR cycles: 98° C. 2 min/98° C. 30 sec, 56° C. 30 sec, 72° C. 4 min, 30 cycles/72° C. 5 min]. Then, the 1st PCR amplification product was diluted 100-fold, and the DNA was amplified by combining the PCR lower primer [RHO20] and the nested primers contained in the above kit. [2nd PCR cycles: 98° C. 2 min/98° C. 30 sec, 56° C. 30 sec, 72° C. 4 min, 30 cycles/72° C. 5 min]. The obtained DNA fragment was cloned in pGEM-T Easy Vector, and after amplification with *E. coli*, the sequence was confirmed using a Dye Terminator Cycle Sequencing Kit (available from Beckman Coulter Inc.).

A DNA fragment of 3377 bp (SEQ ID NO: 105) containing 3181 bp (SEQ ID NO: 104) upstream of OrfA was cloned. It became clear that the OrfA upstream DNA sequence information was a total of 3181 bp.

[Comparative Example 2-2]: PUFA-PKS Pathway Associated Gene: OrfA Downstream Sequence Cloning The genome cassette library produced in Comparative Example 2-1 was used as a template. A PCR upper primer [RHO21: 21mer: 5'-CAG GGC GAG CGA GTG TGG TTC-3' (SEQ ID NO: 106)] was set on the PUFA-PKS pathway associated gene: OrfA described in Patent Document 4, and DNA was amplified by the method described in Comparative Example 2-1. The obtained DNA fragment was cloned in pGEM-T Easy Vector, and after amplification with *E. coli*, the sequence was confirmed using a Dye Terminator Cycle Sequencing Kit (available from Beckman Coulter Inc.). A DNA fragment of 1204 bp (SEQ ID NO: 108) containing 1160 bp (SEQ ID NO: 107) downstream of OrfA was cloned.

A PCR upper primer [RHO28: 20mer: 5'-TGA TGC CGA TGC TAC AAA AG-3' (SEQ ID NO: 109)] was again produced on SEQ ID NO: 94, and DNA was amplified by the method described in Comparative Example 1-2. The obtained DNA fragment was cloned in pGEM-T Easy Vector, and after amplification with *E. coli*, the sequence was confirmed using a Dye Terminator Cycle Sequencing Kit (available from Beckman Coulter Inc.).

Furthermore, a 1488 bp DNA fragment (SEQ ID NO: 110) containing the downstream sequence was cloned. It became clear that the OrfA downstream DNA sequence information is a total of 2551 bp (SEQ ID NO: 111).

[Comparative Example 2-3]: Production of PUFA-PKS Pathway Associated Gene: OrfA Targeting Vector Using *Thraustochytrium aureum* ATCC 34304 genome DNA as a template, an 18S rDNA sequence (1835 bp, SEQ ID NO: 112) was amplified with PrimeSTAR HS DNA Polymerase (available from Takara Bio Inc.). The PCR primers used were as shown below. TMO30 was set on the 18S rDNA sequence. TMO31 includes the 18S rDNA sequence and the EF1α promoter sequence. [TMO30: 30mer: 5'-CGAATA TTC CTG GTT GAT CCT GCC AGT AGT-3' (SEQ ID NO: 113), TMO31: 46mer: 5'-GTAACG GCT TTT TTT GAA TTG CAG GTT CAC TAC GCT TGT TAG AAA C-3' (SEQ ID NO: 114)]. [PCR cycles: 98° C. 10 sec/98° C. 10 sec, 58° C. 30 sec, 72° C. 2 min, 30 cycles/72° C. 2 min].

Furthermore, using *Thraustochytrium aureum* ATCC 34304 genome DNA as a template, an EF1α promoter sequence (661 bp, SEQ ID NO: 115) was amplified with PrimeSTAR HS DNA Polymerase (available from Takara Bio Inc.). The PCR primers used were as shown below. TMO32 includes the 18S rDNA sequence and the EF1α promoter sequence. TMO33 includes the EF1α promoter sequence and an artificially synthesized neomycin resistance gene sequence. [TMO32: 46mer: 5'-GGT TTC CGT AGT GAA CCT GCAATT CAA AAA AAG CCG TTA CTC ACA T-3' (SEQ ID NO: 116), TMO33: 46mer: 5'-GCG TGA AGG CCG TCC TGT TCA ATC ATC TAG CCT TCC TTT GCC GCT G-3' (SEQ ID NO: 117)]. [PCR cycles: 98° C. 10 sec/98° C. 10 sec, 58° C. 30 sec, 72° C. 1 min, 30 cycles/72° C. 1 min].

Using the artificially synthesized neomycin resistance gene sequence as a template, an artificially synthesized neomycin resistance gene sequence (835 bp, SEQ ID NO: 118) was amplified with PrimeSTAR HS DNA Polymerase (available from Takara Bio Inc.). The PCR primers used were as shown below. TMO34 includes the EF1α promoter sequence and the artificially synthesized neomycin resistance gene sequence. TMO35 includes the artificially synthesized neomycin resistance gene sequence and the EF1α terminator sequence. [TMO34: 45mer: 5'-CAT CGG CAA AGG AAG GCT AGA TGA TTG AAC AGG ACG GCC TTC ACG-3' (SEQ ID NO: 119), TMO35: 46mer: 5'-GCG CAT AGC CGG CGC GGA TCT CAA AAG AAC TCG TCC AGG AGG CGG T-3' (SEQ ID NO: 120)]. [PCR cycles: 98° C. 10 sec/98° C. 10 sec, 58° C. 30 sec, 72° C. 1 min, 30 cycles/72° C. 1 min].

Using *Thraustochytrium aureum* ATCC 34304 genome DNA as a template, an EF1α terminator sequence (1249 bp, SEQ ID NO: 121) was amplified with PrimeSTAR HS DNA Polymerase (available from Takara Bio Inc.). The PCR primers used were as shown below. TMO36 includes the artificially synthesized neomycin resistance gene sequence and the EF1α terminator sequence. TMO37 was set within the EF1α terminator. [TMO36: 46mer: 5'-TCC TGG ACG AGT TCT TTT GAG ATC CGC GCC GGC TAT GCG CCC GTG C-3' (SEQ ID NO: 122), TMO37: 30mer: 5'-CAC TGC AGC GAA AGA CGG GCC GTA AGG ACG-3' (SEQ ID NO: 123)]. [PCR cycles: 98° C. 10 sec/98° C. 10 sec, 58° C. 30 sec, 72° C. 2 min, 30 cycles/72° C. 2 min].

Using SEQ ID NOS: 112, 115, 118, and 121 as templates, fusion PCR was performed according to the method described in Non-patent Document 9. LA Taq Hot Start Version (available from Takara Bio Inc.) was used for the enzymes. In the first amplification, the set of TMO30 (SEQ ID NO: 113) and TMO33 (SEQ ID NO: 117) and the set of TMO34 (SEQ ID NO: 119) and TMO37 (SEQ ID NO: 123) were used. In the second amplification, the set of TMO30 (SEQ ID NO: 113) and TMO37 (SEQ ID NO: 123) was used. As conditions of the PCR reaction, denaturation was performed at 98° C. for 10 sec, and annealing and the elongation reaction were performed while adjusting as appropriate according to Tm of the primers and the lengths of the amplification fragments (FIG. 42).

The DNA fragment ligated in this manner (FIG. 44, SEQ ID NO: 124, 4453 bp) was cut at the EcoRI site in *T. aureum* 18S rDNA and at the NcoI site in the *T. aureum* EF1α terminator, and was bound to the vector derived from pGEM-T Easy Vector. This was named pRH5 (FIG. 45).

Using *Thraustochytrium aureum* ATCC 34304 genome DNA as a template, the PCR primers were set in the upstream sequence clarified in Comparative Example 2-1 (SEQ ID NO: 104) and the PUFA-PKS pathway associated gene: OrfA described in Patent Document 4, and DNA was amplified with PrimeSTAR HS DNA Polymerase with GC Buffer (available from Takara Bio Inc.). A 1218 bp DNA fragment (SEQ ID NO: 125) was obtained by this amplification. This was used as the 5' homologous region of the targeting vector. The PCR primers used are as shown below. As a linker sequence, an EcoRI site or a HindIII site was appended to each. [RHO33: 32mer: 5'-CCC GAA TTC GGA CGA TGA CTG ACT GAC TGA TT-3' (SEQ ID NO: 126), RHO34: 28mer: 5'-CCC AAG CTT GTC TGC CTC GGC TCT TGG T-3' (SEQ ID NO: 127)]. [PCR cycles: 98° C. 2 min/98° C. 30 sec, 57° C. 30 sec, 72° C. 1 min, 30 cycles/72° C. 3 min].

Using *Thraustochytrium aureum* ATCC 34304 genome DNA as a template, the PCR primers were set in the downstream sequence clarified in Comparative Example 2-2 (SEQ ID NO: 111), and DNA was amplified with PrimeSTAR HS DNA Polymerase with GC Buffer (available from Takara Bio Inc.). A 1000 bp DNA fragment (SEQ ID NO: 128) was obtained by this amplification. This was used as the 3' homologous region of the targeting vector. The PCR primers used were as shown below. An NcoI site as a linker sequence was appended to each. [RHO29: 28mer: 5'-CCC CCA TGG TGT TGC TGT GGG ATT GGT C-3' (SEQ ID NO: 129), RHO30: 30mer: 5'-CCC CCA TGG CTC GGT TAC ATC TCT GAG GAA-3' (SEQ ID NO: 130)]. [PCR cycles: 98° C. 2 min/98° C. 30 sec, 57° C. 30 sec, 72° C. 1 min, 30 cycles/72° C. 3 min].

The amplified upstream sequence was ligated to the EcoRI site and the HindIII site in pRH5 illustrated in FIG. 43. The amplified downstream sequence was ligated to the NcoI site. This vector was named pRH21.

Figure 44:
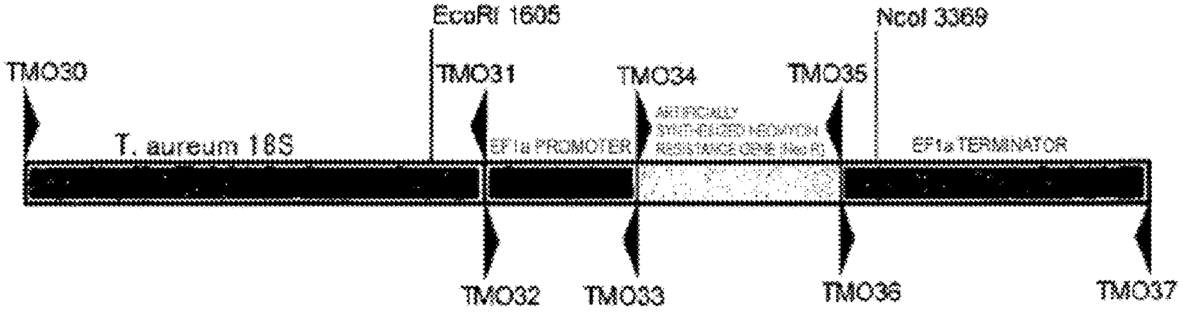
FIG. 44 is a schematic diagram of the primers used in fusion PCR and the products. The final product is a fused sequence of 18S rDNA derived from *Thraustochytrium aureum* ATCC 34304, an EF1α promoter derived from *Thraustochytrium aureum* ATCC 34304, an artificially synthesized neomycin resistance gene, and an EF1α terminator derived from *Thraustochytrium aureum* ATCC 34304.
Figure 45:
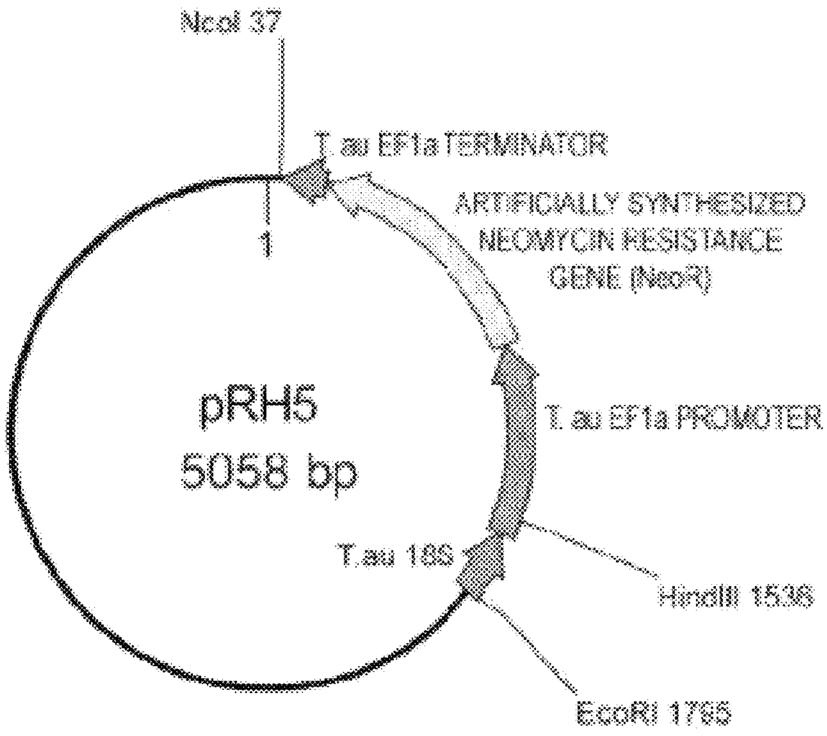
FIG. 45 illustrates a plasmid in which a portion of the ligated DNA fragment in FIG. 42 was cloned. The plasmid contains a partial sequence of the 3' side from the EcoRI site of 18S rDNA derived from *Thraustochytrium aureum* ATCC 34304, an EF1a promoter derived from *Thraustochytrium aureum* ATCC 34304, an artificially synthesized neomycin resistance gene, and a partial sequence of the 5' side from the NcoI site of the EF1a terminator derived from *Thraustochytrium aureum* ATCC 34304.

The targeting vector (pRH21) obtained using the produced artificially synthesized neomycin resistance gene is illustrated in FIG. 44.

[Comparative Example 2-4]: Production of PUFA-PKS Pathway Associated Gene: OrfA Targeting Vector (Hygromycin Resistance Gene)

Using pRH32 (FIG. 6) described in Example 2-3 as a template, a ubiquitin promoter—hygromycin resistance gene fragment (1632 bp, SEQ ID NO: 131) was amplified with PrimeSTAR HS DNA Polymerase with GC Buffer (available from Takara Bio Inc.). The PCR primers used were as shown below. RHO59 was set on the ubiquitin promoter, and a HindIII site was appended as a linker sequence. RHO60 contains a stop codon of the hygromycin resistance gene sequence, and has the linker sequences SphI and SalI. [RHO59: 36mer: 5'-CCC AAG CTT GCC GCA GCG CCT GGT GCA CCC GCC GGG-3' (SEQ ID NO: 132), RHO60: 43mer: 5'-CCC GCA TGC GTC GAC TAT TCC TTT GCC CTC GGA CGA GTG CTG G-3' (SEQ ID NO: 133)]. [PCR cycles: 98° C. 2 min/98° C. 30 sec, 68° C. 2 min, 30 cycles/68° C. 2 min].

Figure 46:
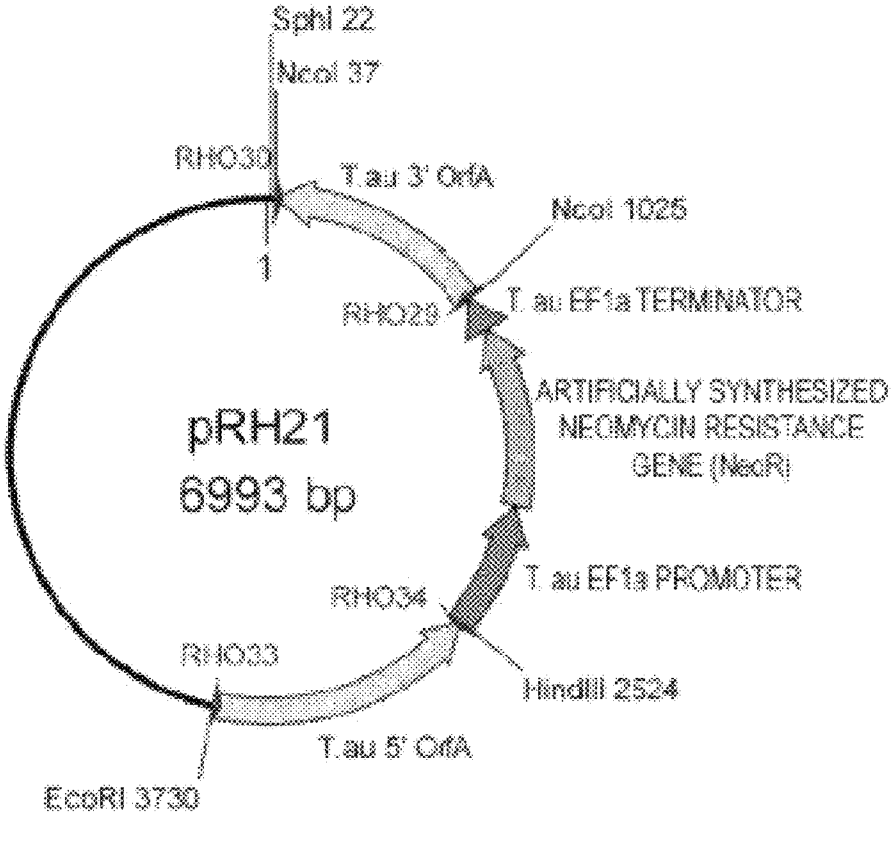
FIG. 46 illustrates the produced targeting vector of *Thraustochytrium aureum* ATCC 34304 PKS pathway associated gene orfA. As a drug resistance marker, the vector has a neomycin resistance gene.
Figure 47:
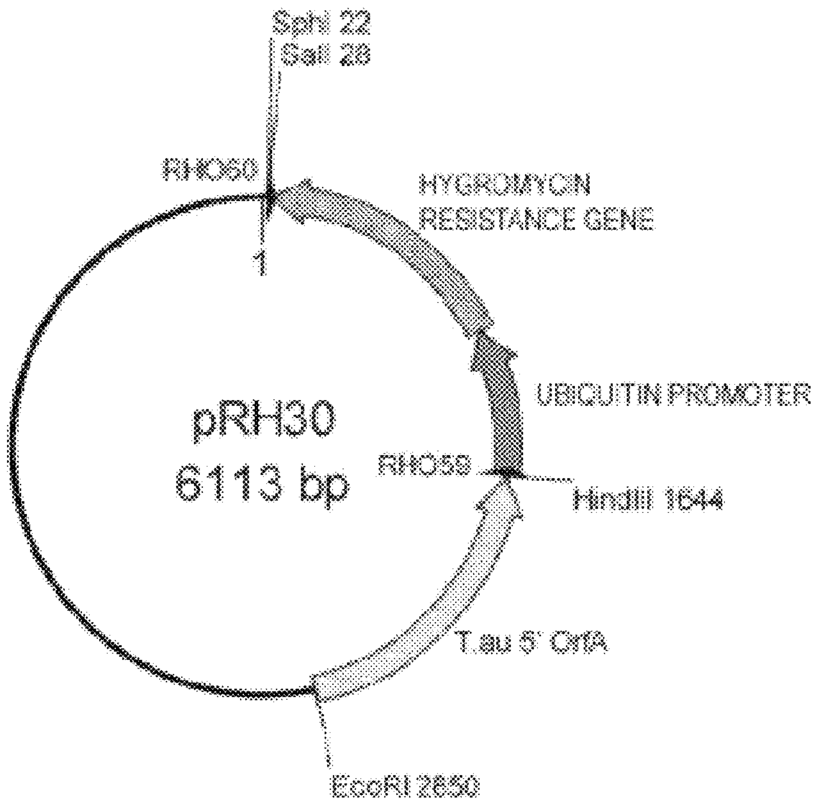
FIG. 47 illustrates a plasmid containing an upstream sequence of the *Thraustochytrium aureum* ATCC 34304 PKS pathway associated gene orfA, a ubiquitin promoter derived from *Thraustochytrium aureum* ATCC 34304, and a hygromycin resistance gene.

The amplified fragment was ligated to the HindIII and SphI sites of pRH21 (FIG. 46) described in Comparative Example 2-3 (FIG. 47, pRH30).

Using *Thraustochytrium aureum* ATCC 34304 genome DNA as a template, the DNA was amplified with PrimeSTAR HS DNA Polymerase with GC Buffer (available from Takara Bio Inc.) using the produced PCR primers in the downstream sequence (SEQ ID NO: 111) clarified in Comparative Example 2-2. A 1000 bp DNA fragment (SEQ ID NO: 134) was obtained by this amplification. This was used as the 3' homologous region of the targeting vector. The PCR primers used were as shown below. A SalI site as a linker sequence was also appended. [RHO61: 29mer: 5'-CCC GTC GAC GTG TTG CTG TGG GAT TGG TC-3' (SEQ ID NO: 135), RHO62: 29mer: 5'-CCC GTC GAC TCG GTT ACA TCT CTG AGG AA-3' (SEQ ID NO: 136)]. [PCR cycles: 98° C. 2 min/98° C. 30 sec, 57° C. 30 sec, 72° C. 1 min, 30 cycles/72° C. 3 min].

Figure 48:
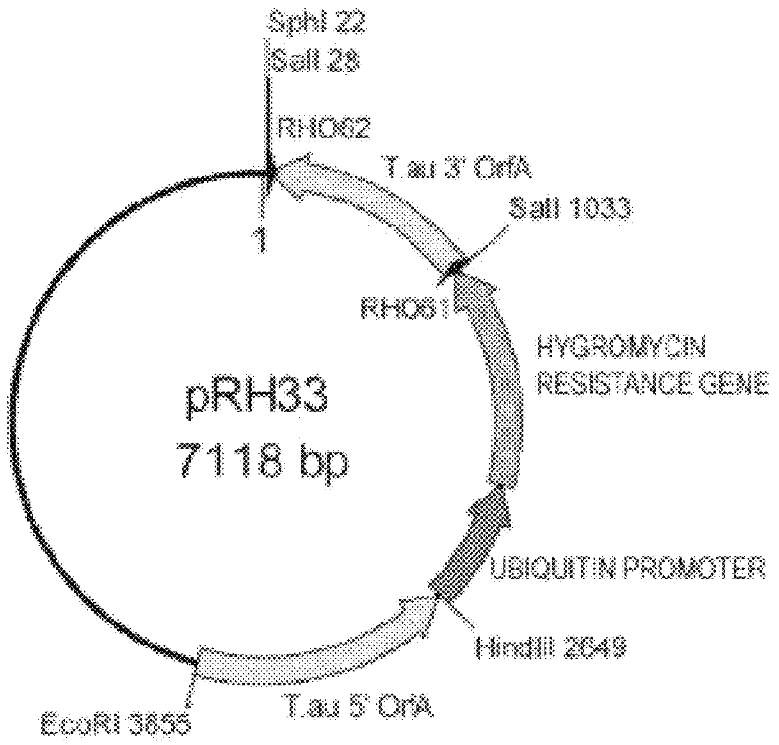
FIG. 48 illustrates the produced targeting vector of *Thraustochytrium aureum* ATCC 34304 PKS pathway associated gene orfA. As a drug resistance marker, the vector has a hygromycin resistance gene.

The amplified downstream sequence was ligated to the SalI site of pRH30 (FIG. 45). This was named pRH33. The targeting vector (pRH33) obtained using the produced hygromycin resistance gene is illustrated in FIG. 48.

[Comparative Example 2-5]: PUFA-PKS Pathway Associated Gene: OrfA Targeting Vector Transfer Using the targeting vectors produced in Comparative Examples 2-3 and 2-4 as templates, the genes were amplified with PrimeSTAR Max DNA Polymerase (available from Takara Bio Inc.) using RHO30 (described in Comparative Example 2-3, SEQ ID NO: 130) and RHO33 (described in Comparative Example 2-3, SEQ ID NO: 126) as primers. [PCR cycles: 98° C. 2 min/98° C. 30 sec, 60° C. 30 sec, 72° C. 1 min, 30 cycles/72° C. 3 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH21 (FIG. 46) described in Comparative Example 2-3 was used as a template was 3705 bp, and resulted in a sequence including *Thraustochytrium aureum* OrfA gene upstream—EF1α promoter sequence—artificially synthesized neomycin resistance gene sequence—*Thraustochytrium aureum* OrfA gene downstream (SEQ ID NO: 137). The transfer fragment obtained when pRH33 (FIG. 46) described in Comparative Example 2-4 was used as a template was 3826 bp, and resulted in a sequence including *Thraustochytrium aureum* OrfA gene upstream—ubiquitin promoter sequence—hygromycin resistance gene sequence—*Thraustochytrium aureum* OrfA gene downstream (SEQ ID NO: 138).

The *Thraustochytrium aureum* ATCC 34304 strain was cultured for 4 days in a GY culture medium, and cells in the logarithmic growth phase were used in gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 1100 psi). After a recovery time of 4 to 6 hr, the transgenic cells were spread on a PDA agar plate culture medium (containing 2 mg/mL of G418 or containing 2 mg/mL of hygromycin). As a result, from 100 to 200 cells of drug resistant strain per shot were obtained.

[Comparative Example 2-6]: Identification of PUFA-PKS Pathway Associated Gene: OrfA Gene Targeting Homologous Recombinant After genome DNA was extracted from *Thraustochytrium aureum* ATCC 34304 and a hetero homologous recombinant and homo homologous recombinant (PKS pathway associated gene disruption strain) by the method described in Example 2-2, A260/280 was measured and the DNA concentration was calculated.

Figure 49:
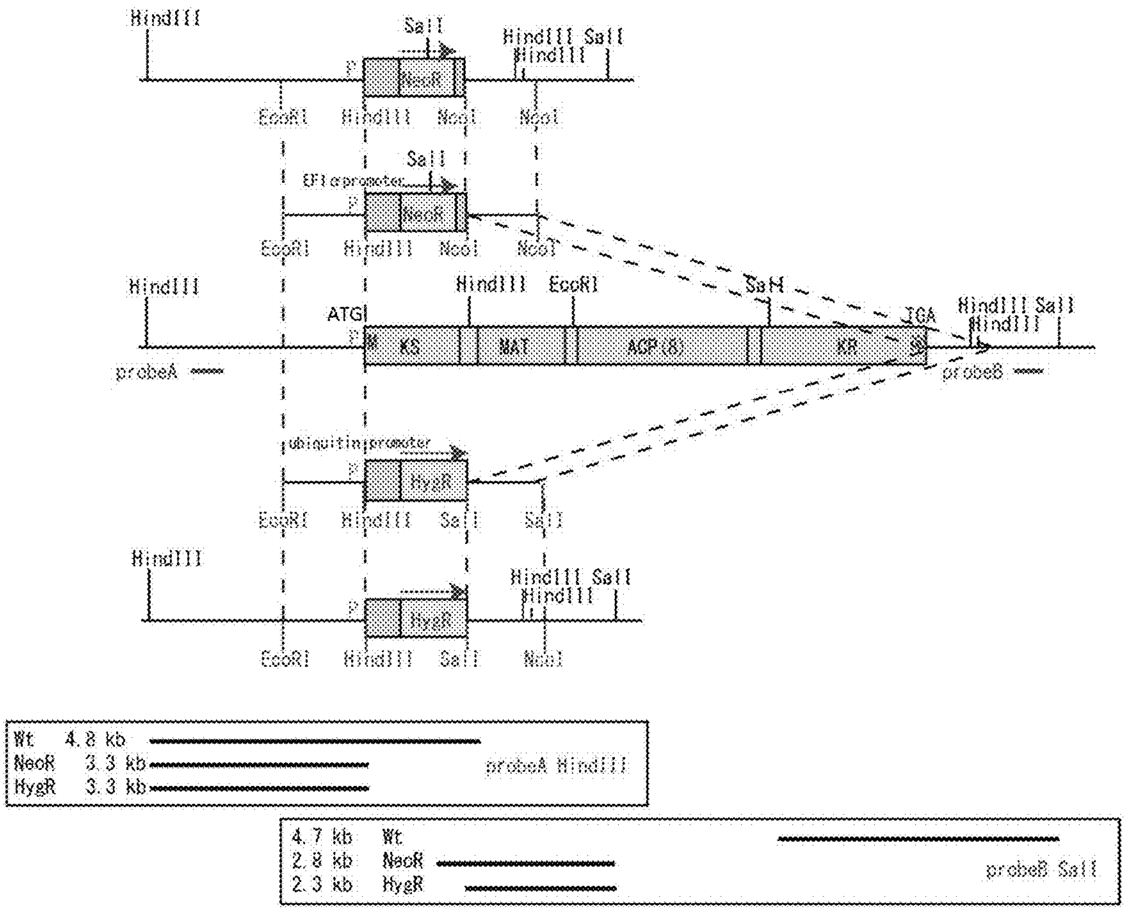
FIG. 49 is a schematic diagram illustrating the positions of the southern hybridization analysis probes used in identification of the PKS pathway associated gene orfA disruption strain of *Thraustochytrium aureum* ATCC 34304, and the expected size of the gene fragment.

After the genome DNA was cut with a restriction enzyme, the obtained genome DNA underwent electrophoresis in approximately 2 to 3 μg per well of 0.7% SeaKem GTG agarose gel (available from Takara Bio Inc.). This was transformed to a nylon membrane, and hybridized at 54° C. for 16 hr with a probe produced using DIG System (available from Roche Applied Science, Inc.). The primers used in probe production were as follows. 5' side [RHO37: 22mer: 5'-GAA GCG TCC CGT AGA TGT GGT C-3' (SEQ ID NO: 139), RHO38: 21mer: 5'-GCC CGA GAG GTC AAA GTA CGC-3' (SEQ ID NO: 140)]; 3' side [RHO39: 20mer: 5'-GCG AGC CCA GGT CCA CTT GC-3' (SEQ ID NO: 141), RHO40: 22mer: 5'-CAG CCC GAT GAA AAA CTT GGT C-3' (SEQ ID NO: 142)]. [PCR cycles: 98° C. 2 min/98° C. 30 sec, 60° C. 30 sec, 72° C. 2 min, 30 cycles/72° C. 3 min]. The positions of the restriction enzymes and the probes used are illustrated in FIG. 49. The hybridized probes were detected using the color development method (NBT/BCIP solution).

Figure 50:
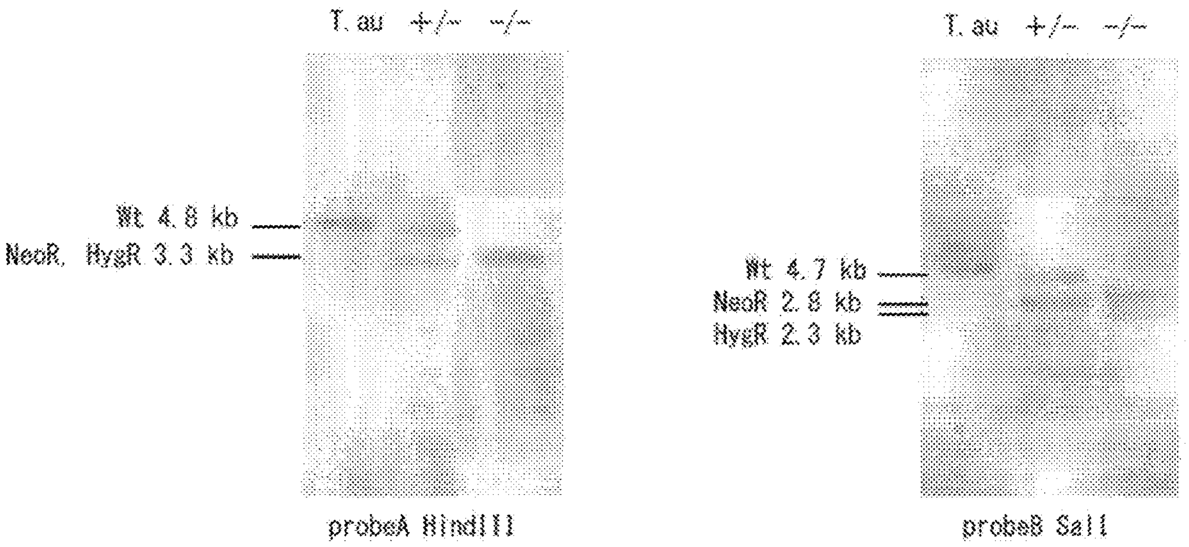
FIG. 50 illustrates an evaluation of PKS pathway associated gene orfA disruption by southern hybridization using *Thraustochytrium aureum* ATCC 34304 genome DNA. (Brief description of symbols) *T. au: Thraustochytrium aureum* ATCC 34304 wild-type strain; +/−: PKS pathway associated gene orfA first allele homologous recombinant derived from *Thraustochytrium aureum* ATCC 34304; −/−: PKS pathway associated gene orfA disruption strain derived from *Thraustochytrium aureum* ATCC 34304

In analysis of both the 5' side and the 3' side, bands were observed at the expected sizes when the drug resistance genes caused homologous recombination (FIG. 50).

Comparative Example 2-7

*Thraustochytrium aureum* ATCC 34304 and the gene disruption strain were cultured according to the method described in Example 2-9, and after freeze drying, the fatty acids were methyl-esterified and analyzed using GC.

Figure 51:
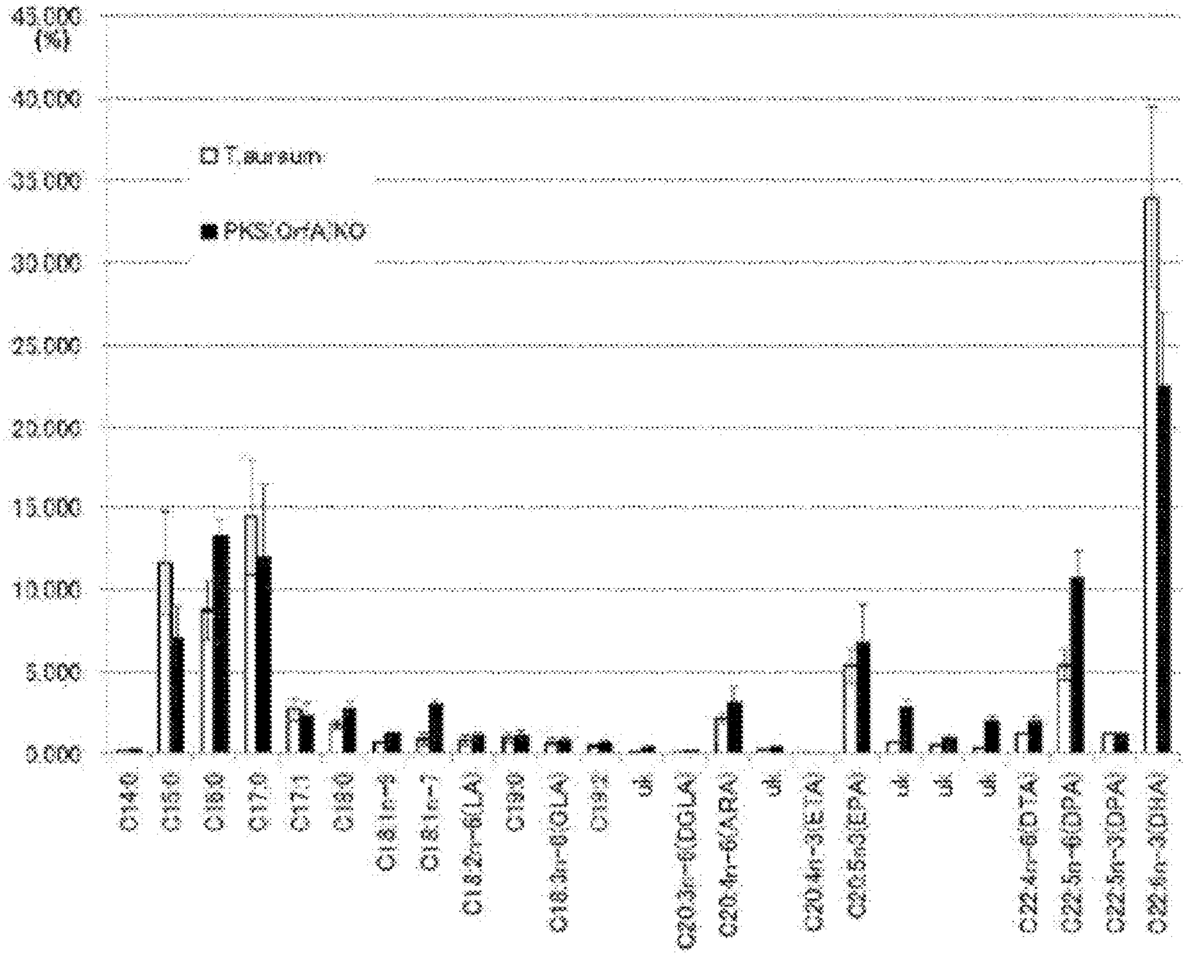
FIG. 51 illustrates a comparison of fatty acid compositions of the *Thraustochytrium aureum* ATCC 34304 wild-type strain and the PKS pathway associated gene orfA disruption strain. The white bars and black bars represent the fatty acid composition of the wild-type strain and the gene disruption strain, respectively. The values are mean±standard deviation.

The changes in the fatty acid composition are shown in FIG. 51. FIG. 52 shows the proportion when the wild-type strain is taken as 100%. FIG. 52 shows that, of the total fatty acid composition, ARA is 3.10%, DGLA is 0.23%, ETA is 0.04%, EPA is 6.82%, n-6 DPA is 10.66%, and DHA is 22.58%. FIG. 52 shows that, by GC area, LA/DHA is 0.05, GLA/DHA is 0.03, DGLA/DHA is 0.01, ARA/DHA is 0.1, EPA/DHA is 0.3, LA/EPA is 0.16, GLA/EPA is 0.11, DTA/EPA is 0.29, DTA/ARA is 0.65, DTA/DGLA is 8.7, LA/n-6 DPA is 0.1, GLA/n-6 DPA is 0.07, DGLA/n-6 DPA is 0.02, ARA/n-6 DPA is 0.3, EPA/n-6 DPA is 0.6, DGLA/LA is 0.2, ARA/LA is 2.9, EPA/LA is 6.4, DTA/LA is 1.9, DGLA/GLA is 0.3, ARA/GLA is 4.0, n-6 DPA/DTA is 5.3, DHA/n-3 DPA is 20.0, C20 PUFA/C22 PUFA is 0.3, and n-6 PUFA/n-3 PUFA is 0.52.

As a result, when the PUFA-PKS pathway associated gene: OrfA was disrupted in *Thraustochytrium aureum*, DPA (C22:5n-6) exhibited an increasing trend and DHA (C22:6n-3) exhibited a decreasing trend.

It is known that in the genus *Schizochytrium* and genus Aurantiochytrium, exogenous PUFAs become necessary when a PUFA-PKS pathway gene is disrupted, and breeding is not possible unless exogenous PUFAs are supplied (Non-patent Document 4). Unlike these organisms, however,

*Thraustochytrium aureum* ATCC 34304 can be cultured without supplementing the culture medium with exogenous PUFAs when a PUFA-PKS pathway associated gene is disrupted. Furthermore, disruption of a PUFA-PKS pathway associated gene, decreased DHA only to approximately ⅔ and slightly increased DPA (C22:5n-6) compared to the wild-type strain.

The above results suggest the possibility that DHA and n-6 DPA are produced via another biosynthesis pathway in addition to the PUFA-PKS pathway in *Thraustochytrium aureum* ATCC 34304. The reason that *Thraustochytrium aureum* ATCC 34304 can be cultured without supplementing the culture medium with exogenous PUFAs is surmised to be that endogenous PUFAs are supplied via a biosynthesis pathway other than the PUFA-PKS pathway.

Comparative Example 3

[Measurement of Fatty Acid Composition of Lipids Produced by PUFA-PKS Gene and C20 Elongase Gene Disruption and Transformation Strain of *Thraustochytrium aureum* ATCC 34304]

[Comparative Example 3-1]: Cloning of Upstream Sequence of *Thraustochytrium aureum* C20 Elongase Gene The genome cassette library produced in Comparative Example 2-1 was used as a template. A PCR lower primer [RHO71: 22mer: 5'-GGG AGC GCA GGG AAA ACG GTC T-3' (SEQ ID NO: 143)] was produced on the C20 elongase gene upstream sequence (SEQ ID NO: 76) described in Comparative Example 1-4, and the gene was amplified by combining with the cassette primers contained in the kit described in Comparative Example 2-1. [1st PCR cycles: 98° C. 2 min/98° C. 30 sec, 56° C. 30 sec, 72° C. 4 min, 30 cycles/72° C. 5 min]. Then, the 1st PCR amplification product was diluted 100-fold, and the gene was amplified by combining a PCR lower primer [RHO72: 20mer: 5'-CCA GCC CAC GTC GTC GGA GC-3' (SEQ ID NO: 144)] and the nested primers contained in the kit described in Comparative Example 2-1. [2nd PCR cycles: 98° C. 2 min/98° C. 30 sec, 56° C. 30 sec, 72° C. 4 min, 30 cycles/72° C. 5 min]. The obtained DNA fragment was cloned in pGEM-T Easy Vector, and after amplification with *E. coli*, the sequence was confirmed using a Dye Terminator Cycle Sequencing Kit (available from Beckman Coulter Inc.).

A 2297 bp DNA fragment (SEQ ID NO: 145) containing the 3277 bp to 981 bp region upstream of the C20 elongase gene was cloned.

[Comparative Example 3-2]: Cloning of Downstream Sequence of C20 Elongase Gene

The genome cassette library produced in Comparative Example 2-1 was used as a template. A PCR upper primer [RHO87: 23mer: 5'-GCC GCT CAT GCC CAC GCT CAA AC-3' (SEQ ID NO: 146)] was produced on the C20 elongase gene downstream sequence (SEQ ID NO: 77) described in Comparative Example 1-4, and the gene was amplified by combining with the cassette primers contained in the kit described in Comparative Example 2-1. [1st PCR cycles: 98° C. 2 min/98° C. 30 sec, 56° C. 30 sec, 72° C. 4 min, 30 cycles/72° C. 5 min]. Then, the 1st PCR amplification product was diluted 100-fold, and the gene was amplified by combining a PCR lower primer [RHO73: 23mer: 5'-CTT TCG GCT GCC AGG AAT CTA CG-3' (SEQ ID NO: 147)] and the nested primers contained in the kit described in Comparative Example 2-1. [2nd PCR cycles: 98° C. 2 min/98° C. 30 sec, 56° C. 30 sec, 72° C. 4 min, 30 cycles/72° C. 5 min]. The obtained DNA fragment was cloned in pGEM-T Easy Vector, and after amplification with *E. coli*, the sequence was confirmed using a Dye Terminator Cycle Sequencing Kit (available from Beckman Coulter Inc.).

A 2189 bp DNA fragment (SEQ ID NO: 148) containing the 1106 bp to 3294 bp region downstream of the C20 elongase gene was cloned.

[Comparative Example 3-3]: Production of Blasticidin Resistance Gene Cassette

Using genome DNA from *Thraustochytrium aureum* ATCC 34304 as a template, an ubiquitin promoter sequence (618 bp, SEQ ID NO: 149) was amplified with PrimeSTAR HS DNA Polymerase with GC Buffer (available from Takara Bio Inc.). The PCR primers used were as shown below. RHO53 was set on the ubiquitin promoter sequence, and includes a BglII linker sequence (Example 2-2, SEQ ID NO: 5). RHO48 includes the ubiquitin promoter sequence and a blasticidin resistance gene sequence. [RHO48: 58mer: 5'-CTT CTT GAG ACA AAG GCT TGG CCA TGT TGG CTA GTG TTG CTT AGG TCG CTT GCT GCT G-3') (SEQ ID NO: 150)]. [PCR cycles: 98° C. 2 min/98° C. 10 sec, 68° C. 1 min, 30 cycles/68° C. 1 min].

Using pTracer-CMV/Bsd/lacZ (available from Invitrogen Corp.) as a template, a blasticidin resistance gene (432 bp, SEQ ID NO: 151) was amplified with PrimeSTAR HS DNA Polymerase with GC Buffer. The PCR primers used were as shown below. RHO47 includes the ubiquitin promoter sequence and the blasticidin resistance gene sequence. RHO49 includes the blasticidin resistance gene sequence and has a BglII linker sequence. [RHO47: 54mer: 5'-AGC GAC CTA AGC AAC ACT AGC CAA CAT GGC CAA GCC TTT GTC TCA AGA AGA ATC-3' (SEQ ID NO: 152), RHO49: 38mer: 5'-CCC AGA TCT TAG CCC TCC CAC ACA TAA CCA GAG GGC AG-3' (SEQ ID NO: 153)]. [PCR cycles: 98° C. 2 min/98° C. 10 sec, 68° C. 1 min, 30 cycles/68° C. 1 min].

Figure 53:
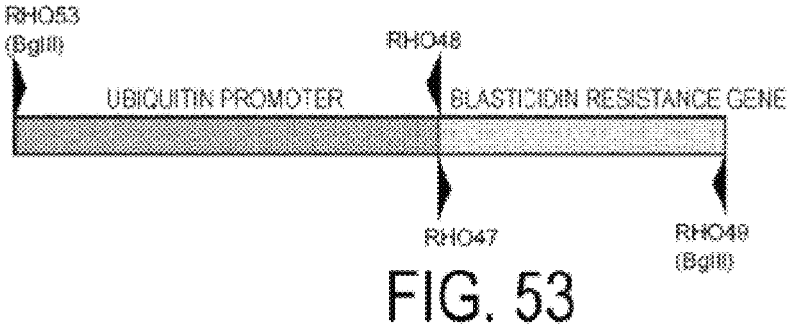
FIG. 53 is a schematic diagram of the primers used in fusion PCR and the products. The final product is a fused sequence of a ubiquitin promoter derived from *Thraustochytrium aureum* ATCC 34304 and a blasticidin resistance gene derived from pTracer-CMV/Bsd/lacZ.

Using SEQ ID NOS: 149 and 151 as templates, fusion PCR was performed using RHO53 (described in Example 2-2, SEQ ID NO: 5) and RHO49 (SEQ ID NO: 153) according to the method described in Non-patent Document 9. Amplification was performed using LA Taq Hot Start Version (available from Takara Bio Inc.) as the enzyme under the following conditions, and then the amplified product was digested with BglII. [PCR cycles: 94° C. 2 min/94° C. 20 sec, 55° C. 30 sec, 68° C. 1 min, 30 cycles/68° C. 1 min (1° C./10 sec from 55° C. to 68° C.)]. (FIG. 53).

The *Thraustochytrium aureum* ATCC 34304-derived ubiquitin promoter -pTracer-CMV/Bsd/lacZ-derived blasticidin resistance gene sequence (1000 bp, SEQ ID NO: 154) fused as described above was digested with BglII, and the resultant was bound to the BamHI site of pRH27 (FIG. 2) described in Example 2-1. After amplification of the produced plasmid with *E. coli*, the sequence was confirmed using a Dye Terminator Cycle Sequencing Kit (available from Beckman Coulter Inc.). This was named pRH38.

Figure 54:
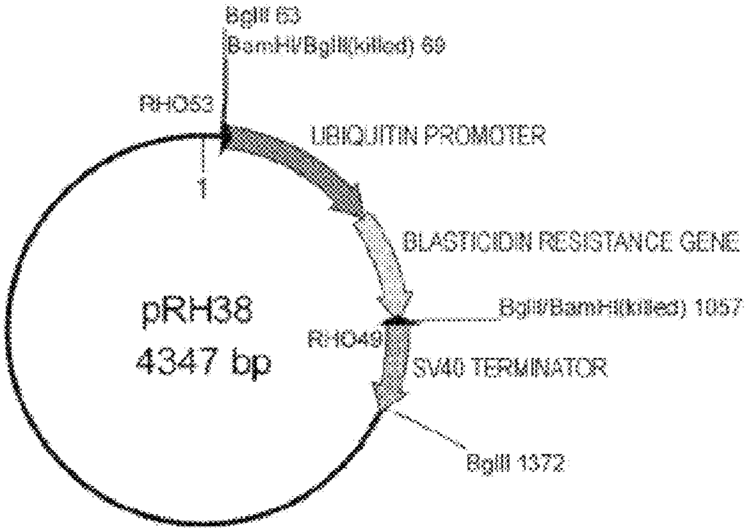
FIG. 54 illustrates the produced BglII cassette of the blasticidin resistance gene derived from pTracer-CMV/Bsd/lac.

The produced blasticidin resistance gene cassette (pRH38) is illustrated in FIG. 54.

[Comparative Example 3-4]: Production of GFP Fusion Zeocin Resistance Gene Cassette Using genome DNA from *Thraustochytrium aureum* ATCC 34304 as a template, a ubiquitin promoter sequence (812 bp, SEQ ID NO: 155) was amplified with PrimeSTAR HS DNA Polymerase with GC Buffer (available from Takara Bio Inc.). The PCR primers used were as shown below. TMO38 was set on the ubiquitin promoter sequence. TMO39 includes the ubiquitin promoter sequence and an enhanced GFP gene sequence. [TMO38: 29mer: 5'-TCG GTA CCC GTT AGA ACG CGT AAT ACG AC-3' (SEQ ID NO: 156), TMO39: 41mer: 5'-TCC TCG CCC TTG CTC ACC ATG TTG GCT AGT GTT GCT TAG GT-3' (SEQ ID NO: 157)]. [PCR cycles: 98° C. 10 sec/98° C. 10 sec, 58° C. 30 sec, 72° C. 1 min, 30 cycles/72° C. 1 min].

Using an enhanced GFP gene sequence (available from Clontech Laboratories, Inc.) as a template, the enhanced GFP gene sequence (748 bp, SEQ ID NO: 158) was amplified with PrimeSTAR HS DNA Polymerase (available from Takara Bio Inc.). The PCR primers used were as shown below. TMO40 includes the ubiquitin promoter sequence and the enhanced GFP gene sequence. RHO91 includes the enhanced GFP sequence and a zeocin resistance gene sequence. [TMO40: 41mer: 5'-ACC TAA GCA ACA CTA GCC AAC ATG GTG AGC AAG GGC GAG GA-3' (SEQ ID NO: 159), RHO91: 58mer: 5'-GAACGGCAC TGGTCAACTTGGCGTCCATGC CGAGAGTGATCC CGG CGG CGG TCA CGA A-3' (SEQ ID NO: 160)]. [PCR cycles: 98° C. 10 sec/98° C. 10 sec, 58° C. 30 sec, 72° C. 2 min, 30 cycles/72° C. 2 min].

Figure 55:
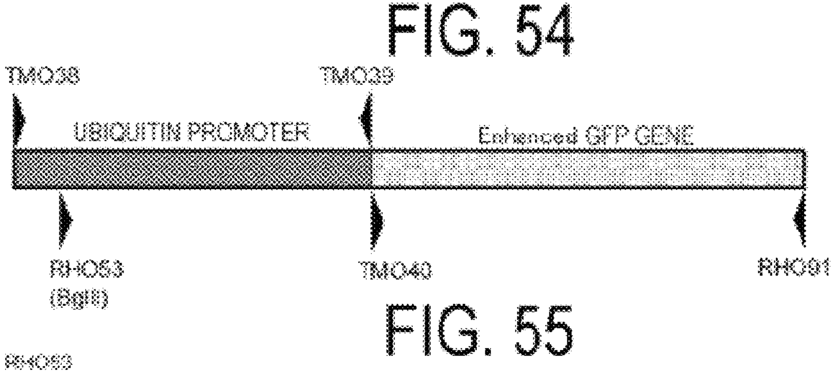
FIG. 55 is a schematic diagram of the primers used in fusion PCR and the products. The final product is a fused sequence of a ubiquitin promoter derived from *Thraustochytrium aureum* ATCC 34304 and an enhanced GFP gene (available from Clontech Laboratories, Inc.).

Using SEQ ID NOS: 156 and 158 as templates, fusion PCR was performed by LA Taq Hot Start Version (available from Takara Bio Inc.) according to the method described in Non-patent Document 9. TMO38 (SEQ ID NO: 156) and RHO91 (SEQ ID NO: 160) were used as primers, and the conditions were as follows: PCR cycles: 94° C. 2 min/94° C. 20 sec, 55° C. 30 sec, 68° C. 2 min, 30 cycles/68° C. 2 min (1° C./10 sec from 55° C. to 68° C.) (FIG. 55, 1519 bp, SEQ ID NO: 161).

Using SEQ ID NO: 161 as a template, the ubiquitin promoter sequence—enhanced GFP gene sequence (1319 bp, SEQ ID NO: 162) was amplified with PrimeSTAR HS DNA Polymerase (available from Takara Bio Inc.). The primers used were as follows. RHO53 (Example 2-2, SEQ ID NO: 5) contains the ubiquitin promoter sequence and has a BglII site. RHO91 (SEQ ID NO: 160) includes the enhanced GFP sequence and a zeocin resistance gene sequence. [PCR cycles: 98° C. 2 min/98° C. 10 sec, 68° C. 2 min, 30 cycles/68° C. 2 min].

Using pcDNA 3.1 Zeo(+) as a template, a zeocin resistance gene sequence (408 bp, SEQ ID NO: 163) was amplified with PrimeSTAR HS DNA Polymerase (available from Takara Bio Inc.). RHO92 includes the enhanced GFP sequence and a zeocin resistance gene sequence. RHO64 contains the zeocin resistance gene sequence and has a BglII site. [RHO92: 54mer: 5'-CGC CGC CGG GAT CAC TCT CGG CAT GGA CGC CAA GTT GAC CAG TGC CGT TCC GGT-3' (SEQ ID NO: 164), RHO64: 38mer: 5'-CCC AGA TCT CAG TCC TGC TCC TCG GCC ACG AAG TGC AC-3' (SEQ ID NO: 165)]. [PCR cycles: 98° C. 2 min/98° C. 10 sec, 68° C. 1 min, 30 cycles/68° C. 1 min].

Figure 56:
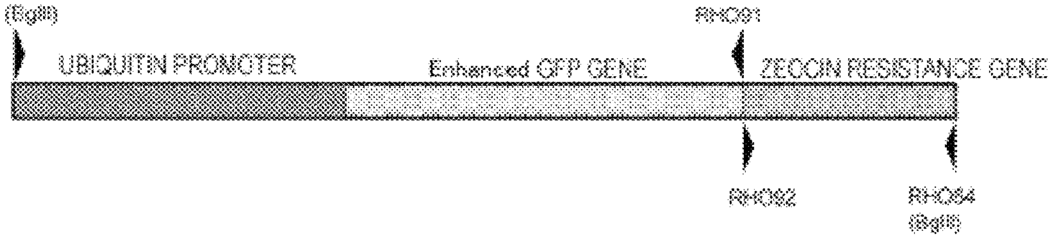
FIG. 56 is a schematic diagram of the primers used in fusion PCR and the products. The final product is a fused sequence of a ubiquitin promoter derived from *Thraustochytrium aureum* ATCC 34304, an enhanced GFP gene (available from Clontech Laboratories, Inc.), and a zeocin resistance gene derived from pcDNA 3.1 Zeo(+).

Using SEQ ID NOS: 162 and 163 as templates, fusion PCR was performed by LA Taq Hot Start Version (available from Takara Bio Inc.) according to the method described in Non-patent Document 9. RHO53 (Example 2-2, SEQ ID NO: 5) and RHO64 (SEQ ID NO: 165) were used as primers, and the conditions were as follows: PCR cycles: 94° C. 2 min/94° C. 20 sec, 68° C. 2 min, 30 cycles/68° C. 2 min (1° C./10 sec from 55° C. to 68° C.) (FIG. 56).

The *Thraustochytrium aureum* ATCC 34304-derived ubiquitin promoter —enhanced GFP gene—pcDNA 3.1 Zeo(+)-derived zeocin resistance gene (FIG. 56, 1677 bp, SEQ ID NO: 166) fused as described above was digested with BglII, and the resultant was bound to the BamHI site of pRH27 (FIG. 2) described in Example 2-1. After amplification of the produced plasmid with *E. coli*, the sequence was confirmed using a Dye Terminator Cycle Sequencing Kit (available from Beckman Coulter Inc.). This was named pRH51.

Figure 57:
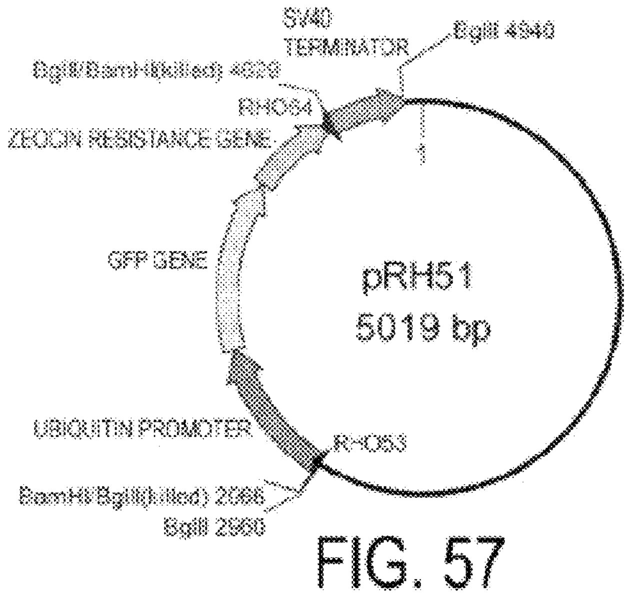
FIG. 57 illustrates the produced BglII cassette of the enhanced GFP-zeocin resistance fusion gene.

The produced GFP fusion zeocin resistance gene cassette (pRH51) is illustrated in FIG. 57.

[Comparative Example 3-5]: Production of Plasmid Serving as Base for Production of C20 Elongase Gene Targeting Vector Using *Thraustochytrium aureum* ATCC 34304 genome DNA as a template, a C20 elongase gene and its surrounding sequence were amplified with PCR by PrimeSTAR HS DNA Polymerase (available from Takara Bio Inc.) (2884 bp, SEQ ID NO: 167). The PCR primers used were as follows. Both primers contained an EcoI linker sequence. KS09 was set in the C20 elongase gene upstream (SEQ ID NO: 76), and KSO10 was set in the C20 elongase gene downstream (SEQ ID NO: 77). [KSO9: 50mer: 5'-CCC GAA TTC ACT AGT GAT TCT CCC GGG TGG ACC TAG CGC GTG TGT CAC CT-3' (SEQ ID NO: 168), KSO10: 40mer: 5'-CCC GAA TTC GAT TAT CCC GGG GCC GAG AAC GGG GTC GCC C-3' (SEQ ID NO: 169)]. [PCR cycles: 98° C. 2 min/98° C. 10 sec, 68° C. 3.5 min, 30 cycles/68° C. 10 min]. PrimeSTAR HS DNA Polymerase (available from Takara Bio Inc.) was used for the enzymes, and after amplification, the amplified products were digested with EcoRI, and then cloned at the vector EcoRI site of pBlueScript (SK) (available from Stratagene Corp.). After amplification with *E. coli*, the sequence was confirmed using a Dye Terminator Cycle Sequencing Kit (available from Beckman Coulter Inc.) (FIG. 58).

Figure 58:
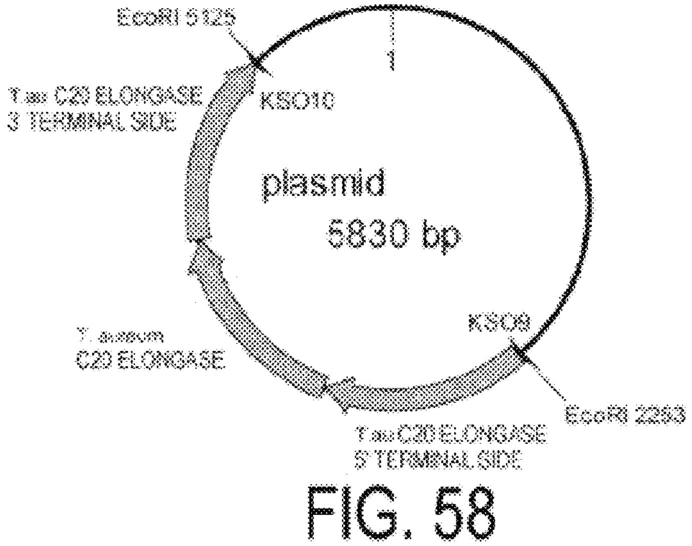
FIG. 58 illustrates a plasmid containing a cloned *Thraustochytrium aureum* ATCC 34304 C20 elongase sequence and the peripheral sequence.

A primer set that was set up in the reverse direction with the objective of deleting a portion of the C20 elongase gene sequence and inserting a BglII site (1939 bp, SEQ ID NO: 170) was prepared using the plasmid illustrated in FIG. 58 as a template, and the set was amplified with PrimeSTAR Max DNA Polymerase (available from Takara Bio Inc.). The PCR primers used were as shown below, both of which have a BglII linker sequence. [RHO69: 38mer: 5'-CCC AGA TCT ACC TGT TTC CGG CTG GCT CCC GAG CCA TG-3' (SEQ ID NO: 171), RHO70: 38mer: 5'-CCC AGA TCT GGT CGC GTT TAC AAA GCA GCG CAG CAA CA-3' (SEQ ID NO: 172)]. [PCR cycles: 98° C. 2 min/98° C. 10 sec, 68° C. 1.5 min, 30 cycles/68° C. 1.5 min]. After amplification under the above conditions, the amplified product was digested with BglII and then self-ligated. After the ligated sample was amplified with *E. coli*, the sequence was confirmed using a Dye Terminator Cycle Sequencing Kit (available from Beckman Coulter Inc.). This was named pRH40.

Figure 59:
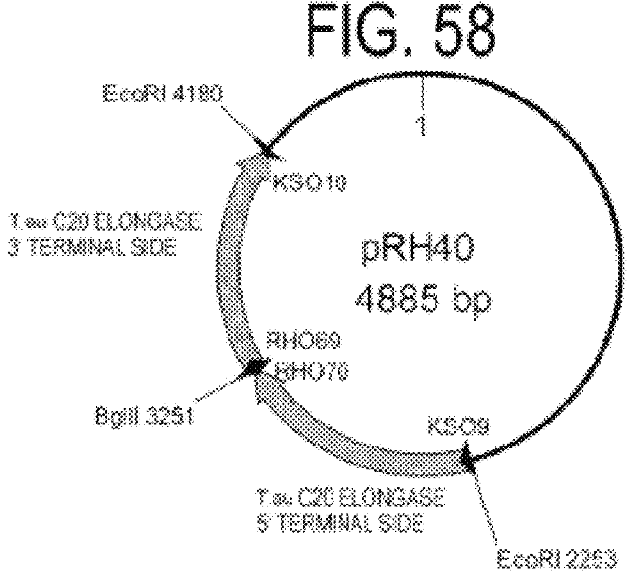
FIG. 59 illustrates a plasmid in which the *Thraustochytrium aureum* ATCC 34304 C20 elongase sequence has been completely deleted from the plasmid illustrated in FIG. 56 and a BglII site has been inserted.

The produced plasmid (pRH40) serving as a base for production of a C20 elongase gene targeting vector is illustrated in FIG. 59.

[Comparative Example 3-6]: Production of Targeting Vectors (Blasticidin Resistance Gene and GFP Fusion Zeocin Resistance Gene)

pRH38 (FIG. 52) described in Comparative Example 3-3 was digested with BglII, and a DNA fragment containing a blasticidin resistance gene cassette was bound to the BglII site of pRH40 (FIG. 59) described in Comparative Example 3-5. This was named pRH43.

pRH51 (FIG. 55) described in Comparative Example 3-4 was digested with BglII, and a DNA fragment containing a GFP fusion zeocin resistance gene cassette was bound to the BglII site of pRH40 (FIG. 57) described in Comparative Example 3-5. This was named pRH54.

Figure 60:
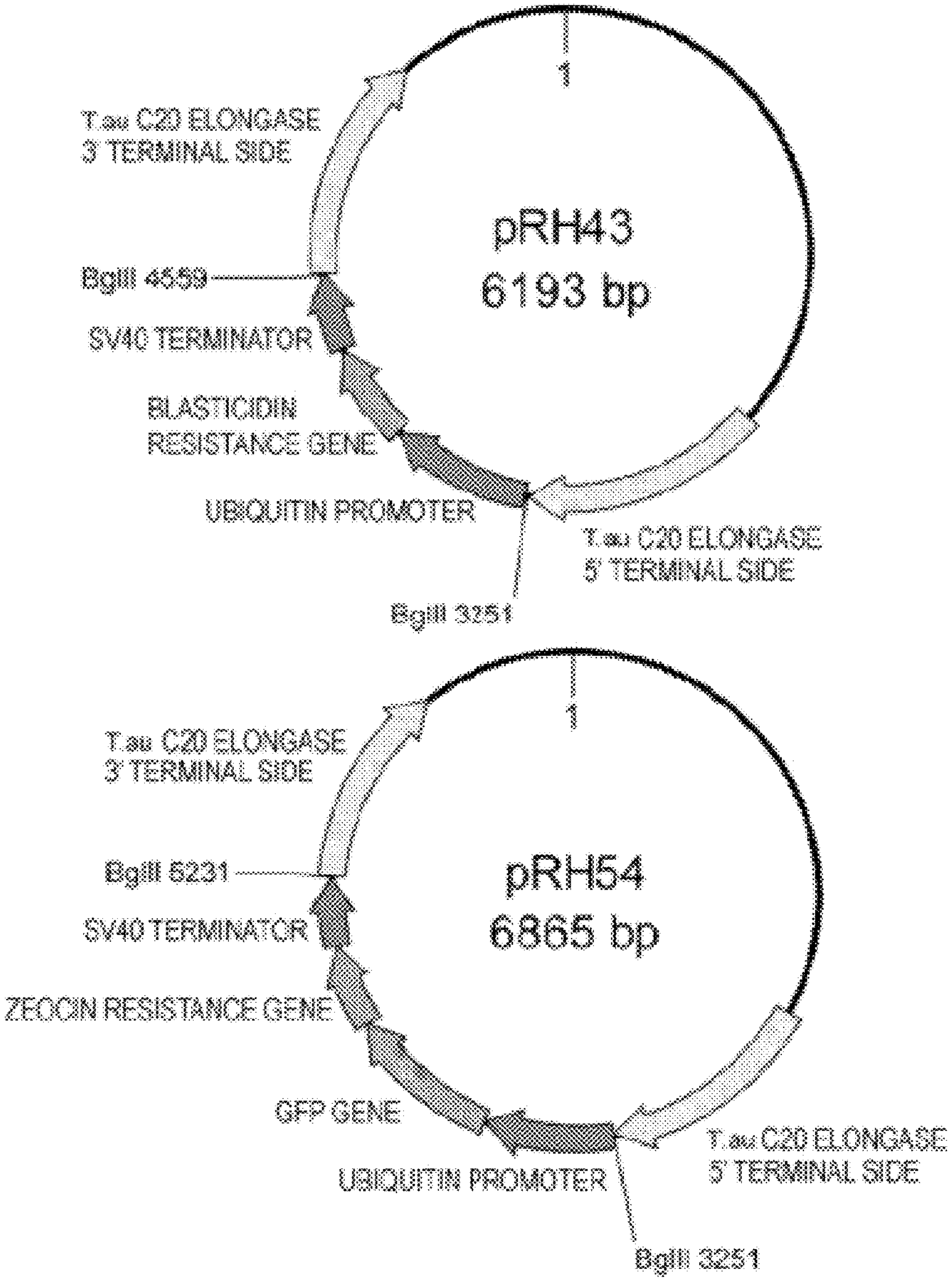
FIG. 60 illustrates the produced *Thraustochytrium aureum* ATCC 34304 C20 elongase gene targeting vectors (two types). As a drug resistance marker, the vectors have a blasticidin resistance gene (pRH43) or an enhanced GFP-zeocin resistance fusion gene (pRH54).

The two produced targeting vectors (pRH43 and 54) are illustrated in FIG. 60.

[Comparative Example 3-7]: Transfer of C20 Elongase Gene Targeting Vectors into *Thraustochytrium aureum* OrfA Disruption Strain Using the two targeting vectors produced in Comparative Example 3-6 as templates, the genes were amplified with PrimeSTAR Max DNA Polymerase (available from Takara Bio Inc.) using KSO11 and KS012 as primers. KSO11 was set upstream of the *Thraustochytrium aureum* C20 elongase gene, and KS012 was set downstream of the *Thraustochytrium aureum* C20 elongase gene. [KSO11: 31mer: 5'-CTC CCG GGT GGA CCT AGC GCG TGT GTC ACC T-3' (SEQ ID NO: 173), KSO12: 27mer: 5'-ATC CCG GGG CCG AGA ACG CCC TCG CCC-3' (SEQ ID NO: 174)]. [PCR cycles: 98° C. 2 min/98° C. 30 sec, 68° C. 2 min, 30 cycles/68° C. 2 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH43 (FIG. 60) described in Comparative Example 3-6 was used as a template was 3215 bp, and resulted in a sequence including *Thraustochytrium aureum* C20 elongase gene upstream—ubiquitin promoter—blasticidin resistance gene sequence—SV40 terminator sequence—*Thraustochytrium aureum* C20 elongase gene downstream (SEQ ID NO: 175). The transfer fragment obtained when pRH54 (FIG. 60) described in Comparative Example 3-6 was used as a template was 3887 bp, and resulted in a sequence including *Thraustochytrium aureum* C20 elongase gene upstream—ubiquitin promoter—enhanced GFP gene sequence—zeocin resistance gene sequence—SV40 terminator sequence—*Thraustochytrium aureum* C20 elongase gene downstream (SEQ ID NO: 176).

The PUFA-PKS pathway associated gene: OrfA gene disruption strain described in Comparative Example 2 was cultured for 4 days in a GY culture medium, and cells in the logarithmic growth phase were used in gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 1100 psi). After a recovery time of 4 to 6 hr, the transgenic cells were spread on a PDA agar plate culture medium (containing 2 mg/mL of G418 or containing 2 mg/mL of hygromycin). As a result, from 100 to 200 cells of drug resistant strain per shot were obtained.

[Comparative Example 3-8]: Identification of C20 Elongase Gene Targeting Homologous Recombinant After genome DNA was extracted from the C20 elongase gene disruption strain in the *Thraustochytrium aureum* OrfA disruption strain and *Thraustochytrium aureum* by the method described in Example 2-2, A260/A280 was measured and the DNA concentration was calculated.

Figure 61:
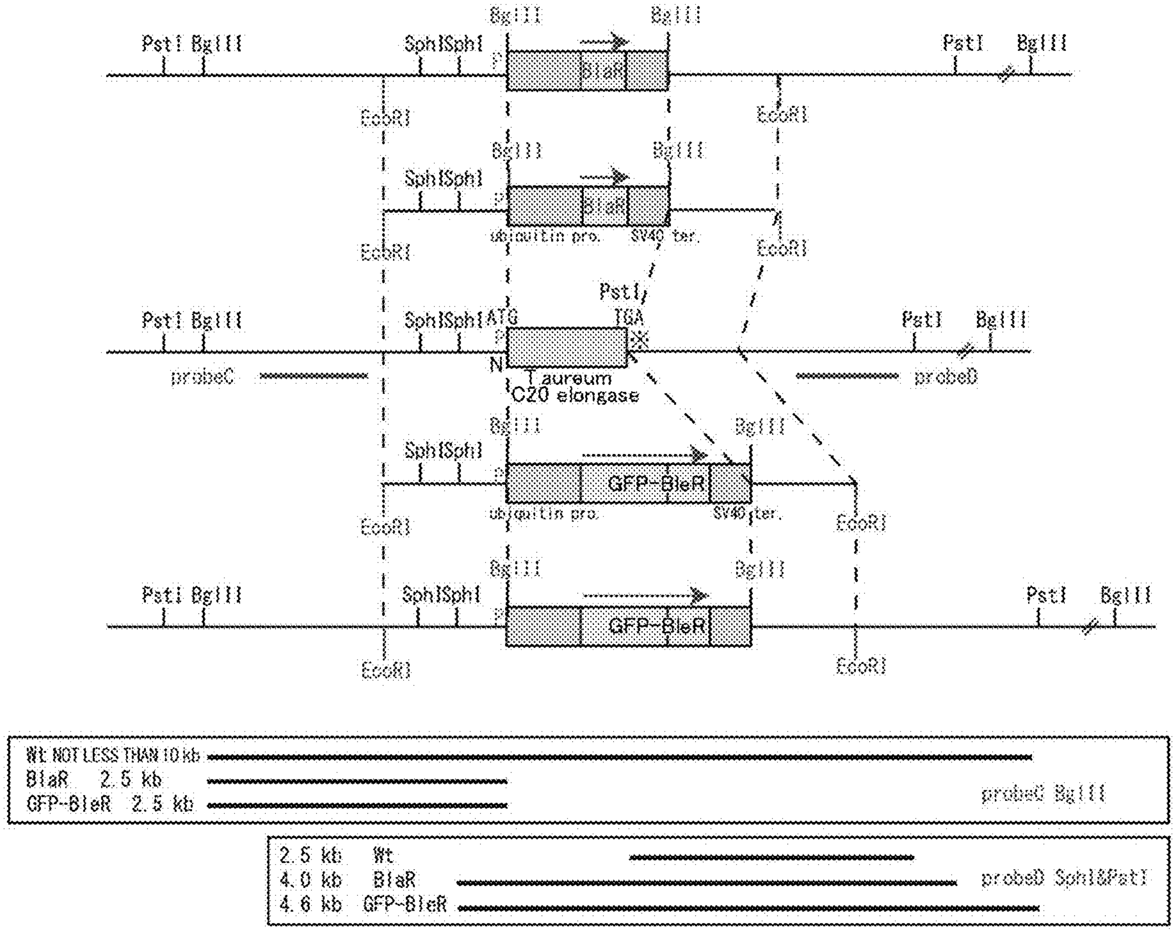
FIG. 61 is a schematic diagram illustrating the position of the southern hybridization analysis probe used in identification of the C20 elongase gene disruption strain of the *Thraustochytrium aureum* ATCC 34304 PKS pathway (orfA gene) disruption strain, and the expected size of the gene fragment.

After the genome DNA was cut with a restriction enzyme, and underwent electrophoresis in approximately 2 to 3 μg per well of 0.7% SeaKem GTG agarose gel (available from Takara Bio Inc.). This was transformed to a nylon membrane, and hybridized for at 51° C. 16 hr with a probe produced using DIG System (available from Roche Applied Science, Inc.). The primers used in probe production were as follows. 5' side [RHO94: 21mer: 5'-ACG TCC GCT TCAAAC ACC TCG-3' (SEQ ID NO: 177), RHO95: 24mer: 5'-TCG GAA CAA CTG GAA CAA CTAAAG-3' (SEQ ID NO: 178)]; 3' side [RHO96: 22mer: 5'-ATG TCG CTC TCC TTC TTC TCA G-3' (SEQ ID NO: 179), RHO97: 21mer: 5'-TCG GCT CCT GGAAAG TGC TCT-3' (SEQ ID NO: 180)]. [PCR cycles: 98° C. 2 min/98° C. 30 sec, 58° C. 30 sec, 72° C. 1 min, 30 cycles/72° C. 3 min]. The positions of the restriction enzymes and the probes used are illustrated in FIG. 61. The hybridized probes were detected using the color development method (NBT/BCIP solution).

Figure 62:
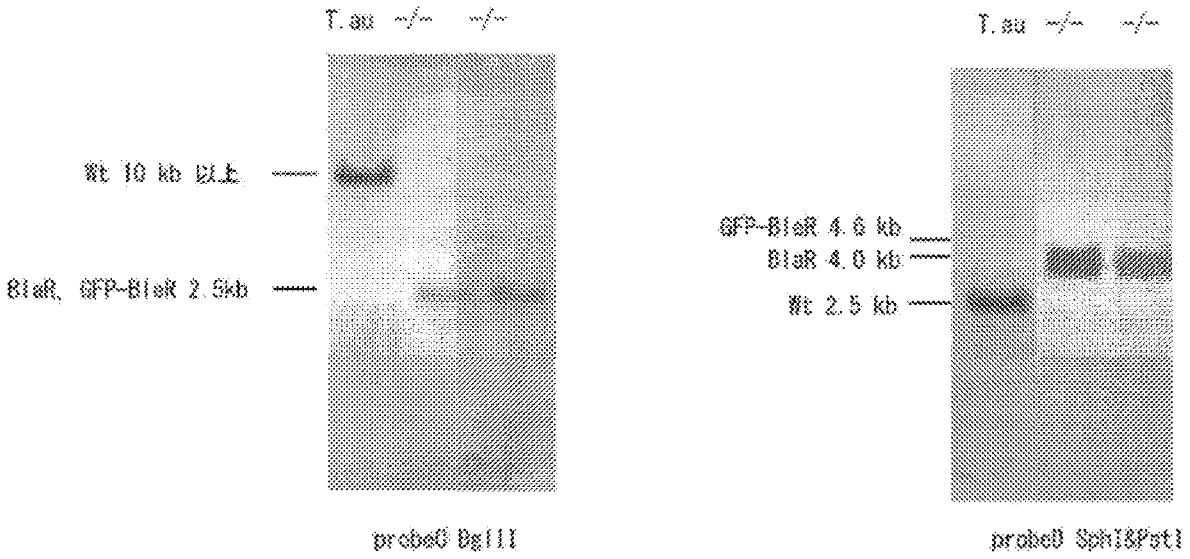
FIG. 62 illustrates an evaluation of C20 elongase gene disruption by southern hybridization using *Thraustochytrium aureum* ATCC 34304 genome DNA. (Brief description of symbols) *T. au: Thraustochytrium aureum* ATCC 34304 wild-type strain; −/−: PKS pathway (orfA gene) and C20 elongase gene double disruption strain derived from *Thraustochytrium aureum* ATCC 34304

In analysis of both the 5' side and the 3' side, bands were observed at the expected sizes when the drug resistance genes caused homologous recombination (FIG. 62). The experiment reveals that the *Thraustochytrium aureum* ATCC 34304 strain does not require nutrients even when the PKS pathway associated gene: OrfA and the C20 elongase gene are deleted.

[Comparative Example 3-9]: Change in Fatty Acid Composition by C20 Elongase Gene Disruption in *Thraustochytrium aureum* OrfA Disruption Strain

*Thraustochytrium aureum* ATCC 34304 and the gene disruption strain were cultured according to the method described in Example 2-9, and after freeze drying, the fatty acids were methyl-esterified and analyzed using GC. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 63:
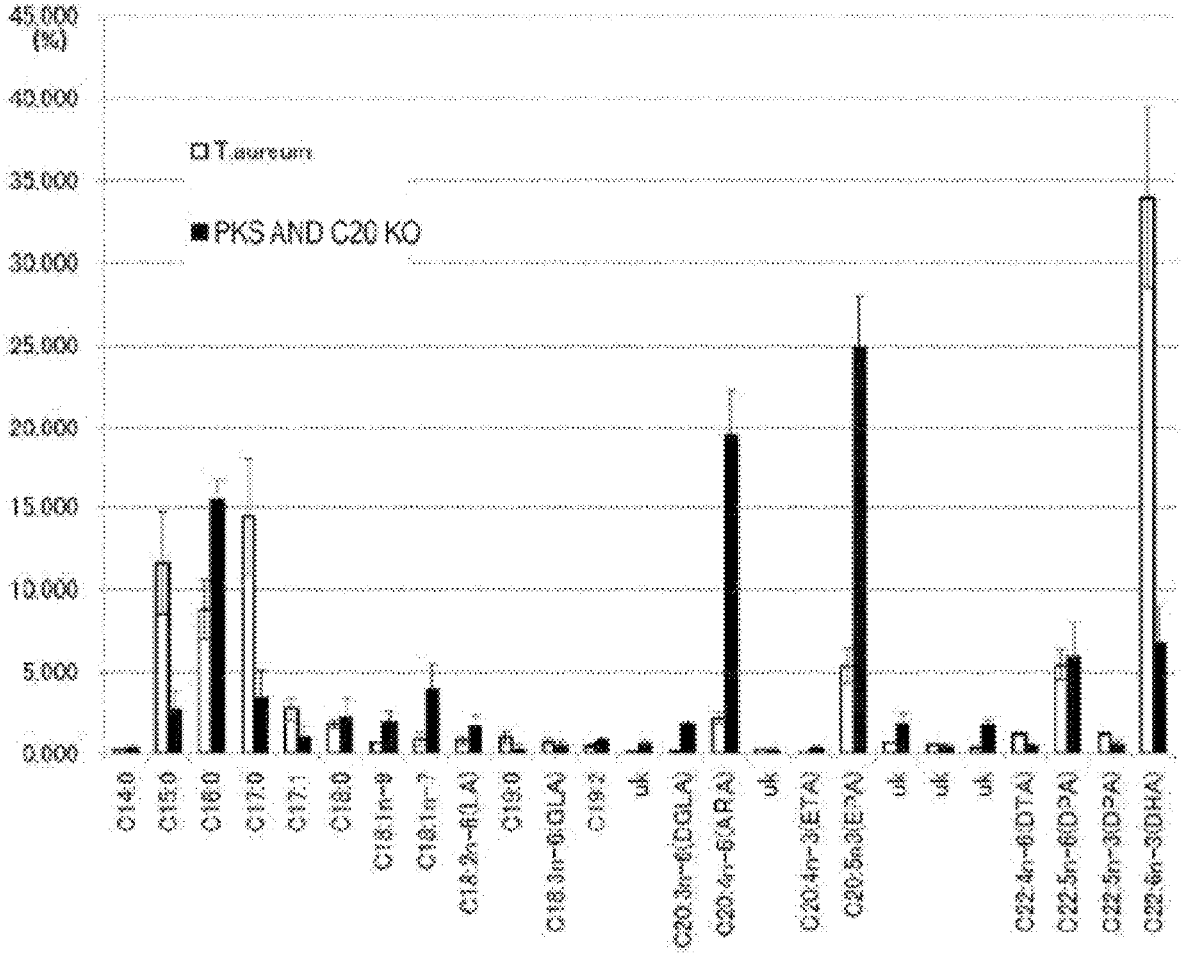
FIG. 63 illustrates a comparison of fatty acid compositions of the *Thraustochytrium aureum* ATCC 34304 wild-type strain and the PKS pathway (orfA gene) and C20 elongase gene double disruption strain. The white bars and black bars represent the fatty acid composition of the wild-type strain and the gene disruption strain, respectively. The values are mean±standard deviation.

The changes in the fatty acid composition are shown in FIG. 63. Furthermore, FIG. 64 shows the proportion when the wild-type strain is taken as 100%. FIG. 64 shows that, of the total fatty acid composition, ARA is 19.50%, DGLA is 1.81%, ETA is 0.31%, EPA is 24.92%, n-6 DPA is 5.90%, and DHA is 6.78%. FIG. 64 shows that, by GC area, LA/DHA is 0.25, GLA/DHA is 0.07, DGLA/DHA is 0.27, ARA/DHA is 2.88, EPA/DHA is 3.68, LA/EPA is 0.07, GLA/EPA is 0.02, DTA/EPA is 0.02, DTA/ARA is 0.02, DTA/DGLA is 0.26, LA/n-6 DPA is 0.29, GLA/n-6 DPA is 0.08, DGLA/n-6 DPA is 0.31, ARA/n-6 DPA is 3.31, EPA/n-6 DPA is 4.22, DGLA/LA is 1.06, ARA/LA is 11.40, EPA/LA is 14.57, DTA/LA is 0.27, DGLA/GLA is 4.02, ARA/GLA is 43.33, n-6 DPA/DTA is 12.55, DHA/n-3 DPA is 11.69, C20 PUFA/C22 PUFA is 3.39, and n-6 PUFA/n-3 PUFA is 0.85.

As a result, when the C20 elongase gene was disrupted in the *Thraustochytrium aureum* OrfA disruption strain, C20:4n-6 (ARA) increased approximately 8-fold, C20:5n-3 (EPA) increased approximately 4-fold, and C22:6n-3 (DHA) decreased to approximately ⅕.

Thus, it was demonstrated that in order to create a strain in which the produced quantity of DHA and DPA n-6 are markedly reduced from *Thraustochytrium aureum* ATCC 34304, which has both an endogenous elongase-desaturase pathway and an endogenous PUFA-PKS pathway, both a gene of an enzyme constituting the elongase-desaturase pathway (for example, the C20 elongase gene) and a PUFA-PKS pathway associated gene need to be disrupted.

Comparative Example 4

[Measurement of Fatty Acid Composition of Lipids Produced by PUFA-PKS Gene and Δ4 Desaturase Gene Disruption and Transformation Strain of *Thraustochytrium aureum* ATCC 34304]

Figure 65:
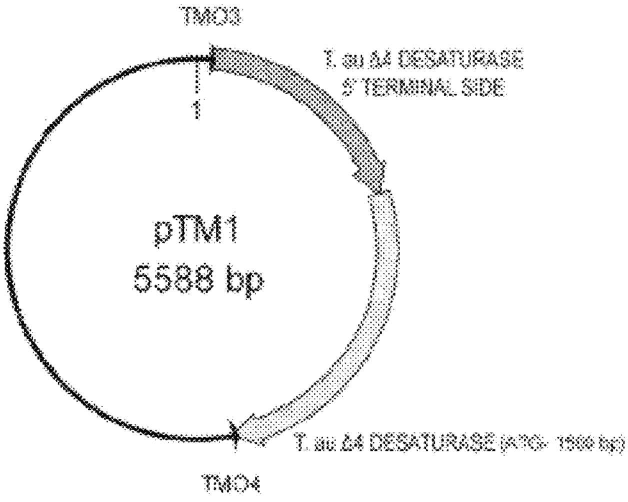
FIG. 65 illustrates a plasmid containing from 1071 bp upstream of the Δ4 desaturase gene to 1500 bp within the Δ4 desaturase gene of a cloned *Thraustochytrium aureum* ATCC 34304 strain.

[Comparative Example 4-1]: Cloning Sequence of 1071 bp Upstream of Δ4 Desaturase Gene to 1500 bp within Δ4 Desaturase Gene of *Thraustochytrium aureum* ATCC 34304 Strain Genome DNA of the *Thraustochytrium aureum* ATCC 34304 strain extracted by the method described in Example 2-2 was read, and a gene sequence having high homology to known Δ4 desaturase was searched for. Two PCR primers were designed based on the search results. TMO3 is a sequence located at 1071 to 1049 bp upstream of the Δ4 desaturase gene of the *Thraustochytrium aureum* ATCC 34304 strain, and TMO4 is a sequence within the protein coding region located at 1477 to 1500 bp counting from the start codon. [TMO3: 23mer: 5'-GGC GGA GCG AAG TGT GAA AGT TA-3' (SEQ ID NO: 181), TMO4: 24mer: 5'-GCG ACA GCA TCT TGA AAT AGG CAG-3' (SEQ ID NO: 182)]. Using genome DNA of the *Thraustochytrium aureum* ATCC 34304 strain as a primer, the sequence of 1071 bp upstream of the Δ4 desaturase gene to 1500 bp within the Δ4 desaturase gene (2571 bp, SEQ ID NO: 183) of *Thraustochytrium aureum* ATCC 34304 strain was amplified using these two primers. The amplification conditions were as follows. [PCR cycles: 98° C. 2 min/98° C. 20 sec, 60° C. 30 sec, 72° C. 3 min, 30 cycles/72° C. 8 min]. The obtained DNA fragment was cloned in pGEM-T Easy Vector, and after amplification with *E. coli*, the sequence was confirmed using a Dye Terminator Cycle Sequencing Kit (available from Beckman Coulter Inc.). This was named pTM1 (FIG. 65).

[Comparative Example 4-2]: Production of Plasmid Serving as Base for Production of Δ4 Desaturase Gene Targeting Vector Using pTM1 (FIG. 65) produced in Comparative Example 4-1 as a template, a primer set set in the reverse direction so as to delete a 556 bp sequence (616 bp, SEQ ID NO: 184) containing 60 bp upstream of the Δ4 desaturase gene and the start codon within the Δ4 desaturase gene and to produce a BglII site in the deleted portion was prepared. TMO7 and TMO8 both contain a BglII sequence. PrimeSTAR Max DNA Polymerase (available from Takara Bio Inc.) was used in amplification. [TMO7: 25mer: 5'-CAG GAG ATC TCC AAG TCG CGA TTC A-3' (SEQ ID NO: 185), TMO8: 26mer: 5'-CTT GGA GAT CTC CTG CCC GTC CCG AA-3' (SEQ ID NO: 186)]. [PCR cycles: 98° C. 3 min/98° C. 10 sec, 55° C. 15 sec, 72° C. 30 sec, 30 cycles/72° C. 30 sec]. After amplification under the above conditions, the amplified product was purified by electrophoresis using agarose gel. After transforming the obtained DNA fragment into *E. coli* and amplifying, the sequence was confirmed using a Dye Terminator Cycle Sequencing Kit (available from Beckman Coulter Inc.). This was named pTM2.

Figure 66:
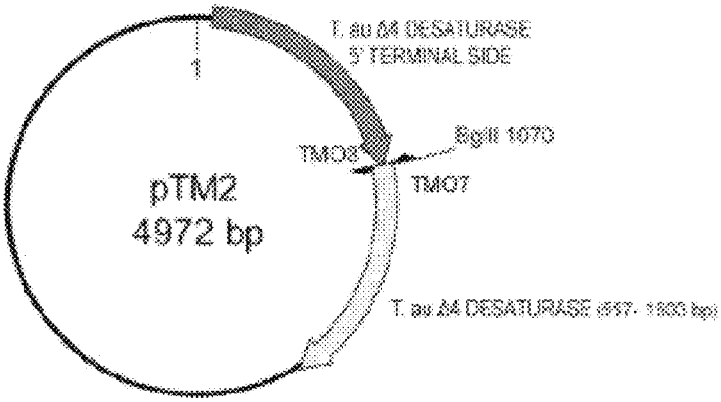
FIG. 66 illustrates a plasmid in which a sequence of 60 bp upstream of the Δ4 desaturase gene of the plasmid illustrated in FIG. 63 and a sequence of 556 bp containing the start codon within the Δ4 desaturase gene (616 bp, SEQ ID NO: 205) have been deleted and a BglII site has been inserted in the deleted portion.

The produced plasmid (pTM2) serving as a base for production of a Δ4 desaturase gene targeting vector is illustrated in FIG. 66.

[Comparative Example 4-3]: Production of Targeting Vectors (Blasticidin Resistance Gene and GFP Fusion Zeocin Resistance Gene)

pRH38 (FIG. 54) described in Comparative Example 3-3 was digested with BglII, and a DNA fragment containing a blasticidin resistance gene cassette was bound to the BglII site of pTM2 (FIG. 66) described in Comparative Example 4-2. This was named pTM6.

pRH51 (FIG. 57) described in Comparative Example 3-4 was digested with BglII, and a DNA fragment containing a GFP fusion zeocin resistance gene cassette was bound to the BglII site of pTM2 (FIG. 66) described in Comparative Example 4-2. This was named pTM8.

Figure 67:
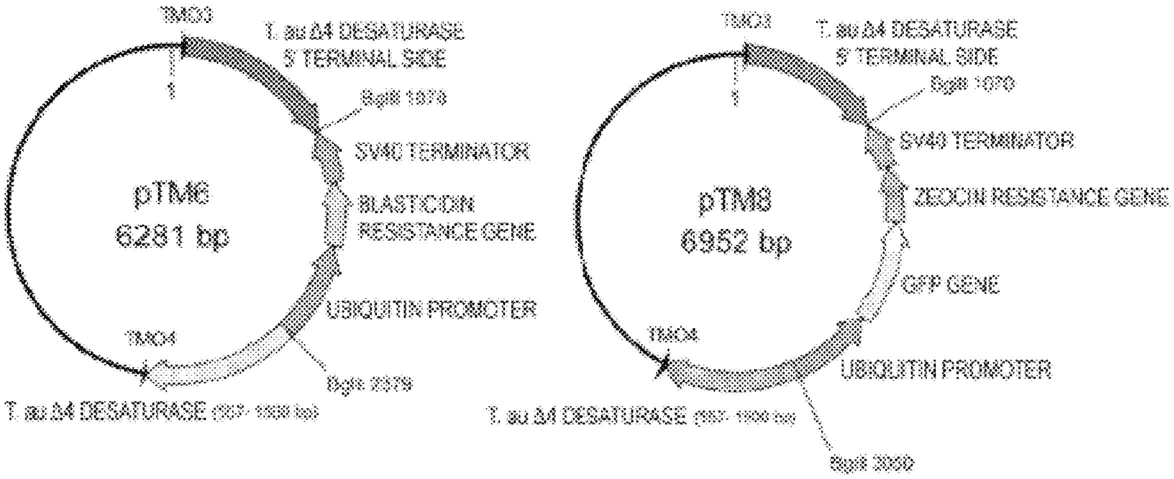
FIG. 67 illustrates the produced *Thraustochytrium aureum* ATCC 34304 strain Δ4 desaturase gene targeting vectors (two types). As a drug resistance marker, the vectors have a blasticidin resistance gene (pTM6) or an enhanced GFP-zeocin resistance fusion gene (pTM8).

The two produced targeting vectors (pTM6 and 8) are illustrated in FIG. 67.

[Comparative Example 4-4]: Transfer of Δ4 Desaturase Gene Targeting Vectors into *Thraustochytrium aureum* OrfA Disruption Strain Using the two targeting vectors produced in Comparative Example 4-3 as templates, the genes were amplified with PrimeSTAR Max DNA Polymerase (available from Takara Bio Inc.) using TMO3 (described in Comparative Example 4-1, SEQ ID NO: 181) and TMO4 (described in Comparative Example 4-1, SEQ ID NO: 182) as primers. [PCR cycles: 98° C. 3 min/98° C. 10 sec, 55° C. 5 sec, 72° C. 4 min, 30 cycles/72° C. 3 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pTM6 (FIG. 67) described in Comparative Example 4-3 was used as a template was 3264 bp, and resulted in a sequence within *Thraustochytrium aureum* Δ4 desaturase gene upstream—SV40 terminator sequence—blasticidin resistance gene sequence—ubiquitin promoter—*Thraustochytrium aureum* Δ4 desaturase gene (SEQ ID NO: 187). The transfer fragment obtained when pTM8 (FIG. 67) described in Comparative Example 4-3 was used as a template was 3935 bp, and resulted in a sequence within *Thraustochytrium aureum* Δ4 desaturase gene upstream—SV40 terminator sequence—zeocin resistance gene sequence—enhanced GFP gene sequence—ubiquitin promoter—*Thraustochytrium aureum* Δ4 desaturase gene (SEQ ID NO: 188).

The PUFA-PKS pathway associated gene: OrfA gene disruption strain described in Comparative Example 2 was cultured for 4 days in a GY culture medium, and cells in the logarithmic growth phase were used in gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 1100 psi). After a recovery time of 4 to 6 hr, the transgenic cells were spread on a PDA agar plate culture medium (containing 20 mg/mL of zeocin or containing 0.2 mg/mL of blasticidin). As a result, from 100 to 200 cells of drug resistant strain per shot were obtained.

Figure 68:
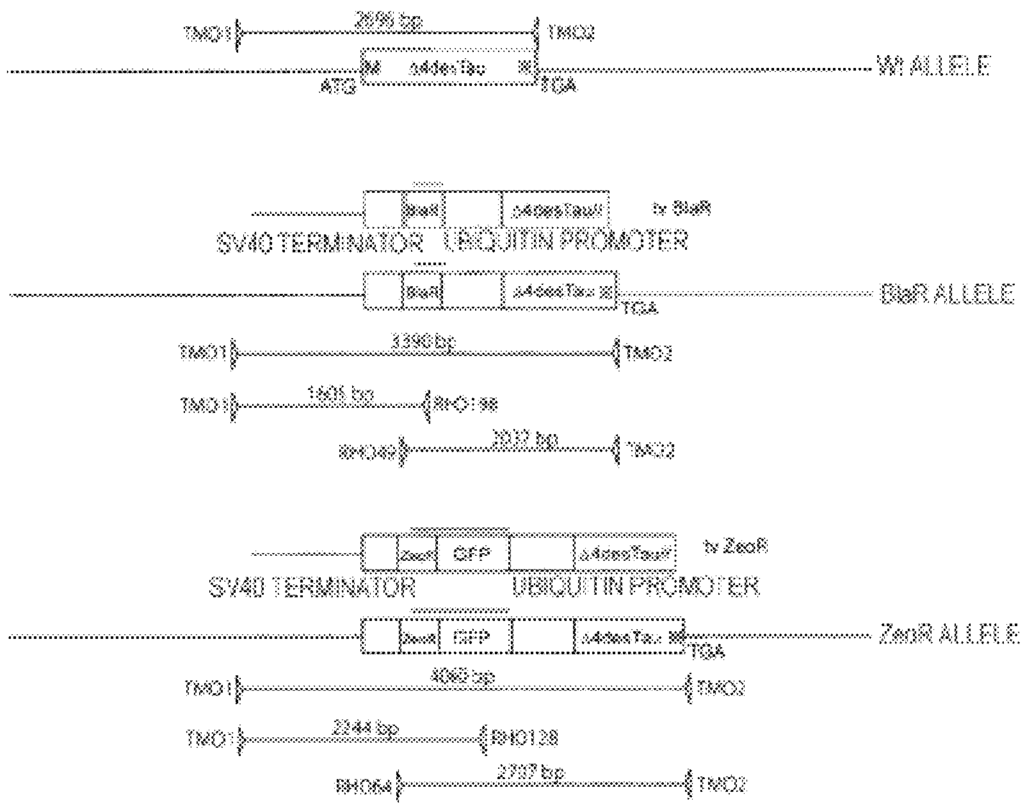
FIG. 68 is a schematic diagram illustrating the positions of the PCR primers used in identification of the Δ4 desaturase gene disruption strain of the *Thraustochytrium aureum* ATCC 34304 PKS pathway (orfA gene) disruption strain, and the expected products.
Figure 69:
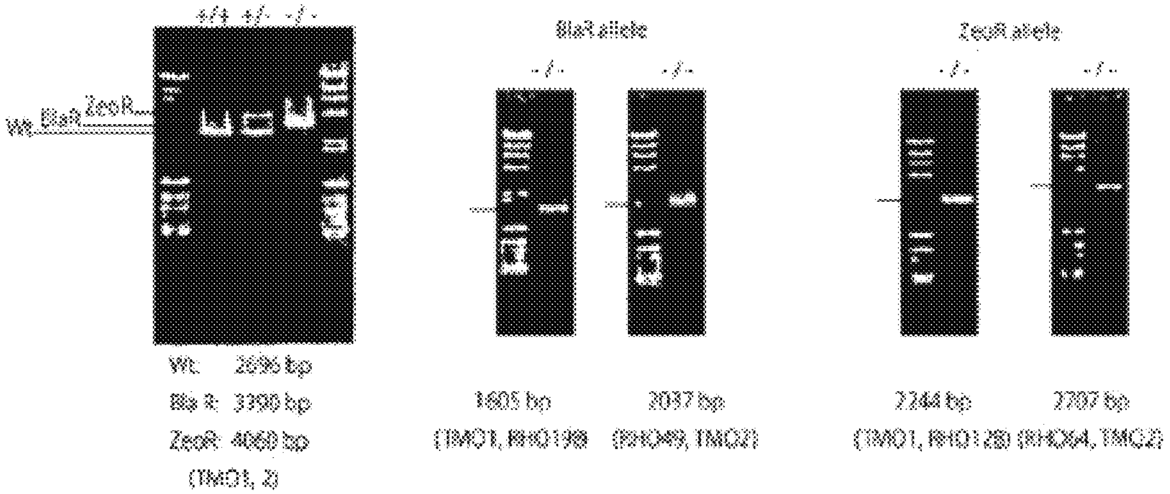
FIG. 69 illustrates an evaluation of Δ4 desaturase gene disruption by PCR using *Thraustochytrium aureum* ATCC 34304 strain genome DNA as a template. (Brief description of symbols)+/+: PKS pathway (orfA gene) disruption strain derived from *Thraustochytrium aureum* ATCC 34304; +/−: Δ4 desaturase first allele homologous recombinant derived from PKS pathway (orfA gene) disruption strain derived from *Thraustochytrium aureum* ATCC 34304; −/−: PKS pathway (orfA gene) and Δ4 desaturase gene double disruption strain derived from *Thraustochytrium aureum* ATCC 34304

[Comparative Example 4-5]: Identification of Δ4 Desaturase Gene Targeting Homologous Recombinant After genome DNA was extracted from the Δ4 desaturase gene disruption strain in the *Thraustochytrium aureum* OrfA disruption strain and *Thraustochytrium aureum* by the method described in Example 2-2, A260/A280 was measured and the DNA concentration was calculated. Using the genome DNA as templates, PCR for genome structure confirmation was performed using Mighty Amp DNA Polymerase (available from Takara Bio Inc.). The positions of the primers used, the combinations used in amplification, and the expected sizes of the amplification products are illustrated in FIG. 68. TMO1 was set upstream of the Δ4 desaturase gene, TMO2 was set downstream of the Δ4 desaturase gene, RHO198 (SEQ ID NO: 191) and RHO49 (described in Comparative Example 3-3, SEQ ID NO: 153) were set on the blasticidin resistance gene, RHO128 was set on the enhanced GFP gene, and RHO64 (described in Comparative Example 3-4, SEQ ID NO: 165) was set on the zeocin resistance gene. [TMO1: 23mer: 5'-AAA AGA ACA AGC CCT CTC CTG GA-3' (SEQ ID NO: 189), TMO2: 23mer: 5'-GAG GTT TGT ATG TTC GGC GGT TT-3' (SEQ ID NO: 190), RHO198: 26mer: 5'-TGG GGG ACC TTG TGC AGA ACT CGT GG-3' (SEQ ID NO: 191), RHO128: 22mer: 5'-GAC CTA CGG CGT GCA GTG CTT C-3' (SEQ ID NO: 192)]. [PCR cycles: 98° C. 2 min/98° C. 10 sec, 68° C. 4 min 30 sec, 30 cycles/68° C. 4 min]. A Δ4 desaturase gene disruption strain was obtained, wherein there was no amplification in the wild-type allele (Wt allele), and there was amplification in the blasticidin resistance gene allele (BlaR allele) and the zeocin resistance gene allele (ZeoR allele) (FIG. 69). The experiment reveals that the *Thraustochytrium aureum* ATCC 34304 strain does not require nutrients even when the PKS pathway associated gene: OrfA and the Δ4 desaturase gene are deleted.

[Comparative Example 4-6]: Change in Fatty Acid Composition by Δ4 Desaturase Gene Disruption in *Thraustochytrium aureum* OrfA Disruption Strain

*Thraustochytrium aureum* ATCC 34304 and the gene disruption strain were cultured according to the method described in Example 2-9, and after freeze drying, the fatty acids were methyl-esterified and analyzed using GC. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 70:
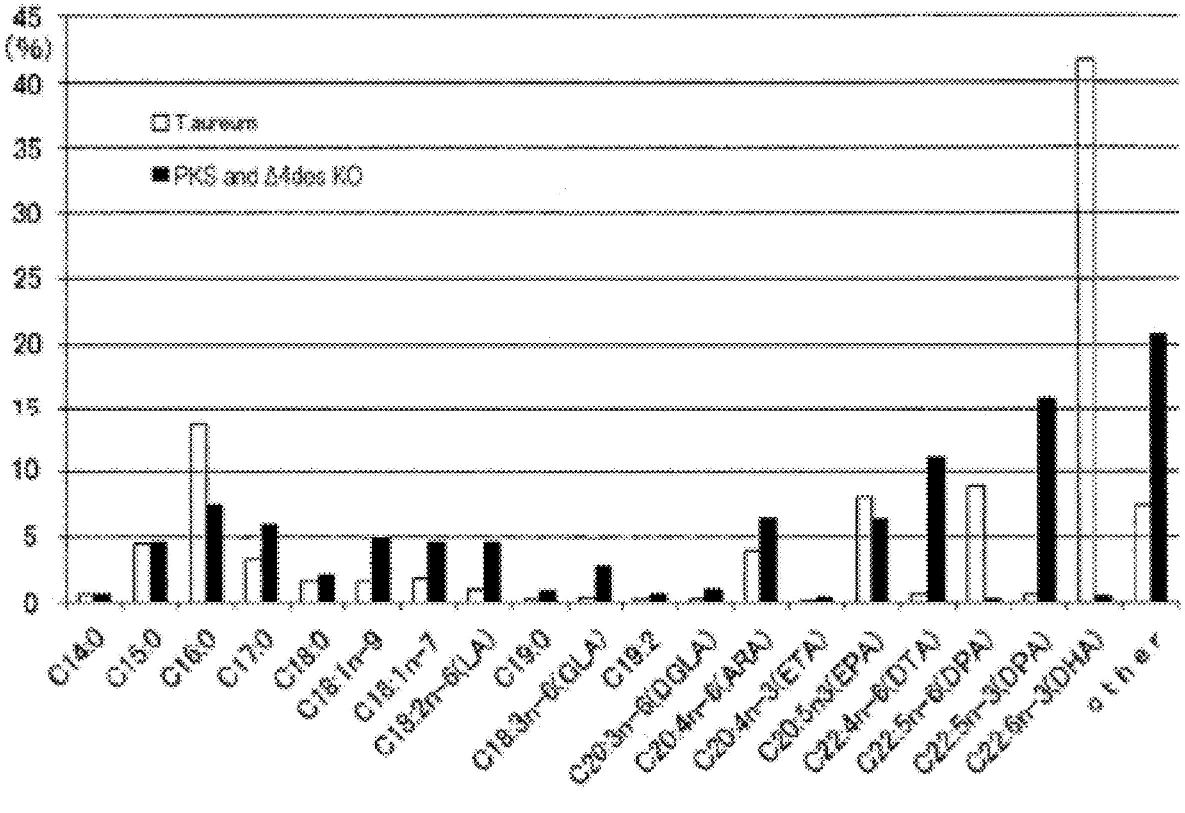
FIG. 70 illustrates a comparison of fatty acid compositions of the *Thraustochytrium aureum* ATCC 34304 wild-type strain and the PKS pathway (orfA gene) and Δ4 desaturase gene double disruption strain. The white bars and black bars represent the fatty acid composition of the wild-type strain and the gene disruption strain, respectively.

The changes in the fatty acid composition are shown in FIG. 70. Furthermore, FIG. 71 shows the proportion when the wild-type strain is taken as 100%. FIG. 71 shows that, of the total fatty acid composition, ARA is 6.35%, DGLA is 0.90%, ETA is 0.28%, EPA is 6.22%, n-6 DPA is 0.21%, and DHA is 0.51%. FIG. 71 shows that, by GC area, LA/DHA is 8.76, GLA/DHA is 1.59, DGLA/DHA is 1.76, ARA/DHA is 12.45, EPA/DHA is 12.20, LA/EPA is 0.72, GLA/EPA is 0.13, DTA/EPA is 1.77, DTA/ARA is 1.73, DTA/DGLA is 12.23, LA/n-6 DPA is 21.29, GLA/n-6 DPA is 3.86, DGLA/n-6 DPA is 4.29, ARA/n-6 DPA is 30.24, EPA/n-6 DPA is 29.62, DGLA/LA is 0.20, ARA/LA is 1.42, EPA/LA is 1.39, DTA/LA is 2.46, DGLA/GLA is 1.11, ARA/GLA is 7.84, n-6 DPA/DTA is 0.02, DHA/n-3 DPA is 0.03, C20 PUFA/C22 PUFA is 0.50, and n-6 PUFA/n-3 PUFA is 0.81.

As a result, when the Δ4 desaturase gene is disrupted in the *Thraustochytrium aureum* OrfA disruption strain, C22:5n-6 (DPA) and C22:6n-3 (DHA) are not substantially biosynthesized, and the Δ4 desaturase substrates C22:4n-6 (DTA) and C22:5n-3 (DPA) are accumulated.

Thus, it was demonstrated that in order to create a strain that cannot substantially biosynthesize DHA and n-6 DPA from *Thraustochytrium aureum* ATCC 34304, which has both an endogenous elongase-desaturase pathway and an endogenous PUFA-PKS pathway, both a gene of an enzyme constituting the elongase-desaturase pathway (for example, the Δ4 desaturase gene) and a PUFA-PKS pathway associated gene needs to be disrupted.

By using the microbial oil obtained in this manner, it is possible to obtain microbial oil having a fatty acid composition in which the composition ratios of PUFAs other than DHA and n-6 DPA are increased. It is possible to produce any PUFAs by modifying the genes of a microorganism that produces a large amount of DHA. Furthermore, by producing microbial oil that contains particularly little DHA and n-6 DPA, it is possible to produce microbial oil that requires little refinement. Additionally, by transforming elongase and desaturase into a microorganism in this manner, it is possible to obtain a microorganism that produces microbial oil.

INDUSTRIAL APPLICABILITY

A new "pattern" of biosynthesis pathway of polyunsaturated fatty acids (PUFAs) was discovered in microorganisms called labyrinthulids. Because it is possible to provide labyrinthulea that produce PUFAs via only the elongase-desaturase pathway, it is anticipated that PUFAs will be mass produced using only the elongase-desaturase pathway.

The invention claimed is:

1. A method for producing a microbial oil, comprising:

genetically modifying a labyrinthulid which belongs to the genus *Parietichytrium* or the genus *Schizochytrium* by disrupting and/or silencing a Δ4 desaturase gene, a C20 elongase gene, and/or a C18 elongase gene, or by being transformed with an ω3 desaturase gene;

culturing the labyrinthulid; and collecting the microbial oil from the labyrinthulid, wherein the labyrinthulid has an activity of synthesizing DHA via a PUFA-PKS pathway in an amount of not more than 1/100 of a total amount of DHA synthesized in the labyrinthulid or no activity of producing PUFAs via the PUFA-PKS pathway, and the labyrinthulid has an activity of producing PUFAs via an endogenous elongase-desaturase pathway.

2. The method according to claim 1, wherein the microbial oil comprises an increased amount of DTA as compared with the microbial oil collected from the labyrinthulid whose Δ4 desaturase gene is not disrupted or silenced.

3. The method according to claim 1, wherein the microbial oil comprises an increased amount of n-3 DPA as compared with the microbial oil collected from the labyrinthulid whose Δ4 desaturase gene is not disrupted or silenced.

4. The method according to claim 1, wherein the microbial oil comprises an increased amount of EPA as compared with the microbial oil collected from the labyrinthulid whose C20 elongase gene is not disrupted or silenced.

5. The method according to claim 1, wherein the microbial oil comprises an increased amount of ARA as compared with the microbial oil collected from the labyrinthulid whose C20 elongase gene is not disrupted or silenced.

6. The method according to claim 1, wherein the microbial oil comprises an increased amount of STA as compared with the microbial oil collected from the labyrinthulid whose C18 elongase gene is not disrupted or silenced.

7. The method according to claim 1, wherein the microbial oil comprises an increased amount of GLA as compared with the microbial oil collected from the labyrinthulid whose C18 elongase gene is not disrupted or silenced.

8. The method according to claim 1, wherein the microbial oil comprises an increased amount of EPA as compared with the microbial oil collected from the labyrinthulid which is not transformed with the 03 desaturase gene.

9. The method according to claim 1, wherein the microbial oil comprises an increased amount of ETA as compared with the microbial oil collected from the labyrinthulid which is not transformed with the 03 desaturase gene.

10. The method according to claim 1, wherein the labyrinthulid belonging to the genus *Parietichytrium* is *Parietichytrium* sp. SEK358 (FERM BP-11405), *Parietichytrium sarkarianum* SEK364 (FERM BP-11298), or *Parietichytrium* sp. SEK571 (FERM BP 11406), and/or wherein the labyrinthulid belonging to the genus *Schizochytrium* is *Schizochytrium aggregatum* ATCC 28209.

* * * * *